(12) United States Patent
De Leys

(10) Patent No.: US 6,210,903 B1
(45) Date of Patent: Apr. 3, 2001

(54) PEPTIDE DERIVED FROM HUMAN IMMUNODEFICIENCY VIRUS TYPE 1 (HIV-1), ISOLATE ANT70, CONTAINING AN IMMUNODOMINANT EPITOPE AND IT'S USE IN IMMUNODIAGNOSTIC ASSAYS

(75) Inventor: Robert De Leys, Grimbergen (BE)

(73) Assignee: N. V. Innogenetics S. A., Ghent (BE)

(*) Notice: Subject to any disclaimer, the term of this patent is extended or adjusted under 35 U.S.C. 154(b) by 0 days.

(21) Appl. No.: 09/112,206

(22) Filed: Jul. 9, 1998

Related U.S. Application Data

(62) Division of application No. 08/146,028, filed as application No. PCT/EP93/00517 on Mar. 8, 1993, now Pat. No. 5,891,640.

(30) Foreign Application Priority Data

Mar. 6, 1992 (EP) .................................................. 92400598

(51) Int. Cl.⁷ .................................................. G01N 33/53
(52) U.S. Cl. .................. 435/7.1; 424/188.1; 424/208.1; 530/326; 435/5
(58) Field of Search .............................. 435/5, 7.1, 69.1, 435/69.3; 520/300, 326; 424/188.1, 208.1

(56) References Cited

U.S. PATENT DOCUMENTS

| 4,833,071 | 5/1989 | Wang et al. | 435/5 |
| 5,001,049 | 3/1991 | Klein et al. | 435/5 |

FOREIGN PATENT DOCUMENTS

| 0 345 375 | 12/1989 | (EP) . |
| 0 388 232 | 9/1990 | (EP) . |
| 0 438 332 | 7/1991 | (EP) . |
| 0 442 394 | 8/1991 | (EP) . |
| 0 448 095 | 9/1991 | (EP) . |
| 0 461 462 | 12/1991 | (EP) . |
| 0 468 527 | 1/1992 | (EP) . |
| 0 484 787 | 5/1992 | (EP) . |
| 0 489 968 | 6/1992 | (EP) . |
| 84/03506 | 9/1984 | (WO) . |

OTHER PUBLICATIONS

De Leys, R., et al, *Journal of Virology*, vol. 64, No. 3, pp. 1207–1216, Mar. 1990, "Isolation and Partial Characterization of an Unusual Human Immunodeficiency Retrovirus from Two Persons of West–Central African Origin".

R. Von Grunigen et al., Journal of Immunological Methods, 125 (1989) 143–146 "Epitope Analysis: Biotinylated Short Peptides As Inhibitors Of Anti–Peptide Antibody".

K.R. Anumula et al., Journal of Immunological Methods, 135 (1990) 199–208 "Immunologic Methods for Quantitative Estimation of Small Peptides and Their Application to Bradykinin".

R. Von Gruenigen et al., Biol. Chem. Hoppe–Seyler, vol. 372, pp. 163–172, Mar. 1991 "Enzyme Immunoassay with Captured Hapten".

Database WPI, Week 9146, Derwent Publications Ltd., London, GB; AN 91–337496 & SU, A, 1 612 264 (Bioorg Chem Inst) Dec. 7, 1990.

Fischer and Howden, 1990 J. Immunoassay 11:311–327.

Rosen et al., 1987, "Detection of Antibodies to HIV Using Synthetic Peptides Derived from the gp41 Envelope Protein", in Vaccines 87, Cold Spring Harbor Laboratory.

Oldstone et al., 1991, J. Virol. 65:1727–1734.

Gnann et al., 1987, J. Virol. 61:2630–2641.

Gnann et al., 1987, J. Infect. Dis. 156:261–267.

D.E. Pollet et al., Clinical Chemistry, 37, No. 6, (1991) 1024–1025 "Development of a Screening Elisa and a Confirmatory Assay for Hepatitis C Antibodies Based on Synthetic Peptides", Abstract No. 0547.

*Primary Examiner*—Laurie Scheiner
*Assistant Examiner*—Jeffrey S. Parkin
(74) *Attorney, Agent, or Firm*—Nixon & Vanderhye PC

(57) ABSTRACT

This invention is directed toward a peptide corresponding to an immunologically important viral epitope. Specifically, the peptide corresponds to an immunodominant epitope identified in the gp120 region of the human immunodeficiency virus type 1 (HIV-1), strain Ant70. This peptide has the following amino acid sequence: $NH_2$-Gln-Ile-Asp-Ile-Gln-Glu-Met-Arg-Ile-Gly-Pro-Met-Ala-Trp-Tyr-Ser-Met-Gly-Ile-Gly-Gly-$CO_2H$. The invention also relates to the use of this peptide, particularly when biotinylated in the form of complexes of streptavidin-biotinylated peptides or of avidin-biotinylated peptides, for the in vitro determination of HIV-1-specific antibodies.

9 Claims, 57 Drawing Sheets

N-terminally biotinylated TM peptide

C-terminally biotinylated TM peptide

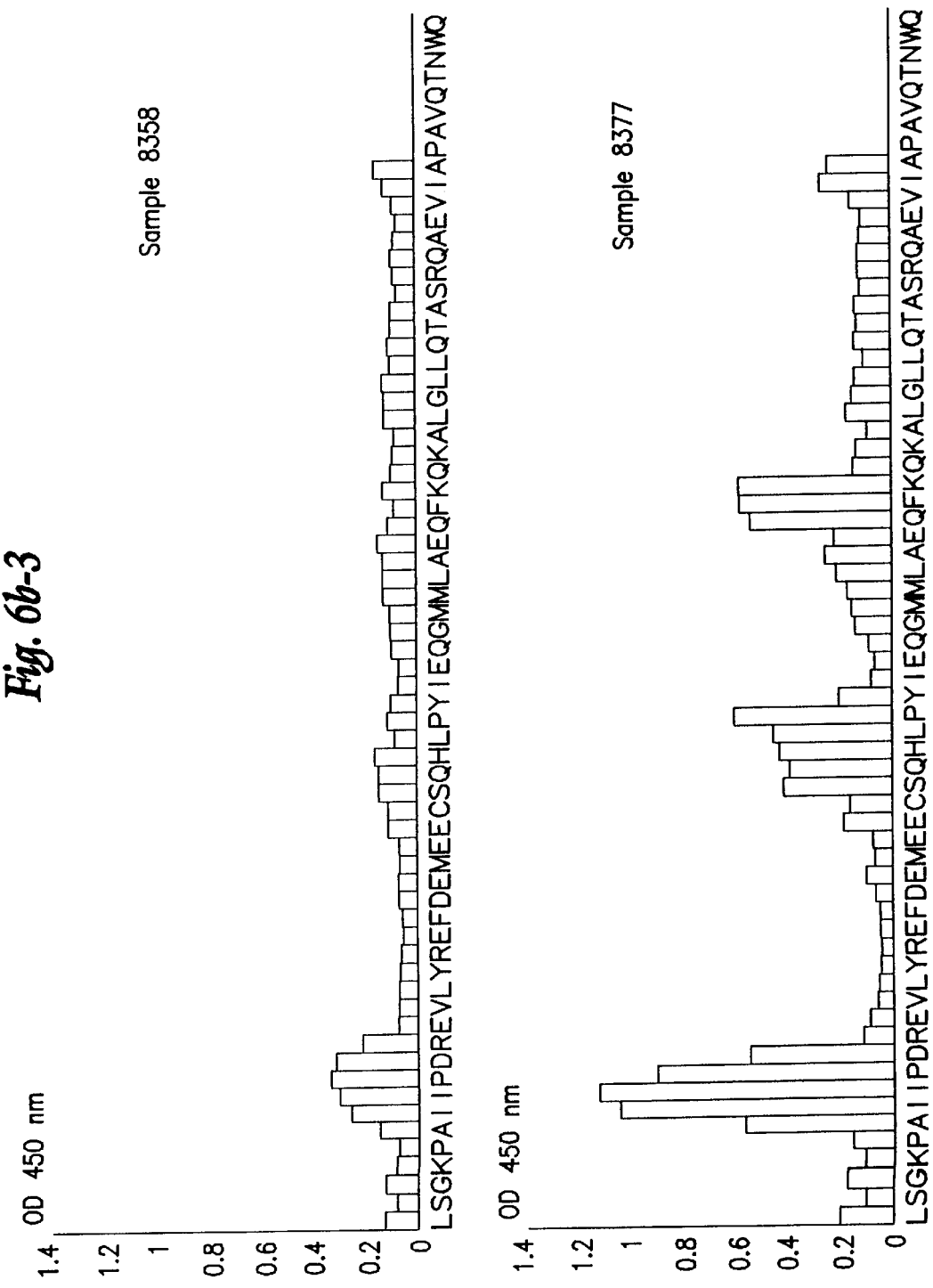

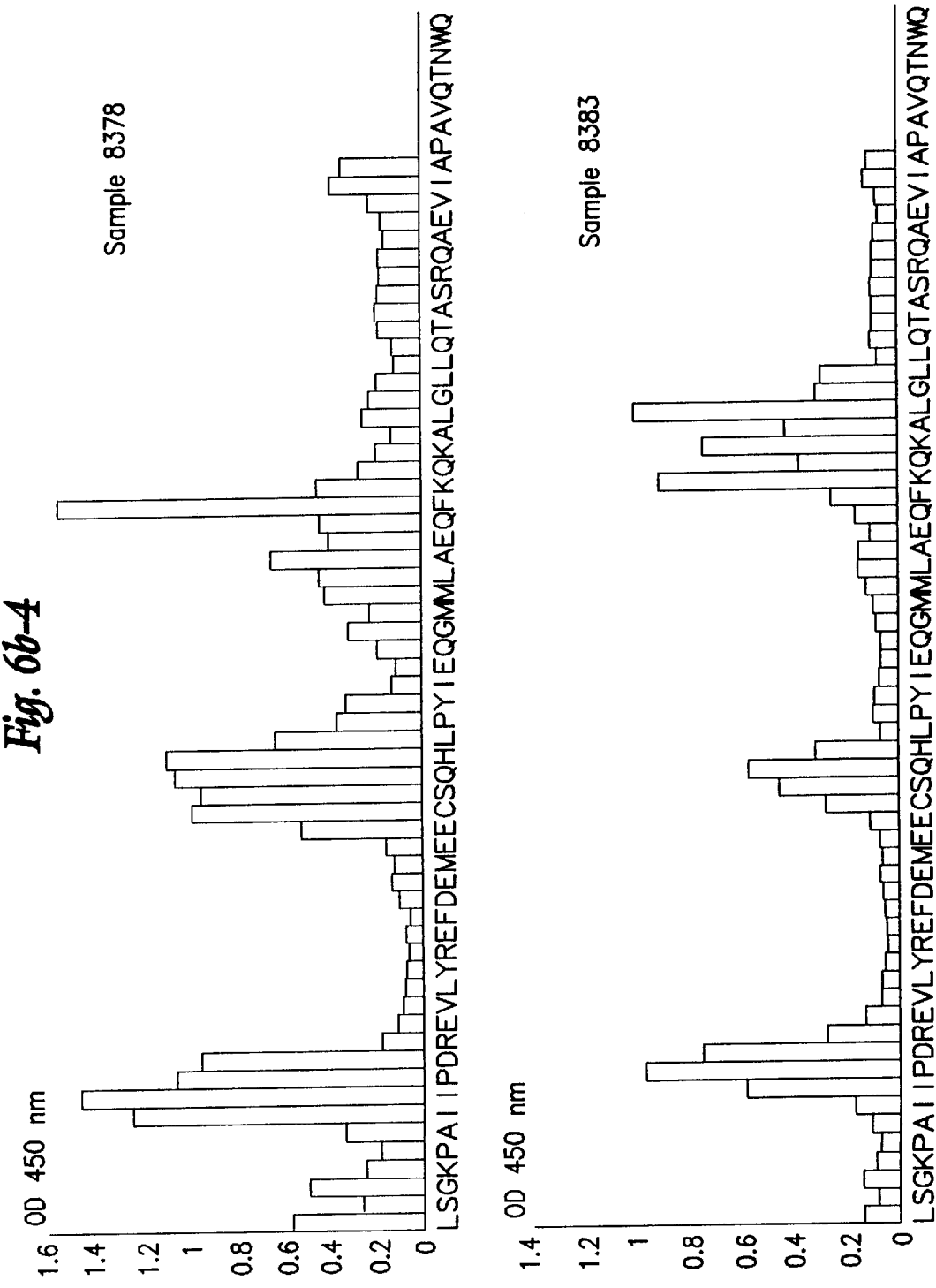

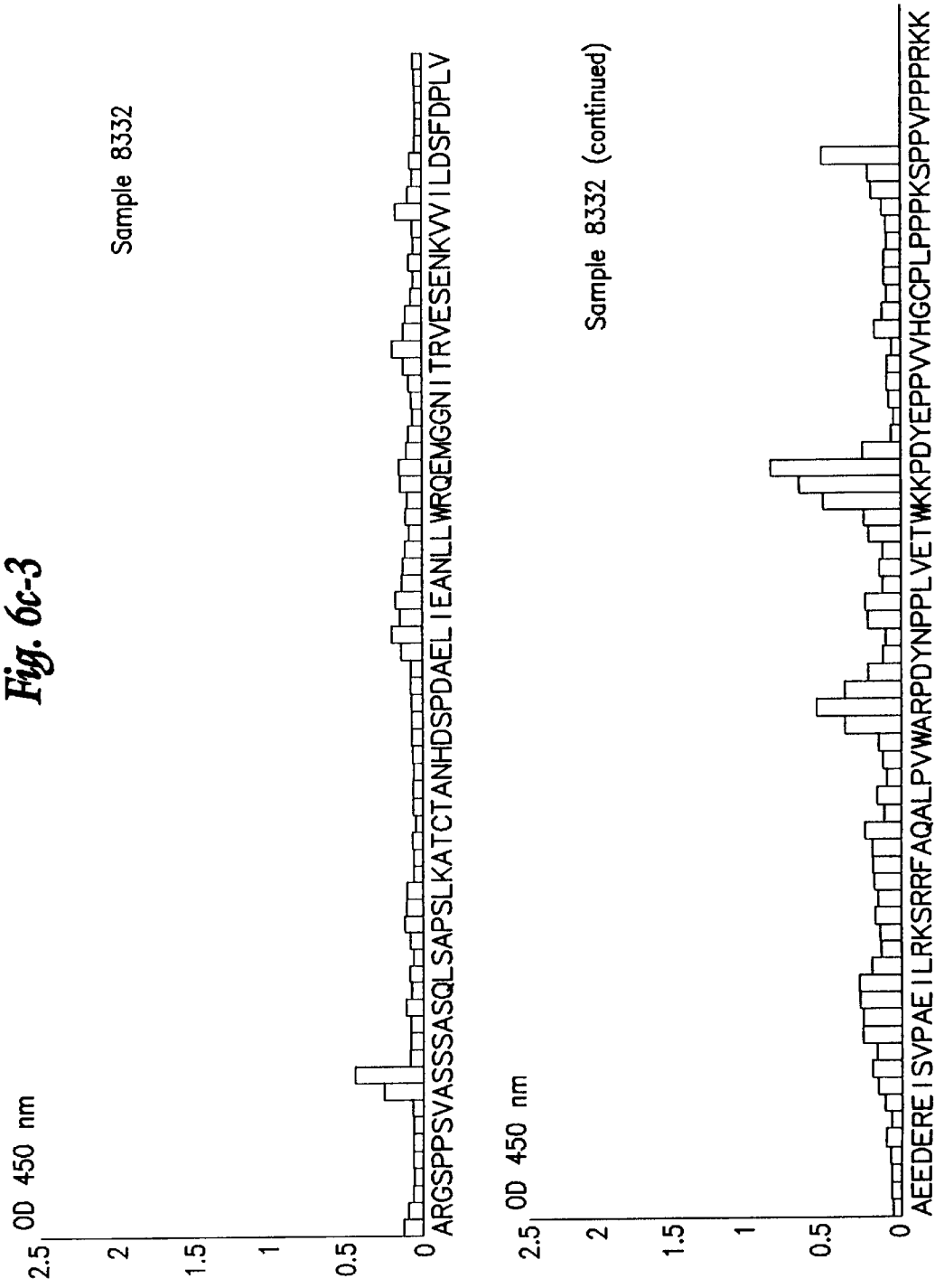

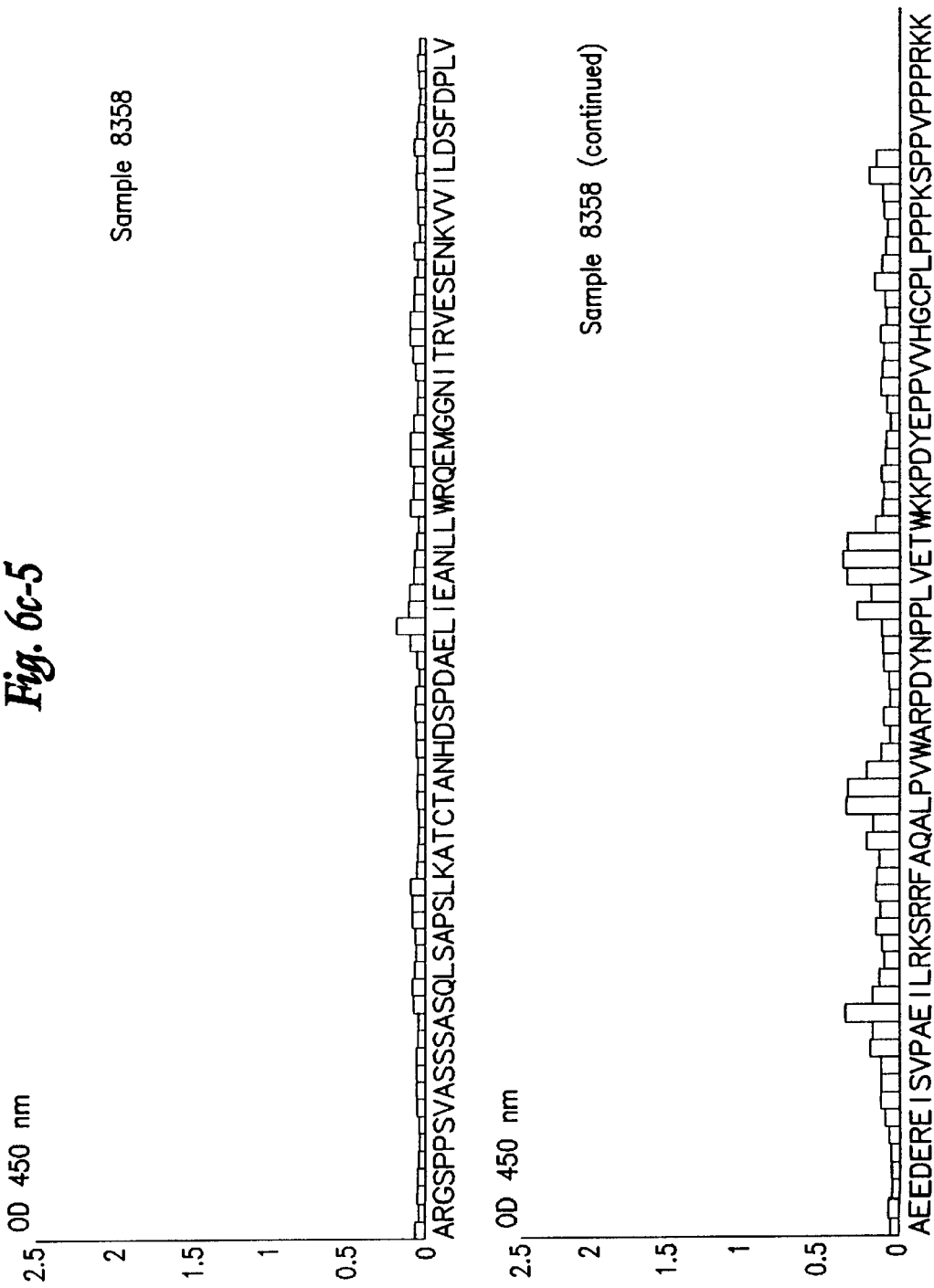

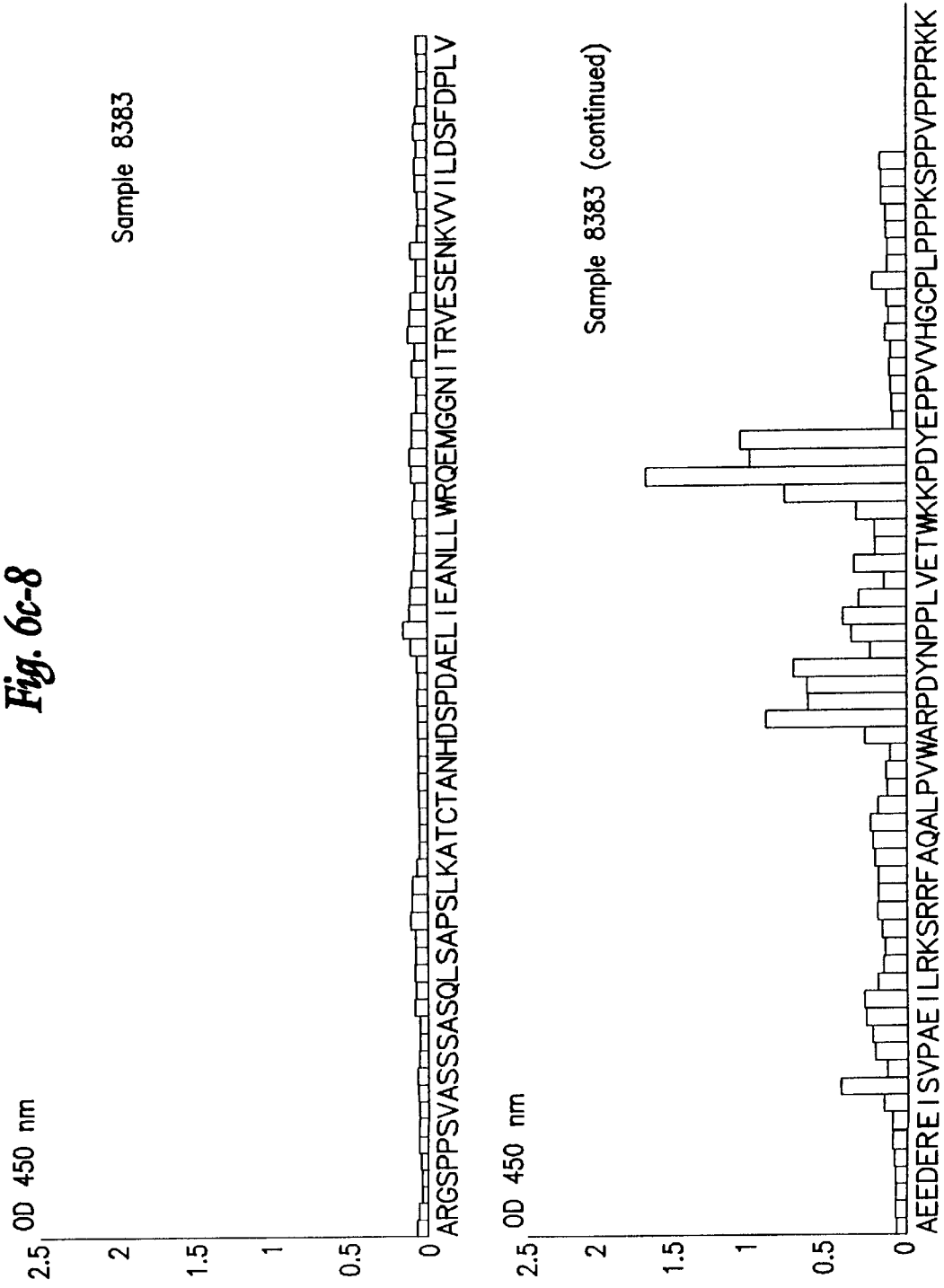

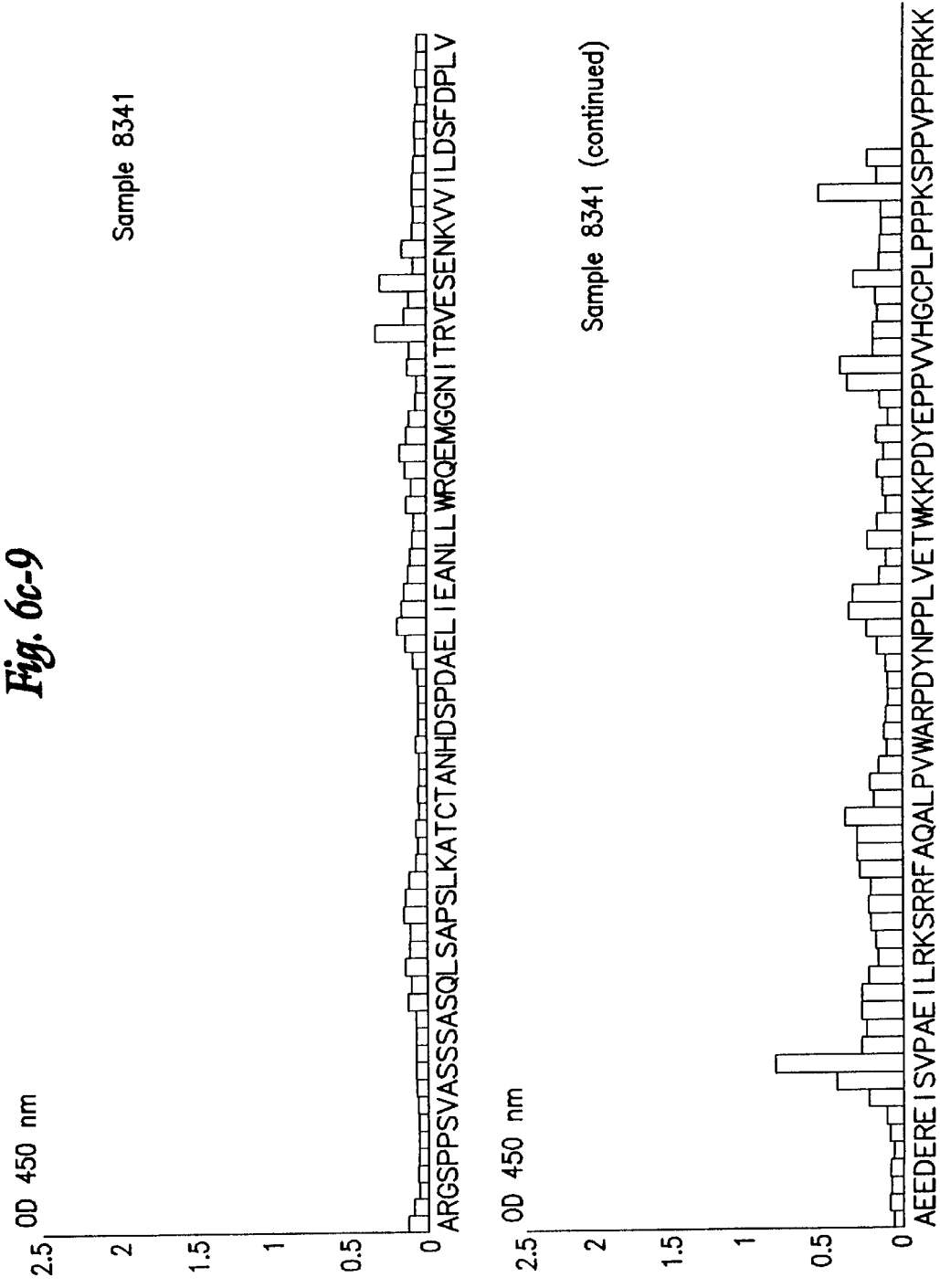

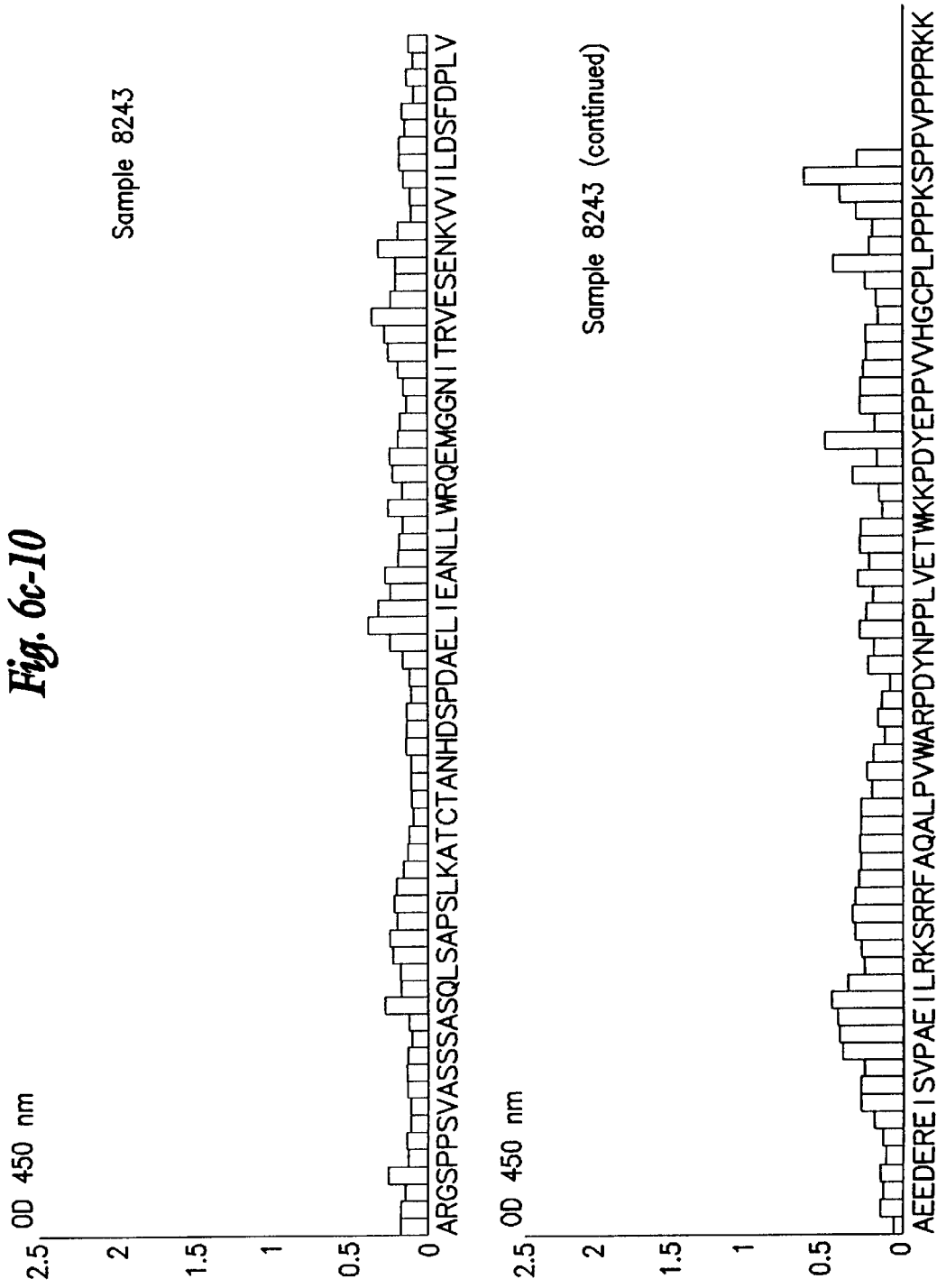

Fig. 7a-1

Peptide I    MSTIPKPQRKTKRNTNRRPQ
Peptide II           PQRKTKRNTNRRPQDVKFPG
Peptide III                  RNTNRRPQDVKFPGGGQIVG

| Peptide I | Peptide II | Peptide III |
|---|---|---|
| MSTIPKPQR | PQRKTKRNT | RNTNRRPQD |
| STIPKPQRK | QRKTKRNTN | NTNRRPQDV |
| TIPKPQRKT | RKTKRNTNR | TNRRPQDVK |
| IPKPQRKTK | KTKRNTNRR | NRRPQDVKF |
| PKPQRKTKR | TKRNTNRRP | RRPQDVKFP |
| KPQRKTKRN | KRNTNRRPQ | RPQDVKFPG |
| PQRKTKRNT | RNTNRRPQD | PQDVKFPGG |
| QRKTKRNTN | NTNRRPQDV | QDVKFPGGG |
| RKTKRNTNR | TNRRPQDVK | DVKFPGGGQ |
| KTKRNTNRR | NRRPQDVKF | VKFPGGGQI |
| TKRNTNRRP | RRPQDVKFP | KFPGGGQIV |
| KRNTNRRPQ | RPQDVKFPG | FPGGGQIVG |

Fig. 7a-2

```
Core 5     PGGGQIVGGVYLLPRRGPRL
Peptide IV        LPRRGPRLGVRATRKTSERS
Peptide V                   TRKTSERSQPRGRRQPIPKV
Peptide VI                           RRQPIPKVRRPEGRTWAQPG
```

| Core 5 | Peptide IV | Peptide V | Peptides VI |
|---|---|---|---|
| PGGGQIVGG | LPRRGPRLG | TRKTSERSQ | RRQPIPKVR |
| GGGQIVGGV | PRRGPRLGV | RKTSERSQP | RQPIPKVRR |
| GGQIVGGVY | RRGPRLGVR | KTSERSQPR | QPIPKVRRP |
| GQIVGGVYL | RGPRLGVRA | TSERSQPRG | PIPKVRRPE |
| QIVGGVYLL | GPRLGVRAT | SERSQPRGR | IPKVRRPEG |
| IVGGVYLLP | PRLGVRATR | ERSQPRGRR | PKVRRPEGR |
| VGGVYLLPR | RLGVRATRK | RSQPRGRRQ | KVRRPEGRT |
| GGVYLLPRR | LGVRATRKT | SQPRGRRQP | VRRPEGRTW |
| GVYLLPRRG | GVRATRKTS | QPRGRRQPI | RRPEGRTWA |
| VYLLPRRGP | VRATRKTSE | PRGRRQPIP | RPEGRTWAQ |
| YLLPRRGPR | RATRKTSER | RGRRQPIPK | PEGRTWAQP |
| LLPRRGPRL | ATRKTSERS | GRRQPIPKV | EGRTWAQPG |

Fig. 7b-1

```
HCV1    LSGKPAIIPDREVLYREFDE
HCV2        IIPDREVLYREFDEMEECSQ
HCV3            VLYREFDEMEECSQHLPYIE
HCV4                DEMEECSQHLPYIEQGMMLA
HCV5                    SQHLPYIEQGMMLAEQFKQK
HCV6                        IEQGMMLAEQFKQKALGLLQ
```

| HCV1 | HCV2 | HCV3 | HCV4 | HCV5 | HCV6 |
|------|------|------|------|------|------|
| LSGKPAIIP | IIPDREVLY | VLYREFDEM | DEMEECSQH | SQHLPYIEQ | IEQGMMLAE |
| SGKPAIIPD | IPDREVLYR | LYREFDEME | EMEECSQHL | QHLPYIEQG | EQGMMLAEQ |
| GKPAIIPDR | PDREVLYRE | YREFDEMEE | MEECSQHLP | HLPYIEQGM | QGMMLAEQF |
| KPAIIPDRE | DREVLYREF | REFDEMEEC | EECSQHLPY | LPYIEQGMM | GMMLAEQFK |
| PAIIPDREV | REVLYREFD | EFDEMEECS | ECSQHLPYI | PYIEQGMML | MMLAEQFKQ |
| AIIPDREVL | EVLYREFDE | FDEMEECSQ | CSQHLPYIE | YIEQGMMLA | MLAEQFKQK |
| IIPDREVLY | VLYREFDEM | DEMEECSQH | SQHLPYIEQ | IEQGMMLAE | LAEQFKQKA |
| IPDREVLYR | LYREFDEME | EMEECSQHL | QHLPYIEQG | EQGMMLAEQ | AEQFKQKAL |
| PDREVLYRE | YREFDEMEE | MEECSQHLP | HLPYIEQGM | QGMMLAEQF | EQFKQKALG |
| DREVLYREF | REFDEMEEC | EECSQHLPY | LPYIEQGMM | GMMLAEQFK | QFKQKALGL |
| REVLYREFD | EFDEMEECS | ECSQHLPYI | PYIEQGMML | MMLAEQFKQ | FKQKALGLL |
| EVLYREFDE | FDEMEECSQ | CSQHLPYIE | YIEQGMMLA | MLAEQFKQK | KQKALGLLQ |

Fig. 7b-2

HCV7 LAEQFKQKALGLLQTASRQA
HCV8 QKALGLLQTASRQAEVIAPA
HCV9 LQTASRQAEVIAPAVQTNWQ

HCV7

LAEQFKQKA
AEQFKQKAL
EQFKQKALG
QFKQKALGL
FKQKALGLL
KQKALGLLQ
QKALGLLQT
KALGLLQTA
ALGLLQTAS
LGLLQTASR
GLLQTASRQ
LLQTASRQA

HCV8

QKALGLLQT
KALGLLQTA
ALGLLQTAS
LGLLQTASR
GLLQTASRQ
LLQTASRQA
LQTASRQAE
QTASRQAEV
TASRQAEVI
ASRQAEVIA
SRQAEVIAP
RQAEVIAPA

HCV9

LQTASRQAE
QTASRQAEV
TASRQAEVI
ASRQAEVIA
SRQAEVIAP
RQAEVIAPA
QAEVIAPAV
AEVIAPAVQ
EVIAPAVQT
VIAPAVQTN
IAPAVQTNW
APAVQTNWQ

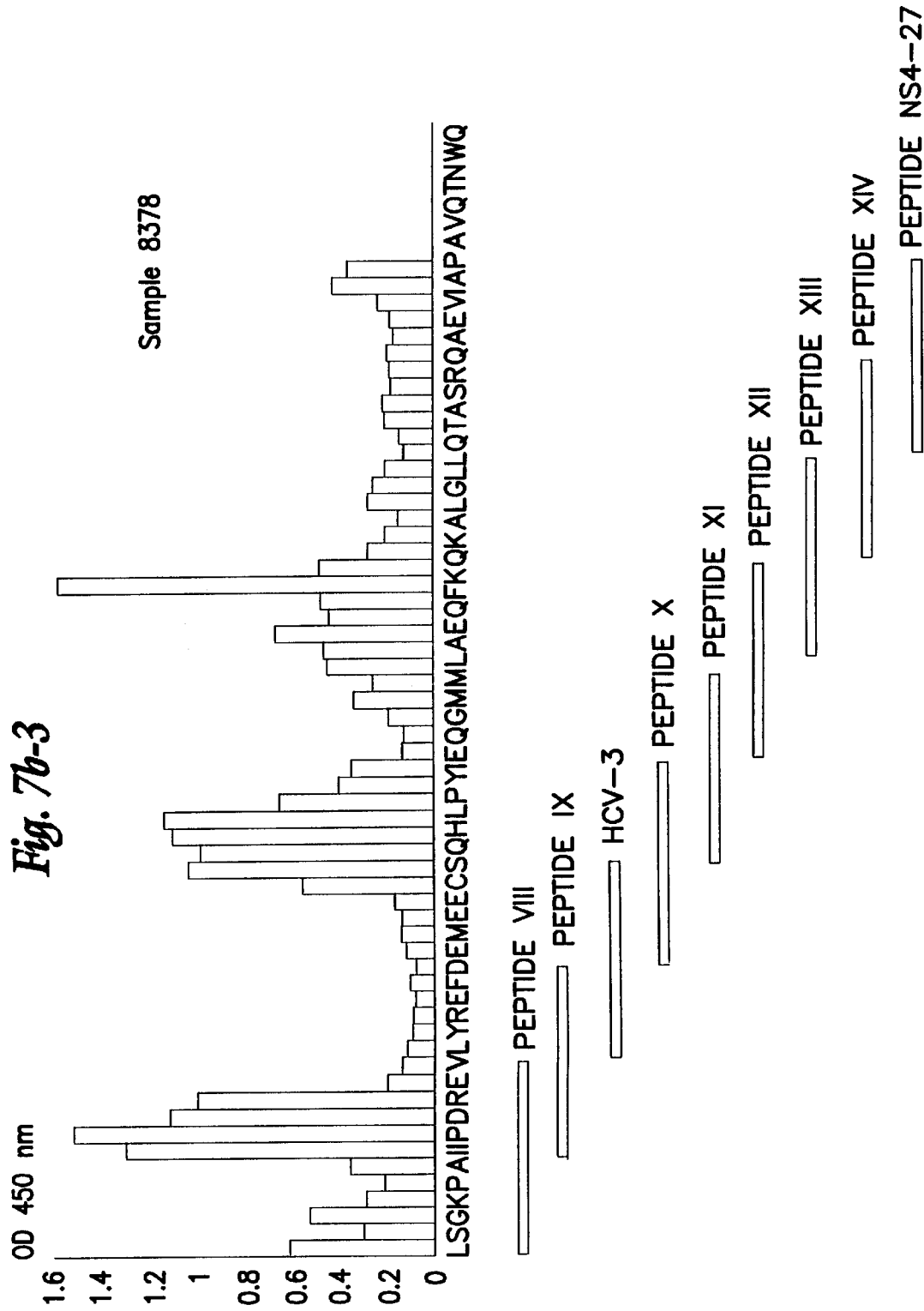

Fig. 7c-1

NS5-21 GNITRYESENKVVILDSFDP
NS5-23 　　　　　　VILDSFDPLVAEEDEREISV
NS5-25 　　　　　　　　　　　　EDEREISVPAEILRKSRRFA
NS5-27 　　　　　　　　　　　　　　　　　　　　LRKSRRFAQALPVWARPDYN
NS5-29 　　　　　　　　　　　　　　　　　　　　　　　　　　　　VWARPDYNPPLVETWKKPDY

| NS5-21 | NS5-23 | NS5-25 | NS5-27 | NS5-29 |
|---|---|---|---|---|
| GNITRYESE | VILDSFDPL | EDEREISVP | LRKSRRFAQ | VWARPDYNP |
| NITRYESEN | ILDSFDPLV | DEREISVPA | RKSRRFAQA | WARPDYNPP |
| ITRYESENK | LDSFDPLVA | EREISVPAE | KSRRFAQAL | ARPDYNPPL |
| TRYESENKV | DSFDPLVAE | REISVPAEI | SRRFAQALP | RPDYNPPLV |
| RYESENKVV | SFDPLVAEE | EISVPAEIL | RRFAQALPV | PDYNPPLVE |
| YESENKVVI | FDPLVAEED | ISVPAEILR | RFAQALPVW | DYNPPLVET |
| ESENKVVIL | DPLVAEEDE | SVPAEILRK | FAQALPVWA | YNPPLVETW |
| SENKVVILD | PLVAEEDER | VPAEILRKS | AQALPVWAR | NPPLVETWK |
| ENKVVILDS | LVAEEDERE | PAEILRKSR | QALPVWARP | PPLVETWKK |
| NKVVILDSF | VAEEDEREI | AEILRKSRR | ALPVWARPD | PLVETWKKP |
| KVVILDSFD | AEEDEREIS | EILRKSRRF | LPVWARPDY | LVETWKKPD |
| VVILDSFDP | EEDEREISV | ILRKSRRFA | PVWARPDYN | VETWKKPDY |

Fig. 7c-2

NS5-31  ETWKKPDYEPPVVHGCPLPP
NS5-33  VHGCPLPPKSPPVPPPRKK

NS5-31

ETWKKPDYE
TWKKPDYEP
WKKPDYEPP
KKPDYEPPV
KPDYEPPVV
PDYEPPVVH
DYEPPVVHG
YEPPVVHGC
EPPVVHGCP
PPVVHGCPL
PVVHGCPLP
VVHGCPLPP

NS5-33

VHGCPLPPK
HGCPLPPKS
GCPLPPKSP
CPLPPKSPP
PLPPKSPPV
LPPPKSPPVP

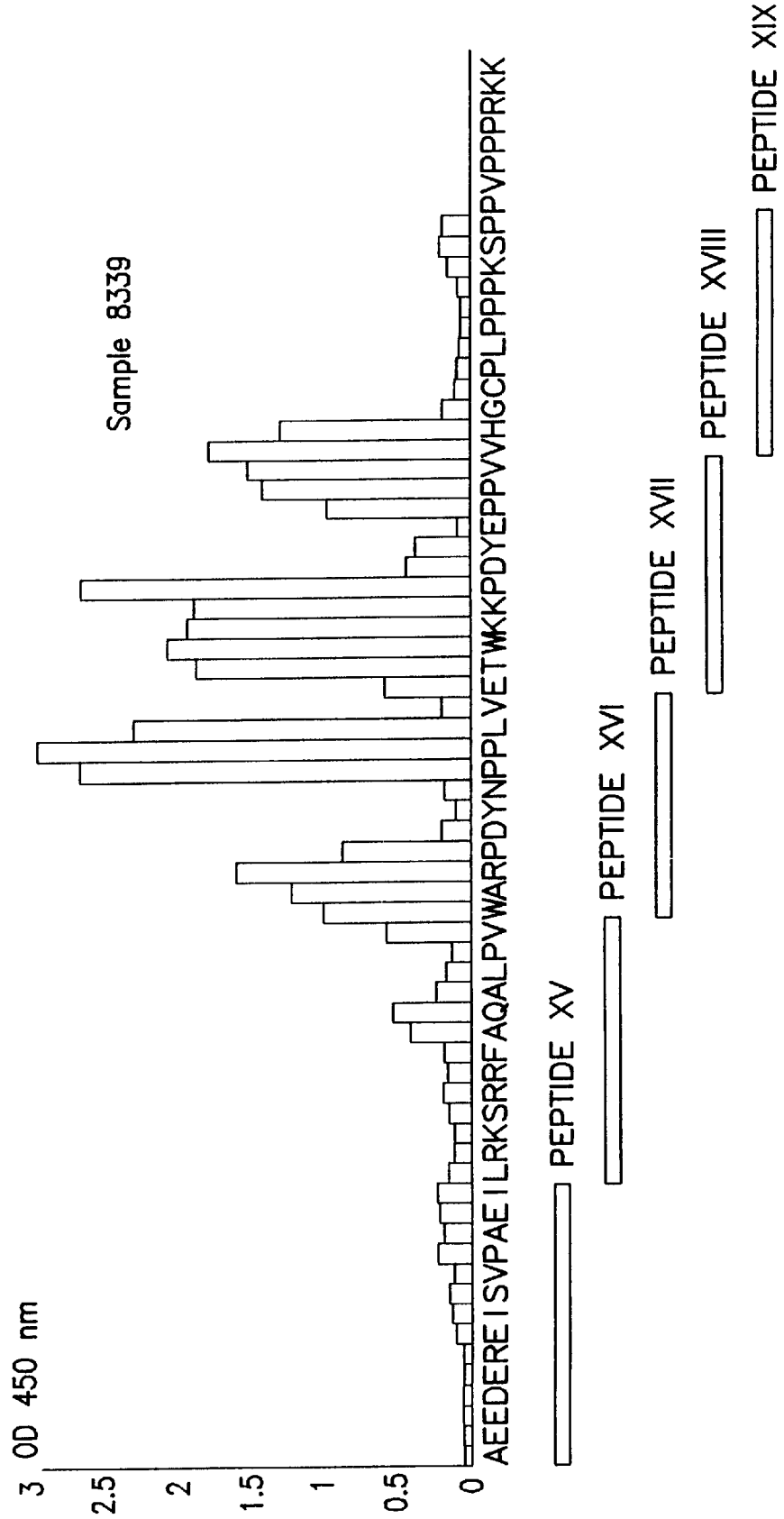

a: High intensity control
b: Low intensity control
c: Medium intensity control
d: Peptide XXg-1, unbiotinylated
e: Peptide XXg-2, unbiotinylated
f: Biotinylated peptide XXg-1: streptavidin complex
g: Biotinylated peptide XXg-2: streptavidin complex

Fig. 11

| Peptide | Sequence |
|---------|----------|
| NS4-a | GALVAFKIMSGEVPSTEDLV |
| NS4-b | VPSTEDLVNLLPAILSPGAL |
| NS4-c | AILSPGALVVGVVCAAILRR |
| NS4-d | VCAAILRRHVGPGEGAVQWM |
| NS4-e | GEGAVQWMNRLIAFASRGNH |

Fig. 12

| Peptide | Amino Acid Sequence |
|---|---|
| Epi-152 | Bio-GG-IPDREVLYRGGKKPDYEPPVGGRRPQDVKFP<br>　　　　　└─NS4 epitope 1─┘└─NS5 epitope 5─┘└─Core epitope 2─┘ |
| Epi-33B3A | Bio-GG-WARPDYNPPGGQFKQKALGLGSGVYLLPRRG<br>　　　　　└─NS5 epitope 3─┘└─NS4 epitope 3B─┘└─Core epitope 3A─┘ |
| Epi-4B2A6 | Bio-GG-RGRRQPIPKGGSQHLPYIEQSGPVVHGCPLP<br>　　　　　└─Core epitope 4B─┘└─NS4 epitope 2A─┘└─NS5 epitope 6─┘ |

Synthesis of peptide sequence

Cleavage and side-chain deprotection

Oxidation and dimerization

RABBIT 325, 326: XXb-2-MAP
RABBIT 327, 328: XXg-2-MAP

```
                        SEQUENCE LISTING (1) GENERAL INFORMATION:

(iii) NUMBER OF SEQUENCES: 453

(2) INFORMATION FOR SEQ ID NO: 1:

(i) SEQUENCE CHARACTERISTICS:
         (A) LENGTH: 11 amino acids
         (B) TYPE: amino acid
         (D) TOPOLOGY: linear (ii) MOLECULE TYPE: peptide (iii) HYPOTHETICAL: NO (vi) ORIGINAL SOURCE:
         (C) INDIVIDUAL ISOLATE: HTLV-IIIB (ix) FEATURE:
         (A) NAME/KEY: Modified-site
         (B) LOCATION: 1

(ix) FEATURE:
         (A) NAME/KEY: Modified-site
         (B) LOCATION: 11

(xi) SEQUENCE DESCRIPTION: SEQ ID NO: 1:

Xaa Ile Trp Gly Cys Ser Gly Lys Ile Cys Xaa
```

```
1               5                  10
```

(2) INFORMATION FOR SEQ ID NO: 2:

(i) SEQUENCE CHARACTERISTICS:
        (A) LENGTH: 21 amino acids
        (B) TYPE: amino acid
        (D) TOPOLOGY: linear (ii) MOLECULE TYPE: peptide (iii) HYPOTHETICAL: NO (vi) ORIGINAL SOURCE:
        (C) INDIVIDUAL ISOLATE: HIV-1

(ix) FEATURE:
        (A) NAME/KEY: Modified-site
        (B) LOCATION: 1

(ix) FEATURE:
        (A) NAME/KEY: Modified-site
        (B) LOCATION: 21

(xi) SEQUENCE DESCRIPTION: SEQ ID NO: 2:

```
Xaa Ile Trp Gly Cys Ser Gly Lys Leu Ile Cys Thr Thr Ala Val Pro
1               5                  10                  15

Trp Asn Ala Ser Xaa
            20
```

(2) INFORMATION FOR SEQ ID NO: 3:

(i) SEQUENCE CHARACTERISTICS:
        (A) LENGTH: 22 amino acids
        (B) TYPE: amino acid
        (D) TOPOLOGY: linear (ii) MOLECULE TYPE: peptide (iii) HYPOTHETICAL: NO (vi) ORIGINAL SOURCE:
        (C) INDIVIDUAL ISOLATE: HIV-1

(ix) FEATURE:
        (A) NAME/KEY: Modified-site
        (B) LOCATION: 1

(ix) FEATURE:
        (A) NAME/KEY: Modified-site
        (B) LOCATION: 22

(xi) SEQUENCE DESCRIPTION: SEQ ID NO: 3:

```
Xaa Glu Arg Tyr Leu Lys Asp Gln Gln Leu Leu Gly Ile Trp Gly Cys
1               5                  10                  15

Ser Gly Lys Leu Ile Xaa
            20
```

(2) INFORMATION FOR SEQ ID NO: 4:

(i) SEQUENCE CHARACTERISTICS:
        (A) LENGTH: 19 amino acids
        (B) TYPE: amino acid
        (D) TOPOLOGY: linear (ii) MOLECULE TYPE: peptide (iii) HYPOTHETICAL: NO (vi) ORIGINAL SOURCE:
        (C) INDIVIDUAL ISOLATE: HIV-1

```
    (ix) FEATURE:
         (A) NAME/KEY: Modified-site
         (B) LOCATION: 1

(ix) FEATURE:
         (A) NAME/KEY: Modified-site
         (B) LOCATION: 19

(xi) SEQUENCE DESCRIPTION: SEQ ID NO: 4:

Xaa Leu Gln Ala Arg Ile Leu Ala Val Glu Arg Tyr Leu Lys Asp Gln
1               5                   10                  15

Gln Leu Xaa (2) INFORMATION FOR SEQ ID NO: 5:

(i) SEQUENCE CHARACTERISTICS:
        (A) LENGTH: 12 amino acids
        (B) TYPE: amino acid
        (D) TOPOLOGY: linear (ii) MOLECULE TYPE: peptide (iii) HYPOTHETICAL: NO (vi) ORIGINAL SOURCE:
         (C) INDIVIDUAL ISOLATE: Ant70

(ix) FEATURE:
         (A) NAME/KEY: Modified-site
         (B) LOCATION: 1

(ix) FEATURE:
         (A) NAME/KEY: Modified-site
         (B) LOCATION: 12

(xi) SEQUENCE DESCRIPTION: SEQ ID NO: 5:

Xaa Leu Trp Gly Cys Lys Gly Lys Leu Val Cys Xaa
1               5                   10

(2) INFORMATION FOR SEQ ID NO: 6:

(i) SEQUENCE CHARACTERISTICS:
        (A) LENGTH: 25 amino acids
        (B) TYPE: amino acid
        (D) TOPOLOGY: linear (ii) MOLECULE TYPE: peptide (iii) HYPOTHETICAL: NO (vi) ORIGINAL SOURCE:
         (C) INDIVIDUAL ISOLATE: ELI (ix) FEATURE:
         (A) NAME/KEY: Modified-site
         (B) LOCATION: 1

(ix) FEATURE:
         (A) NAME/KEY: Modified-site
         (B) LOCATION: 25

(xi) SEQUENCE DESCRIPTION: SEQ ID NO: 6:

Xaa Asp Gln Gln Leu Leu Gly Ile Trp Gly Cys Ser Gly Lys His Ile
1               5                   10                  15

Cys Thr Thr Asn Val Pro Trp Asn Xaa
                20                  25

(2) INFORMATION FOR SEQ ID NO: 7:

(i) SEQUENCE CHARACTERISTICS:
        (A) LENGTH: 25 amino acids
```

```
      (B) TYPE: amino acid
      (D) TOPOLOGY: linear (ii) MOLECULE TYPE: peptide (iii) HYPOTHETICAL: YES (ix) FEATURE:
      (A) NAME/KEY: Modified-site
      (B) LOCATION: 1

(ix) FEATURE:
      (A) NAME/KEY: Modified-site
      (B) LOCATION: 25

(xi) SEQUENCE DESCRIPTION: SEQ ID NO: 7:

Xaa Asn Asn Thr Arg Lys Ser Ile His Ile Gly Pro Gly Arg Ala Phe
1               5                  10                  15

Tyr Thr Thr Gly Glu Ile Ile Gly Xaa
            20                  25

(2) INFORMATION FOR SEQ ID NO: 8:

(i) SEQUENCE CHARACTERISTICS:
      (A) LENGTH: 37 amino acids
      (B) TYPE: amino acid
      (D) TOPOLOGY: linear (ii) MOLECULE TYPE: peptide (iii) HYPOTHETICAL: YES (ix) FEATURE:
      (A) NAME/KEY: Modified-site
      (B) LOCATION: 1

(ix) FEATURE:
      (A) NAME/KEY: Modified-site
      (B) LOCATION: 37

(xi) SEQUENCE DESCRIPTION: SEQ ID NO: 8:

Xaa Cys Thr Arg Pro Asn Asn Asn Thr Arg Lys Ser Ile His Ile Gly
1               5                  10                  15

Pro Gly Arg Ala Phe Tyr Thr Thr Gly Glu Ile Ile Gly Asp Ile Arg
                20                  25                  30

Gln Ala His Cys Xaa
            35

(2) INFORMATION FOR SEQ ID NO: 9:

(i) SEQUENCE CHARACTERISTICS:
      (A) LENGTH: 25 amino acids
      (B) TYPE: amino acid
      (D) TOPOLOGY: linear (ii) MOLECULE TYPE: peptide (iii) HYPOTHETICAL: NO (vi) ORIGINAL SOURCE:
      (C) INDIVIDUAL ISOLATE: HIV-1 SF2

(ix) FEATURE:
      (A) NAME/KEY: Modified-site
      (B) LOCATION: 1

(ix) FEATURE:
      (A) NAME/KEY: Modified-site
      (B) LOCATION: 25

(xi) SEQUENCE DESCRIPTION: SEQ ID NO: 9:
```

```
Xaa Asn Asn Thr Arg Lys Ser Ile Tyr Ile Gly Pro Gly Arg Ala Phe
 1               5                  10                  15

His Thr Thr Gly Arg Ile Ile Gly Xaa
            20                  25
```

(2) INFORMATION FOR SEQ ID NO: 10:

(i) SEQUENCE CHARACTERISTICS:
        (A) LENGTH: 25 amino acids
        (B) TYPE: amino acid
        (D) TOPOLOGY: linear (ii) MOLECULE TYPE: peptide (iii) HYPOTHETICAL: NO (vi) ORIGINAL SOURCE:
       (C) INDIVIDUAL ISOLATE: HIV-1 SC (ix) FEATURE:
       (A) NAME/KEY: Modified-site
       (B) LOCATION: 1

(ix) FEATURE:
       (A) NAME/KEY: Modified-site
       (B) LOCATION: 25

(xi) SEQUENCE DESCRIPTION: SEQ ID NO: 10:

```
Xaa Asn Asn Thr Thr Arg Ser Ile His Ile Gly Pro Gly Arg Ala Phe
 1               5                  10                  15

Tyr Ala Thr Gly Asp Ile Ile Gly Xaa
            20                  25
```

(2) INFORMATION FOR SEQ ID NO: 11:

(i) SEQUENCE CHARACTERISTICS:
        (A) LENGTH: 25 amino acids
        (B) TYPE: amino acid
        (D) TOPOLOGY: linear (ii) MOLECULE TYPE: peptide (iii) HYPOTHETICAL: NO (vi) ORIGINAL SOURCE:
       (C) INDIVIDUAL ISOLATE: HIV-1 MN (ix) FEATURE:
       (A) NAME/KEY: Modified-site
       (B) LOCATION: 1

(ix) FEATURE:
       (A) NAME/KEY: Modified-site
       (B) LOCATION: 25

(xi) SEQUENCE DESCRIPTION: SEQ ID NO: 11:

```
Xaa Tyr Asn Lys Arg Lys Arg Ile His Ile Gly Pro Gly Arg Ala Phe
 1               5                  10                  15

Tyr Thr Thr Lys Asn Ile Ile Gly Xaa
            20                  25
```

(2) INFORMATION FOR SEQ ID NO: 12:

(i) SEQUENCE CHARACTERISTICS:
        (A) LENGTH: 25 amino acids
        (B) TYPE: amino acid
        (D) TOPOLOGY: linear (ii) MOLECULE TYPE: peptide (iii) HYPOTHETICAL: NO (vi) ORIGINAL SOURCE:
    (C) INDIVIDUAL ISOLATE: HIV-1 RF (ix) FEATURE:
    (A) NAME/KEY: Modified-site
    (B) LOCATION: 1

(ix) FEATURE:
    (A) NAME/KEY: Modified-site
    (B) LOCATION: 25

(xi) SEQUENCE DESCRIPTION: SEQ ID NO: 12:

```
Xaa Asn Asn Thr Arg Lys Ser Ile Thr Lys Gly Pro Gly Arg Val Ile
1               5                   10                  15

Tyr Ala Thr Gly Gln Ile Ile Gly Xaa
            20                  25
```

(2) INFORMATION FOR SEQ ID NO: 13:

(i) SEQUENCE CHARACTERISTICS:
        (A) LENGTH: 24 amino acids
        (B) TYPE: amino acid
        (D) TOPOLOGY: linear (ii) MOLECULE TYPE: peptide (iii) HYPOTHETICAL: NO (vi) ORIGINAL SOURCE:
        (C) INDIVIDUAL ISOLATE: HIV-1 mal (ix) FEATURE:
        (A) NAME/KEY: Modified-site
        (B) LOCATION: 1

(ix) FEATURE:
        (A) NAME/KEY: Modified-site
        (B) LOCATION: 24

(xi) SEQUENCE DESCRIPTION: SEQ ID NO: 13:

```
Xaa Asn Asn Thr Arg Arg Gly Ile His Phe Gly Pro Gly Gln Ala Leu
1               5                   10                  15

Tyr Thr Thr Gly Ile Val Gly Xaa
            20
```

(2) INFORMATION FOR SEQ ID NO: 14:

(i) SEQUENCE CHARACTERISTICS:
        (A) LENGTH: 26 amino acids
        (B) TYPE: amino acid
        (D) TOPOLOGY: linear (ii) MOLECULE TYPE: peptide (iii) HYPOTHETICAL: NO (vi) ORIGINAL SOURCE:
        (C) INDIVIDUAL ISOLATE: HTLV-IIIB (ix) FEATURE:
        (A) NAME/KEY: Modified-site
        (B) LOCATION: 1

(ix) FEATURE:
        (A) NAME/KEY: Modified-site
        (B) LOCATION: 26

(xi) SEQUENCE DESCRIPTION: SEQ ID NO: 14:

```
Xaa Asn Asn Thr Arg Lys Ser Ile Arg Ile Gln Arg Gly Pro Gly Arg
1               5                   10                  15
```

```
Ala Phe Val Thr Ile Gly Lys Ile Gly Xaa
            20                  25

(2) INFORMATION FOR SEQ ID NO: 15:

(i) SEQUENCE CHARACTERISTICS:
        (A) LENGTH: 24 amino acids
        (B) TYPE: amino acid
        (D) TOPOLOGY: linear (ii) MOLECULE TYPE: peptide (iii) HYPOTHETICAL: NO (vi) ORIGINAL SOURCE:
        (C) INDIVIDUAL ISOLATE: HIV-1 ELI (ix) FEATURE:
        (A) NAME/KEY: Modified-site
        (B) LOCATION: 1

(ix) FEATURE:
        (A) NAME/KEY: Modified-site
        (B) LOCATION: 24

(xi) SEQUENCE DESCRIPTION: SEQ ID NO: 15:

Xaa Gln Asn Thr Arg Gln Arg Thr Pro Ile Gly Leu Gly Gln Ser Leu
1               5                  10                  15

Tyr Thr Thr Arg Ser Arg Ser Xaa
            20

(2) INFORMATION FOR SEQ ID NO: 16:

(i) SEQUENCE CHARACTERISTICS:
        (A) LENGTH: 23 amino acids
        (B) TYPE: amino acid
        (D) TOPOLOGY: linear (ii) MOLECULE TYPE: peptide (iii) HYPOTHETICAL: NO (vi) ORIGINAL SOURCE:
        (C) INDIVIDUAL ISOLATE: Ant70

(ix) FEATURE:
        (A) NAME/KEY: Modified-site
        (B) LOCATION: 1

(ix) FEATURE:
        (A) NAME/KEY: Modified-site
        (B) LOCATION: 23

(xi) SEQUENCE DESCRIPTION: SEQ ID NO: 16:

Xaa Gln Ile Asp Ile Gln Glu Met Arg Ile Gly Pro Met Ala Trp Tyr
1               5                  10                  15

Ser Met Gly Ile Gly Gly Xaa
            20

(2) INFORMATION FOR SEQ ID NO: 17:

(i) SEQUENCE CHARACTERISTICS:
        (A) LENGTH: 25 amino acids
        (B) TYPE: amino acid
        (D) TOPOLOGY: linear (ii) MOLECULE TYPE: peptide (iii) HYPOTHETICAL: YES (ix) FEATURE:
        (A) NAME/KEY: Modified-site
```

(B) LOCATION: 1

(ix) FEATURE:
            (A) NAME/KEY: Modified-site
            (B) LOCATION: 25

(xi) SEQUENCE DESCRIPTION: SEQ ID NO: 17:

Xaa Asn Asn Thr Arg Arg Gly Ile His Met Gly Trp Gly Arg Thr Phe
1               5                   10                  15

Tyr Ala Thr Gly Glu Ile Ile Gly Xaa
            20                  25

(2) INFORMATION FOR SEQ ID NO: 18:

(i) SEQUENCE CHARACTERISTICS:
            (A) LENGTH: 38 amino acids
            (B) TYPE: amino acid
            (D) TOPOLOGY: linear (ii) MOLECULE TYPE: peptide (iii) HYPOTHETICAL: NO (vi) ORIGINAL SOURCE:
            (C) INDIVIDUAL ISOLATE: HIV-1 gp120

(ix) FEATURE:
            (A) NAME/KEY: Modified-site
            (B) LOCATION: 1

(ix) FEATURE:
            (A) NAME/KEY: Modified-site
            (B) LOCATION: 38

(xi) SEQUENCE DESCRIPTION: SEQ ID NO: 18:

Xaa Arg Asp Asn Trp Arg Ser Glu Leu Tyr Lys Tyr Lys Val Val Lys
1               5                   10                  15

Ile Glu Pro Leu Gly Val Ala Pro Thr Lys Ala Lys Arg Arg Val Val
            20                  25                  30

Gln Arg Glu Lys Arg Xaa
        35

(2) INFORMATION FOR SEQ ID NO: 19:

(i) SEQUENCE CHARACTERISTICS:
            (A) LENGTH: 12 amino acids
            (B) TYPE: amino acid
            (D) TOPOLOGY: linear (ii) MOLECULE TYPE: peptide (iii) HYPOTHETICAL: NO (vi) ORIGINAL SOURCE:
            (C) INDIVIDUAL ISOLATE: HIV-2 rod (ix) FEATURE:
            (A) NAME/KEY: Modified-site
            (B) LOCATION: 1

(ix) FEATURE:
            (A) NAME/KEY: Modified-site
            (B) LOCATION: 12

(xi) SEQUENCE DESCRIPTION: SEQ ID NO: 19:

Xaa Ser Trp Gly Cys Ala Phe Arg Gln Val Cys Xaa
1               5                   10

(2) INFORMATION FOR SEQ ID NO: 20:

```
        (i) SEQUENCE CHARACTERISTICS:
            (A) LENGTH: 22 amino acids
            (B) TYPE: amino acid
            (D) TOPOLOGY: linear (ii) MOLECULE TYPE: peptide (iii) HYPOTHETICAL: NO (vi) ORIGINAL SOURCE:
            (C) INDIVIDUAL ISOLATE: HIV-2

(ix) FEATURE:
            (A) NAME/KEY: Modified-site
            (B) LOCATION: 1

(ix) FEATURE:
            (A) NAME/KEY: Modified-site
            (B) LOCATION: 22

(xi) SEQUENCE DESCRIPTION: SEQ ID NO: 20:

Xaa Lys Tyr Leu Gln Asp Gln Ala Arg Leu Asn Ser Trp Gly Cys Ala
1               5                   10                  15

Phe Arg Gln Val Cys Xaa
            20

(2) INFORMATION FOR SEQ ID NO: 21:

(i) SEQUENCE CHARACTERISTICS:
            (A) LENGTH: 25 amino acids
            (B) TYPE: amino acid
            (D) TOPOLOGY: linear (ii) MOLECULE TYPE: peptide (iii) HYPOTHETICAL: NO (vi) ORIGINAL SOURCE:
            (C) INDIVIDUAL ISOLATE: HIV-2 NIHZ (ix) FEATURE:
            (A) NAME/KEY: Modified-site
            (B) LOCATION: 1

(ix) FEATURE:
            (A) NAME/KEY: Modified-site
            (B) LOCATION: 25

(xi) SEQUENCE DESCRIPTION: SEQ ID NO: 21:

Xaa Asn Lys Thr Val Leu Pro Ile Thr Phe Met Ser Gly Phe Lys Phe
1               5                   10                  15

His Ser Gln Pro Val Ile Asn Lys Xaa
            20                  25

(2) INFORMATION FOR SEQ ID NO: 22:

(i) SEQUENCE CHARACTERISTICS:
            (A) LENGTH: 24 amino acids
            (B) TYPE: amino acid
            (D) TOPOLOGY: linear (ii) MOLECULE TYPE: peptide (iii) HYPOTHETICAL: NO (vi) ORIGINAL SOURCE:
            (C) INDIVIDUAL ISOLATE: HIV-2

(ix) FEATURE:
            (A) NAME/KEY: Modified-site
            (B) LOCATION: 1
```

```
    (ix) FEATURE:
         (A) NAME/KEY: Modified-site
         (B) LOCATION: 24

(xi) SEQUENCE DESCRIPTION: SEQ ID NO: 22:

Xaa Asn Lys Thr Val Val Pro Ile Thr Leu Met Ser Gly Leu Val Phe
1               5                   10                  15

His Ser Gln Pro Ile Asn Lys Xaa
            20

(2) INFORMATION FOR SEQ ID NO: 23:

(i) SEQUENCE CHARACTERISTICS:
        (A) LENGTH: 24 amino acids
        (B) TYPE: amino acid
        (D) TOPOLOGY: linear (ii) MOLECULE TYPE: peptide (iii) HYPOTHETICAL: NO (vi) ORIGINAL SOURCE:
         (C) INDIVIDUAL ISOLATE: HIV-2

(ix) FEATURE:
         (A) NAME/KEY: Modified-site
         (B) LOCATION: 1

(ix) FEATURE:
         (A) NAME/KEY: Modified-site
         (B) LOCATION: 24

(xi) SEQUENCE DESCRIPTION: SEQ ID NO: 23:

Xaa Asn Lys Thr Val Leu Pro Val Thr Ile Met Ser Gly Leu Val Phe
1               5                   10                  15

His Ser Gln Pro Ile Asn Asp Xaa
            20

(2) INFORMATION FOR SEQ ID NO: 24:

(i) SEQUENCE CHARACTERISTICS:
        (A) LENGTH: 12 amino acids
        (B) TYPE: amino acid
        (D) TOPOLOGY: linear (ii) MOLECULE TYPE: peptide (iii) HYPOTHETICAL: NO (vi) ORIGINAL SOURCE:
         (C) INDIVIDUAL ISOLATE: Chimpanzee immunodeficiency Virus (ix) FEATURE:
         (A) NAME/KEY: Modified-site
         (B) LOCATION: 1

(ix) FEATURE:
         (A) NAME/KEY: Modified-site
         (B) LOCATION: 12

(xi) SEQUENCE DESCRIPTION: SEQ ID NO: 24:

Xaa Leu Trp Gly Cys Ser Gly Lys Ala Val Cys Xaa
1               5                   10

(2) INFORMATION FOR SEQ ID NO: 25:

(i) SEQUENCE CHARACTERISTICS:
        (A) LENGTH: 12 amino acids
        (B) TYPE: amino acid
        (D) TOPOLOGY: linear
```

```
    (ii) MOLECULE TYPE: peptide (iii) HYPOTHETICAL: NO (vi) ORIGINAL SOURCE:
          (C) INDIVIDUAL ISOLATE: SIV agm (TY01)

(ix) FEATURE:
          (A) NAME/KEY: Modified-site
          (B) LOCATION: 1

(ix) FEATURE:
          (A) NAME/KEY: Modified-site
          (B) LOCATION: 12

(xi) SEQUENCE DESCRIPTION: SEQ ID NO: 25:

Xaa Ser Trp Gly Cys Ala Trp Lys Gln Val Cys Xaa
1               5                   10

(2) INFORMATION FOR SEQ ID NO: 26:

(i) SEQUENCE CHARACTERISTICS:
          (A) LENGTH: 12 amino acids
          (B) TYPE: amino acid
          (D) TOPOLOGY: linear (ii) MOLECULE TYPE: peptide (iii) HYPOTHETICAL: NO (vi) ORIGINAL SOURCE:
          (C) INDIVIDUAL ISOLATE: SIV mnd (ix) FEATURE:
          (A) NAME/KEY: Modified-site
          (B) LOCATION: 1

(ix) FEATURE:
          (A) NAME/KEY: Modified-site
          (B) LOCATION: 12

(xi) SEQUENCE DESCRIPTION: SEQ ID NO: 26:

Xaa Gln Trp Gly Cys Ser Trp Ala Gln Val Cys Xaa
1               5                   10

(2) INFORMATION FOR SEQ ID NO: 27:

(i) SEQUENCE CHARACTERISTICS:
          (A) LENGTH: 24 amino acids
          (B) TYPE: amino acid
          (D) TOPOLOGY: linear (ii) MOLECULE TYPE: peptide (iii) HYPOTHETICAL: NO (vi) ORIGINAL SOURCE:
          (C) INDIVIDUAL ISOLATE: HTLV (ix) FEATURE:
          (A) NAME/KEY: Modified-site
          (B) LOCATION: 1

(ix) FEATURE:
          (A) NAME/KEY: Modified-site
          (B) LOCATION: 24

(xi) SEQUENCE DESCRIPTION: SEQ ID NO: 27:

Xaa Val Leu Tyr Ser Pro Asn Val Ser Val Pro Ser Ser Ser Ser Thr
1               5                   10                  15
Leu Leu Tyr Pro Ser Leu Ala Xaa
                20
```

(2) INFORMATION FOR SEQ ID NO: 28:

(i) SEQUENCE CHARACTERISTICS:
        (A) LENGTH: 23 amino acids
        (B) TYPE: amino acid
        (D) TOPOLOGY: linear (ii) MOLECULE TYPE: peptide (iii) HYPOTHETICAL: NO (vi) ORIGINAL SOURCE:
        (C) INDIVIDUAL ISOLATE: HTLV (ix) FEATURE:
        (A) NAME/KEY: Modified-site
        (B) LOCATION: 1

(ix) FEATURE:
        (A) NAME/KEY: Modified-site
        (B) LOCATION: 23

(xi) SEQUENCE DESCRIPTION: SEQ ID NO: 28:

Xaa Tyr Thr Cys Ile Val Cys Ile Asp Arg Ala Ser Leu Ser Thr Trp
1               5                   10                  15

His Val Leu Tyr Ser Pro Xaa
            20

(2) INFORMATION FOR SEQ ID NO: 29:

(i) SEQUENCE CHARACTERISTICS:
        (A) LENGTH: 24 amino acids
        (B) TYPE: amino acid
        (D) TOPOLOGY: linear (ii) MOLECULE TYPE: peptide (iii) HYPOTHETICAL: NO (vi) ORIGINAL SOURCE:
        (C) INDIVIDUAL ISOLATE: HTLV (ix) FEATURE:
        (A) NAME/KEY: Modified-site
        (B) LOCATION: 1

(ix) FEATURE:
        (A) NAME/KEY: Modified-site
        (B) LOCATION: 24

(xi) SEQUENCE DESCRIPTION: SEQ ID NO: 29:

Xaa Asn Ser Leu Ile Leu Pro Pro Phe Ser Leu Ser Pro Val Pro Thr
1               5                   10                  15

Leu Gly Ser Arg Ser Arg Arg Xaa
            20

(2) INFORMATION FOR SEQ ID NO: 30:

(i) SEQUENCE CHARACTERISTICS:
        (A) LENGTH: 38 amino acids
        (B) TYPE: amino acid
        (D) TOPOLOGY: linear (ii) MOLECULE TYPE: peptide (iii) HYPOTHETICAL: NO (vi) ORIGINAL SOURCE:
        (C) INDIVIDUAL ISOLATE: HTLV (ix) FEATURE:
        (A) NAME/KEY: Modified-site (B) LOCATION: 1

(ix) FEATURE:
        (A) NAME/KEY: Modified-site
        (B) LOCATION: 38

(xi) SEQUENCE DESCRIPTION: SEQ ID NO: 30:

Xaa Asp Ala Pro Gly Tyr Asp Pro Ile Trp Phe Leu Asn Thr Glu Pro
1               5                  10                  15

Ser Gln Leu Pro Pro Thr Ala Pro Pro Leu Leu Pro His Ser Asn Leu
            20                  25                  30

Asp His Ile Leu Glu Xaa
            35

(2) INFORMATION FOR SEQ ID NO: 31:

(i) SEQUENCE CHARACTERISTICS:
        (A) LENGTH: 33 amino acids
        (B) TYPE: amino acid
        (D) TOPOLOGY: linear (ii) MOLECULE TYPE: peptide (iii) HYPOTHETICAL: NO (vi) ORIGINAL SOURCE:
        (C) INDIVIDUAL ISOLATE: HTLV (ix) FEATURE:
        (A) NAME/KEY: Modified-site
        (B) LOCATION: 1

(ix) FEATURE:
        (A) NAME/KEY: Modified-site
        (B) LOCATION: 33

(xi) SEQUENCE DESCRIPTION: SEQ ID NO: 31:

Xaa Gln Tyr Ala Ala Gln Asn Arg Arg Gly Leu Asp Leu Leu Phe Trp
1               5                  10                  15

Glu Gln Gly Gly Leu Cys Lys Ala Leu Gln Glu Gln Cys Arg Phe Pro
            20                  25                  30

Xaa (2) INFORMATION FOR SEQ ID NO: 32:

(i) SEQUENCE CHARACTERISTICS:
        (A) LENGTH: 33 amino acids
        (B) TYPE: amino acid
        (D) TOPOLOGY: linear (ii) MOLECULE TYPE: peptide (iii) HYPOTHETICAL: NO (vi) ORIGINAL SOURCE:
        (C) INDIVIDUAL ISOLATE: HTLV (ix) FEATURE:
        (A) NAME/KEY: Modified-site
        (B) LOCATION: 1

(ix) FEATURE:
        (A) NAME/KEY: Modified-site
        (B) LOCATION: 33

(xi) SEQUENCE DESCRIPTION: SEQ ID NO: 32:

Xaa Pro Pro Pro Pro Ser Ser Pro Thr His Asp Pro Asp Ser Asp
1               5                  10                  15

Pro Gln Ile Pro Pro Pro Tyr Val Glu Pro Thr Ala Pro Gln Val Leu

```
               20                  25                  30
Xaa (2) INFORMATION FOR SEQ ID NO: 33:

(i) SEQUENCE CHARACTERISTICS:
        (A) LENGTH: 20 amino acids
        (B) TYPE: amino acid
        (D) TOPOLOGY: linear (ii) MOLECULE TYPE: peptide (iii) HYPOTHETICAL: NO (vi) ORIGINAL SOURCE:
        (C) INDIVIDUAL ISOLATE: HTLV (ix) FEATURE:
        (A) NAME/KEY: Modified-site
        (B) LOCATION: 1

(ix) FEATURE:
        (A) NAME/KEY: Modified-site
        (B) LOCATION: 20

(xi) SEQUENCE DESCRIPTION: SEQ ID NO: 33:

Xaa Lys Lys Pro Asn Arg Gln Gly Leu Gly Tyr Tyr Ser Pro Ser Tyr
1               5                  10                  15

Asn Asp Pro Xaa
            20

(2) INFORMATION FOR SEQ ID NO: 34:

(i) SEQUENCE CHARACTERISTICS:
        (A) LENGTH: 38 amino acids
        (B) TYPE: amino acid
        (D) TOPOLOGY: linear (ii) MOLECULE TYPE: peptide (iii) HYPOTHETICAL: NO (vi) ORIGINAL SOURCE:
        (C) INDIVIDUAL ISOLATE: HTLV (ix) FEATURE:
        (A) NAME/KEY: Modified-site
        (B) LOCATION: 1

(ix) FEATURE:
        (A) NAME/KEY: Modified-site
        (B) LOCATION: 38

(xi) SEQUENCE DESCRIPTION: SEQ ID NO: 34:

Xaa Asp Ala Pro Gly Tyr Asp Pro Leu Trp Phe Ile Thr Ser Glu Pro
1               5                  10                  15

Thr Gln Pro Pro Pro Thr Ser Pro Pro Leu Val His Asp Ser Asp Leu
            20                  25                  30

Glu His Val Leu Thr Xaa
            35

(2) INFORMATION FOR SEQ ID NO: 35:

(i) SEQUENCE CHARACTERISTICS:
        (A) LENGTH: 40 amino acids
        (B) TYPE: amino acid
        (D) TOPOLOGY: linear (ii) MOLECULE TYPE: peptide
```

(iii) HYPOTHETICAL: NO (vi) ORIGINAL SOURCE:
            (C) INDIVIDUAL ISOLATE: HTLV (ix) FEATURE:
            (A) NAME/KEY: Modified-site
            (B) LOCATION: 1

(ix) FEATURE:
            (A) NAME/KEY: Modified-site
            (B) LOCATION: 40

(xi) SEQUENCE DESCRIPTION: SEQ ID NO: 35:

Xaa Tyr Ser Cys Met Val Cys Val Asp Arg Ser Ser Leu Ser Ser Trp
1               5                   10                  15

His Val Leu Tyr Thr Pro Asn Ile Ser Ile Pro Gln Gln Thr Ser Ser
            20                  25                  30

Arg Thr Ile Leu Phe Pro Ser Xaa
        35                  40

(2) INFORMATION FOR SEQ ID NO: 36:

(i) SEQUENCE CHARACTERISTICS:
            (A) LENGTH: 32 amino acids
            (B) TYPE: amino acid
            (D) TOPOLOGY: linear (ii) MOLECULE TYPE: peptide (iii) HYPOTHETICAL: NO (vi) ORIGINAL SOURCE:
            (C) INDIVIDUAL ISOLATE: HTLV (ix) FEATURE:
            (A) NAME/KEY: Modified-site
            (B) LOCATION: 1

(ix) FEATURE:
            (A) NAME/KEY: Modified-site
            (B) LOCATION: 32

(xi) SEQUENCE DESCRIPTION: SEQ ID NO: 36:

Xaa Pro Thr Thr Thr Pro Pro Pro Pro Pro Pro Ser Pro Glu Ala
1               5                   10                  15

His Val Pro Pro Pro Tyr Val Glu Pro Thr Thr Thr Gln Cys Phe Xaa
            20                  25                  30

(2) INFORMATION FOR SEQ ID NO: 37:

(i) SEQUENCE CHARACTERISTICS:
            (A) LENGTH: 22 amino acids
            (B) TYPE: amino acid
            (D) TOPOLOGY: linear (ii) MOLECULE TYPE: peptide (iii) HYPOTHETICAL: NO (vi) ORIGINAL SOURCE:
            (C) INDIVIDUAL ISOLATE: HCV (ix) FEATURE:
            (A) NAME/KEY: Modified-site
            (B) LOCATION: 1

(ix) FEATURE:
            (A) NAME/KEY: Modified-site
            (B) LOCATION: 22

(xi) SEQUENCE DESCRIPTION: SEQ ID NO: 37:

```
Xaa Met Ser Thr Ile Pro Lys Pro Gln Arg Lys Thr Lys Arg Asn Thr
 1               5                  10                  15

Asn Arg Arg Pro Gln Xaa
                 20
```

(2) INFORMATION FOR SEQ ID NO: 38:

(i) SEQUENCE CHARACTERISTICS:
        (A) LENGTH: 22 amino acids
        (B) TYPE: amino acid
        (D) TOPOLOGY: linear (ii) MOLECULE TYPE: peptide (iii) HYPOTHETICAL: NO (vi) ORIGINAL SOURCE:
        (C) INDIVIDUAL ISOLATE: HCV (ix) FEATURE:
        (A) NAME/KEY: Modified-site
        (B) LOCATION: 1

(ix) FEATURE:
        (A) NAME/KEY: Modified-site
        (B) LOCATION: 22

(xi) SEQUENCE DESCRIPTION: SEQ ID NO: 38:

```
Xaa Pro Gln Arg Lys Thr Lys Arg Asn Thr Asn Arg Arg Pro Gln Asp
 1               5                  10                  15

Val Lys Phe Pro Gly Xaa
                 20
```

(2) INFORMATION FOR SEQ ID NO: 39:

(i) SEQUENCE CHARACTERISTICS:
        (A) LENGTH: 13 amino acids
        (B) TYPE: amino acid
        (D) TOPOLOGY: linear (ii) MOLECULE TYPE: peptide (iii) HYPOTHETICAL: NO (vi) ORIGINAL SOURCE:
        (C) INDIVIDUAL ISOLATE: HCV (ix) FEATURE:
        (A) NAME/KEY: Modified-site
        (B) LOCATION: 1

(ix) FEATURE:
        (A) NAME/KEY: Modified-site
        (B) LOCATION: 13

(xi) SEQUENCE DESCRIPTION: SEQ ID NO: 39:

```
Xaa Gln Arg Lys Thr Lys Arg Asn Thr Asn Arg Arg Xaa
 1               5                  10
```

(2) INFORMATION FOR SEQ ID NO: 40:

(i) SEQUENCE CHARACTERISTICS:
        (A) LENGTH: 22 amino acids
        (B) TYPE: amino acid
        (D) TOPOLOGY: linear (ii) MOLECULE TYPE: peptide (iii) HYPOTHETICAL: NO (vi) ORIGINAL SOURCE:

(C) INDIVIDUAL ISOLATE: HCV (ix) FEATURE:
            (A) NAME/KEY: Modified-site
            (B) LOCATION: 1

(ix) FEATURE:
            (A) NAME/KEY: Modified-site
            (B) LOCATION: 22

(xi) SEQUENCE DESCRIPTION: SEQ ID NO: 40:

Xaa Arg Asn Thr Asn Arg Arg Pro Gln Asp Val Lys Phe Pro Gly Gly
1               5                  10                  15

Gly Gln Ile Val Gly Xaa
            20

(2) INFORMATION FOR SEQ ID NO: 41:

(i) SEQUENCE CHARACTERISTICS:
            (A) LENGTH: 22 amino acids
            (B) TYPE: amino acid
            (D) TOPOLOGY: linear (ii) MOLECULE TYPE: peptide (iii) HYPOTHETICAL: NO (vi) ORIGINAL SOURCE:
            (C) INDIVIDUAL ISOLATE: HCV (ix) FEATURE:
            (A) NAME/KEY: Modified-site
            (B) LOCATION: 1

(ix) FEATURE:
            (A) NAME/KEY: Modified-site
            (B) LOCATION: 22

(xi) SEQUENCE DESCRIPTION: SEQ ID NO: 41:

Xaa Leu Pro Arg Arg Gly Pro Arg Leu Gly Val Arg Ala Thr Arg Lys
1               5                  10                  15

Thr Ser Glu Arg Ser Xaa
            20

(2) INFORMATION FOR SEQ ID NO: 42:

(i) SEQUENCE CHARACTERISTICS:
            (A) LENGTH: 22 amino acids
            (B) TYPE: amino acid
            (D) TOPOLOGY: linear (ii) MOLECULE TYPE: peptide (iii) HYPOTHETICAL: NO (vi) ORIGINAL SOURCE:
            (C) INDIVIDUAL ISOLATE: HCV (ix) FEATURE:
            (A) NAME/KEY: Modified-site
            (B) LOCATION: 1

(ix) FEATURE:
            (A) NAME/KEY: Modified-site
            (B) LOCATION: 22

(xi) SEQUENCE DESCRIPTION: SEQ ID NO: 42:

Xaa Val Gly Gly Val Tyr Leu Leu Pro Arg Arg Gly Pro Arg Leu Gly
1               5                  10                  15

Val Arg Ala Thr Arg Xaa
            20

(2) INFORMATION FOR SEQ ID NO: 43:

(i) SEQUENCE CHARACTERISTICS:
        (A) LENGTH: 22 amino acids
        (B) TYPE: amino acid
        (D) TOPOLOGY: linear (ii) MOLECULE TYPE: peptide (iii) HYPOTHETICAL: NO (vi) ORIGINAL SOURCE:
        (C) INDIVIDUAL ISOLATE: HCV (ix) FEATURE:
        (A) NAME/KEY: Modified-site
        (B) LOCATION: 1

(ix) FEATURE:
        (A) NAME/KEY: Modified-site
        (B) LOCATION: 22

(xi) SEQUENCE DESCRIPTION: SEQ ID NO: 43:

```
Xaa Thr Arg Lys Thr Ser Glu Arg Ser Gln Pro Arg Gly Arg Arg Gln
1               5                   10                  15
Pro Ile Pro Lys Val Xaa
            20
```

(2) INFORMATION FOR SEQ ID NO: 44:

(i) SEQUENCE CHARACTERISTICS:
        (A) LENGTH: 22 amino acids
        (B) TYPE: amino acid
        (D) TOPOLOGY: linear (ii) MOLECULE TYPE: peptide (iii) HYPOTHETICAL: NO (vi) ORIGINAL SOURCE:
        (C) INDIVIDUAL ISOLATE: HCV (ix) FEATURE:
        (A) NAME/KEY: Modified-site
        (B) LOCATION: 1

(ix) FEATURE:
        (A) NAME/KEY: Modified-site
        (B) LOCATION: 22

(xi) SEQUENCE DESCRIPTION: SEQ ID NO: 44:

```
Xaa Arg Ser Gln Pro Arg Gly Arg Arg Gln Pro Ile Pro Lys Val Arg
1               5                   10                  15
Arg Pro Glu Gly Arg Xaa
            20
```

(2) INFORMATION FOR SEQ ID NO: 45:

(i) SEQUENCE CHARACTERISTICS:
        (A) LENGTH: 22 amino acids
        (B) TYPE: amino acid
        (D) TOPOLOGY: linear (ii) MOLECULE TYPE: peptide (iii) HYPOTHETICAL: NO (vi) ORIGINAL SOURCE:
        (C) INDIVIDUAL ISOLATE: HCV (ix) FEATURE:

```
            (A) NAME/KEY: Modified-site
            (B) LOCATION: 1

(ix) FEATURE:
            (A) NAME/KEY: Modified-site
            (B) LOCATION: 22

(xi) SEQUENCE DESCRIPTION: SEQ ID NO: 45:

Xaa Arg Arg Gln Pro Ile Pro Lys Val Arg Arg Pro Glu Gly Arg Thr
1               5                  10                  15

Trp Ala Gln Pro Gly Xaa
            20

(2) INFORMATION FOR SEQ ID NO: 46:

(i) SEQUENCE CHARACTERISTICS:
            (A) LENGTH: 22 amino acids
            (B) TYPE: amino acid
            (D) TOPOLOGY: linear (ii) MOLECULE TYPE: peptide (iii) HYPOTHETICAL: NO (vi) ORIGINAL SOURCE:
            (C) INDIVIDUAL ISOLATE: HCV (ix) FEATURE:
            (A) NAME/KEY: Modified-site
            (B) LOCATION: 1

(ix) FEATURE:
            (A) NAME/KEY: Modified-site
            (B) LOCATION: 22

(xi) SEQUENCE DESCRIPTION: SEQ ID NO: 46:

Xaa Gly Arg Thr Trp Ala Gln Pro Gly Tyr Pro Trp Pro Leu Tyr Gly
1               5                  10                  15

Asn Glu Gly Cys Gly Xaa
            20

(2) INFORMATION FOR SEQ ID NO: 47:

(i) SEQUENCE CHARACTERISTICS:
            (A) LENGTH: 32 amino acids
            (B) TYPE: amino acid
            (D) TOPOLOGY: linear (ii) MOLECULE TYPE: peptide (iii) HYPOTHETICAL: NO (vi) ORIGINAL SOURCE:
            (C) INDIVIDUAL ISOLATE: HCV (ix) FEATURE:
            (A) NAME/KEY: Modified-site
            (B) LOCATION: 1

(ix) FEATURE:
            (A) NAME/KEY: Modified-site
            (B) LOCATION: 32

(xi) SEQUENCE DESCRIPTION: SEQ ID NO: 47:

Xaa Met Ser Thr Ile Pro Gln Arg Lys Thr Lys Arg Asn Thr Asn Arg
1               5                  10                  15

Arg Pro Gln Asp Val Lys Phe Pro Gly Gly Gly Gln Ile Val Gly Xaa
                20                  25                  30

(2) INFORMATION FOR SEQ ID NO: 48:
```

```
    (i) SEQUENCE CHARACTERISTICS:
        (A) LENGTH: 42 amino acids
        (B) TYPE: amino acid
        (D) TOPOLOGY: linear (ii) MOLECULE TYPE: peptide (iii) HYPOTHETICAL: NO (vi) ORIGINAL SOURCE:
        (C) INDIVIDUAL ISOLATE: HCV (ix) FEATURE:
        (A) NAME/KEY: Modified-site
        (B) LOCATION: 1

(ix) FEATURE:
        (A) NAME/KEY: Modified-site
        (B) LOCATION: 42

(xi) SEQUENCE DESCRIPTION: SEQ ID NO: 48:

Xaa Gly Gly Val Tyr Leu Leu Pro Arg Arg Gly Pro Arg Leu Gly Val
1               5                   10                  15

Arg Arg Ala Thr Arg Lys Thr Ser Glu Arg Ser Gln Pro Arg Gly Arg
            20                  25                  30

Arg Gln Pro Ile Pro Lys Val Arg Arg Xaa
        35                  40

(2) INFORMATION FOR SEQ ID NO: 49:

(i) SEQUENCE CHARACTERISTICS:
        (A) LENGTH: 22 amino acids
        (B) TYPE: amino acid
        (D) TOPOLOGY: linear (ii) MOLECULE TYPE: peptide (iii) HYPOTHETICAL: NO (vi) ORIGINAL SOURCE:
        (C) INDIVIDUAL ISOLATE: HCV (ix) FEATURE:
        (A) NAME/KEY: Modified-site
        (B) LOCATION: 1

(ix) FEATURE:
        (A) NAME/KEY: Modified-site
        (B) LOCATION: 22

(xi) SEQUENCE DESCRIPTION: SEQ ID NO: 49:

Xaa Leu Ser Gly Lys Pro Ala Ile Ile Pro Asp Arg Glu Val Leu Tyr
1               5                   10                  15

Arg Glu Phe Asp Glu Xaa
            20

(2) INFORMATION FOR SEQ ID NO: 50:

(i) SEQUENCE CHARACTERISTICS:
        (A) LENGTH: 22 amino acids
        (B) TYPE: amino acid
        (D) TOPOLOGY: linear (ii) MOLECULE TYPE: peptide (iii) HYPOTHETICAL: NO (vi) ORIGINAL SOURCE:
        (C) INDIVIDUAL ISOLATE: HCV (ix) FEATURE:
```

(A) NAME/KEY: Modified-site
            (B) LOCATION: 1

(ix) FEATURE:
            (A) NAME/KEY: Modified-site
            (B) LOCATION: 22

(xi) SEQUENCE DESCRIPTION: SEQ ID NO: 50:

Xaa Ile Ile Pro Asp Arg Glu Val Leu Tyr Arg Glu Phe Asp Glu Met
1               5                   10                  15

Glu Glu Cys Ser Gln Xaa
            20

(2) INFORMATION FOR SEQ ID NO: 51:

(i) SEQUENCE CHARACTERISTICS:
            (A) LENGTH: 22 amino acids
            (B) TYPE: amino acid
            (D) TOPOLOGY: linear (ii) MOLECULE TYPE: peptide (iii) HYPOTHETICAL: NO (vi) ORIGINAL SOURCE:
            (C) INDIVIDUAL ISOLATE: HCV (ix) FEATURE:
            (A) NAME/KEY: Modified-site
            (B) LOCATION: 1

(ix) FEATURE:
            (A) NAME/KEY: Modified-site
            (B) LOCATION: 22

(xi) SEQUENCE DESCRIPTION: SEQ ID NO: 51:

Xaa Val Leu Tyr Arg Glu Phe Asp Glu Met Glu Glu Cys Ser Gln His
1               5                   10                  15

Leu Pro Tyr Ile Glu Xaa
            20

(2) INFORMATION FOR SEQ ID NO: 52:

(i) SEQUENCE CHARACTERISTICS:
            (A) LENGTH: 22 amino acids
            (B) TYPE: amino acid
            (D) TOPOLOGY: linear (ii) MOLECULE TYPE: peptide (iii) HYPOTHETICAL: NO (vi) ORIGINAL SOURCE:
            (C) INDIVIDUAL ISOLATE: HCV (ix) FEATURE:
            (A) NAME/KEY: Modified-site
            (B) LOCATION: 1

(ix) FEATURE:
            (A) NAME/KEY: Modified-site
            (B) LOCATION: 22

(xi) SEQUENCE DESCRIPTION: SEQ ID NO: 52:

Xaa Asp Glu Met Glu Glu Cys Ser Gln His Leu Pro Tyr Ile Glu Gln
1               5                   10                  15

Gly Met Met Leu Ala Xaa
            20

(2) INFORMATION FOR SEQ ID NO: 53:

(i) SEQUENCE CHARACTERISTICS:
            (A) LENGTH: 22 amino acids
            (B) TYPE: amino acid
            (D) TOPOLOGY: linear (ii) MOLECULE TYPE: peptide (iii) HYPOTHETICAL: NO (vi) ORIGINAL SOURCE:
            (C) INDIVIDUAL ISOLATE: HCV (ix) FEATURE:
            (A) NAME/KEY: Modified-site
            (B) LOCATION: 1

( (ix) FEATURE:
            (A) NAME/KEY: Modified-site
            (B) LOCATION: 22

(xi) SEQUENCE DESCRIPTION: SEQ ID NO: 55:

Xaa Leu Ala Glu Gln Phe Lys Gln Lys Ala Leu Gly Leu Leu Gln Thr
1               5                   10                  15

Ala Ser Arg Gln Ala Xaa
            20

(2) INFORMATION FOR SEQ ID NO: 56:

(i) SEQUENCE CHARACTERISTICS:
            (A) LENGTH: 22 amino acids
            (B) TYPE: amino acid
            (D) TOPOLOGY: linear (ii) MOLECULE TYPE: peptide (iii) HYPOTHETICAL: NO (vi) ORIGINAL SOURCE:
            (C) INDIVIDUAL ISOLATE: HCV (ix) FEATURE:
            (A) NAME/KEY: Modified-site
            (B) LOCATION: 1

(ix) FEATURE:
            (A) NAME/KEY: Modified-site
            (B) LOCATION: 22

(xi) SEQUENCE DESCRIPTION: SEQ ID NO: 56:

Xaa Gln Lys Ala Leu Gly Leu Leu Gln Thr Ala Ser Arg Gln Ala Glu
1               5                   10                  15

Val Ile Ala Pro Ala Xaa
            20

(2) INFORMATION FOR SEQ ID NO: 57:

(i) SEQUENCE CHARACTERISTICS:
            (A) LENGTH: 33 amino acids
            (B) TYPE: amino acid
            (D) TOPOLOGY: linear (ii) MOLECULE TYPE: peptide (iii) HYPOTHETICAL: NO (vi) ORIGINAL SOURCE:
            (C) INDIVIDUAL ISOLATE: HCV (ix) FEATURE:
            (A) NAME/KEY: Modified-site
            (B) LOCATION: 1

(ix) FEATURE:
            (A) NAME/KEY: Modified-site
            (B) LOCATION: 33

(xi) SEQUENCE DESCRIPTION: SEQ ID NO: 57:

Xaa Ser Gln His Leu Pro Tyr Ile Glu Gln Glu Met Leu Ala Glu Glu
1               5                   10                  15

Phe Lys Gln Lys Ala Leu Gly Leu Leu Gln Thr Ala Ser Arg Gln Ala
            20                  25                  30

Xaa (2) INFORMATION FOR SEQ ID NO: 58:

```
    (i) SEQUENCE CHARACTERISTICS:
         (A) LENGTH: 22 amino acids
         (B) TYPE: amino acid
         (D) TOPOLOGY: linear (ii) MOLECULE TYPE: peptide (iii) HYPOTHETICAL: NO (vi) ORIGINAL SOURCE:
         (C) INDIVIDUAL ISOLATE: HCV (ix) FEATURE:
         (A) NAME/KEY: Modified-site
         (B) LOCATION: 1

(ix) FEATURE:
         (A) NAME/KEY: Modified-site
         (B) LOCATION: 22

(xi) SEQUENCE DESCRIPTION: SEQ ID NO: 58:

Xaa Gly Glu Gly Ala Val Gln Trp Met Asn Arg Leu Ile Ala Phe Ala
1               5                  10                  15

Ser Arg Gly Asn His Xaa
            20

(2) INFORMATION FOR SEQ ID NO: 59:

(i) SEQUENCE CHARACTERISTICS:
         (A) LENGTH: 22 amino acids
         (B) TYPE: amino acid
         (D) TOPOLOGY: linear (ii) MOLECULE TYPE: peptide (iii) HYPOTHETICAL: NO (vi) ORIGINAL SOURCE:
         (C) INDIVIDUAL ISOLATE: HCV (ix) FEATURE:
         (A) NAME/KEY: Modified-site
         (B) LOCATION: 1

(ix) FEATURE:
         (A) NAME/KEY: Modified-site
         (B) LOCATION: 22

(xi) SEQUENCE DESCRIPTION: SEQ ID NO: 59:

Xaa Glu Asp Glu Arg Glu Ile Ser Val Pro Ala Glu Ile Leu Arg Lys
1               5                  10                  15

Ser Arg Arg Phe Ala Xaa
            20

(2) INFORMATION FOR SEQ ID NO: 60:

(i) SEQUENCE CHARACTERISTICS:
         (A) LENGTH: 22 amino acids
         (B) TYPE: amino acid
         (D) TOPOLOGY: linear (ii) MOLECULE TYPE: peptide (iii) HYPOTHETICAL: NO (vi) ORIGINAL SOURCE:
         (C) INDIVIDUAL ISOLATE: HCV (ix) FEATURE:
         (A) NAME/KEY: Modified-site
         (B) LOCATION: 1

(ix) FEATURE:
```

(A) NAME/KEY: Modified-site
         (B) LOCATION: 22

(xi) SEQUENCE DESCRIPTION: SEQ ID NO: 60:

Xaa Leu Arg Lys Ser Arg Arg Phe Ala Gln Ala Leu Pro Val Trp Ala
1               5                  10                  15

Arg Pro Asp Tyr Asn Xaa
            20

(2) INFORMATION FOR SEQ ID NO: 61:

(i) SEQUENCE CHARACTERISTICS:
         (A) LENGTH: 22 amino acids
         (B) TYPE: amino acid
         (D) TOPOLOGY: linear (ii) MOLECULE TYPE: peptide (iii) HYPOTHETICAL: NO (vi) ORIGINAL SOURCE:
         (C) INDIVIDUAL ISOLATE: HCV (ix) FEATURE:
         (A) NAME/KEY: Modified-site
         (B) LOCATION: 1

(ix) FEATURE:
         (A) NAME/KEY: Modified-site
         (B) LOCATION: 22

(xi) SEQUENCE DESCRIPTION: SEQ ID NO: 61:

Xaa Val Trp Ala Arg Pro Asp Tyr Asn Pro Pro Leu Val Glu Thr Trp
1               5                  10                  15

Lys Lys Pro Asp Tyr Xaa
            20

(2) INFORMATION FOR SEQ ID NO: 62:

(i) SEQUENCE CHARACTERISTICS:
         (A) LENGTH: 22 amino acids
         (B) TYPE: amino acid
         (D) TOPOLOGY: linear (ii) MOLECULE TYPE: peptide (iii) HYPOTHETICAL: NO (vi) ORIGINAL SOURCE:
         (C) INDIVIDUAL ISOLATE: HCV (ix) FEATURE:
         (A) NAME/KEY: Modified-site
         (B) LOCATION: 1

(ix) FEATURE:
         (A) NAME/KEY: Modified-site
         (B) LOCATION: 22

(xi) SEQUENCE DESCRIPTION: SEQ ID NO: 62:

Xaa Glu Thr Trp Lys Lys Pro Asp Tyr Glu Pro Pro Val Val His Gly
1               5                  10                  15

Cys Pro Leu Pro Pro Xaa
            20

(2) INFORMATION FOR SEQ ID NO: 63:

(i) SEQUENCE CHARACTERISTICS:
         (A) LENGTH: 22 amino acids
         (B) TYPE: amino acid

```
        (D) TOPOLOGY: linear (ii) MOLECULE TYPE: peptide (iii) HYPOTHETICAL: NO (vi) ORIGINAL SOURCE:
         (C) INDIVIDUAL ISOLATE: HCV (ix) FEATURE:
         (A) NAME/KEY: Modified-site
         (B) LOCATION: 1

(ix) FEATURE:
         (A) NAME/KEY: Modified-site
         (B) LOCATION: 22

(xi) SEQUENCE DESCRIPTION: SEQ ID NO: 63:

Xaa Val His Gly Cys Pro Leu Pro Pro Pro Lys Ser Pro Pro Val Pro
1               5                   10                  15

Pro Pro Arg Lys Lys Xaa
            20

(2) INFORMATION FOR SEQ ID NO: 64:

(i) SEQUENCE CHARACTERISTICS:
        (A) LENGTH: 39 amino acids
        (B) TYPE: amino acid
        (D) TOPOLOGY: linear (ii) MOLECULE TYPE: peptide (iii) HYPOTHETICAL: NO (vi) ORIGINAL SOURCE:
         (C) INDIVIDUAL ISOLATE: HCV type 1

(ix) FEATURE:
         (A) NAME/KEY: Modified-site
         (B) LOCATION: 1

(ix) FEATURE:
         (A) NAME/KEY: Modified-site
         (B) LOCATION: 39

(xi) SEQUENCE DESCRIPTION: SEQ ID NO: 64:

Xaa Glu Asp Glu Arg Glu Ile Ser Val Pro Ala Glu Ile Leu Arg Lys
1               5                   10                  15

Ser Arg Lys Ser Arg Arg Phe Ala Gln Ala Leu Pro Val Trp Ala Arg
            20                  25                  30

Pro Asp Tyr Asp Tyr Asn Xaa
            35

(2) INFORMATION FOR SEQ ID NO: 65:

(i) SEQUENCE CHARACTERISTICS:
        (A) LENGTH: 36 amino acids
        (B) TYPE: amino acid
        (D) TOPOLOGY: linear (ii) MOLECULE TYPE: peptide (iii) HYPOTHETICAL: NO (vi) ORIGINAL SOURCE:
         (C) INDIVIDUAL ISOLATE: HCV (ix) FEATURE:
         (A) NAME/KEY: Modified-site
         (B) LOCATION: 1

(ix) FEATURE:
```

```
            (A) NAME/KEY: Modified-site
            (B) LOCATION: 36

(xi) SEQUENCE DESCRIPTION: SEQ ID NO: 65:

Xaa Gly Glu Thr Tyr Thr Ser Gly Gly Ala Ala Ser His Thr Thr Ser
1               5                   10                  15

Thr Leu Ala Ser Leu Phe Ser Pro Gly Ala Ser Gln Arg Ile Gln Leu
            20                  25                  30

Val Asn Thr Xaa
        35

(2) INFORMATION FOR SEQ ID NO: 66:

(i) SEQUENCE CHARACTERISTICS:
            (A) LENGTH: 24 amino acids
            (B) TYPE: amino acid
            (D) TOPOLOGY: linear (ii) MOLECULE TYPE: peptide (iii) HYPOTHETICAL: NO (vi) ORIGINAL SOURCE:
            (C) INDIVIDUAL ISOLATE: HCV (ix) FEATURE:
            (A) NAME/KEY: Modified-site
            (B) LOCATION: 1

(ix) FEATURE:
            (A) NAME/KEY: Modified-site
            (B) LOCATION: 24

(xi) SEQUENCE DESCRIPTION: SEQ ID NO: 66:

Xaa Gly Glu Thr Tyr Thr Ser Gly Gly Ala Ala Ser His Thr Thr Ser
1               5                   10                  15

Thr Leu Ala Ser Leu Phe Ser Xaa
            20

(2) INFORMATION FOR SEQ ID NO: 67:

(i) SEQUENCE CHARACTERISTICS:
            (A) LENGTH: 26 amino acids
            (B) TYPE: amino acid
            (D) TOPOLOGY: linear (ii) MOLECULE TYPE: peptide (iii) HYPOTHETICAL: NO (vi) ORIGINAL SOURCE:
            (C) INDIVIDUAL ISOLATE: HCV (ix) FEATURE:
            (A) NAME/KEY: Modified-site
            (B) LOCATION: 1

(ix) FEATURE:
            (A) NAME/KEY: Modified-site
            (B) LOCATION: 26

(xi) SEQUENCE DESCRIPTION: SEQ ID NO: 67:

Xaa Ser His Thr Thr Ser Thr Leu Ala Ser Leu Phe Ser Pro Gly Ala
1               5                   10                  15

Ser Gln Arg Ile Gln Leu Val Asn Thr Xaa
            20                  25

(2) INFORMATION FOR SEQ ID NO: 68:
```

```
      (i) SEQUENCE CHARACTERISTICS:
          (A) LENGTH: 36 amino acids
          (B) TYPE: amino acid
          (D) TOPOLOGY: linear (ii) MOLECULE TYPE: peptide (iii) HYPOTHETICAL: NO (vi) ORIGINAL SOURCE:
          (C) INDIVIDUAL ISOLATE: HCV (ix) FEATURE:
          (A) NAME/KEY: Modified-site
          (B) LOCATION: 1

(ix) FEATURE:
          (A) NAME/KEY: Modified-site
          (B) LOCATION: 36

(xi) SEQUENCE DESCRIPTION: SEQ ID NO: 68:

Xaa Gly His Thr Arg Val Ser Gly Gly Ala Ala Ala Ser Asp Thr Arg
1               5                   10                  15

Gly Leu Val Ser Leu Phe Ser Pro Gly Ser Ala Gln Lys Ile Gln Leu
            20                  25                  30

Val Asn Thr Xaa
        35

(2) INFORMATION FOR SEQ ID NO: 69:

(i) SEQUENCE CHARACTERISTICS:
          (A) LENGTH: 24 amino acids
          (B) TYPE: amino acid
          (D) TOPOLOGY: linear (ii) MOLECULE TYPE: peptide (iii) HYPOTHETICAL: NO (vi) ORIGINAL SOURCE:
          (C) INDIVIDUAL ISOLATE: HCV (ix) FEATURE:
          (A) NAME/KEY: Modified-site
          (B) LOCATION: 1

(ix) FEATURE:
          (A) NAME/KEY: Modified-site
          (B) LOCATION: 24

(xi) SEQUENCE DESCRIPTION: SEQ ID NO: 69:

Xaa Gly His Thr Arg Val Ser Gly Gly Ala Ala Ala Ser Asp Thr Arg
1               5                   10                  15

Gly Leu Val Ser Leu Phe Ser Xaa
            20

(2) INFORMATION FOR SEQ ID NO: 70:

(i) SEQUENCE CHARACTERISTICS:
          (A) LENGTH: 26 amino acids
          (B) TYPE: amino acid
          (D) TOPOLOGY: linear (ii) MOLECULE TYPE: peptide (iii) HYPOTHETICAL: NO (vi) ORIGINAL SOURCE:
          (C) INDIVIDUAL ISOLATE: HCV (ix) FEATURE:
          (A) NAME/KEY: Modified-site
```

(B) LOCATION: 1

(ix) FEATURE:
        (A) NAME/KEY: Modified-site
        (B) LOCATION: 26

(xi) SEQUENCE DESCRIPTION: SEQ ID NO: 70:

Xaa Ala Ser Asp Thr Arg Gly Leu Val Ser Leu Phe Ser Pro Gly Ser
1               5                  10                  15

Ala Gln Lys Ile Gln Leu Val Asn Thr Xaa
            20                  25

(2) INFORMATION FOR SEQ ID NO: 71:

(i) SEQUENCE CHARACTERISTICS:
        (A) LENGTH: 36 amino acids
        (B) TYPE: amino acid
        (D) TOPOLOGY: linear (ii) MOLECULE TYPE: peptide (iii) HYPOTHETICAL: NO (vi) ORIGINAL SOURCE:
        (C) INDIVIDUAL ISOLATE: HCV (ix) FEATURE:
        (A) NAME/KEY: Modified-site
        (B) LOCATION: 1

(ix) FEATURE:
        (A) NAME/KEY: Modified-site
        (B) LOCATION: 36

(xi) SEQUENCE DESCRIPTION: SEQ ID NO: 71:

Xaa Gly His Thr Arg Val Thr Gly Gly Val Gln Gly His Val Thr Cys
1               5                  10                  15

Thr Leu Thr Ser Leu Phe Arg Pro Gly Ala Ser Gln Lys Ile Gln Leu
            20                  25                  30

Val Asn Thr Xaa
        35

(2) INFORMATION FOR SEQ ID NO: 72:

(i) SEQUENCE CHARACTERISTICS:
        (A) LENGTH: 24 amino acids
        (B) TYPE: amino acid
        (D) TOPOLOGY: linear (ii) MOLECULE TYPE: peptide (iii) HYPOTHETICAL: NO (vi) ORIGINAL SOURCE:
        (C) INDIVIDUAL ISOLATE: HCV (ix) FEATURE:
        (A) NAME/KEY: Modified-site
        (B) LOCATION: 1

(ix) FEATURE:
        (A) NAME/KEY: Modified-site
        (B) LOCATION: 24

(xi) SEQUENCE DESCRIPTION: SEQ ID NO: 72:

Xaa Gly His Thr Arg Val Thr Gly Gly Val Gln Gly His Val Thr Cys
1               5                  10                  15

Thr Leu Thr Ser Leu Phe Arg Xaa
            20

(2) INFORMATION FOR SEQ ID NO: 73:

(i) SEQUENCE CHARACTERISTICS:
        (A) LENGTH: 26 amino acids
        (B) TYPE: amino acid
        (D) TOPOLOGY: linear (ii) MOLECULE TYPE: peptide (iii) HYPOTHETICAL: NO (vi) ORIGINAL SOURCE:
        (C) INDIVIDUAL ISOLATE: HCV (ix) FEATURE:
        (A) NAME/KEY: Modified-site
        (B) LOCATION: 1

(ix) FEATURE:
        (A) NAME/KEY: Modified-site
        (B) LOCATION: 26

(xi) SEQUENCE DESCRIPTION: SEQ ID NO: 73:

Xaa Gly His Val Thr Cys Thr Leu Thr Ser Leu Phe Arg Pro Gly Ala
1             5                  10             15

Ser Gln Lys Ile Gln Leu Val Asn Thr Xaa
        20              25

(2) INFORMATION FOR SEQ ID NO: 74:

(i) SEQUENCE CHARACTERISTICS:
        (A) LENGTH: 36 amino acids
        (B) TYPE: amino acid
        (D) TOPOLOGY: linear (ii) MOLECULE TYPE: peptide (iii) HYPOTHETICAL: NO (vi) ORIGINAL SOURCE:
        (C) INDIVIDUAL ISOLATE: HCV (ix) FEATURE:
        (A) NAME/KEY: Modified-site
        (B) LOCATION: 1

(ix) FEATURE:
        (A) NAME/KEY: Modified-site
        (B) LOCATION: 36

(xi) SEQUENCE DESCRIPTION: SEQ ID NO: 74:

Xaa Gly His Thr His Val Thr Gly Gly Arg Val Ala Ser Ser Thr Gln
1             5                  10             15

Ser Leu Val Ser Trp Leu Ser Gln Gly Pro Ser Gln Lys Ile Gln Leu
        20              25             30

Val Asn Thr Xaa
       35

(2) INFORMATION FOR SEQ ID NO: 75:

(i) SEQUENCE CHARACTERISTICS:
        (A) LENGTH: 24 amino acids
        (B) TYPE: amino acid
        (D) TOPOLOGY: linear (ii) MOLECULE TYPE: peptide (iii) HYPOTHETICAL: NO (vi) ORIGINAL SOURCE:
        (C) INDIVIDUAL ISOLATE: HCV

```
       (ix) FEATURE:
             (A) NAME/KEY: Modified-site
             (B) LOCATION: 1

(ix) FEATURE:
             (A) NAME/KEY: Modified-site
             (B) LOCATION: 24

(xi) SEQUENCE DESCRIPTION: SEQ ID NO: 75:

Xaa Gly His Thr His Val Thr Gly Gly Arg Val Ala Ser Ser Thr Gln
1               5                  10                  15

Ser Leu Val Ser Trp Leu Ser Xaa
            20

(2) INFORMATION FOR SEQ ID NO: 76:

(i) SEQUENCE CHARACTERISTICS:
             (A) LENGTH: 26 amino acids
             (B) TYPE: amino acid
             (D) TOPOLOGY: linear (ii) MOLECULE TYPE: peptide (iii) HYPOTHETICAL: NO (vi) ORIGINAL SOURCE:
             (C) INDIVIDUAL ISOLATE: HCV (ix) FEATURE:
             (A) NAME/KEY: Modified-site
             (B) LOCATION: 1

(ix) FEATURE:
             (A) NAME/KEY: Modified-site
             (B) LOCATION: 26

(xi) SEQUENCE DESCRIPTION: SEQ ID NO: 76:

Xaa Ala Ser Ser Thr Gln Ser Leu Val Ser Trp Leu Ser Gln Gly Pro
1               5                  10                  15

Ser Gln Lys Ile Gln Leu Val Asn Thr Xaa
            20                  25

(2) INFORMATION FOR SEQ ID NO: 77:

(i) SEQUENCE CHARACTERISTICS:
             (A) LENGTH: 36 amino acids
             (B) TYPE: amino acid
             (D) TOPOLOGY: linear (ii) MOLECULE TYPE: peptide (iii) HYPOTHETICAL: NO (vi) ORIGINAL SOURCE:
             (C) INDIVIDUAL ISOLATE: HCV (ix) FEATURE:
             (A) NAME/KEY: Modified-site
             (B) LOCATION: 1

(ix) FEATURE:
             (A) NAME/KEY: Modified-site
             (B) LOCATION: 36

(xi) SEQUENCE DESCRIPTION: SEQ ID NO: 77:

Xaa Gly Asp Thr His Val Thr Gly Gly Ala Gln Ala Lys Thr Thr Asn
1               5                  10                  15

Arg Leu Val Ser Met Phe Ala Ser Gly Pro Ser Gln Lys Ile Gln Leu
            20                  25                  30
```

```
Ile Asn Thr Xaa
        35

(2) INFORMATION FOR SEQ ID NO: 78:

(i) SEQUENCE CHARACTERISTICS:
        (A) LENGTH: 24 amino acids
        (B) TYPE: amino acid
        (D) TOPOLOGY: linear (ii) MOLECULE TYPE: peptide (iii) HYPOTHETICAL: NO (vi) ORIGINAL SOURCE:
        (C) INDIVIDUAL ISOLATE: HCV (ix) FEATURE:
        (A) NAME/KEY: Modified-site
        (B) LOCATION: 1

(ix) FEATURE:
        (A) NAME/KEY: Modified-site
        (B) LOCATION: 24

(xi) SEQUENCE DESCRIPTION: SEQ ID NO: 78:

Xaa Gly Asp Thr His Val Thr Gly Gly Ala Gln Ala Lys Thr Thr Asn
1               5                   10                  15

Arg Leu Val Ser Met Phe Ala Xaa
            20

(2) INFORMATION FOR SEQ ID NO: 79:

(i) SEQUENCE CHARACTERISTICS:
        (A) LENGTH: 26 amino acids
        (B) TYPE: amino acid
        (D) TOPOLOGY: linear (ii) MOLECULE TYPE: peptide (iii) HYPOTHETICAL: NO (vi) ORIGINAL SOURCE:
        (C) INDIVIDUAL ISOLATE: HCV (ix) FEATURE:
        (A) NAME/KEY: Modified-site
        (B) LOCATION: 1

(ix) FEATURE:
        (A) NAME/KEY: Modified-site
        (B) LOCATION: 26

(xi) SEQUENCE DESCRIPTION: SEQ ID NO: 79:

Xaa Ala Lys Thr Thr Asn Arg Leu Val Ser Met Phe Ala Ser Gly Pro
1               5                   10                  15

Ser Gln Lys Ile Gln Leu Ile Asn Thr Xaa
            20                  25

(2) INFORMATION FOR SEQ ID NO: 80:

(i) SEQUENCE CHARACTERISTICS:
        (A) LENGTH: 36 amino acids
        (B) TYPE: amino acid
        (D) TOPOLOGY: linear (ii) MOLECULE TYPE: peptide (iii) HYPOTHETICAL: NO (vi) ORIGINAL SOURCE:
        (C) INDIVIDUAL ISOLATE: HCV
```

```
    (ix) FEATURE:
         (A) NAME/KEY: Modified-site
         (B) LOCATION: 1

(ix) FEATURE:
         (A) NAME/KEY: Modified-site
         (B) LOCATION: 36

(xi) SEQUENCE DESCRIPTION: SEQ ID NO: 80:

Xaa Ala Glu Thr Tyr Thr Ser Gly Gly Asn Ala Gly His Thr Met Thr
1               5                  10                  15

Gly Ile Val Arg Phe Phe Ala Pro Gly Pro Lys Gln Asn Val His Leu
            20                  25                  30

Ile Asn Thr Xaa
        35

(2) INFORMATION FOR SEQ ID NO: 81:

(i) SEQUENCE CHARACTERISTICS:
         (A) LENGTH: 24 amino acids
         (B) TYPE: amino acid
         (D) TOPOLOGY: linear (ii) MOLECULE TYPE: peptide (iii) HYPOTHETICAL: NO (vi) ORIGINAL SOURCE:
         (C) INDIVIDUAL ISOLATE: HCV (ix) FEATURE:
         (A) NAME/KEY: Modified-site
         (B) LOCATION: 1

(ix) FEATURE:
         (A) NAME/KEY: Modified-site
         (B) LOCATION: 24

(xi) SEQUENCE DESCRIPTION: SEQ ID NO: 81:

Xaa Ala Glu Thr Tyr Thr Ser Gly Gly Asn Ala Gly His Thr Met Thr
1               5                  10                  15

Gly Ile Val Arg Phe Phe Ala Xaa
            20

(2) INFORMATION FOR SEQ ID NO: 82:

(i) SEQUENCE CHARACTERISTICS:
         (A) LENGTH: 26 amino acids
         (B) TYPE: amino acid
         (D) TOPOLOGY: linear (ii) MOLECULE TYPE: peptide (iii) HYPOTHETICAL: NO (vi) ORIGINAL SOURCE:
         (C) INDIVIDUAL ISOLATE: HCV (ix) FEATURE:
         (A) NAME/KEY: Modified-site
         (B) LOCATION: 1

(ix) FEATURE:
         (A) NAME/KEY: Modified-site
         (B) LOCATION: 26

(xi) SEQUENCE DESCRIPTION: SEQ ID NO: 82:

Xaa Gly His Thr Met Thr Gly Ile Val Arg Phe Phe Ala Pro Gly Pro
1               5                  10                  15
```

```
Lys Gln Asn Val His Leu Ile Asn Thr Xaa
            20                  25

(2) INFORMATION FOR SEQ ID NO: 83:

(i) SEQUENCE CHARACTERISTICS:
        (A) LENGTH: 36 amino acids
        (B) TYPE: amino acid
        (D) TOPOLOGY: linear (ii) MOLECULE TYPE: peptide (iii) HYPOTHETICAL: NO (vi) ORIGINAL SOURCE:
        (C) INDIVIDUAL ISOLATE: HCV (ix) FEATURE:
        (A) NAME/KEY: Modified-site
        (B) LOCATION: 1

(ix) FEATURE:
        (A) NAME/KEY: Modified-site
        (B) LOCATION: 36

(xi) SEQUENCE DESCRIPTION: SEQ ID NO: 83:

Xaa Ala Glu Thr Ile Val Ser Gly Gly Gln Ala Ala Arg Ala Met Ser
1               5                   10                  15

Gly Leu Val Ser Leu Phe Thr Pro Gly Ala Lys Gln Asn Ile Gln Leu
            20                  25                  30

Ile Asn Thr Xaa
        35

(2) INFORMATION FOR SEQ ID NO: 84:

(i) SEQUENCE CHARACTERISTICS:
        (A) LENGTH: 24 amino acids
        (B) TYPE: amino acid
        (D) TOPOLOGY: linear (ii) MOLECULE TYPE: peptide (iii) HYPOTHETICAL: NO (vi) ORIGINAL SOURCE:
        (C) INDIVIDUAL ISOLATE: HCV (ix) FEATURE:
        (A) NAME/KEY: Modified-site
        (B) LOCATION: 1

(ix) FEATURE:
        (A) NAME/KEY: Modified-site
        (B) LOCATION: 24

(xi) SEQUENCE DESCRIPTION: SEQ ID NO: 84:

Xaa Ala Glu Thr Ile Val Ser Gly Gly Gln Ala Ala Arg Ala Met Ser
1               5                   10                  15

Gly Leu Val Ser Leu Phe Thr Xaa
            20

(2) INFORMATION FOR SEQ ID NO: 85:

(i) SEQUENCE CHARACTERISTICS:
        (A) LENGTH: 26 amino acids
        (B) TYPE: amino acid
        (D) TOPOLOGY: linear (ii) MOLECULE TYPE: peptide (iii) HYPOTHETICAL: NO
```

(vi) ORIGINAL SOURCE:
              (C) INDIVIDUAL ISOLATE: HCV (ix) FEATURE:
              (A) NAME/KEY: Modified-site
              (B) LOCATION: 1

(ix) FEATURE:
              (A) NAME/KEY: Modified-site
              (B) LOCATION: 26

(xi) SEQUENCE DESCRIPTION: SEQ ID NO: 85:

Xaa Ala Arg Ala Met Ser Gly Leu Val Ser Leu Phe Thr Pro Gly Ala
1               5                   10                  15

Lys Gln Asn Ile Gln Leu Ile Asn Thr Xaa
            20                  25

(2) INFORMATION FOR SEQ ID NO: 86:

(i) SEQUENCE CHARACTERISTICS:
              (A) LENGTH: 36 amino acids
              (B) TYPE: amino acid
              (D) TOPOLOGY: linear (ii) MOLECULE TYPE: peptide (iii) HYPOTHETICAL: NO (vi) ORIGINAL SOURCE:
              (C) INDIVIDUAL ISOLATE: HCV (ix) FEATURE:
              (A) NAME/KEY: Modified-site
              (B) LOCATION: 1

(ix) FEATURE:
              (A) NAME/KEY: Modified-site
              (B) LOCATION: 36

(xi) SEQUENCE DESCRIPTION: SEQ ID NO: 86:

Xaa Ala Glu Thr Tyr Thr Thr Gly Gly Ser Thr Ala Arg Thr Thr Gln
1               5                   10                  15

Gly Leu Val Ser Leu Phe Ser Arg Gly Ala Lys Gln Asp Ile Gln Leu
            20                  25                  30

Ile Asn Thr Xaa
        35

(2) INFORMATION FOR SEQ ID NO: 87:

(i) SEQUENCE CHARACTERISTICS:
              (A) LENGTH: 24 amino acids
              (B) TYPE: amino acid
              (D) TOPOLOGY: linear (ii) MOLECULE TYPE: peptide (iii) HYPOTHETICAL: NO (vi) ORIGINAL SOURCE:
              (C) INDIVIDUAL ISOLATE: HCV (ix) FEATURE:
              (A) NAME/KEY: Modified-site
              (B) LOCATION: 1

(ix) FEATURE:
              (A) NAME/KEY: Modified-site
              (B) LOCATION: 24

(xi) SEQUENCE DESCRIPTION: SEQ ID NO: 87:

```
Xaa Ala Glu Thr Tyr Thr Thr Gly Gly Ser Thr Ala Arg Thr Thr Gln
1               5                   10                  15

Gly Leu Val Ser Leu Phe Ser Xaa
                20
```

(2) INFORMATION FOR SEQ ID NO: 88:

(i) SEQUENCE CHARACTERISTICS:
        (A) LENGTH: 26 amino acids
        (B) TYPE: amino acid
        (D) TOPOLOGY: linear (ii) MOLECULE TYPE: peptide (iii) HYPOTHETICAL: NO (vi) ORIGINAL SOURCE:
        (C) INDIVIDUAL ISOLATE: HCV (ix) FEATURE:
        (A) NAME/KEY: Modified-site
        (B) LOCATION: 1

(ix) FEATURE:
        (A) NAME/KEY: Modified-site
        (B) LOCATION: 26

(xi) SEQUENCE DESCRIPTION: SEQ ID NO: 88:

```
Xaa Ala Arg Thr Thr Gln Gly Leu Val Ser Leu Phe Ser Arg Gly Ala
1               5                   10                  15

Lys Gln Asp Ile Gln Leu Ile Asn Thr Xaa
                20                  25
```

(2) INFORMATION FOR SEQ ID NO: 89:

(i) SEQUENCE CHARACTERISTICS:
        (A) LENGTH: 36 amino acids
        (B) TYPE: amino acid
        (D) TOPOLOGY: linear (ii) MOLECULE TYPE: peptide (iii) HYPOTHETICAL: NO (vi) ORIGINAL SOURCE:
        (C) INDIVIDUAL ISOLATE: HCV type 2

(ix) FEATURE:
        (A) NAME/KEY: Modified-site
        (B) LOCATION: 1

(ix) FEATURE:
        (A) NAME/KEY: Modified-site
        (B) LOCATION: 36

(xi) SEQUENCE DESCRIPTION: SEQ ID NO: 89:

```
Xaa Ala Gln Thr His Thr Val Gly Gly Ser Thr Ala His Asn Ala Arg
1               5                   10                  15

Thr Leu Thr Gly Met Phe Ser Leu Gly Ala Arg Gln Lys Ile Gln Leu
                20                  25                  30

Ile Asn Thr Xaa
            35
```

(2) INFORMATION FOR SEQ ID NO: 90:

(i) SEQUENCE CHARACTERISTICS:
        (A) LENGTH: 24 amino acids
        (B) TYPE: amino acid
        (D) TOPOLOGY: linear (ii) MOLECULE TYPE: peptide (iii) HYPOTHETICAL: NO (vi) ORIGINAL SOURCE:
             (C) INDIVIDUAL ISOLATE: HCV type 2

(ix) FEATURE:
             (A) NAME/KEY: Modified-site
             (B) LOCATION: 1

(ix) FEATURE:
             (A) NAME/KEY: Modified-site
             (B) LOCATION: 24

(xi) SEQUENCE DESCRIPTION: SEQ ID NO: 90:

Xaa Ala Gln Thr His Thr Val Gly Gly Ser Thr Ala His Asn Ala Arg
1               5                   10                  15

Thr Leu Thr Gly Met Phe Ser Xaa
            20

(2) INFORMATION FOR SEQ ID NO: 91:

(i) SEQUENCE CHARACTERISTICS:
            (A) LENGTH: 26 amino acids
            (B) TYPE: amino acid
            (D) TOPOLOGY: linear (ii) MOLECULE TYPE: peptide (iii) HYPOTHETICAL: NO (vi) ORIGINAL SOURCE:
            (C) INDIVIDUAL ISOLATE: HCV type 2

(ix) FEATURE:
            (A) NAME/KEY: Modified-site
            (B) LOCATION: 1

(ix) FEATURE:
            (A) NAME/KEY: Modified-site
            (B) LOCATION: 26

(xi) SEQUENCE DESCRIPTION: SEQ ID NO: 91:

Xaa Ala His Asn Ala Arg Thr Leu Thr Gly Met Phe Ser Leu Gly Ala
1               5                   10                  15

Arg Gln Lys Ile Gln Leu Ile Asn Thr Xaa
            20                  25

(2) INFORMATION FOR SEQ ID NO: 92:

(i) SEQUENCE CHARACTERISTICS:
            (A) LENGTH: 22 amino acids
            (B) TYPE: amino acid
            (D) TOPOLOGY: linear (ii) MOLECULE TYPE: peptide (iii) HYPOTHETICAL: NO (vi) ORIGINAL SOURCE:
            (C) INDIVIDUAL ISOLATE: HCV type 2

(ix) FEATURE:
            (A) NAME/KEY: Modified-site
            (B) LOCATION: 1

(ix) FEATURE:
            (A) NAME/KEY: Modified-site
            (B) LOCATION: 22

(xi) SEQUENCE DESCRIPTION: SEQ ID NO: 92:

```
Xaa Val Asn Gln Arg Ala Val Val Ala Pro Asp Lys Glu Val Leu Tyr
1               5                   10                  15
Glu Ala Phe Asp Glu Xaa
            20

(2) INFORMATION FOR SEQ ID NO: 93:

(i) SEQUENCE CHARACTERISTICS:
        (A) LENGTH: 22 amino acids
        (B) TYPE: amino acid
        (D) TOPOLOGY: linear (ii) MOLECULE TYPE: peptide (iii) HYPOTHETICAL: NO (vi) ORIGINAL SOURCE:
        (C) INDIVIDUAL ISOLATE: HCV type 2

(ix) FEATURE:
        (A) NAME/KEY: Modified-site
        (B) LOCATION: 1

(ix) FEATURE:
        (A) NAME/KEY: Modified-site
        (B) LOCATION: 22

(xi) SEQUENCE DESCRIPTION: SEQ ID NO: 93:

Xaa Val Ala Pro Asp Lys Glu Val Leu Tyr Glu Ala Phe Asp Glu Met
1               5                   10                  15
Glu Glu Cys Ala Ser Xaa
            20

(2) INFORMATION FOR SEQ ID NO: 94:

(i) SEQUENCE CHARACTERISTICS:
        (A) LENGTH: 22 amino acids
        (B) TYPE: amino acid
        (D) TOPOLOGY: linear (ii) MOLECULE TYPE: peptide (iii) HYPOTHETICAL: NO (vi) ORIGINAL SOURCE:
        (C) INDIVIDUAL ISOLATE: HCV type 2

(ix) FEATURE:
        (A) NAME/KEY: Modified-site
        (B) LOCATION: 1

(ix) FEATURE:
        (A) NAME/KEY: Modified-site
        (B) LOCATION: 22

(xi) SEQUENCE DESCRIPTION: SEQ ID NO: 94:

Xaa Asp Glu Met Glu Glu Cys Ala Ser Arg Ala Ala Leu Ile Glu Glu
1               5                   10                  15
Gly Gln Arg Ile Ala Xaa
            20

(2) INFORMATION FOR SEQ ID NO: 95:

(i) SEQUENCE CHARACTERISTICS:
        (A) LENGTH: 22 amino acids
        (B) TYPE: amino acid
        (D) TOPOLOGY: linear (ii) MOLECULE TYPE: peptide (iii) HYPOTHETICAL: NO
```

```
    (vi) ORIGINAL SOURCE:
        (C) INDIVIDUAL ISOLATE: HCV type 2

(ix) FEATURE:
        (A) NAME/KEY: Modified-site
        (B) LOCATION: 1

(ix) FEATURE:
        (A) NAME/KEY: Modified-site
        (B) LOCATION: 22

(xi) SEQUENCE DESCRIPTION: SEQ ID NO: 95:

Xaa Ala Ser Arg Ala Ala Leu Ile Glu Glu Gly Gln Arg Ile Ala Glu
1               5                   10                  15

Met Leu Lys Ser Lys Xaa
            20

(2) INFORMATION FOR SEQ ID NO: 96:

(i) SEQUENCE CHARACTERISTICS:
        (A) LENGTH: 22 amino acids
        (B) TYPE: amino acid
        (D) TOPOLOGY: linear (ii) MOLECULE TYPE: peptide (iii) HYPOTHETICAL: NO (vi) ORIGINAL SOURCE:
        (C) INDIVIDUAL ISOLATE: HCV type 2

(ix) FEATURE:
        (A) NAME/KEY: Modified-site
        (B) LOCATION: 1

(ix) FEATURE:
        (A) NAME/KEY: Modified-site
        (B) LOCATION: 22

(xi) SEQUENCE DESCRIPTION: SEQ ID NO: 96:

Xaa Ile Glu Glu Gly Gln Arg Ile Ala Glu Met Leu Lys Ser Lys Ile
1               5                   10                  15

Gln Gly Leu Leu Gln Xaa
            20

(2) INFORMATION FOR SEQ ID NO: 97:

(i) SEQUENCE CHARACTERISTICS:
        (A) LENGTH: 22 amino acids
        (B) TYPE: amino acid
        (D) TOPOLOGY: linear (ii) MOLECULE TYPE: peptide (iii) HYPOTHETICAL: NO (vi) ORIGINAL SOURCE:
        (C) INDIVIDUAL ISOLATE: HCV type 2

(ix) FEATURE:
        (A) NAME/KEY: Modified-site
        (B) LOCATION: 1

(ix) FEATURE:
        (A) NAME/KEY: Modified-site
        (B) LOCATION: 22

(xi) SEQUENCE DESCRIPTION: SEQ ID NO: 97:

Xaa Ile Ala Glu Met Leu Lys Ser Lys Ile Gln Gly Leu Leu Gln Gln
1               5                   10                  15
```

```
Ala Ser Lys Gln Ala Xaa
            20

(2) INFORMATION FOR SEQ ID NO: 98:

(i) SEQUENCE CHARACTERISTICS:
         (A) LENGTH: 22 amino acids
         (B) TYPE: amino acid
         (D) TOPOLOGY: linear (ii) MOLECULE TYPE: peptide (iii) HYPOTHETICAL: NO (vi) ORIGINAL SOURCE:
         (C) INDIVIDUAL ISOLATE: HCV type 2

(ix) FEATURE:
         (A) NAME/KEY: Modified-site
         (B) LOCATION: 1

(ix) FEATURE:
         (A) NAME/KEY: Modified-site
         (B) LOCATION: 22

(xi) SEQUENCE DESCRIPTION: SEQ ID NO: 98:

Xaa Ser Lys Ile Gln Gly Leu Leu Gln Gln Ala Ser Lys Gln Ala Gln
1               5                  10                  15

Asp Ile Gln Pro Ala Xaa
            20

(2) INFORMATION FOR SEQ ID NO: 99:

(i) SEQUENCE CHARACTERISTICS:
         (A) LENGTH: 21 amino acids
         (B) TYPE: amino acid
         (D) TOPOLOGY: linear (ii) MOLECULE TYPE: peptide (iii) HYPOTHETICAL: NO (vi) ORIGINAL SOURCE:
         (C) INDIVIDUAL ISOLATE: HCV type 2

(ix) FEATURE:
         (A) NAME/KEY: Modified-site
         (B) LOCATION: 1

(ix) FEATURE:
         (A) NAME/KEY: Modified-site
         (B) LOCATION: 21

(xi) SEQUENCE DESCRIPTION: SEQ ID NO: 99:

Xaa Arg Ser Asp Leu Glu Pro Ser Ile Pro Ser Glu Tyr Met Leu Pro
1               5                  10                  15

Lys Lys Arg Phe Xaa
            20

(2) INFORMATION FOR SEQ ID NO: 100:

(i) SEQUENCE CHARACTERISTICS:
         (A) LENGTH: 22 amino acids
         (B) TYPE: amino acid
         (D) TOPOLOGY: linear (ii) MOLECULE TYPE: peptide (iii) HYPOTHETICAL: NO (vi) ORIGINAL SOURCE:
         (C) INDIVIDUAL ISOLATE: HCV type 2
```

(ix) FEATURE:
         (A) NAME/KEY: Modified-site
         (B) LOCATION: 1

(ix) FEATURE:
         (A) NAME/KEY: Modified-site
         (B) LOCATION: 22

(xi) SEQUENCE DESCRIPTION: SEQ ID NO: 100:

Xaa Met Leu Pro Lys Lys Arg Phe Pro Pro Ala Leu Pro Ala Trp Ala
1               5                   10                  15

Arg Pro Asp Tyr Asn Xaa
            20

(2) INFORMATION FOR SEQ ID NO: 101:

(i) SEQUENCE CHARACTERISTICS:
        (A) LENGTH: 22 amino acids
        (B) TYPE: amino acid
        (D) TOPOLOGY: linear (ii) MOLECULE TYPE: peptide (iii) HYPOTHETICAL: NO (vi) ORIGINAL SOURCE:
         (C) INDIVIDUAL ISOLATE: HCV type 2

(ix) FEATURE:
         (A) NAME/KEY: Modified-site
         (B) LOCATION: 1

(ix) FEATURE:
         (A) NAME/KEY: Modified-site
         (B) LOCATION: 22

(xi) SEQUENCE DESCRIPTION: SEQ ID NO: 101:

Xaa Ala Trp Ala Arg Pro Asp Tyr Asn Pro Pro Leu Val Glu Ser Trp
1               5                   10                  15

Lys Arg Pro Asp Tyr Xaa
            20

(2) INFORMATION FOR SEQ ID NO: 102:

(i) SEQUENCE CHARACTERISTICS:
        (A) LENGTH: 22 amino acids
        (B) TYPE: amino acid
        (D) TOPOLOGY: linear (ii) MOLECULE TYPE: peptide (iii) HYPOTHETICAL: NO (vi) ORIGINAL SOURCE:
         (C) INDIVIDUAL ISOLATE: HCV type 2

(ix) FEATURE:
         (A) NAME/KEY: Modified-site
         (B) LOCATION: 1

(ix) FEATURE:
         (A) NAME/KEY: Modified-site
         (B) LOCATION: 22

(xi) SEQUENCE DESCRIPTION: SEQ ID NO: 102:

Xaa Glu Ser Trp Lys Arg Pro Asp Tyr Gln Pro Ala Thr Val Ala Gly
1               5                   10                  15

Cys Ala Leu Pro Pro Xaa
            20

(2) INFORMATION FOR SEQ ID NO: 103:

(i) SEQUENCE CHARACTERISTICS:
        (A) LENGTH: 22 amino acids
        (B) TYPE: amino acid
        (D) TOPOLOGY: linear (ii) MOLECULE TYPE: peptide (iii) HYPOTHETICAL: NO (vi) ORIGINAL SOURCE:
        (C) INDIVIDUAL ISOLATE: HCV type 2

(ix) FEATURE:
        (A) NAME/KEY: Modified-site
        (B) LOCATION: 1

(ix) FEATURE:
        (A) NAME/KEY: Modified-site
        (B) LOCATION: 22

(xi) SEQUENCE DESCRIPTION: SEQ ID NO: 103:

```
Xaa Val Ala Gly Cys Ala Leu Pro Pro Pro Lys Lys Thr Pro Thr Pro
1               5                  10                  15

Pro Pro Arg Arg Arg Xaa
            20
```

(2) INFORMATION FOR SEQ ID NO: 104:

(i) SEQUENCE CHARACTERISTICS:
        (A) LENGTH: 33 amino acids
        (B) TYPE: amino acid
        (D) TOPOLOGY: linear (ii) MOLECULE TYPE: peptide (iii) HYPOTHETICAL: NO (vi) ORIGINAL SOURCE:
        (C) INDIVIDUAL ISOLATE: HCV (ix) FEATURE:
        (A) NAME/KEY: Modified-site
        (B) LOCATION: 1

(ix) FEATURE:
        (A) NAME/KEY: Modified-site
        (B) LOCATION: 33

(xi) SEQUENCE DESCRIPTION: SEQ ID NO: 104:

```
Xaa Ile Pro Asp Arg Glu Val Leu Tyr Arg Gly Gly Lys Lys Pro Asp
1               5                  10                  15

Tyr Glu Pro Pro Val Gly Gly Arg Arg Pro Gln Asp Val Lys Phe Pro
            20                  25                  30

Xaa
```

(2) INFORMATION FOR SEQ ID NO: 105:

(i) SEQUENCE CHARACTERISTICS:
        (A) LENGTH: 33 amino acids
        (B) TYPE: amino acid
        (D) TOPOLOGY: linear (ii) MOLECULE TYPE: peptide (iii) HYPOTHETICAL: NO (vi) ORIGINAL SOURCE:
        (C) INDIVIDUAL ISOLATE: HCV (ix) FEATURE:
            (A) NAME/KEY: Modified-site
            (B) LOCATION: 1

(ix) FEATURE:
            (A) NAME/KEY: Modified-site
            (B) LOCATION: 33

(xi) SEQUENCE DESCRIPTION: SEQ ID NO: 105:

Xaa Trp Ala Arg Pro Asp Tyr Asn Pro Pro Gly Gly Gln Phe Lys Gln
1               5                  10                  15

Lys Ala Leu Gly Leu Gly Ser Gly Val Tyr Leu Leu Pro Arg Arg Gly
             20                  25                  30

Xaa (2) INFORMATION FOR SEQ ID NO: 106:

(i) SEQUENCE CHARACTERISTICS:
            (A) LENGTH: 33 amino acids
            (B) TYPE: amino acid
            (D) TOPOLOGY: linear (ii) MOLECULE TYPE: peptide (iii) HYPOTHETICAL: NO (vi) ORIGINAL SOURCE:
            (C) INDIVIDUAL ISOLATE: HCV (ix) FEATURE:
            (A) NAME/KEY: Modified-site
            (B) LOCATION: 1

(ix) FEATURE:
            (A) NAME/KEY: Modified-site
            (B) LOCATION: 33

(xi) SEQUENCE DESCRIPTION: SEQ ID NO: 106:

Xaa Arg Gly Arg Arg Gln Pro Ile Pro Lys Gly Gly Ser Gln His Leu
1               5                  10                  15

Pro Tyr Ile Glu Gln Ser Gly Pro Val Val His Gly Cys Pro Leu Pro
             20                  25                  30

Xaa (2) INFORMATION FOR SEQ ID NO: 107:

(i) SEQUENCE CHARACTERISTICS:
            (A) LENGTH: 22 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO: 107:

Xaa Leu Gly Gly Lys Pro Ala Ile Val Pro Asp Lys Glu Val Leu Tyr
1               5                  10                  15

Gln Gln Tyr Asp Glu Xaa
             20

(2) INFORMATION FOR SEQ ID NO: 108:

(i) SEQUENCE CHARACTERISTICS:
            (A) LENGTH: 22 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO: 108:

Xaa Ser Gln Ala Ala Pro Tyr Ile Glu Gln Ala Gln Val Ile Ala His
1               5                   10                  15

Gln Phe Lys Glu Lys Xaa
            20

(2) INFORMATION FOR SEQ ID NO: 109:

(i) SEQUENCE CHARACTERISTICS:
        (A) LENGTH: 24 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 109:

Xaa Ile Ala His Gln His Gln Phe Lys Glu Lys Val Leu Gly Leu Leu
1               5                   10                  15

Gln Arg Ala Thr Gln Gln Gln Xaa
            20

(2) INFORMATION FOR SEQ ID NO: 110:

(i) SEQUENCE CHARACTERISTICS:
        (A) LENGTH: 11 amino acids
        (B) TYPE: amino acid
        (D) TOPOLOGY: linear (ii) MOLECULE TYPE: peptide (iii) HYPOTHETICAL: NO (vi) ORIGINAL SOURCE:
        (C) INDIVIDUAL ISOLATE: HTLV-IIIB (ix) FEATURE:
        (A) NAME/KEY: Xaa is Ac
        (B) LOCATION: 1

(ix) FEATURE:
        (A) NAME/KEY: Xaa is NH2
        (B) LOCATION: 11

(xi) SEQUENCE DESCRIPTION: SEQ ID NO: 110:

Xaa Ile Trp Gly Cys Ser Gly Lys Ile Cys Xaa
1               5                   10

(2) INFORMATION FOR SEQ ID NO: 111:

(i) SEQUENCE CHARACTERISTICS:
        (A) LENGTH: 11 amino acids
        (B) TYPE: amino acid
        (D) TOPOLOGY: linear (ii) MOLECULE TYPE: peptide (iii) HYPOTHETICAL: NO (vi) ORIGINAL SOURCE:
        (C) INDIVIDUAL ISOLATE: HTLV-IIIB (ix) FEATURE:
        (A) NAME/KEY: Xaa is Bio-Gly-Gly-Gly
        (B) LOCATION: 1

(ix) FEATURE:
        (A) NAME/KEY: Xaa is NH2
        (B) LOCATION: 11

(xi) SEQUENCE DESCRIPTION: SEQ ID NO: 111:

Xaa Ile Trp Gly Cys Ser Gly Lys Ile Cys Xaa
1               5                   10

(2) INFORMATION FOR SEQ ID NO: 112:

(i) SEQUENCE CHARACTERISTICS:
      (A) LENGTH: 12 amino acids
      (B) TYPE: amino acid
      (D) TOPOLOGY: linear (ii) MOLECULE TYPE: peptide (iii) HYPOTHETICAL: NO (vi) ORIGINAL SOURCE:
      (C) INDIVIDUAL ISOLATE: HIV-2 rod (ix) FEATURE:
      (A) NAME/KEY: Xaa is Ac
      (B) LOCATION: 1

(ix) FEATURE:
      (A) NAME/KEY: Xaa is NH2
      (B) LOCATION: 12

(xi) SEQUENCE DESCRIPTION: SEQ ID NO: 112:

Xaa Ser Trp Gly Cys Ala Phe Arg Gln Val Cys Xaa
1               5                   10

(2) INFORMATION FOR SEQ ID NO: 113:

(i) SEQUENCE CHARACTERISTICS:
      (A) LENGTH: 12 amino acids
      (B) TYPE: amino acid
      (D) TOPOLOGY: linear (ii) MOLECULE TYPE: peptide (iii) HYPOTHETICAL: NO (vi) ORIGINAL SOURCE:
      (C) INDIVIDUAL ISOLATE: HIV-2 rod (ix) FEATURE:
      (A) NAME/KEY: Xaa is Bio-Gly-Gly-Gly
      (B) LOCATION: 1

(ix) FEATURE:
      (A) NAME/KEY: Xaa is NH2
      (B) LOCATION: 12

(xi) SEQUENCE DESCRIPTION: SEQ ID NO: 113:

Xaa Ser Trp Gly Cys Ala Phe Arg Gln Val Cys Xaa
1               5                   10

(2) INFORMATION FOR SEQ ID NO: 114:

(i) SEQUENCE CHARACTERISTICS:
      (A) LENGTH: 25 amino acids
      (B) TYPE: amino acid
      (D) TOPOLOGY: linear (ii) MOLECULE TYPE: peptide (iii) HYPOTHETICAL: NO (vi) ORIGINAL SOURCE:
      (C) INDIVIDUAL ISOLATE: HIV-1 MN (ix) FEATURE:
      (A) NAME/KEY: Xaa is Ac (B) LOCATION: 1

(ix) FEATURE:
            (A) NAME/KEY: Xaa is NH2
            (B) LOCATION: 25

(xi) SEQUENCE DESCRIPTION: SEQ ID NO: 114:

Xaa Tyr Asn Lys Arg Lys Arg Ile His Ile Gly Pro Gly Arg Ala Phe
1               5                   10                  15

Tyr Thr Thr Lys Asn Ile Ile Gly Xaa
            20                  25

(2) INFORMATION FOR SEQ ID NO: 115:

(i) SEQUENCE CHARACTERISTICS:
            (A) LENGTH: 25 amino acids
            (B) TYPE: amino acid
            (D) TOPOLOGY: linear (ii) MOLECULE TYPE: peptide (iii) HYPOTHETICAL: NO (vi) ORIGINAL SOURCE:
            (C) INDIVIDUAL ISOLATE: HIV-1 MN (ix) FEATURE:
            (A) NAME/KEY: Xaa is Bio-Gly-Gly
            (B) LOCATION: 1

(ix) FEATURE:
            (A) NAME/KEY: Xaa is NH2
            (B) LOCATION: 25

(xi) SEQUENCE DESCRIPTION: SEQ ID NO: 115:

Xaa Tyr Asn Lys Arg Lys Arg Ile His Ile Gly Pro Gly Arg Ala Phe
1               5                   10                  15

Tyr Thr Thr Lys Asn Ile Ile Gly Xaa
            20                  25

(2) INFORMATION FOR SEQ ID NO: 116:

(i) SEQUENCE CHARACTERISTICS:
            (A) LENGTH: 22 amino acids
            (B) TYPE: amino acid
            (D) TOPOLOGY: linear (ii) MOLECULE TYPE: peptide (iii) HYPOTHETICAL: NO (vi) ORIGINAL SOURCE:
            (C) INDIVIDUAL ISOLATE: HCV (ix) FEATURE:
            (A) NAME/KEY: Xaa is absent
            (B) LOCATION: 1

(ix) FEATURE:
            (A) NAME/KEY: Xaa is absent
            (B) LOCATION: 22

(xi) SEQUENCE DESCRIPTION: SEQ ID NO: 116:

Xaa Ser Gln His Leu Pro Tyr Ile Glu Gln Gly Met Met Leu Ala Glu
1               5                   10                  15

Gln Phe Lys Gln Lys Xaa
            20

(2) INFORMATION FOR SEQ ID NO: 117:

```
        (i) SEQUENCE CHARACTERISTICS:
            (A) LENGTH: 22 amino acids
            (B) TYPE: amino acid
            (D) TOPOLOGY: linear (ii) MOLECULE TYPE: peptide (iii) HYPOTHETICAL: NO (vi) ORIGINAL SOURCE:
            (C) INDIVIDUAL ISOLATE: HCV (ix) FEATURE:
            (A) NAME/KEY: Xaa is absent
            (B) LOCATION: 1

(ix) FEATURE:
            (A) NAME/KEY: Xaa is absent
            (B) LOCATION: 22

(xi) SEQUENCE DESCRIPTION: SEQ ID NO: 117:

Xaa Leu Arg Lys Ser Arg Arg Phe Ala Gln Ala Leu Pro Val Trp Ala
1               5                  10                  15

Arg Pro Asp Tyr Asn Xaa
            20

(2) INFORMATION FOR SEQ ID NO: 118:

(i) SEQUENCE CHARACTERISTICS:
            (A) LENGTH: 22 amino acids
            (B) TYPE: amino acid
            (D) TOPOLOGY: linear (ii) MOLECULE TYPE: peptide (iii) HYPOTHETICAL: NO (vi) ORIGINAL SOURCE:
            (C) INDIVIDUAL ISOLATE: HCV (ix) FEATURE:
            (A) NAME/KEY: Xaa is absent
            (B) LOCATION: 1

(ix) FEATURE:
            (A) NAME/KEY: Xaa is absent
            (B) LOCATION: 22

(xi) SEQUENCE DESCRIPTION: SEQ ID NO: 118:

Xaa Pro Gln Arg Lys Thr Lys Arg Asn Thr Asn Arg Arg Pro Gln Asp
1               5                  10                  15

Val Lys Phe Pro Gly Xaa
            20

(2) INFORMATION FOR SEQ ID NO: 119:

(i) SEQUENCE CHARACTERISTICS:
            (A) LENGTH: 22 amino acids
            (B) TYPE: amino acid
            (D) TOPOLOGY: linear (ii) MOLECULE TYPE: peptide (iii) HYPOTHETICAL: NO (vi) ORIGINAL SOURCE:
            (C) INDIVIDUAL ISOLATE: HCV (ix) FEATURE:
            (A) NAME/KEY: Xaa is absent
            (B) LOCATION: 1

(ix) FEATURE:
```

```
            (A) NAME/KEY: Xaa is absent
            (B) LOCATION: 22

(xi) SEQUENCE DESCRIPTION: SEQ ID NO: 119:

Xaa Arg Asn Thr Asn Arg Arg Pro Gln Asp Val Lys Phe Pro Gly Gly
1               5                   10                  15

Gly Gln Ile Val Gly Xaa
            20

(2) INFORMATION FOR SEQ ID NO: 120:

(i) SEQUENCE CHARACTERISTICS:
        (A) LENGTH: 22 amino acids
        (B) TYPE: amino acid
        (D) TOPOLOGY: linear (ii) MOLECULE TYPE: peptide (iii) HYPOTHETICAL: NO (vi) ORIGINAL SOURCE:
        (C) INDIVIDUAL ISOLATE: HCV (ix) FEATURE:
        (A) NAME/KEY: Xaa is absent
        (B) LOCATION: 1

(ix) FEATURE:
        (A) NAME/KEY: Xaa is absent
        (B) LOCATION: 22

(xi) SEQUENCE DESCRIPTION: SEQ ID NO: 120:

Xaa Thr Arg Lys Thr Ser Glu Arg Ser Gln Pro Arg Gly Arg Arg Gln
1               5                   10                  15

Pro Ile Pro Lys Val Xaa
            20

(2) INFORMATION FOR SEQ ID NO: 121:

(i) SEQUENCE CHARACTERISTICS:
        (A) LENGTH: 22 amino acids
        (B) TYPE: amino acid
        (D) TOPOLOGY: linear (ii) MOLECULE TYPE: peptide (iii) HYPOTHETICAL: NO (vi) ORIGINAL SOURCE:
        (C) INDIVIDUAL ISOLATE: HCV (ix) FEATURE:
        (A) NAME/KEY: Xaa is absent
        (B) LOCATION: 1

(ix) FEATURE:
        (A) NAME/KEY: Xaa is absent
        (B) LOCATION: 22

(xi) SEQUENCE DESCRIPTION: SEQ ID NO: 121:

Xaa Ile Ile Pro Asp Arg Glu Val Leu Tyr Arg Glu Phe Asp Glu Met
1               5                   10                  15

Glu Glu Cys Ser Gln Xaa
            20

(2) INFORMATION FOR SEQ ID NO: 122:

(i) SEQUENCE CHARACTERISTICS:
        (A) LENGTH: 22 amino acids
        (B) TYPE: amino acid
```

```
            (D) TOPOLOGY: linear (ii) MOLECULE TYPE: peptide (iii) HYPOTHETICAL: NO (vi) ORIGINAL SOURCE:
            (C) INDIVIDUAL ISOLATE: HCV (ix) FEATURE:
            (A) NAME/KEY: Xaa is absent
            (B) LOCATION: 1

(ix) FEATURE:
            (A) NAME/KEY: Xaa is absent
            (B) LOCATION: 22

(xi) SEQUENCE DESCRIPTION: SEQ ID NO: 122:

Xaa Glu Thr Trp Lys Lys Pro Asp Tyr Glu Pro Pro Val Val His Gly
1               5                  10                  15

Cys Pro Leu Pro Pro Xaa
            20

(2) INFORMATION FOR SEQ ID NO: 123:

(i) SEQUENCE CHARACTERISTICS:
            (A) LENGTH: 22 amino acids
            (B) TYPE: amino acid
            (D) TOPOLOGY: linear (ii) MOLECULE TYPE: peptide (iii) HYPOTHETICAL: NO (vi) ORIGINAL SOURCE:
            (C) INDIVIDUAL ISOLATE: HCV (ix) FEATURE:
            (A) NAME/KEY: Xaa is H2N
            (B) LOCATION: 1

(ix) FEATURE:
            (A) NAME/KEY: Xaa is CONH2
            (B) LOCATION: 22

(xi) SEQUENCE DESCRIPTION: SEQ ID NO: 123:

Xaa Met Ser Thr Ile Pro Lys Pro Gln Arg Lys Thr Lys Arg Asn Thr
1               5                  10                  15

Asn Arg Arg Pro Gln Xaa
            20

(2) INFORMATION FOR SEQ ID NO: 124:

(i) SEQUENCE CHARACTERISTICS:
            (A) LENGTH: 22 amino acids
            (B) TYPE: amino acid
            (D) TOPOLOGY: linear (ii) MOLECULE TYPE: peptide (iii) HYPOTHETICAL: NO (vi) ORIGINAL SOURCE:
            (C) INDIVIDUAL ISOLATE: HCV (ix) FEATURE:
            (A) NAME/KEY: Xaa is H2N
            (B) LOCATION: 1

(ix) FEATURE:
            (A) NAME/KEY: Xaa is Gly-Gly-Lys(Bio)-CONH2
            (B) LOCATION: 22
```

(xi) SEQUENCE DESCRIPTION: SEQ ID NO: 124:

Xaa Met Ser Thr Ile Pro Lys Pro Gln Arg Lys Thr Lys Arg Asn Thr
1               5                   10                  15

Asn Arg Arg Pro Gln Xaa
                20

(2) INFORMATION FOR SEQ ID NO: 125:

(i) SEQUENCE CHARACTERISTICS:
        (A) LENGTH: 36 amino acids
        (B) TYPE: amino acid
        (D) TOPOLOGY: linear (ii) MOLECULE TYPE: peptide (iii) HYPOTHETICAL: NO (vi) ORIGINAL SOURCE:
        (C) INDIVIDUAL ISOLATE: HCV (ix) FEATURE:
        (A) NAME/KEY: Xaa is absent
        (B) LOCATION: 1

(ix) FEATURE:
        (A) NAME/KEY: Xaa is absent
        (B) LOCATION: 36

(xi) SEQUENCE DESCRIPTION: SEQ ID NO: 125:

Xaa Gly Glu Thr Tyr Thr Ser Gly Gly Ala Ala Ser His Thr Thr Ser
1               5                   10                  15

Thr Leu Ala Ser Leu Phe Ser Pro Gly Ala Ser Gln Arg Ile Gln Leu
                20                  25                  30

Val Asn Thr Xaa
            35

(2) INFORMATION FOR SEQ ID NO: 126:

(i) SEQUENCE CHARACTERISTICS:
        (A) LENGTH: 36 amino acids
        (B) TYPE: amino acid
        (D) TOPOLOGY: linear (ii) MOLECULE TYPE: peptide (iii) HYPOTHETICAL: NO (vi) ORIGINAL SOURCE:
        (C) INDIVIDUAL ISOLATE: HCV (ix) FEATURE:
        (A) NAME/KEY: Xaa is absent
        (B) LOCATION: 1

(ix) FEATURE:
        (A) NAME/KEY: Xaa is absent
        (B) LOCATION: 36

(xi) SEQUENCE DESCRIPTION: SEQ ID NO: 126:

Xaa Gly His Thr Arg Val Ser Gly Gly Ala Ala Ala Ser Asp Thr Arg
1               5                   10                  15

Gly Leu Val Ser Leu Phe Ser Pro Gly Ser Ala Gln Lys Ile Gln Leu
                20                  25                  30

Val Asn Thr Xaa
            35

(2) INFORMATION FOR SEQ ID NO: 127:

(i) SEQUENCE CHARACTERISTICS:
            (A) LENGTH: 36 amino acids
            (B) TYPE: amino acid
            (D) TOPOLOGY: linear (ii) MOLECULE TYPE: peptide (iii) HYPOTHETICAL: NO (vi) ORIGINAL SOURCE:
            (C) INDIVIDUAL ISOLATE: HCV (ix) FEATURE:
            (A) NAME/KEY: Xaa is absent
            (B) LOCATION: 1

(ix) FEATURE:
            (A) NAME/KEY: Xaa is absent
            (B) LOCATION: 36

(xi) SEQUENCE DESCRIPTION: SEQ ID NO: 127:

Xaa Gly His Thr Arg Val Thr Gly Gly Val Gln Gly His Val Thr Cys
1               5                   10                  15

Thr Leu Thr Ser Leu Phe Arg Pro Gly Ala Ser Gln Lys Ile Gln Leu
            20                  25                  30

Val Asn Thr Xaa
        35

(2) INFORMATION FOR SEQ ID NO: 128:

(i) SEQUENCE CHARACTERISTICS:
            (A) LENGTH: 36 amino acids
            (B) TYPE: amino acid
            (D) TOPOLOGY: linear (ii) MOLECULE TYPE: peptide (iii) HYPOTHETICAL: NO (vi) ORIGINAL SOURCE:
            (C) INDIVIDUAL ISOLATE: HCV (ix) FEATURE:
            (A) NAME/KEY: Xaa is absent
            (B) LOCATION: 1

(ix) FEATURE:
            (A) NAME/KEY: Xaa is absent
            (B) LOCATION: 36

(xi) SEQUENCE DESCRIPTION: SEQ ID NO: 128:

Xaa Gly His Thr His Val Thr Gly Gly Arg Val Ala Ser Ser Thr Gln
1               5                   10                  15

Ser Leu Val Ser Trp Leu Ser Gln Gly Pro Ser Gln Lys Ile Gln Leu
            20                  25                  30

Val Asn Thr Xaa
        35

(2) INFORMATION FOR SEQ ID NO: 129:

(i) SEQUENCE CHARACTERISTICS:
            (A) LENGTH: 36 amino acids
            (B) TYPE: amino acid
            (D) TOPOLOGY: linear (ii) MOLECULE TYPE: peptide (iii) HYPOTHETICAL: NO (vi) ORIGINAL SOURCE:
            (C) INDIVIDUAL ISOLATE: HCV (ix) FEATURE:
            (A) NAME/KEY: Xaa is absent
            (B) LOCATION: 1

(ix) FEATURE:
            (A) NAME/KEY: Xaa is absent
            (B) LOCATION: 36

(xi) SEQUENCE DESCRIPTION: SEQ ID NO: 129:

Xaa Gly Asp Thr His Val Thr Gly Gly Ala Gln Ala Lys Thr Thr Asn
1               5                  10                  15

Arg Leu Val Ser Met Phe Ala Ser Gly Pro Ser Gln Lys Ile Gln Leu
            20                  25                  30

Ile Asn Thr Xaa
            35

(2) INFORMATION FOR SEQ ID NO: 130:

(i) SEQUENCE CHARACTERISTICS:
            (A) LENGTH: 36 amino acids
            (B) TYPE: amino acid
            (D) TOPOLOGY: linear (ii) MOLECULE TYPE: peptide (iii) HYPOTHETICAL: NO (vi) ORIGINAL SOURCE:
            (C) INDIVIDUAL ISOLATE: HCV (ix) FEATURE:
            (A) NAME/KEY: Xaa is absent
            (B) LOCATION: 1

(ix) FEATURE:
            (A) NAME/KEY: Xaa is absent
            (B) LOCATION: 36

(xi) SEQUENCE DESCRIPTION: SEQ ID NO: 130:

Xaa Ala Glu Thr Tyr Thr Ser Gly Gly Asn Ala Gly His Thr Met Thr
1               5                  10                  15

Gly Ile Val Arg Phe Phe Ala Pro Gly Pro Lys Gln Asn Val His Leu
            20                  25                  30

Ile Asn Thr Xaa
            35

(2) INFORMATION FOR SEQ ID NO: 131:

(i) SEQUENCE CHARACTERISTICS:
            (A) LENGTH: 36 amino acids
            (B) TYPE: amino acid
            (D) TOPOLOGY: linear (ii) MOLECULE TYPE: peptide (iii) HYPOTHETICAL: NO (vi) ORIGINAL SOURCE:
            (C) INDIVIDUAL ISOLATE: HCV (ix) FEATURE:
            (A) NAME/KEY: Xaa is absent
            (B) LOCATION: 1

(ix) FEATURE:
            (A) NAME/KEY: Xaa is absent
            (B) LOCATION: 36

(xi) SEQUENCE DESCRIPTION: SEQ ID NO: 131:

```
Xaa Ala Glu Thr Ile Val Ser Gly Gly Gln Ala Ala Arg Ala Met Ser
1               5                   10                  15

Gly Leu Val Ser Leu Phe Thr Pro Gly Ala Lys Gln Asn Ile Gln Leu
            20                  25                  30

Ile Asn Thr Xaa
            35

(2) INFORMATION FOR SEQ ID NO: 132:

(i) SEQUENCE CHARACTERISTICS:
        (A) LENGTH: 36 amino acids
        (B) TYPE: amino acid
        (D) TOPOLOGY: linear (ii) MOLECULE TYPE: peptide (iii) HYPOTHETICAL: NO (vi) ORIGINAL SOURCE:
         (C) INDIVIDUAL ISOLATE: HCV (ix) FEATURE:
         (A) NAME/KEY: Xaa is absent
         (B) LOCATION: 1

(ix) FEATURE:
         (A) NAME/KEY: Xaa is absent
         (B) LOCATION: 36

(xi) SEQUENCE DESCRIPTION: SEQ ID NO: 132:

Xaa Ala Glu Thr Tyr Thr Thr Gly Gly Ser Thr Ala Arg Thr Thr Gln
1               5                   10                  15

Gly Leu Val Ser Leu Phe Ser Arg Gly Ala Lys Gln Asp Ile Gln Leu
            20                  25                  30

Ile Asn Thr Xaa
            35

(2) INFORMATION FOR SEQ ID NO: 133:

(i) SEQUENCE CHARACTERISTICS:
        (A) LENGTH: 22 amino acids
        (B) TYPE: amino acid
        (D) TOPOLOGY: linear (ii) MOLECULE TYPE: peptide (iii) HYPOTHETICAL: NO (vi) ORIGINAL SOURCE:
         (C) INDIVIDUAL ISOLATE: HCV (ix) FEATURE:
         (A) NAME/KEY: Xaa is absent
         (B) LOCATION: 1

(ix) FEATURE:
         (A) NAME/KEY: Xaa is absent
         (B) LOCATION: 22

(xi) SEQUENCE DESCRIPTION: SEQ ID NO: 133:

Xaa Met Ser Thr Ile Pro Lys Pro Gln Arg Lys Thr Lys Arg Asn Thr
1               5                   10                  15

Asn Arg Arg Pro Gln Xaa
            20

(2) INFORMATION FOR SEQ ID NO: 134:

(i) SEQUENCE CHARACTERISTICS:
        (A) LENGTH: 22 amino acids
```

```
            (B) TYPE: amino acid
            (D) TOPOLOGY: linear (ii) MOLECULE TYPE: peptide (iii) HYPOTHETICAL: NO (vi) ORIGINAL SOURCE:
            (C) INDIVIDUAL ISOLATE: HCV (ix) FEATURE:
            (A) NAME/KEY: Xaa is absent
            (B) LOCATION: 1

(ix) FEATURE:
            (A) NAME/KEY: Xaa is absent
            (B) LOCATION: 22

(xi) SEQUENCE DESCRIPTION: SEQ ID NO: 134:

Xaa Pro Gln Arg Lys Thr Lys Arg Asn Thr Asn Arg Arg Pro Gln Asp
1               5                  10                  15

Val Lys Phe Pro Gly Xaa
            20

(2) INFORMATION FOR SEQ ID NO: 135:

(i) SEQUENCE CHARACTERISTICS:
            (A) LENGTH: 22 amino acids
            (B) TYPE: amino acid
            (D) TOPOLOGY: linear (ii) MOLECULE TYPE: peptide (iii) HYPOTHETICAL: NO (vi) ORIGINAL SOURCE:
            (C) INDIVIDUAL ISOLATE: HCV (ix) FEATURE:
            (A) NAME/KEY: Xaa is absent
            (B) LOCATION: 1

(ix) FEATURE:
            (A) NAME/KEY: Xaa is absent
            (B) LOCATION: 22

(xi) SEQUENCE DESCRIPTION: SEQ ID NO: 135:

Xaa Arg Asn Thr Asn Arg Arg Pro Gln Asp Val Lys Phe Pro Gly Gly
1               5                  10                  15

Gly Gln Ile Val Gly Xaa
            20

(2) INFORMATION FOR SEQ ID NO: 136:

(i) SEQUENCE CHARACTERISTICS:
            (A) LENGTH: 32 amino acids
            (B) TYPE: amino acid
            (D) TOPOLOGY: linear (ii) MOLECULE TYPE: peptide (iii) HYPOTHETICAL: NO (vi) ORIGINAL SOURCE:
            (C) INDIVIDUAL ISOLATE: HCV (ix) FEATURE:
            (A) NAME/KEY: Xaa is absent
            (B) LOCATION: 1

(ix) FEATURE:
            (A) NAME/KEY: Xaa is absent
            (B) LOCATION: 32
```

(xi) SEQUENCE DESCRIPTION: SEQ ID NO: 136:

Xaa Met Ser Thr Ile Pro Gln Arg Lys Thr Lys Arg Asn Thr Asn Arg
1               5                   10                  15

Arg Pro Gln Asp Val Lys Phe Pro Gly Gly Gln Ile Val Gly Xaa
                20                  25                  30

(2) INFORMATION FOR SEQ ID NO: 137:

(i) SEQUENCE CHARACTERISTICS:
        (A) LENGTH: 22 amino acids
        (B) TYPE: amino acid
        (D) TOPOLOGY: linear (ii) MOLECULE TYPE: peptide (iii) HYPOTHETICAL: NO (vi) ORIGINAL SOURCE:
        (C) INDIVIDUAL ISOLATE: HCV (ix) FEATURE:
        (A) NAME/KEY: Xaa is absent
        (B) LOCATION: 1

(ix) FEATURE:
        (A) NAME/KEY: Xaa is absent
        (B) LOCATION: 22

(xi) SEQUENCE DESCRIPTION: SEQ ID NO: 137:

Xaa Val Gly Gly Val Tyr Leu Leu Pro Arg Arg Gly Pro Arg Leu Gly
1               5                   10                  15

Val Arg Ala Thr Arg Xaa
                20

(2) INFORMATION FOR SEQ ID NO: 138:

(i) SEQUENCE CHARACTERISTICS:
        (A) LENGTH: 22 amino acids
        (B) TYPE: amino acid
        (D) TOPOLOGY: linear (ii) MOLECULE TYPE: peptide (iii) HYPOTHETICAL: NO (vi) ORIGINAL SOURCE:
        (C) INDIVIDUAL ISOLATE: HCV (ix) FEATURE:
        (A) NAME/KEY: Xaa is absent
        (B) LOCATION: 1

(ix) FEATURE:
        (A) NAME/KEY: Xaa is absent
        (B) LOCATION: 22

(xi) SEQUENCE DESCRIPTION: SEQ ID NO: 138:

Xaa Leu Pro Arg Arg Gly Pro Arg Leu Gly Val Arg Ala Thr Arg Lys
1               5                   10                  15

Thr Ser Glu Arg Ser Xaa
                20

(2) INFORMATION FOR SEQ ID NO: 139:

(i) SEQUENCE CHARACTERISTICS:
        (A) LENGTH: 22 amino acids
        (B) TYPE: amino acid
        (D) TOPOLOGY: linear

```
        (ii) MOLECULE TYPE: peptide (iii) HYPOTHETICAL: NO (vi) ORIGINAL SOURCE:
              (C) INDIVIDUAL ISOLATE: HCV (ix) FEATURE:
              (A) NAME/KEY: Xaa is absent
              (B) LOCATION: 1

(ix) FEATURE:
              (A) NAME/KEY: Xaa is absent
              (B) LOCATION: 22

(xi) SEQUENCE DESCRIPTION: SEQ ID NO: 139:

Xaa Thr Arg Lys Thr Ser Glu Arg Ser Gln Pro Arg Gly Arg Arg Gln
1               5                   10                  15

Pro Ile Pro Lys Val Xaa
              20

(2) INFORMATION FOR SEQ ID NO: 140:

(i) SEQUENCE CHARACTERISTICS:
              (A) LENGTH: 22 amino acids
              (B) TYPE: amino acid
              (D) TOPOLOGY: linear (ii) MOLECULE TYPE: peptide (iii) HYPOTHETICAL: NO (vi) ORIGINAL SOURCE:
              (C) INDIVIDUAL ISOLATE: HCV (ix) FEATURE:
              (A) NAME/KEY: Xaa is absent
              (B) LOCATION: 1

(ix) FEATURE:
              (A) NAME/KEY: Xaa is absent
              (B) LOCATION: 22

(xi) SEQUENCE DESCRIPTION: SEQ ID NO: 140:

Xaa Arg Ser Gln Pro Arg Gly Arg Arg Gln Pro Ile Pro Lys Val Arg
1               5                   10                  15

Arg Pro Glu Gly Arg Xaa
              20

(2) INFORMATION FOR SEQ ID NO: 141:

(i) SEQUENCE CHARACTERISTICS:
              (A) LENGTH: 42 amino acids
              (B) TYPE: amino acid
              (D) TOPOLOGY: linear (ii) MOLECULE TYPE: peptide (iii) HYPOTHETICAL: NO (vi) ORIGINAL SOURCE:
              (C) INDIVIDUAL ISOLATE: HCV (ix) FEATURE:
              (A) NAME/KEY: Xaa is absent
              (B) LOCATION: 1

(ix) FEATURE:
              (A) NAME/KEY: Xaa is absent
              (B) LOCATION: 42

(xi) SEQUENCE DESCRIPTION: SEQ ID NO: 141:
```

```
Xaa Gly Gly Val Tyr Leu Leu Pro Arg Arg Gly Pro Arg Leu Gly Val
1               5                   10                  15

Arg Arg Ala Thr Arg Lys Thr Ser Glu Arg Ser Gln Pro Arg Gly Arg
            20                  25                  30

Arg Gln Pro Ile Pro Lys Val Arg Arg Xaa
            35                  40
```

(2) INFORMATION FOR SEQ ID NO: 142:

(i) SEQUENCE CHARACTERISTICS:
        (A) LENGTH: 22 amino acids
        (B) TYPE: amino acid
        (D) TOPOLOGY: linear (ii) MOLECULE TYPE: peptide (iii) HYPOTHETICAL: NO (vi) ORIGINAL SOURCE:
        (C) INDIVIDUAL ISOLATE: HCV (ix) FEATURE:
        (A) NAME/KEY: Xaa is absent
        (B) LOCATION: 1

(ix) FEATURE:
        (A) NAME/KEY: Xaa is absent
        (B) LOCATION: 22

(xi) SEQUENCE DESCRIPTION: SEQ ID NO: 142:

```
Xaa Ser Gln His Leu Pro Tyr Ile Glu Gln Gly Met Met Leu Ala Glu
1               5                   10                  15

Gln Phe Lys Gln Lys Xaa
            20
```

(2) INFORMATION FOR SEQ ID NO: 143:

(i) SEQUENCE CHARACTERISTICS:
        (A) LENGTH: 22 amino acids
        (B) TYPE: amino acid
        (D) TOPOLOGY: linear (ii) MOLECULE TYPE: peptide (iii) HYPOTHETICAL: NO (vi) ORIGINAL SOURCE:
        (C) INDIVIDUAL ISOLATE: HCV (ix) FEATURE:
        (A) NAME/KEY: Xaa is absent
        (B) LOCATION: 1

(ix) FEATURE:
        (A) NAME/KEY: Xaa is absent
        (B) LOCATION: 22

(xi) SEQUENCE DESCRIPTION: SEQ ID NO: 143:

```
Xaa Leu Ala Glu Gln Phe Lys Gln Lys Ala Leu Gly Leu Leu Gln Thr
1               5                   10                  15

Ala Ser Arg Gln Ala Xaa
            20
```

(2) INFORMATION FOR SEQ ID NO: 144:

(i) SEQUENCE CHARACTERISTICS:
        (A) LENGTH: 33 amino acids
        (B) TYPE: amino acid
        (D) TOPOLOGY: linear (ii) MOLECULE TYPE: peptide (iii) HYPOTHETICAL: NO (vi) ORIGINAL SOURCE:
            (C) INDIVIDUAL ISOLATE: HCV (ix) FEATURE:
            (A) NAME/KEY: Xaa is absent
            (B) LOCATION: 1

(ix) FEATURE:
            (A) NAME/KEY: Xaa is absent
            (B) LOCATION: 33

(xi) SEQUENCE DESCRIPTION: SEQ ID NO: 144:

Xaa Ser Gln His Leu Pro Tyr Ile Glu Gln Glu Met Leu Ala Glu Glu
1               5                  10                  15

Phe Lys Gln Lys Ala Leu Gly Leu Leu Gln Thr Ala Ser Arg Gln Ala
                20                  25                  30

Xaa (2) INFORMATION FOR SEQ ID NO: 145:

(i) SEQUENCE CHARACTERISTICS:
            (A) LENGTH: 22 amino acids
            (B) TYPE: amino acid
            (D) TOPOLOGY: linear (ii) MOLECULE TYPE: peptide (iii) HYPOTHETICAL: NO (vi) ORIGINAL SOURCE:
            (C) INDIVIDUAL ISOLATE: HCV (ix) FEATURE:
            (A) NAME/KEY: Xaa is absent
            (B) LOCATION: 1

(ix) FEATURE:
            (A) NAME/KEY: Xaa is absent
            (B) LOCATION: 22

(xi) SEQUENCE DESCRIPTION: SEQ ID NO: 145:

Xaa Glu Asp Glu Arg Glu Ile Ser Val Pro Ala Glu Ile Leu Arg Lys
1               5                  10                  15

Ser Arg Arg Phe Ala Xaa
                20

(2) INFORMATION FOR SEQ ID NO: 146:

(i) SEQUENCE CHARACTERISTICS:
            (A) LENGTH: 22 amino acids
            (B) TYPE: amino acid
            (D) TOPOLOGY: linear (ii) MOLECULE TYPE: peptide (iii) HYPOTHETICAL: NO (vi) ORIGINAL SOURCE:
            (C) INDIVIDUAL ISOLATE: HCV (ix) FEATURE:
            (A) NAME/KEY: Xaa is absent
            (B) LOCATION: 1

(ix) FEATURE:
            (A) NAME/KEY: Xaa is absent
            (B) LOCATION: 22

(xi) SEQUENCE DESCRIPTION: SEQ ID NO: 146:

Xaa Leu Arg Lys Ser Arg Arg Phe Ala Gln Ala Leu Pro Val Trp Ala
 1               5                  10                  15

Arg Pro Asp Tyr Asn Xaa
            20

(2) INFORMATION FOR SEQ ID NO: 147:

(i) SEQUENCE CHARACTERISTICS:
        (A) LENGTH: 39 amino acids
        (B) TYPE: amino acid
        (D) TOPOLOGY: linear (ii) MOLECULE TYPE: peptide (iii) HYPOTHETICAL: NO (vi) ORIGINAL SOURCE:
        (C) INDIVIDUAL ISOLATE: HCV type 1

(ix) FEATURE:
        (A) NAME/KEY: Xaa is absent
        (B) LOCATION: 1

(ix) FEATURE:
        (A) NAME/KEY: Xaa is absent
        (B) LOCATION: 39

(xi) SEQUENCE DESCRIPTION: SEQ ID NO: 147:

Xaa Glu Asp Glu Arg Glu Ile Ser Val Pro Ala Glu Ile Leu Arg Lys
 1               5                  10                  15

Ser Arg Lys Ser Arg Arg Phe Ala Gln Ala Leu Pro Val Trp Ala Arg
            20                  25                  30

Pro Asp Tyr Asp Tyr Asn Xaa
            35

(2) INFORMATION FOR SEQ ID NO: 148:

(i) SEQUENCE CHARACTERISTICS:
        (A) LENGTH: 22 amino acids
        (B) TYPE: amino acid
        (D) TOPOLOGY: linear (ii) MOLECULE TYPE: peptide (iii) HYPOTHETICAL: NO (vi) ORIGINAL SOURCE:
        (C) INDIVIDUAL ISOLATE: HCV (ix) FEATURE:
        (A) NAME/KEY: Xaa is absent
        (B) LOCATION: 1

(ix) FEATURE:
        (A) NAME/KEY: Xaa is absent
        (B) LOCATION: 22

(xi) SEQUENCE DESCRIPTION: SEQ ID NO: 148:

Xaa Leu Ser Gly Lys Pro Ala Ile Ile Pro Asp Arg Glu Val Leu Tyr
 1               5                  10                  15

Arg Glu Phe Asp Glu Xaa
            20

(2) INFORMATION FOR SEQ ID NO: 149:

(i) SEQUENCE CHARACTERISTICS:
        (A) LENGTH: 22 amino acids
        (B) TYPE: amino acid

```
        (D) TOPOLOGY: linear (ii) MOLECULE TYPE: peptide (iii) HYPOTHETICAL: NO (vi) ORIGINAL SOURCE:
         (C) INDIVIDUAL ISOLATE: HCV type 2

(ix) FEATURE:
         (A) NAME/KEY: Xaa is absent
         (B) LOCATION: 1

(ix) FEATURE:
         (A) NAME/KEY: Xaa is absent
         (B) LOCATION: 22

(xi) SEQUENCE DESCRIPTION: SEQ ID NO: 149:

Xaa Val Asn Gln Arg Ala Val Val Ala Pro Asp Lys Glu Val Leu Tyr
1               5                   10                  15

Glu Ala Phe Asp Glu Xaa
            20

(2) INFORMATION FOR SEQ ID NO: 150:

(i) SEQUENCE CHARACTERISTICS:
        (A) LENGTH: 22 amino acids
        (B) TYPE: amino acid
        (D) TOPOLOGY: linear (ii) MOLECULE TYPE: peptide (iii) HYPOTHETICAL: NO (vi) ORIGINAL SOURCE:
         (C) INDIVIDUAL ISOLATE: HCV (ix) FEATURE:
         (A) NAME/KEY: Xaa is absent
         (B) LOCATION: 1

(ix) FEATURE:
         (A) NAME/KEY: Xaa is absent
         (B) LOCATION: 22

(xi) SEQUENCE DESCRIPTION: SEQ ID NO: 150:

Xaa Ser Gln His Leu Pro Tyr Ile Glu Gln Gly Met Met Leu Ala Glu
1               5                   10                  15

Gln Phe Lys Gln Lys Xaa
            20

(2) INFORMATION FOR SEQ ID NO: 151:

(i) SEQUENCE CHARACTERISTICS:
        (A) LENGTH: 22 amino acids
        (B) TYPE: amino acid
        (D) TOPOLOGY: linear (ii) MOLECULE TYPE: peptide (iii) HYPOTHETICAL: NO (vi) ORIGINAL SOURCE:
         (C) INDIVIDUAL ISOLATE: HCV type 2

(ix) FEATURE:
         (A) NAME/KEY: Xaa is absent
         (B) LOCATION: 1

(ix) FEATURE:
         (A) NAME/KEY: Xaa is absent
         (B) LOCATION: 22
```

(xi) SEQUENCE DESCRIPTION: SEQ ID NO: 151:

Xaa Ala Ser Arg Ala Ala Leu Ile Glu Glu Gly Gln Arg Ile Ala Glu
1               5                   10                  15

Met Leu Lys Ser Lys Xaa
            20

(2) INFORMATION FOR SEQ ID NO: 152:

(i) SEQUENCE CHARACTERISTICS:
        (A) LENGTH: 22 amino acids
        (B) TYPE: amino acid
        (D) TOPOLOGY: linear (ii) MOLECULE TYPE: peptide (iii) HYPOTHETICAL: NO (vi) ORIGINAL SOURCE:
        (C) INDIVIDUAL ISOLATE: HCV (ix) FEATURE:
        (A) NAME/KEY: Xaa is absent
        (B) LOCATION: 1

(ix) FEATURE:
        (A) NAME/KEY: Xaa is absent
        (B) LOCATION: 22

(xi) SEQUENCE DESCRIPTION: SEQ ID NO: 152:

Xaa Leu Ala Glu Gln Phe Lys Gln Lys Ala Leu Gly Leu Leu Gln Thr
1               5                   10                  15

Ala Ser Arg Gln Ala Xaa
            20

(2) INFORMATION FOR SEQ ID NO: 153:

(i) SEQUENCE CHARACTERISTICS:
        (A) LENGTH: 22 amino acids
        (B) TYPE: amino acid
        (D) TOPOLOGY: linear (ii) MOLECULE TYPE: peptide (iii) HYPOTHETICAL: NO (vi) ORIGINAL SOURCE:
        (C) INDIVIDUAL ISOLATE: HCV type 2

(ix) FEATURE:
        (A) NAME/KEY: Xaa is absent
        (B) LOCATION: 1

(ix) FEATURE:
        (A) NAME/KEY: Xaa is absent
        (B) LOCATION: 22

(xi) SEQUENCE DESCRIPTION: SEQ ID NO: 153:

Xaa Ile Ala Glu Met Leu Lys Ser Lys Ile Gln Gly Leu Leu Gln Gln
1               5                   10                  15

Ala Ser Lys Gln Ala Xaa
            20

(2) INFORMATION FOR SEQ ID NO: 154:

(i) SEQUENCE CHARACTERISTICS:
        (A) LENGTH: 25 amino acids
        (B) TYPE: amino acid
        (D) TOPOLOGY: linear (ii) MOLECULE TYPE: peptide (iii) HYPOTHETICAL: YES (ix) FEATURE:
             (A) NAME/KEY: Xaa is absent
             (B) LOCATION: 1

(ix) FEATURE:
             (A) NAME/KEY: Xaa is absent
             (B) LOCATION: 25

(xi) SEQUENCE DESCRIPTION: SEQ ID NO: 154:

Xaa Asn Asn Thr Arg Lys Ser Ile His Ile Gly Pro Gly Arg Ala Phe
1               5                  10                  15

Tyr Thr Thr Gly Glu Ile Ile Gly Xaa
            20                  25

(2) INFORMATION FOR SEQ ID NO: 155:

(i) SEQUENCE CHARACTERISTICS:
            (A) LENGTH: 25 amino acids
            (B) TYPE: amino acid
            (D) TOPOLOGY: linear (ii) MOLECULE TYPE: peptide (iii) HYPOTHETICAL: NO (vi) ORIGINAL SOURCE:
             (C) INDIVIDUAL ISOLATE: HIV-1 SF2

(ix) FEATURE:
             (A) NAME/KEY: Xaa is absent
             (B) LOCATION: 1

(ix) FEATURE:
             (A) NAME/KEY: Xaa is absent
             (B) LOCATION: 25

(xi) SEQUENCE DESCRIPTION: SEQ ID NO: 155:

Xaa Asn Asn Thr Arg Lys Ser Ile Tyr Ile Gly Pro Gly Arg Ala Phe
1               5                  10                  15

His Thr Thr Gly Arg Ile Ile Gly Xaa
            20                  25

(2) INFORMATION FOR SEQ ID NO: 156:

(i) SEQUENCE CHARACTERISTICS:
            (A) LENGTH: 25 amino acids
            (B) TYPE: amino acid
            (D) TOPOLOGY: linear (ii) MOLECULE TYPE: peptide (iii) HYPOTHETICAL: NO (vi) ORIGINAL SOURCE:
             (C) INDIVIDUAL ISOLATE: HIV-1 SC (ix) FEATURE:
             (A) NAME/KEY: Xaa is absent
             (B) LOCATION: 1

(ix) FEATURE:
             (A) NAME/KEY: Xaa is absent
             (B) LOCATION: 25

(xi) SEQUENCE DESCRIPTION: SEQ ID NO: 156:

Xaa Asn Asn Thr Thr Arg Ser Ile His Ile Gly Pro Gly Arg Ala Phe
1               5                  10                  15

Tyr Ala Thr Gly Asp Ile Ile Gly Xaa 20                  25

(2) INFORMATION FOR SEQ ID NO: 157:

(i) SEQUENCE CHARACTERISTICS:
        (A) LENGTH: 25 amino acids
        (B) TYPE: amino acid
        (D) TOPOLOGY: linear (ii) MOLECULE TYPE: peptide (iii) HYPOTHETICAL: NO (vi) ORIGINAL SOURCE:
        (C) INDIVIDUAL ISOLATE: HIV-1 MN (ix) FEATURE:
        (A) NAME/KEY: Xaa is absent
        (B) LOCATION: 1

(ix) FEATURE:
        (A) NAME/KEY: Xaa is absent
        (B) LOCATION: 25

(xi) SEQUENCE DESCRIPTION: SEQ ID NO: 157:

Xaa Tyr Asn Lys Arg Lys Arg Ile His Ile Gly Pro Gly Arg Ala Phe
1               5                   10                  15

Tyr Thr Thr Lys Asn Ile Ile Gly Xaa
            20                  25

(2) INFORMATION FOR SEQ ID NO: 158:

(i) SEQUENCE CHARACTERISTICS:
        (A) LENGTH: 25 amino acids
        (B) TYPE: amino acid
        (D) TOPOLOGY: linear (ii) MOLECULE TYPE: peptide (iii) HYPOTHETICAL: NO (vi) ORIGINAL SOURCE:
        (C) INDIVIDUAL ISOLATE: HIV-1 RF (ix) FEATURE:
        (A) NAME/KEY: Xaa is absent
        (B) LOCATION: 1

(ix) FEATURE:
        (A) NAME/KEY: Xaa is absent
        (B) LOCATION: 25

(xi) SEQUENCE DESCRIPTION: SEQ ID NO: 158:

Xaa Asn Asn Thr Arg Lys Ser Ile Thr Lys Gly Pro Gly Arg Val Ile
1               5                   10                  15

Tyr Ala Thr Gly Gln Ile Ile Gly Xaa
            20                  25

(2) INFORMATION FOR SEQ ID NO: 159:

(i) SEQUENCE CHARACTERISTICS:
        (A) LENGTH: 24 amino acids
        (B) TYPE: amino acid
        (D) TOPOLOGY: linear (ii) MOLECULE TYPE: peptide (iii) HYPOTHETICAL: NO (vi) ORIGINAL SOURCE:
        (C) INDIVIDUAL ISOLATE: HIV-1 mal

```
    (ix) FEATURE:
        (A) NAME/KEY: Xaa is absent
        (B) LOCATION: 1

(ix) FEATURE:
        (A) NAME/KEY: Xaa is absent
        (B) LOCATION: 24

(xi) SEQUENCE DESCRIPTION: SEQ ID NO: 159:

Xaa Asn Asn Thr Arg Arg Gly Ile His Phe Gly Pro Gly Gln Ala Leu
1               5                   10                  15

Tyr Thr Thr Gly Ile Val Gly Xaa
            20

(2) INFORMATION FOR SEQ ID NO: 160:

(i) SEQUENCE CHARACTERISTICS:
        (A) LENGTH: 24 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 160:

Asn Asn Thr Arg Lys Ser Ile Arg Ile Gln Arg Gly Pro Gly Arg Ala
1               5                   10                  15

Phe Val Thr Ile Gly Lys Ile Gly
            20

(2) INFORMATION FOR SEQ ID NO: 161:

(i) SEQUENCE CHARACTERISTICS:
        (A) LENGTH: 24 amino acids
        (B) TYPE: amino acid
        (D) TOPOLOGY: linear (ii) MOLECULE TYPE: peptide (iii) HYPOTHETICAL: NO (vi) ORIGINAL SOURCE:
        (C) INDIVIDUAL ISOLATE: HIV-1 ELI (ix) FEATURE:
        (A) NAME/KEY: Xaa is absent
        (B) LOCATION: 1

(ix) FEATURE:
        (A) NAME/KEY: Xaa is absent
        (B) LOCATION: 24

(xi) SEQUENCE DESCRIPTION: SEQ ID NO: 161:

Xaa Gln Asn Thr Arg Gln Arg Thr Pro Ile Gly Leu Gly Gln Ser Leu
1               5                   10                  15

Tyr Thr Thr Arg Ser Arg Ser Xaa
            20

(2) INFORMATION FOR SEQ ID NO: 162:

(i) SEQUENCE CHARACTERISTICS:
        (A) LENGTH: 23 amino acids
        (B) TYPE: amino acid
        (D) TOPOLOGY: linear (ii) MOLECULE TYPE: peptide (iii) HYPOTHETICAL: NO (vi) ORIGINAL SOURCE:
```

(C) INDIVIDUAL ISOLATE: Ant70

(ix) FEATURE:
                (A) NAME/KEY: Xaa is absent
                (B) LOCATION: 1

(ix) FEATURE:
                (A) NAME/KEY: Xaa is absent
                (B) LOCATION: 23

(xi) SEQUENCE DESCRIPTION: SEQ ID NO: 162:

Xaa Gln Ile Asp Ile Gln Glu Met Arg Ile Gly Pro Met Ala Trp Tyr
1               5                   10                  15

Ser Met Gly Ile Gly Gly Xaa
            20

(2) INFORMATION FOR SEQ ID NO: 163:

(i) SEQUENCE CHARACTERISTICS:
                (A) LENGTH: 25 amino acids
                (B) TYPE: amino acid
                (D) TOPOLOGY: linear (ii) MOLECULE TYPE: peptide (iii) HYPOTHETICAL: YES (ix) FEATURE:
                (A) NAME/KEY: Xaa is absent
                (B) LOCATION: 1

(ix) FEATURE:
                (A) NAME/KEY: Xaa is absent
                (B) LOCATION: 25

(xi) SEQUENCE DESCRIPTION: SEQ ID NO: 163:

Xaa Asn Asn Thr Arg Arg Gly Ile His Met Gly Trp Gly Arg Thr Phe
1               5                   10                  15

Tyr Ala Thr Gly Glu Ile Ile Gly Xaa
            20                  25

(2) INFORMATION FOR SEQ ID NO: 164:

(i) SEQUENCE CHARACTERISTICS:
                (A) LENGTH: 24 amino acids
                (B) TYPE: amino acid
                (D) TOPOLOGY: linear (ii) MOLECULE TYPE: peptide (iii) HYPOTHETICAL: NO (vi) ORIGINAL SOURCE:
                (C) INDIVIDUAL ISOLATE: HIV-2

(ix) FEATURE:
                (A) NAME/KEY: Xaa is absent
                (B) LOCATION: 1

(ix) FEATURE:
                (A) NAME/KEY: Xaa is absent
                (B) LOCATION: 24

(xi) SEQUENCE DESCRIPTION: SEQ ID NO: 164:

Xaa Asn Lys Thr Val Val Pro Ile Thr Leu Met Ser Gly Leu Val Phe
1               5                   10                  15

His Ser Gln Pro Ile Asn Lys Xaa
            20

(2) INFORMATION FOR SEQ ID NO: 165:

(i) SEQUENCE CHARACTERISTICS:
        (A) LENGTH: 24 amino acids
        (B) TYPE: amino acid
        (D) TOPOLOGY: linear (ii) MOLECULE TYPE: peptide (iii) HYPOTHETICAL: NO (vi) ORIGINAL SOURCE:
        (C) INDIVIDUAL ISOLATE: HIV-2

(ix) FEATURE:
        (A) NAME/KEY: Xaa is absent
        (B) LOCATION: 1

(ix) FEATURE:
        (A) NAME/KEY: Xaa is absent
        (B) LOCATION: 24

(xi) SEQUENCE DESCRIPTION: SEQ ID NO: 165:

Xaa Asn Lys Thr Val Leu Pro Val Thr Ile Met Ser Gly Leu Val Phe
1               5                   10                  15

His Ser Gln Pro Ile Asn Asp Xaa
            20

(2) INFORMATION FOR SEQ ID NO: 166:

(i) SEQUENCE CHARACTERISTICS:
        (A) LENGTH: 24 amino acids
        (B) TYPE: amino acid
        (D) TOPOLOGY: linear (ii) MOLECULE TYPE: peptide (iii) HYPOTHETICAL: NO (vi) ORIGINAL SOURCE:
        (C) INDIVIDUAL ISOLATE: HTLV (ix) FEATURE:
        (A) NAME/KEY: Xaa is Bio Gly Gly
        (B) LOCATION: 1

(ix) FEATURE:
        (A) NAME/KEY: Xaa is absent
        (B) LOCATION: 24

(xi) SEQUENCE DESCRIPTION: SEQ ID NO: 166:

Xaa Val Leu Tyr Ser Pro Asn Val Ser Val Pro Ser Ser Ser Ser Thr
1               5                   10                  15

Leu Leu Tyr Pro Ser Leu Ala Xaa
            20

(2) INFORMATION FOR SEQ ID NO: 167:

(i) SEQUENCE CHARACTERISTICS:
        (A) LENGTH: 23 amino acids
        (B) TYPE: amino acid
        (D) TOPOLOGY: linear (ii) MOLECULE TYPE: peptide (iii) HYPOTHETICAL: NO (vi) ORIGINAL SOURCE:
        (C) INDIVIDUAL ISOLATE: HTLV (ix) FEATURE:
        (A) NAME/KEY: Xaa is Bio Gly Gly
        (B) LOCATION: 1

```
    (ix) FEATURE:
         (A) NAME/KEY: Xaa is absent
         (B) LOCATION: 23

(xi) SEQUENCE DESCRIPTION: SEQ ID NO: 167:

Xaa Tyr Thr Cys Ile Val Cys Ile Asp Arg Ala Ser Leu Ser Thr Trp
1               5                   10                  15

His Val Leu Tyr Ser Pro Xaa
            20

(2) INFORMATION FOR SEQ ID NO: 168:

(i) SEQUENCE CHARACTERISTICS:
         (A) LENGTH: 24 amino acids
         (B) TYPE: amino acid
         (D) TOPOLOGY: linear (ii) MOLECULE TYPE: peptide (iii) HYPOTHETICAL: NO (vi) ORIGINAL SOURCE:
         (C) INDIVIDUAL ISOLATE: HTLV (ix) FEATURE:
         (A) NAME/KEY: Xaa is Bio Gly Gly
         (B) LOCATION: 1

(ix) FEATURE:
         (A) NAME/KEY: Xaa is absent
         (B) LOCATION: 24

(xi) SEQUENCE DESCRIPTION: SEQ ID NO: 168:

Xaa Asn Ser Leu Ile Leu Pro Pro Phe Ser Leu Ser Pro Val Pro Thr
1               5                   10                  15

Leu Gly Ser Arg Ser Arg Arg Xaa
            20

(2) INFORMATION FOR SEQ ID NO: 169:

(i) SEQUENCE CHARACTERISTICS:
         (A) LENGTH: 38 amino acids
         (B) TYPE: amino acid
         (D) TOPOLOGY: linear (ii) MOLECULE TYPE: peptide (iii) HYPOTHETICAL: NO (vi) ORIGINAL SOURCE:
         (C) INDIVIDUAL ISOLATE: HTLV (ix) FEATURE:
         (A) NAME/KEY: Xaa is Bio Gly Gly
         (B) LOCATION: 1

(ix) FEATURE:
         (A) NAME/KEY: Xaa is absent
         (B) LOCATION: 38

(xi) SEQUENCE DESCRIPTION: SEQ ID NO: 169:

Xaa Asp Ala Pro Gly Tyr Asp Pro Ile Trp Phe Leu Asn Thr Glu Pro
1               5                   10                  15

Ser Gln Leu Pro Pro Thr Ala Pro Pro Leu Leu Pro His Ser Asn Leu
            20                  25                  30

Asp His Ile Leu Glu Xaa
            35

(2) INFORMATION FOR SEQ ID NO: 170:
```

(i) SEQUENCE CHARACTERISTICS:
            (A) LENGTH: 33 amino acids
            (B) TYPE: amino acid
            (D) TOPOLOGY: linear (ii) MOLECULE TYPE: peptide (iii) HYPOTHETICAL: NO (vi) ORIGINAL SOURCE:
            (C) INDIVIDUAL ISOLATE: HTLV (ix) FEATURE:
            (A) NAME/KEY: Xaa is Bio Gly Gly
            (B) LOCATION: 1

(ix) FEATURE:
            (A) NAME/KEY: Xaa is absent
            (B) LOCATION: 33

(xi) SEQUENCE DESCRIPTION: SEQ ID NO: 170:

Xaa Gln Tyr Ala Ala Gln Asn Arg Arg Gly Leu Asp Leu Leu Phe Trp
1               5                  10                  15

Glu Gln Gly Gly Leu Cys Lys Ala Leu Gln Glu Gln Cys Arg Phe Pro
            20                  25                  30

Xaa (2) INFORMATION FOR SEQ ID NO: 171:

(i) SEQUENCE CHARACTERISTICS:
            (A) LENGTH: 33 amino acids
            (B) TYPE: amino acid
            (D) TOPOLOGY: linear (ii) MOLECULE TYPE: peptide (iii) HYPOTHETICAL: NO (vi) ORIGINAL SOURCE:
            (C) INDIVIDUAL ISOLATE: HTLV (ix) FEATURE:
            (A) NAME/KEY: Xaa is Bio Gly Gly
            (B) LOCATION: 1

(ix) FEATURE:
            (A) NAME/KEY: Xaa is absent
            (B) LOCATION: 33

(xi) SEQUENCE DESCRIPTION: SEQ ID NO: 171:

Xaa Pro Pro Pro Pro Ser Ser Pro Thr His Asp Pro Asp Ser Asp
1               5                  10                  15

Pro Gln Ile Pro Pro Pro Tyr Val Glu Pro Thr Ala Pro Gln Val Leu
            20                  25                  30

Xaa (2) INFORMATION FOR SEQ ID NO: 172:

(i) SEQUENCE CHARACTERISTICS:
            (A) LENGTH: 20 amino acids
            (B) TYPE: amino acid
            (D) TOPOLOGY: linear (ii) MOLECULE TYPE: peptide (iii) HYPOTHETICAL: NO (vi) ORIGINAL SOURCE:
            (C) INDIVIDUAL ISOLATE: HTLV

```
    (ix) FEATURE:
        (A) NAME/KEY: Xaa is Bio Gly Gly
        (B) LOCATION: 1

(ix) FEATURE:
        (A) NAME/KEY: Xaa is absent
        (B) LOCATION: 20

(xi) SEQUENCE DESCRIPTION: SEQ ID NO: 172:

Xaa Lys Lys Pro Asn Arg Gln Gly Leu Gly Tyr Tyr Ser Pro Ser Tyr
1               5                  10                  15

Asn Asp Pro Xaa
            20

(2) INFORMATION FOR SEQ ID NO: 173:

(i) SEQUENCE CHARACTERISTICS:
        (A) LENGTH: 38 amino acids
        (B) TYPE: amino acid
        (D) TOPOLOGY: linear (ii) MOLECULE TYPE: peptide (iii) HYPOTHETICAL: NO (vi) ORIGINAL SOURCE:
        (C) INDIVIDUAL ISOLATE: HTLV (ix) FEATURE:
        (A) NAME/KEY: Xaa is Bio Gly Gly
        (B) LOCATION: 1

(ix) FEATURE:
        (A) NAME/KEY: Xaa is absent
        (B) LOCATION: 38

(xi) SEQUENCE DESCRIPTION: SEQ ID NO: 173:

Xaa Asp Ala Pro Gly Tyr Asp Pro Leu Trp Phe Ile Thr Ser Glu Pro
1               5                  10                  15

Thr Gln Pro Pro Pro Thr Ser Pro Pro Leu Val His Asp Ser Asp Leu
            20                  25                  30

Glu His Val Leu Thr Xaa
            35

(2) INFORMATION FOR SEQ ID NO: 174:

(i) SEQUENCE CHARACTERISTICS:
        (A) LENGTH: 40 amino acids
        (B) TYPE: amino acid
        (D) TOPOLOGY: linear (ii) MOLECULE TYPE: peptide (iii) HYPOTHETICAL: NO (vi) ORIGINAL SOURCE:
        (C) INDIVIDUAL ISOLATE: HTLV (ix) FEATURE:
        (A) NAME/KEY: Xaa is Bio Gly Gly
        (B) LOCATION: 1

(ix) FEATURE:
        (A) NAME/KEY: Xaa is absent
        (B) LOCATION: 40

(xi) SEQUENCE DESCRIPTION: SEQ ID NO: 174:

Xaa Tyr Ser Cys Met Val Cys Val Asp Arg Ser Ser Leu Ser Ser Trp
1               5                  10                  15

His Val Leu Tyr Thr Pro Asn Ile Ser Ile Pro Gln Gln Thr Ser Ser
```

```
                20                  25                  30
Arg Thr Ile Leu Phe Pro Ser Xaa
            35                  40
```

(2) INFORMATION FOR SEQ ID NO: 175:

(i) SEQUENCE CHARACTERISTICS:
        (A) LENGTH: 32 amino acids
        (B) TYPE: amino acid
        (D) TOPOLOGY: linear (ii) MOLECULE TYPE: peptide (iii) HYPOTHETICAL: NO (vi) ORIGINAL SOURCE:
        (C) INDIVIDUAL ISOLATE: HTLV (ix) FEATURE:
        (A) NAME/KEY: Xaa is Bio Gly Gly
        (B) LOCATION: 1

(ix) FEATURE:
        (A) NAME/KEY: Xaa is absent
        (B) LOCATION: 32

(xi) SEQUENCE DESCRIPTION: SEQ ID NO: 175:

```
Xaa Pro Thr Thr Thr Pro Pro Pro Pro Pro Pro Ser Pro Glu Ala
1               5                   10                  15
His Val Pro Pro Pro Tyr Val Glu Pro Thr Thr Thr Gln Cys Phe Xaa
            20                  25                  30
```

(2) INFORMATION FOR SEQ ID NO: 176:

(i) SEQUENCE CHARACTERISTICS:
        (A) LENGTH: 12 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Xaa is Bio Gly Gly Gly
        (B) LOCATION: 1

(ix) FEATURE:
        (A) NAME/KEY: Xaa is absent
        (B) LOCATION: 12

(ix) FEATURE:
        (A) NAME/KEY: Disulfide-bond
        (B) LOCATION: 4..10

(xi) SEQUENCE DESCRIPTION: SEQ ID NO: 176:

```
Xaa Ile Trp Gly Cys Ser Gly Lys Leu Ile Cys Xaa
1               5                   10
```

(2) INFORMATION FOR SEQ ID NO: 177:

(i) SEQUENCE CHARACTERISTICS:
        (A) LENGTH: 12 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Xaa is absent
        (B) LOCATION: 1

```
    (ix) FEATURE:
         (A) NAME/KEY: Xaa is Gly Gly Lys(Bio)
         (B) LOCATION: 12

(ix) FEATURE:
         (A) NAME/KEY: Disulfide-bond
         (B) LOCATION: 4..10

(xi) SEQUENCE DESCRIPTION: SEQ ID NO: 177:

Xaa Ile Trp Gly Cys Ser Gly Lys Leu Ile Cys Xaa
1               5                   10

(2) INFORMATION FOR SEQ ID NO: 178:

(i) SEQUENCE CHARACTERISTICS:
         (A) LENGTH: 9 amino acids
         (B) TYPE: amino acid
         (C) STRANDEDNESS: single
         (D) TOPOLOGY: linear (ii) MOLECULE TYPE: peptide (xi) SEQUENCE DESCRIPTION: SEQ ID NO: 178:

Met Ser Thr Ile Pro Lys Pro Gln Arg
1               5

(2) INFORMATION FOR SEQ ID NO: 179:

(i) SEQUENCE CHARACTERISTICS:
         (A) LENGTH: 9 amino acids
         (B) TYPE: amino acid
         (C) STRANDEDNESS: single
         (D) TOPOLOGY: linear (ii) MOLECULE TYPE: peptide (xi) SEQUENCE DESCRIPTION: SEQ ID NO: 179:

Ser Thr Ile Pro Lys Pro Gln Arg Lys
1               5

(2) INFORMATION FOR SEQ ID NO: 180:

(i) SEQUENCE CHARACTERISTICS:
         (A) LENGTH: 9 amino acids
         (B) TYPE: amino acid
         (C) STRANDEDNESS: single
         (D) TOPOLOGY: linear (ii) MOLECULE TYPE: peptide (xi) SEQUENCE DESCRIPTION: SEQ ID NO: 180:

Thr Ile Pro Lys Pro Gln Arg Lys Thr
1               5

(2) INFORMATION FOR SEQ ID NO: 181:

(i) SEQUENCE CHARACTERISTICS:
         (A) LENGTH: 9 amino acids
         (B) TYPE: amino acid
         (C) STRANDEDNESS: single
         (D) TOPOLOGY: linear (ii) MOLECULE TYPE: peptide (xi) SEQUENCE DESCRIPTION: SEQ ID NO: 181:

Ile Pro Lys Pro Gln Arg Lys Thr Lys
1               5

(2) INFORMATION FOR SEQ ID NO: 182:
```

(i) SEQUENCE CHARACTERISTICS:
    (A) LENGTH: 9 amino acids
    (B) TYPE: amino acid
    (C) STRANDEDNESS: single
    (D) TOPOLOGY: linear (ii) MOLECULE TYPE: peptide (xi) SEQUENCE DESCRIPTION: SEQ ID NO: 182:

Pro Lys Pro Gln Arg Lys Thr Lys Arg
1               5

(2) INFORMATION FOR SEQ ID NO: 183:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 183:

Lys Pro Gln Arg Lys Thr Lys Arg Asn
1               5

(2) INFORMATION FOR SEQ ID NO: 184:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 184:

Pro Gln Arg Lys Thr Lys Arg Asn Thr
1               5

(2) INFORMATION FOR SEQ ID NO: 185:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 185:

Gln Arg Lys Thr Lys Arg Asn Thr Asn
1               5

(2) INFORMATION FOR SEQ ID NO: 186:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 186:

Arg Lys Thr Lys Arg Asn Thr Asn Arg
1               5

(2) INFORMATION FOR SEQ ID NO: 187:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 187:

Lys Thr Lys Arg Asn Thr Asn Arg Arg
1               5

(2) INFORMATION FOR SEQ ID NO: 188:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 188:

Thr Lys Arg Asn Thr Asn Arg Arg Pro
1               5

(2) INFORMATION FOR SEQ ID NO: 189:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 189:

Lys Arg Asn Thr Asn Arg Arg Pro Gln
1               5

(2) INFORMATION FOR SEQ ID NO: 190:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 190:

Pro Gln Arg Lys Thr Lys Arg Asn Thr
1               5

(2) INFORMATION FOR SEQ ID NO: 191:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 191:

Gln Arg Lys Thr Lys Arg Asn Thr Asn
1               5

(2) INFORMATION FOR SEQ ID NO: 192:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 192:

Arg Lys Thr Lys Arg Asn Thr Asn Arg
1               5

(2) INFORMATION FOR SEQ ID NO: 193:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 193:

Lys Thr Lys Arg Asn Thr Asn Arg Arg
1               5

(2) INFORMATION FOR SEQ ID NO: 194:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 194:

Thr Lys Arg Asn Thr Asn Arg Arg Pro
1               5

(2) INFORMATION FOR SEQ ID NO: 195:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 195:

Lys Arg Asn Thr Asn Arg Arg Pro Gln
1               5

(2) INFORMATION FOR SEQ ID NO: 196:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 196:

Arg Asn Thr Asn Arg Arg Pro Gln Asp
1               5

(2) INFORMATION FOR SEQ ID NO: 197:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 197:

Asn Thr Asn Arg Arg Pro Gln Asp Val
1               5

(2) INFORMATION FOR SEQ ID NO: 198:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 198:

Thr Asn Arg Arg Pro Gln Asp Val Lys
1               5

(2) INFORMATION FOR SEQ ID NO: 199:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 199:

Asn Arg Arg Pro Gln Asp Val Lys Phe
1               5

(2) INFORMATION FOR SEQ ID NO: 200:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 200:

Arg Arg Pro Gln Asp Val Lys Phe Pro
1               5

(2) INFORMATION FOR SEQ ID NO: 201:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 201:

Arg Pro Gln Asp Val Lys Phe Pro Gly 1               5

(2) INFORMATION FOR SEQ ID NO: 202:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 202:

Arg Thr Asn Asn Arg Arg Pro Gln Asp
1               5

(2) INFORMATION FOR SEQ ID NO: 203:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 203:

Asn Thr Asn Arg Arg Pro Gln Asp Val
1               5

(2) INFORMATION FOR SEQ ID NO: 204:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 204:

Thr Asn Arg Arg Pro Gln Asp Val Lys
1               5

(2) INFORMATION FOR SEQ ID NO: 205:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 205:

Asn Arg Arg Pro Gln Asp Val Lys Phe
1               5

(2) INFORMATION FOR SEQ ID NO: 206:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 206:

```
Arg Arg Pro Gln Asp Val Lys Phe Pro
1               5
```

(2) INFORMATION FOR SEQ ID NO: 207:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 207:

```
Arg Pro Gln Asp Val Lys Phe Pro Gly
1               5
```

(2) INFORMATION FOR SEQ ID NO: 208:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 208:

```
Pro Gln Asp Val Lys Phe Pro Gly Gly
1               5
```

(2) INFORMATION FOR SEQ ID NO: 209:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 209:

```
Gln Asp Val Lys Phe Pro Gly Gly Gly
1               5
```

(2) INFORMATION FOR SEQ ID NO: 210:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 210:

```
Asp Val Lys Phe Pro Gly Gly Gly Gln
1               5
```

(2) INFORMATION FOR SEQ ID NO: 211:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 211:

```
Val Lys Phe Pro Gly Gly Gly Gln Ile
1               5
```

(2) INFORMATION FOR SEQ ID NO: 212:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 212:

```
Lys Phe Pro Gly Gly Gly Gln Ile Val
1               5
```

(2) INFORMATION FOR SEQ ID NO: 213:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 213:

```
Phe Pro Gly Gly Gly Gln Ile Val Gly
1               5
```

(2) INFORMATION FOR SEQ ID NO: 214:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 214:

```
Pro Gly Gly Gly Gln Ile Val Gly Gly
1               5
```

(2) INFORMATION FOR SEQ ID NO: 215:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 215:

```
Gly Gly Gly Gln Ile Val Gly Gly Val
1               5
```

(2) INFORMATION FOR SEQ ID NO: 216:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 216:

Gly Gly Gln Ile Val Gly Gly Val Tyr
1               5

(2) INFORMATION FOR SEQ ID NO: 217:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 217:

Gly Gln Ile Val Gly Gly Val Tyr Leu
1               5

(2) INFORMATION FOR SEQ ID NO: 218:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 218:

Gln Ile Val Gly Gly Val Tyr Leu Leu
1               5

(2) INFORMATION FOR SEQ ID NO: 219:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 219:

Ile Val Gly Gly Val Tyr Leu Leu Pro
1               5

(2) INFORMATION FOR SEQ ID NO: 220:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 220:

Val Gly Gly Val Tyr Leu Leu Pro Arg
1               5

(2) INFORMATION FOR SEQ ID NO: 221:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 221:

Gly Gly Val Tyr Leu Leu Pro Arg Arg
1               5

(2) INFORMATION FOR SEQ ID NO: 222:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 222:

Gly Val Tyr Leu Leu Pro Arg Arg Gly
1               5

(2) INFORMATION FOR SEQ ID NO: 223:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 223:

Val Tyr Leu Leu Pro Arg Arg Gly Pro
1               5

(2) INFORMATION FOR SEQ ID NO: 224:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 224:

Tyr Leu Leu Pro Arg Arg Gly Pro Arg
1               5

(2) INFORMATION FOR SEQ ID NO: 225:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 225:

Leu Leu Pro Arg Arg Gly Pro Arg Leu
1               5

(2) INFORMATION FOR SEQ ID NO: 226:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 226:

Leu Pro Arg Arg Gly Pro Arg Leu Gly
1               5

(2) INFORMATION FOR SEQ ID NO: 227:

(i) SEQUENCE CHARACTERISTICS:
            (A) LENGTH: 9 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO: 227:

Pro Arg Arg Gly Pro Arg Leu Gly Val
1               5

(2) INFORMATION FOR SEQ ID NO: 228:

(i) SEQUENCE CHARACTERISTICS:
            (A) LENGTH: 9 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO: 228:

Arg Arg Gly Pro Arg Leu Gly Val Arg
1               5

(2) INFORMATION FOR SEQ ID NO: 229:

(i) SEQUENCE CHARACTERISTICS:
            (A) LENGTH: 9 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO: 229:

Arg Gly Pro Arg Leu Gly Val Arg Ala
1               5

(2) INFORMATION FOR SEQ ID NO: 230:

(i) SEQUENCE CHARACTERISTICS:
            (A) LENGTH: 9 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO: 230:

Gly Pro Arg Leu Gly Val Arg Ala Thr
1               5

(2) INFORMATION FOR SEQ ID NO: 231:

(i) SEQUENCE CHARACTERISTICS:
            (A) LENGTH: 9 amino acids
            (B) TYPE: amino acid
            (C) STRANDEDNESS: single
            (D) TOPOLOGY: linear

```
        (ii) MOLECULE TYPE: peptide (xi) SEQUENCE DESCRIPTION: SEQ ID NO: 231:

Pro Arg Leu Gly Val Arg Ala Thr Arg
1               5

(2) INFORMATION FOR SEQ ID NO: 232:

(i) SEQUENCE CHARACTERISTICS:
            (A) LENGTH: 9 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO: 232:

Arg Leu Gly Val Arg Ala Thr Arg Lys
1               5

(2) INFORMATION FOR SEQ ID NO: 233:

(i) SEQUENCE CHARACTERISTICS:
            (A) LENGTH: 9 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO: 233:

Leu Gly Val Arg Ala Thr Arg Lys Thr
1               5

(2) INFORMATION FOR SEQ ID NO: 234:

(i) SEQUENCE CHARACTERISTICS:
            (A) LENGTH: 9 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO: 234:

Gly Val Arg Ala Thr Arg Lys Thr Ser
1               5

(2) INFORMATION FOR SEQ ID NO: 235:

(i) SEQUENCE CHARACTERISTICS:
            (A) LENGTH: 9 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO: 235:

Val Arg Ala Thr Arg Lys Thr Ser Glu
1               5

(2) INFORMATION FOR SEQ ID NO: 236:

(i) SEQUENCE CHARACTERISTICS:
            (A) LENGTH: 9 amino acids
            (B) TYPE: amino acid
            (C) STRANDEDNESS: single
```

(D) TOPOLOGY: linear (ii) MOLECULE TYPE: peptide (xi) SEQUENCE DESCRIPTION: SEQ ID NO: 236:

Arg Ala Thr Arg Lys Thr Ser Glu Arg
1               5

(2) INFORMATION FOR SEQ ID NO: 237:

(i) SEQUENCE CHARACTERISTICS:
            (A) LENGTH: 9 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO: 237:

Ala Thr Arg Lys Thr Ser Glu Arg Ser
1               5

(2) INFORMATION FOR SEQ ID NO: 238:

(i) SEQUENCE CHARACTERISTICS:
            (A) LENGTH: 9 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO: 238:

Thr Arg Lys Thr Ser Glu Arg Ser Gln
1               5

(2) INFORMATION FOR SEQ ID NO: 239:

(i) SEQUENCE CHARACTERISTICS:
            (A) LENGTH: 9 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO: 239:

Arg Lys Thr Ser Glu Arg Ser Gln Pro
1               5

(2) INFORMATION FOR SEQ ID NO: 240:

(i) SEQUENCE CHARACTERISTICS:
            (A) LENGTH: 9 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO: 240:

Lys Thr Ser Glu Arg Ser Gln Pro Arg
1               5

(2) INFORMATION FOR SEQ ID NO: 241:

(i) SEQUENCE CHARACTERISTICS:
            (A) LENGTH: 9 amino acids
            (B) TYPE: amino acid

```
            (C) STRANDEDNESS: single
            (D) TOPOLOGY: linear (ii) MOLECULE TYPE: peptide (xi) SEQUENCE DESCRIPTION: SEQ ID NO: 241:

Thr Ser Glu Arg Ser Gln Pro Arg Gly
1               5

(2) INFORMATION FOR SEQ ID NO: 242:

(i) SEQUENCE CHARACTERISTICS:
            (A) LENGTH: 9 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO: 242:

Ser Glu Arg Ser Gln Pro Arg Gly Arg
1               5

(2) INFORMATION FOR SEQ ID NO: 243:

(i) SEQUENCE CHARACTERISTICS:
            (A) LENGTH: 9 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO: 243:

Glu Arg Ser Gln Pro Arg Gly Arg Arg
1               5

(2) INFORMATION FOR SEQ ID NO: 244:

(i) SEQUENCE CHARACTERISTICS:
            (A) LENGTH: 9 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO: 244:

Arg Ser Gln Pro Arg Gly Arg Arg Gln
1               5

(2) INFORMATION FOR SEQ ID NO: 245:

(i) SEQUENCE CHARACTERISTICS:
            (A) LENGTH: 9 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO: 245:

Ser Gln Pro Arg Gly Arg Arg Gln Pro
1               5

(2) INFORMATION FOR SEQ ID NO: 246:

(i) SEQUENCE CHARACTERISTICS:
            (A) LENGTH: 9 amino acids
```

-continued (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 246:

Gln Pro Arg Gly Arg Arg Gln Pro Ile
1               5

(2) INFORMATION FOR SEQ ID NO: 247:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 247:

Pro Arg Gly Arg Arg Gln Pro Ile Pro
1               5

(2) INFORMATION FOR SEQ ID NO: 248:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 248:

Arg Gly Arg Arg Gln Pro Ile Pro Lys
1               5

(2) INFORMATION FOR SEQ ID NO: 249:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 249:

Gly Arg Arg Gln Pro Ile Pro Lys Val
1               5

(2) INFORMATION FOR SEQ ID NO: 250:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 250:

Arg Arg Gln Pro Ile Pro Lys Val Arg
1               5

(2) INFORMATION FOR SEQ ID NO: 251:

(i) SEQUENCE CHARACTERISTICS:

(A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 251:

Arg Gln Pro Ile Pro Lys Val Arg Arg
1               5

(2) INFORMATION FOR SEQ ID NO: 252:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 252:

Gln Pro Ile Pro Lys Val Arg Arg Pro
1               5

(2) INFORMATION FOR SEQ ID NO: 253:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 253:

Pro Ile Pro Lys Val Arg Arg Pro Glu
1               5

(2) INFORMATION FOR SEQ ID NO: 254:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 254:

Ile Pro Lys Val Arg Arg Pro Glu Gly
1               5

(2) INFORMATION FOR SEQ ID NO: 255:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 255:

Pro Lys Val Arg Arg Pro Glu Gly Arg
1               5

(2) INFORMATION FOR SEQ ID NO: 256:

```
        (i) SEQUENCE CHARACTERISTICS:
            (A) LENGTH: 9 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO: 256:

Lys Val Arg Arg Pro Glu Gly Arg Thr
1               5

(2) INFORMATION FOR SEQ ID NO: 257:

(i) SEQUENCE CHARACTERISTICS:
            (A) LENGTH: 9 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO: 257:

Val Arg Arg Pro Glu Gly Arg Thr Trp
1               5

(2) INFORMATION FOR SEQ ID NO: 258:

(i) SEQUENCE CHARACTERISTICS:
            (A) LENGTH: 9 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO: 258:

Arg Arg Pro Glu Gly Arg Thr Trp Ala
1               5

(2) INFORMATION FOR SEQ ID NO: 259:

(i) SEQUENCE CHARACTERISTICS:
            (A) LENGTH: 9 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO: 259:

Arg Pro Glu Gly Arg Thr Trp Ala Gln
1               5

(2) INFORMATION FOR SEQ ID NO: 260:

(i) SEQUENCE CHARACTERISTICS:
            (A) LENGTH: 9 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO: 260:

Pro Glu Gly Arg Thr Trp Ala Gln Pro
1               5

(2) INFORMATION FOR SEQ ID NO: 261:
```

(i) SEQUENCE CHARACTERISTICS:
            (A) LENGTH: 9 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO: 261:

Glu Gly Arg Thr Trp Ala Gln Pro Gly
1               5

(2) INFORMATION FOR SEQ ID NO: 262:

(i) SEQUENCE CHARACTERISTICS:
            (A) LENGTH: 9 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO: 262:

Leu Ser Gly Lys Pro Ala Ile Ile Pro
1               5

(2) INFORMATION FOR SEQ ID NO: 263:

(i) SEQUENCE CHARACTERISTICS:
            (A) LENGTH: 9 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO: 263:

Ser Gly Lys Pro Ala Ile Ile Pro Asp
1               5

(2) INFORMATION FOR SEQ ID NO: 264:

(i) SEQUENCE CHARACTERISTICS:
            (A) LENGTH: 9 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO: 264:

Gly Lys Pro Ala Ile Ile Pro Asp Arg
1               5

(2) INFORMATION FOR SEQ ID NO: 265:

(i) SEQUENCE CHARACTERISTICS:
            (A) LENGTH: 9 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO: 265:

Lys Pro Ala Ile Ile Pro Asp Arg Glu
1               5

```
(2) INFORMATION FOR SEQ ID NO: 266:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 266:

Pro Ala Ile Ile Pro Asp Arg Glu Val
1               5

(2) INFORMATION FOR SEQ ID NO: 267:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 267:

Ala Ile Ile Pro Asp Arg Glu Val Leu
1               5

(2) INFORMATION FOR SEQ ID NO: 268:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 268:

Ile Ile Pro Asp Arg Glu Val Leu Tyr
1               5

(2) INFORMATION FOR SEQ ID NO: 269:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 269:

Ile Pro Asp Arg Glu Val Leu Tyr Arg
1               5

(2) INFORMATION FOR SEQ ID NO: 270:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 270:

Pro Asp Arg Glu Val Leu Tyr Arg Glu
1               5
```

(2) INFORMATION FOR SEQ ID NO: 271:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 271:

Asp Arg Glu Val Leu Tyr Arg Glu Phe
1               5

(2) INFORMATION FOR SEQ ID NO: 272:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 272:

Arg Glu Val Leu Tyr Arg Glu Phe Asp
1               5

(2) INFORMATION FOR SEQ ID NO: 273:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 273:

Glu Val Leu Tyr Arg Glu Phe Asp Glu
1               5

(2) INFORMATION FOR SEQ ID NO: 274:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 274:

Ile Ile Pro Asp Arg Glu Val Leu Tyr
1               5

(2) INFORMATION FOR SEQ ID NO: 275:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 275:

Ile Pro Asp Arg Glu Val Leu Tyr Arg
1               5

(2) INFORMATION FOR SEQ ID NO: 276:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 276:

Pro Asp Arg Glu Val Leu Tyr Arg Glu
1               5

(2) INFORMATION FOR SEQ ID NO: 277:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 277:

Asp Arg Glu Val Leu Tyr Arg Glu Phe
1               5

(2) INFORMATION FOR SEQ ID NO: 278:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 278:

Arg Glu Val Leu Tyr Arg Glu Phe Asp
1               5

(2) INFORMATION FOR SEQ ID NO: 279:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 279:

Glu Val Leu Tyr Arg Glu Phe Asp Glu
1               5

(2) INFORMATION FOR SEQ ID NO: 280:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 280:

Val Leu Tyr Arg Glu Phe Asp Glu Met 1           5

(2) INFORMATION FOR SEQ ID NO: 281:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 281:

Leu Tyr Arg Glu Phe Asp Glu Met Glu
1               5

(2) INFORMATION FOR SEQ ID NO: 282:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 282:

Tyr Arg Glu Phe Asp Glu Met Glu Glu
1               5

(2) INFORMATION FOR SEQ ID NO: 283:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 283:

Arg Glu Phe Asp Glu Met Glu Glu Cys
1               5

(2) INFORMATION FOR SEQ ID NO: 284:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 284:

Glu Phe Asp Glu Met Glu Glu Cys Ser
1               5

(2) INFORMATION FOR SEQ ID NO: 285:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 285:

```
Phe Asp Glu Met Glu Glu Cys Ser Gln
1               5
```

(2) INFORMATION FOR SEQ ID NO: 286:

(i) SEQUENCE CHARACTERISTICS:
　　　　　(A) LENGTH: 9 amino acids
　　　　　(B) TYPE: amino acid
　　　　　(C) STRANDEDNESS: single
　　　　　(D) TOPOLOGY: linear (ii) MOLECULE TYPE: peptide (xi) SEQUENCE DESCRIPTION: SEQ ID NO: 286:

```
Val Leu Tyr Arg Glu Phe Asp Glu Met
1               5
```

(2) INFORMATION FOR SEQ ID NO: 287:

(i) SEQUENCE CHARACTERISTICS:
　　　　　(A) LENGTH: 9 amino acids
　　　　　(B) TYPE: amino acid
　　　　　(C) STRANDEDNESS: single
　　　　　(D) TOPOLOGY: linear (ii) MOLECULE TYPE: peptide (xi) SEQUENCE DESCRIPTION: SEQ ID NO: 287:

```
Leu Tyr Arg Glu Phe Asp Glu Met Glu
1               5
```

(2) INFORMATION FOR SEQ ID NO: 288:

(i) SEQUENCE CHARACTERISTICS:
　　　　　(A) LENGTH: 9 amino acids
　　　　　(B) TYPE: amino acid
　　　　　(C) STRANDEDNESS: single
　　　　　(D) TOPOLOGY: linear (ii) MOLECULE TYPE: peptide (xi) SEQUENCE DESCRIPTION: SEQ ID NO: 288:

```
Tyr Arg Glu Phe Asp Glu Met Glu Glu
1               5
```

(2) INFORMATION FOR SEQ ID NO: 289:

(i) SEQUENCE CHARACTERISTICS:
　　　　　(A) LENGTH: 9 amino acids
　　　　　(B) TYPE: amino acid
　　　　　(C) STRANDEDNESS: single
　　　　　(D) TOPOLOGY: linear (ii) MOLECULE TYPE: peptide (xi) SEQUENCE DESCRIPTION: SEQ ID NO: 289:

```
Arg Glu Phe Asp Glu Met Glu Glu Cys
1               5
```

(2) INFORMATION FOR SEQ ID NO: 290:

(i) SEQUENCE CHARACTERISTICS:
　　　　　(A) LENGTH: 9 amino acids
　　　　　(B) TYPE: amino acid
　　　　　(C) STRANDEDNESS: single
　　　　　(D) TOPOLOGY: linear (ii) MOLECULE TYPE: peptide (xi) SEQUENCE DESCRIPTION: SEQ ID NO: 290:

```
Glu Phe Asp Glu Met Glu Glu Cys Ser
1               5
```

(2) INFORMATION FOR SEQ ID NO: 291:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 291:

```
Phe Asp Glu Met Glu Glu Cys Ser Gln
1               5
```

(2) INFORMATION FOR SEQ ID NO: 292:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 292:

```
Asp Glu Met Glu Glu Cys Ser Gln His
1               5
```

(2) INFORMATION FOR SEQ ID NO: 293:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 293:

```
Glu Met Glu Glu Cys Ser Gln His Leu
1               5
```

(2) INFORMATION FOR SEQ ID NO: 294:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 294:

```
Met Glu Glu Cys Ser Gln His Leu Pro
1               5
```

(2) INFORMATION FOR SEQ ID NO: 295:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 295:

Glu Glu Cys Ser Gln His Leu Pro Tyr
1               5

(2) INFORMATION FOR SEQ ID NO: 296:

(i) SEQUENCE CHARACTERISTICS:
            (A) LENGTH: 9 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO: 296:

Glu Cys Ser Gln His Leu Pro Tyr Ile
1               5

(2) INFORMATION FOR SEQ ID NO: 297:

(i) SEQUENCE CHARACTERISTICS:
            (A) LENGTH: 9 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO: 297:

Cys Ser Gln His Leu Pro Tyr Ile Glu
1               5

(2) INFORMATION FOR SEQ ID NO: 298:

(i) SEQUENCE CHARACTERISTICS:
            (A) LENGTH: 9 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO: 298:

Asp Glu Met Glu Glu Cys Ser Gln His
1               5

(2) INFORMATION FOR SEQ ID NO: 299:

(i) SEQUENCE CHARACTERISTICS:
            (A) LENGTH: 9 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO: 299:

Glu Met Glu Glu Cys Ser Gln His Leu
1               5

(2) INFORMATION FOR SEQ ID NO: 300:

(i) SEQUENCE CHARACTERISTICS:
            (A) LENGTH: 9 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO: 300:

Met Glu Glu Cys Ser Gln His Leu Pro
1               5

(2) INFORMATION FOR SEQ ID NO: 301:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 301:

Glu Glu Cys Ser Gln His Leu Pro Tyr
1               5

(2) INFORMATION FOR SEQ ID NO: 302:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 302:

Glu Cys Ser Gln His Leu Pro Tyr Ile
1               5

(2) INFORMATION FOR SEQ ID NO: 303:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 303:

Cys Ser Gln His Leu Pro Tyr Ile Glu
1               5

(2) INFORMATION FOR SEQ ID NO: 304:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 304:

Ser Gln His Leu Pro Tyr Ile Glu Gln
1               5

(2) INFORMATION FOR SEQ ID NO: 305:

(i) SEQUENCE CHARACTERISTICS:
        (A) LENGTH: 9 amino acids
        (B) TYPE: amino acid
        (C) STRANDEDNESS: single
        (D) TOPOLOGY: linear

```
        (ii) MOLECULE TYPE: peptide (xi) SEQUENCE DESCRIPTION: SEQ ID NO: 305:

Gln His Leu Pro Tyr Ile Glu Gln Gly
1               5

(2) INFORMATION FOR SEQ ID NO: 306:

(i) SEQUENCE CHARACTERISTICS:
            (A) LENGTH: 9 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO: 306:

His Leu Pro Tyr Ile Glu Gln Gly Met
1               5

(2) INFORMATION FOR SEQ ID NO: 307:

(i) SEQUENCE CHARACTERISTICS:
            (A) LENGTH: 9 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO: 307:

Leu Pro Tyr Ile Glu Gln Gly Met Met
1               5

(2) INFORMATION FOR SEQ ID NO: 308:

(i) SEQUENCE CHARACTERISTICS:
            (A) LENGTH: 9 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO: 308:

Pro Tyr Ile Glu Gln Gly Met Met Leu
1               5

(2) INFORMATION FOR SEQ ID NO: 309:

(i) SEQUENCE CHARACTERISTICS:
            (A) LENGTH: 9 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO: 309:

Tyr Ile Glu Gln Gly Met Met Leu Ala
1               5

(2) INFORMATION FOR SEQ ID NO: 310:

(i) SEQUENCE CHARACTERISTICS:
            (A) LENGTH: 9 amino acids
            (B) TYPE: amino acid
            (C) STRANDEDNESS: single
            (D) TOPOLOGY: linear
```

```
    (ii) MOLECULE TYPE: peptide (xi) SEQUENCE DESCRIPTION: SEQ ID NO: 310:

Ser Gln His Leu Pro Tyr Ile Glu Gln
1               5

(2) INFORMATION FOR SEQ ID NO: 311:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 311:

Gln His Leu Pro Tyr Ile Glu Gln Gly
1               5

(2) INFORMATION FOR SEQ ID NO: 312:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 312:

His Leu Pro Tyr Ile Glu Gln Gly Met
1               5

(2) INFORMATION FOR SEQ ID NO: 313:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 313:

Leu Pro Tyr Ile Glu Gln Gly Met Met
1               5

(2) INFORMATION FOR SEQ ID NO: 314:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 314:

Pro Tyr Ile Glu Gln Gly Met Met Leu
1               5

(2) INFORMATION FOR SEQ ID NO: 315:

(i) SEQUENCE CHARACTERISTICS:
        (A) LENGTH: 9 amino acids
        (B) TYPE: amino acid
        (C) STRANDEDNESS: single
```

(D) TOPOLOGY: linear (ii) MOLECULE TYPE: peptide (xi) SEQUENCE DESCRIPTION: SEQ ID NO: 315:

Tyr Ile Glu Gln Gly Met Met Leu Ala
    1               5

(2) INFORMATION FOR SEQ ID NO: 316:

(i) SEQUENCE CHARACTERISTICS:
            (A) LENGTH: 9 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO: 316:

Ile Glu Gln Gly Met Met Leu Ala Glu
    1               5

(2) INFORMATION FOR SEQ ID NO: 317:

(i) SEQUENCE CHARACTERISTICS:
            (A) LENGTH: 9 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO: 317:

Glu Gln Gly Met Met Leu Ala Glu Gln
    1               5

(2) INFORMATION FOR SEQ ID NO: 318:

(i) SEQUENCE CHARACTERISTICS:
            (A) LENGTH: 9 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO: 318:

Gln Gly Met Met Leu Ala Glu Gln Phe
    1               5

(2) INFORMATION FOR SEQ ID NO: 319:

(i) SEQUENCE CHARACTERISTICS:
            (A) LENGTH: 9 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO: 319:

Gly Met Met Leu Ala Glu Gln Phe Lys
    1               5

(2) INFORMATION FOR SEQ ID NO: 320:

(i) SEQUENCE CHARACTERISTICS:
            (A) LENGTH: 9 amino acids
            (B) TYPE: amino acid

```
            (C) STRANDEDNESS: single
            (D) TOPOLOGY: linear (ii) MOLECULE TYPE: peptide (xi) SEQUENCE DESCRIPTION: SEQ ID NO: 320:

Met Met Leu Ala Glu Gln Phe Lys Gln
1               5

(2) INFORMATION FOR SEQ ID NO: 321:

(i) SEQUENCE CHARACTERISTICS:
            (A) LENGTH: 9 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO: 321:

Met Leu Ala Glu Gln Phe Lys Gln Lys
1               5

(2) INFORMATION FOR SEQ ID NO: 322:

(i) SEQUENCE CHARACTERISTICS:
            (A) LENGTH: 9 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO: 322:

Ile Glu Gln Gly Met Met Leu Ala Glu
1               5

(2) INFORMATION FOR SEQ ID NO: 323:

(i) SEQUENCE CHARACTERISTICS:
            (A) LENGTH: 9 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO: 323:

Glu Gln Gly Met Met Leu Ala Glu Gln
1               5

(2) INFORMATION FOR SEQ ID NO: 324:

(i) SEQUENCE CHARACTERISTICS:
            (A) LENGTH: 9 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO: 324:

Gln Gly Met Met Leu Ala Glu Gln Phe
1               5

(2) INFORMATION FOR SEQ ID NO: 325:

(i) SEQUENCE CHARACTERISTICS:
            (A) LENGTH: 9 amino acids
```

```
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO: 325:

Gly Met Met Leu Ala Glu Gln Phe Lys
1               5

(2) INFORMATION FOR SEQ ID NO: 326:

(i) SEQUENCE CHARACTERISTICS:
            (A) LENGTH: 9 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO: 326:

Met Met Leu Ala Glu Gln Phe Lys Gln
1               5

(2) INFORMATION FOR SEQ ID NO: 327:

(i) SEQUENCE CHARACTERISTICS:
            (A) LENGTH: 9 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO: 327:

Met Leu Ala Glu Gln Phe Lys Gln Lys
1               5

(2) INFORMATION FOR SEQ ID NO: 328:

(i) SEQUENCE CHARACTERISTICS:
            (A) LENGTH: 9 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO: 328:

Leu Ala Glu Gln Phe Lys Gln Lys Ala
1               5

(2) INFORMATION FOR SEQ ID NO: 329:

(i) SEQUENCE CHARACTERISTICS:
            (A) LENGTH: 9 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO: 329:

Ala Glu Gln Phe Lys Gln Lys Ala Leu
1               5

(2) INFORMATION FOR SEQ ID NO: 330:

(i) SEQUENCE CHARACTERISTICS:
```

(A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 330:

Glu Gln Phe Lys Gln Lys Ala Leu Gly
1               5

(2) INFORMATION FOR SEQ ID NO: 331:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 331:

Gln Phe Lys Gln Lys Ala Leu Gly Leu
1               5

(2) INFORMATION FOR SEQ ID NO: 332:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 332:

Phe Lys Gln Lys Ala Leu Gly Leu Leu
1               5

(2) INFORMATION FOR SEQ ID NO: 333:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 333:

Lys Gln Lys Ala Leu Gly Leu Leu Gln
1               5

(2) INFORMATION FOR SEQ ID NO: 334:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 334:

Leu Ala Glu Gln Phe Lys Gln Lys Ala
1               5

(2) INFORMATION FOR SEQ ID NO: 335:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 335:

Ala Glu Gln Phe Lys Gln Lys Ala Leu
1               5

(2) INFORMATION FOR SEQ ID NO: 336:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 336:

Glu Gln Phe Lys Gln Lys Ala Leu Gly
1               5

(2) INFORMATION FOR SEQ ID NO: 337:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 337:

Gln Phe Lys Gln Lys Ala Leu Gly Leu
1               5

(2) INFORMATION FOR SEQ ID NO: 338:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 338:

Phe Lys Gln Lys Ala Leu Gly Leu Leu
1               5

(2) INFORMATION FOR SEQ ID NO: 339:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 339:

Lys Gln Lys Ala Leu Gly Leu Leu Gln
1               5

(2) INFORMATION FOR SEQ ID NO: 340:

(i) SEQUENCE CHARACTERISTICS:
            (A) LENGTH: 9 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO: 340:

Gln Lys Ala Leu Gly Leu Leu Gln Thr
1               5

(2) INFORMATION FOR SEQ ID NO: 341:

(i) SEQUENCE CHARACTERISTICS:
            (A) LENGTH: 9 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO: 341:

Lys Ala Leu Gly Leu Leu Gln Thr Ala
1               5

(2) INFORMATION FOR SEQ ID NO: 342:

(i) SEQUENCE CHARACTERISTICS:
            (A) LENGTH: 9 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO: 342:

Ala Leu Gly Leu Leu Gln Thr Ala Ser
1               5

(2) INFORMATION FOR SEQ ID NO: 343:

(i) SEQUENCE CHARACTERISTICS:
            (A) LENGTH: 9 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO: 343:

Leu Gly Leu Leu Gln Thr Ala Ser Arg
1               5

(2) INFORMATION FOR SEQ ID NO: 344:

(i) SEQUENCE CHARACTERISTICS:
            (A) LENGTH: 9 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO: 344:

Gly Leu Leu Gln Thr Ala Ser Arg Gln
1               5

(2) INFORMATION FOR SEQ ID NO: 345:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 345:

Leu Leu Gln Thr Ala Ser Arg Gln Ala
1               5

(2) INFORMATION FOR SEQ ID NO: 346:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 346:

Gln Lys Ala Leu Gly Leu Leu Gln Thr
1               5

(2) INFORMATION FOR SEQ ID NO: 347:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 347:

Lys Ala Leu Gly Leu Leu Gln Thr Ala
1               5

(2) INFORMATION FOR SEQ ID NO: 348:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 348:

Ala Leu Gly Leu Leu Gln Thr Ala Ser
1               5

(2) INFORMATION FOR SEQ ID NO: 349:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 349:

Leu Gly Leu Leu Gln Thr Ala Ser Arg
1               5

(2) INFORMATION FOR SEQ ID NO: 350:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 350:

Gly Leu Leu Gln Thr Ala Ser Arg Gln
1            5

(2) INFORMATION FOR SEQ ID NO: 351:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 351:

Leu Leu Gln Thr Ala Ser Arg Gln Ala
1            5

(2) INFORMATION FOR SEQ ID NO: 352:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 352:

Leu Gln Thr Ala Ser Arg Gln Ala Glu
1            5

(2) INFORMATION FOR SEQ ID NO: 353:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 353:

Gln Thr Ala Ser Arg Gln Ala Glu Val
1            5

(2) INFORMATION FOR SEQ ID NO: 354:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 354:

Thr Ala Ser Arg Gln Ala Glu Val Ile
1            5

(2) INFORMATION FOR SEQ ID NO: 355:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 355:

Ala Ser Arg Gln Ala Glu Val Ile Ala
1               5

(2) INFORMATION FOR SEQ ID NO: 356:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 356:

Ser Arg Gln Ala Glu Val Ile Ala Pro
1               5

(2) INFORMATION FOR SEQ ID NO: 357:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 357:

Arg Gln Ala Glu Val Ile Ala Pro Ala
1               5

(2) INFORMATION FOR SEQ ID NO: 358:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 358:

Leu Gln Thr Ala Ser Arg Gln Ala Glu
1               5

(2) INFORMATION FOR SEQ ID NO: 359:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 359:

Gln Thr Ala Ser Arg Gln Ala Glu Val 1               5

(2) INFORMATION FOR SEQ ID NO: 360:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 360:

Thr Ala Ser Arg Gln Ala Glu Val Ile
1               5

(2) INFORMATION FOR SEQ ID NO: 361:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 361:

Ala Ser Arg Gln Ala Glu Val Ile Ala
1               5

(2) INFORMATION FOR SEQ ID NO: 362:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 362:

Ser Arg Gln Ala Glu Val Ile Ala Pro
1               5

(2) INFORMATION FOR SEQ ID NO: 363:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 363:

Arg Gln Ala Glu Val Ile Ala Pro Ala
1               5

(2) INFORMATION FOR SEQ ID NO: 364:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 364:

```
Gln Ala Glu Val Ile Ala Pro Ala Val
1               5
```

(2) INFORMATION FOR SEQ ID NO: 365:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 365:

```
Ala Glu Val Ile Ala Pro Ala Val Gly
1               5
```

(2) INFORMATION FOR SEQ ID NO: 366:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 366:

```
Glu Val Ile Ala Pro Ala Val Gly Thr
1               5
```

(2) INFORMATION FOR SEQ ID NO: 367:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 367:

```
Val Ile Ala Pro Ala Val Gly Thr Lys
1               5
```

(2) INFORMATION FOR SEQ ID NO: 368:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 368:

```
Ile Ala Pro Ala Val Gly Thr Lys Lys
1               5
```

(2) INFORMATION FOR SEQ ID NO: 369:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 369:

```
Ala Pro Ala Val Gly Thr Lys Lys Gln
1               5
```

(2) INFORMATION FOR SEQ ID NO: 370:

(i) SEQUENCE CHARACTERISTICS:
       (A) LENGTH: 9 amino acids
       (B) TYPE: amino acid
       (C) STRANDEDNESS: single
       (D) TOPOLOGY: linear (ii) MOLECULE TYPE: peptide (xi) SEQUENCE DESCRIPTION: SEQ ID NO: 370:

```
Gly Asn Ile Thr Arg Tyr Glu Ser Glu
1               5
```

(2) INFORMATION FOR SEQ ID NO: 371:

(i) SEQUENCE CHARACTERISTICS:
       (A) LENGTH: 9 amino acids
       (B) TYPE: amino acid
       (C) STRANDEDNESS: single
       (D) TOPOLOGY: linear (ii) MOLECULE TYPE: peptide (xi) SEQUENCE DESCRIPTION: SEQ ID NO: 371:

```
Asn Ile Thr Arg Tyr Glu Ser Glu Asn
1               5
```

(2) INFORMATION FOR SEQ ID NO: 372:

(i) SEQUENCE CHARACTERISTICS:
       (A) LENGTH: 9 amino acids
       (B) TYPE: amino acid
       (C) STRANDEDNESS: single
       (D) TOPOLOGY: linear (ii) MOLECULE TYPE: peptide (xi) SEQUENCE DESCRIPTION: SEQ ID NO: 372:

```
Ile Thr Arg Tyr Glu Ser Glu Asn Lys
1               5
```

(2) INFORMATION FOR SEQ ID NO: 373:

(i) SEQUENCE CHARACTERISTICS:
       (A) LENGTH: 9 amino acids
       (B) TYPE: amino acid
       (C) STRANDEDNESS: single
       (D) TOPOLOGY: linear (ii) MOLECULE TYPE: peptide (xi) SEQUENCE DESCRIPTION: SEQ ID NO: 373:

```
Thr Arg Tyr Glu Ser Glu Asn Lys Val
1               5
```

(2) INFORMATION FOR SEQ ID NO: 374:

(i) SEQUENCE CHARACTERISTICS:
       (A) LENGTH: 9 amino acids
       (B) TYPE: amino acid
       (C) STRANDEDNESS: single
       (D) TOPOLOGY: linear (ii) MOLECULE TYPE: peptide (xi) SEQUENCE DESCRIPTION: SEQ ID NO: 374:

Arg Tyr Glu Ser Glu Asn Lys Val Val
1               5

(2) INFORMATION FOR SEQ ID NO: 375:

(i) SEQUENCE CHARACTERISTICS:
            (A) LENGTH: 9 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO: 375:

Tyr Glu Ser Glu Asn Lys Val Val Ile
1               5

(2) INFORMATION FOR SEQ ID NO: 376:

(i) SEQUENCE CHARACTERISTICS:
            (A) LENGTH: 9 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO: 376:

Glu Ser Glu Asn Lys Val Val Ile Leu
1               5

(2) INFORMATION FOR SEQ ID NO: 377:

(i) SEQUENCE CHARACTERISTICS:
            (A) LENGTH: 9 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO: 377:

Ser Glu Asn Lys Val Val Ile Leu Asp
1               5

(2) INFORMATION FOR SEQ ID NO: 378:

(i) SEQUENCE CHARACTERISTICS:
            (A) LENGTH: 9 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO: 378:

Glu Asn Lys Val Val Ile Leu Asp Ser
1               5

(2) INFORMATION FOR SEQ ID NO: 379:

(i) SEQUENCE CHARACTERISTICS:
            (A) LENGTH: 9 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO: 379:

Asn Lys Val Val Ile Leu Asp Ser Phe
1               5

(2) INFORMATION FOR SEQ ID NO: 380:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 380:

Lys Val Val Ile Leu Asp Ser Phe Asp
1               5

(2) INFORMATION FOR SEQ ID NO: 381:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 381:

Val Val Ile Leu Asp Ser Phe Asp Pro
1               5

(2) INFORMATION FOR SEQ ID NO: 382:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 382:

Val Ile Leu Asp Ser Phe Asp Pro Leu
1               5

(2) INFORMATION FOR SEQ ID NO: 383:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 383:

Ile Leu Asp Ser Phe Asp Pro Leu Val
1               5

(2) INFORMATION FOR SEQ ID NO: 384:

(i) SEQUENCE CHARACTERISTICS:
        (A) LENGTH: 9 amino acids
        (B) TYPE: amino acid
        (C) STRANDEDNESS: single
        (D) TOPOLOGY: linear

```
        (ii) MOLECULE TYPE: peptide (xi) SEQUENCE DESCRIPTION: SEQ ID NO: 384:

Leu Asp Ser Phe Asp Pro Leu Val Ala
1               5

(2) INFORMATION FOR SEQ ID NO: 385:

(i) SEQUENCE CHARACTERISTICS:
            (A) LENGTH: 9 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO: 385:

Asp Ser Phe Asp Pro Leu Val Ala Glu
1               5

(2) INFORMATION FOR SEQ ID NO: 386:

(i) SEQUENCE CHARACTERISTICS:
            (A) LENGTH: 9 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO: 386:

Ser Phe Asp Pro Leu Val Ala Glu Glu
1               5

(2) INFORMATION FOR SEQ ID NO: 387:

(i) SEQUENCE CHARACTERISTICS:
            (A) LENGTH: 9 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO: 387:

Phe Asp Pro Leu Val Ala Glu Glu Asp
1               5

(2) INFORMATION FOR SEQ ID NO: 388:

(i) SEQUENCE CHARACTERISTICS:
            (A) LENGTH: 9 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO: 388:

Asp Pro Leu Val Ala Glu Glu Asp Glu
1               5

(2) INFORMATION FOR SEQ ID NO: 389:

(i) SEQUENCE CHARACTERISTICS:
            (A) LENGTH: 9 amino acids
            (B) TYPE: amino acid
            (C) STRANDEDNESS: single
            (D) TOPOLOGY: linear
```

(ii) MOLECULE TYPE: peptide (xi) SEQUENCE DESCRIPTION: SEQ ID NO: 389:

Pro Leu Val Ala Glu Glu Asp Glu Arg
1               5

(2) INFORMATION FOR SEQ ID NO: 390:

(i) SEQUENCE CHARACTERISTICS:
            (A) LENGTH: 9 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO: 390:

Leu Val Ala Glu Glu Asp Glu Arg Glu
1               5

(2) INFORMATION FOR SEQ ID NO: 391:

(i) SEQUENCE CHARACTERISTICS:
            (A) LENGTH: 9 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO: 391:

Val Ala Glu Glu Asp Glu Arg Glu Ile
1               5

(2) INFORMATION FOR SEQ ID NO: 392:

(i) SEQUENCE CHARACTERISTICS:
            (A) LENGTH: 9 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO: 392:

Ala Glu Glu Asp Glu Arg Glu Ile Ser
1               5

(2) INFORMATION FOR SEQ ID NO: 393:

(i) SEQUENCE CHARACTERISTICS:
            (A) LENGTH: 9 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO: 393:

Glu Glu Asp Glu Arg Glu Ile Ser Val
1               5

(2) INFORMATION FOR SEQ ID NO: 394:

(i) SEQUENCE CHARACTERISTICS:
            (A) LENGTH: 9 amino acids
            (B) TYPE: amino acid
            (C) STRANDEDNESS: single

```
            (D) TOPOLOGY: linear (ii) MOLECULE TYPE: peptide (xi) SEQUENCE DESCRIPTION: SEQ ID NO: 394:

Glu Asp Glu Arg Glu Ile Ser Val Pro
1               5

(2) INFORMATION FOR SEQ ID NO: 395:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 395:

Asp Glu Arg Glu Ile Ser Val Pro Ala
1               5

(2) INFORMATION FOR SEQ ID NO: 396:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 396:

Glu Arg Glu Ile Ser Val Pro Ala Glu
1               5

(2) INFORMATION FOR SEQ ID NO: 397:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 397:

Arg Glu Ile Ser Val Ala Pro Glu Ile
1               5

(2) INFORMATION FOR SEQ ID NO: 398:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 398:

Glu Ile Ser Val Pro Ala Glu Ile Leu
1               5

(2) INFORMATION FOR SEQ ID NO: 399:

(i) SEQUENCE CHARACTERISTICS:
        (A) LENGTH: 9 amino acids
        (B) TYPE: amino acid
```

```
        (C) STRANDEDNESS: single
        (D) TOPOLOGY: linear (ii) MOLECULE TYPE: peptide (xi) SEQUENCE DESCRIPTION: SEQ ID NO: 399:

Ile Ser Val Pro Ala Glu Ile Leu Arg
1               5

(2) INFORMATION FOR SEQ ID NO: 400:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 400:

Ser Val Pro Ala Glu Ile Leu Arg Lys
1               5

(2) INFORMATION FOR SEQ ID NO: 401:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 401:

Val Pro Ala Glu Ile Leu Arg Lys Ser
1               5

(2) INFORMATION FOR SEQ ID NO: 402:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 402:

Pro Ala Glu Ile Leu Arg Lys Ser Arg
1               5

(2) INFORMATION FOR SEQ ID NO: 403:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 403:

Ala Glu Ile Leu Arg Lys Ser Arg Arg
1               5

(2) INFORMATION FOR SEQ ID NO: 404:

(i) SEQUENCE CHARACTERISTICS:
        (A) LENGTH: 9 amino acids
```

-continued (B) TYPE: amino acid
          (C) STRANDEDNESS: single
          (D) TOPOLOGY: linear (ii) MOLECULE TYPE: peptide (xi) SEQUENCE DESCRIPTION: SEQ ID NO: 404:

Glu Ile Leu Arg Lys Ser Arg Arg Phe
1               5

(2) INFORMATION FOR SEQ ID NO: 405:

(i) SEQUENCE CHARACTERISTICS:
          (A) LENGTH: 9 amino acids
          (B) TYPE: amino acid
          (C) STRANDEDNESS: single
          (D) TOPOLOGY: linear (ii) MOLECULE TYPE: peptide (xi) SEQUENCE DESCRIPTION: SEQ ID NO: 405:

Ile Leu Arg Lys Ser Arg Arg Phe Ala
1               5

(2) INFORMATION FOR SEQ ID NO: 406:

(i) SEQUENCE CHARACTERISTICS:
          (A) LENGTH: 9 amino acids
          (B) TYPE: amino acid
          (C) STRANDEDNESS: single
          (D) TOPOLOGY: linear (ii) MOLECULE TYPE: peptide (xi) SEQUENCE DESCRIPTION: SEQ ID NO: 406:

Leu Arg Lys Ser Arg Arg Phe Ala Gln
1               5

(2) INFORMATION FOR SEQ ID NO: 407:

(i) SEQUENCE CHARACTERISTICS:
          (A) LENGTH: 9 amino acids
          (B) TYPE: amino acid
          (C) STRANDEDNESS: single
          (D) TOPOLOGY: linear (ii) MOLECULE TYPE: peptide (xi) SEQUENCE DESCRIPTION: SEQ ID NO: 407:

Arg Lys Ser Arg Arg Phe Ala Gln Ala
1               5

(2) INFORMATION FOR SEQ ID NO: 408:

(i) SEQUENCE CHARACTERISTICS:
          (A) LENGTH: 9 amino acids
          (B) TYPE: amino acid
          (C) STRANDEDNESS: single
          (D) TOPOLOGY: linear (ii) MOLECULE TYPE: peptide (xi) SEQUENCE DESCRIPTION: SEQ ID NO: 408:

Lys Ser Arg Arg Phe Ala Gln Ala Leu
1               5

(2) INFORMATION FOR SEQ ID NO: 409:

(i) SEQUENCE CHARACTERISTICS:

(A) LENGTH: 9 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO: 409:

Ser Arg Arg Phe Ala Gln Ala Leu Pro
1               5

(2) INFORMATION FOR SEQ ID NO: 410:

(i) SEQUENCE CHARACTERISTICS:
            (A) LENGTH: 9 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO: 410:

Arg Arg Phe Ala Gln Ala Leu Pro Val
1               5

(2) INFORMATION FOR SEQ ID NO: 411:

(i) SEQUENCE CHARACTERISTICS:
            (A) LENGTH: 9 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO: 411:

Arg Phe Ala Gln Ala Leu Pro Val Trp
1               5

(2) INFORMATION FOR SEQ ID NO: 412:

(i) SEQUENCE CHARACTERISTICS:
            (A) LENGTH: 9 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO: 412:

Phe Ala Gln Ala Leu Pro Val Trp Ala
1               5

(2) INFORMATION FOR SEQ ID NO: 413:

(i) SEQUENCE CHARACTERISTICS:
            (A) LENGTH: 9 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO: 413:

Ala Gln Ala Leu Pro Val Trp Ala Arg
1               5

(2) INFORMATION FOR SEQ ID NO: 414:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 414:

Gln Ala Leu Pro Val Trp Ala Arg Pro
1               5

(2) INFORMATION FOR SEQ ID NO: 415:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 415:

Ala Leu Pro Val Trp Ala Arg Pro Asp
1               5

(2) INFORMATION FOR SEQ ID NO: 416:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 416:

Leu Pro Val Trp Ala Arg Pro Asp Tyr
1               5

(2) INFORMATION FOR SEQ ID NO: 417:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 417:

Pro Val Trp Ala Arg Pro Asp Tyr Asn
1               5

(2) INFORMATION FOR SEQ ID NO: 418:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 418:

Val Trp Ala Arg Pro Asp Tyr Asn Pro
1               5

(2) INFORMATION FOR SEQ ID NO: 419:

(i) SEQUENCE CHARACTERISTICS:
    (A) LENGTH: 9 amino acids
    (B) TYPE: amino acid
    (C) STRANDEDNESS: single
    (D) TOPOLOGY: linear (ii) MOLECULE TYPE: peptide (xi) SEQUENCE DESCRIPTION: SEQ ID NO: 419:

Trp Ala Arg Pro Asp Tyr Asn Pro Pro
1               5

(2) INFORMATION FOR SEQ ID NO: 420:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 420:

Ala Arg Pro Asp Tyr Asn Pro Pro Leu
1               5

(2) INFORMATION FOR SEQ ID NO: 421:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 421:

Arg Pro Asp Tyr Asn Pro Pro Leu Val
1               5

(2) INFORMATION FOR SEQ ID NO: 422:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 422:

Pro Asp Tyr Asn Pro Pro Leu Val Glu
1               5

(2) INFORMATION FOR SEQ ID NO: 423:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 423:

Asp Tyr Asn Pro Pro Leu Val Glu Thr
1               5

(2) INFORMATION FOR SEQ ID NO: 424:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 424:

Tyr Asn Pro Pro Leu Val Glu Thr Trp
1               5

(2) INFORMATION FOR SEQ ID NO: 425:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 425:

Asn Pro Pro Leu Val Glu Thr Trp Lys
1               5

(2) INFORMATION FOR SEQ ID NO: 426:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 426:

Pro Pro Leu Val Glu Thr Trp Lys Lys
1               5

(2) INFORMATION FOR SEQ ID NO: 427:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 427:

Pro Leu Val Glu Thr Trp Lys Lys Pro
1               5

(2) INFORMATION FOR SEQ ID NO: 428:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 428:

Leu Val Glu Thr Trp Lys Lys Pro Asp
1               5

(2) INFORMATION FOR SEQ ID NO: 429:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 429:

Val Glu Thr Trp Lys Lys Pro Asp Tyr
1               5

(2) INFORMATION FOR SEQ ID NO: 430:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 430:

Glu Thr Trp Lys Lys Pro Asp Tyr Glu
1               5

(2) INFORMATION FOR SEQ ID NO: 431:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 431:

Thr Trp Lys Lys Pro Asp Tyr Glu Pro
1               5

(2) INFORMATION FOR SEQ ID NO: 432:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 432:

Trp Lys Lys Pro Asp Tyr Glu Pro Pro
1               5

(2) INFORMATION FOR SEQ ID NO: 433:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 433:

Lys Lys Pro Asp Tyr Glu Pro Pro Val
1               5

(2) INFORMATION FOR SEQ ID NO: 434:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 434:

Lys Pro Asp Tyr Glu Pro Pro Val Val
1               5

(2) INFORMATION FOR SEQ ID NO: 435:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 435:

Pro Asp Tyr Glu Pro Pro Val Val His
1               5

(2) INFORMATION FOR SEQ ID NO: 436:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 436:

Asp Tyr Glu Pro Pro Val Val His Gly
1               5

(2) INFORMATION FOR SEQ ID NO: 437:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 437:

Tyr Glu Pro Pro Val Val His Gly Cys
1               5

(2) INFORMATION FOR SEQ ID NO: 438:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 438:

Glu Pro Pro Val Val His Gly Cys Pro 1          5

(2) INFORMATION FOR SEQ ID NO: 439:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 439:

Pro Pro Val Val His Gly Cys Pro Leu
1               5

(2) INFORMATION FOR SEQ ID NO: 440:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 440:

Pro Val Val His Gly Cys Pro Leu Pro
1               5

(2) INFORMATION FOR SEQ ID NO: 441:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 441:

Val Val His Gly Cys Pro Leu Pro Pro
1               5

(2) INFORMATION FOR SEQ ID NO: 442:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 442:

Val His Gly Cys Pro Leu Pro Pro Pro
1               5

(2) INFORMATION FOR SEQ ID NO: 443:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 443:

```
His Gly Cys Pro Leu Pro Pro Pro Lys
1               5
```

(2) INFORMATION FOR SEQ ID NO: 444:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 444:

```
Gly Cys Pro Leu Pro Pro Pro Lys Ser
1               5                   10
```

(2) INFORMATION FOR SEQ ID NO: 445:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 445:

```
Cys Pro Leu Pro Pro Pro Lys Ser Pro
1               5
```

(2) INFORMATION FOR SEQ ID NO: 446:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 446:

```
Pro Leu Pro Pro Pro Lys Ser Pro Pro
1               5
```

(2) INFORMATION FOR SEQ ID NO: 447:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 447:

```
Leu Pro Pro Pro Lys Ser Pro Pro Val
1               5
```

(2) INFORMATION FOR SEQ ID NO: 448:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 448:

```
Pro Pro Pro Lys Ser Pro Pro Val Pro
1               5
```

(2) INFORMATION FOR SEQ ID NO: 449:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 449:

```
Pro Pro Lys Ser Pro Pro Val Pro Pro
1               5
```

(2) INFORMATION FOR SEQ ID NO: 450:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 450:

```
Pro Lys Ser Pro Pro Val Pro Pro Pro
1               5
```

(2) INFORMATION FOR SEQ ID NO: 451:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 451:

```
Lys Ser Pro Pro Val Pro Pro Pro Arg
1               5
```

(2) INFORMATION FOR SEQ ID NO: 452:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 452:

```
Ser Pro Pro Val Pro Pro Pro Arg Lys
1               5
```

(2) INFORMATION FOR SEQ ID NO: 453:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide -continued (xi) SEQUENCE DESCRIPTION: SEQ ID NO: 453:

Pro Pro Val Pro Pro Pro Arg Lys Lys
1               5

PEPTIDE DERIVED FROM HUMAN IMMUNODEFICIENCY VIRUS TYPE 1 (HIV-1), ISOLATE ANT70, CONTAINING AN IMMUNODOMINANT EPITOPE AND IT'S USE IN IMMUNODIAGNOSTIC ASSAYS

This is a divisional of application Ser. No. 08/146,028, filed Nov. 22, 1993, now U.S. Pat. No. 5,891,640; which is a U.S. national phase application based on PCT/EP93/00517, filed Mar. 8, 1993.

The technical problem underlying the present invention is to provide peptides corresponding to immunologically important epitopes on bacterial and viral proteins, as well as the use of said peptides in diagnostic or immunogenic compositions.

Recent developments in genetic engineering as well as the chemistry of solid phase peptide synthesis have led to the increasingly wider use of synthetic peptides in biochemistry and immunology. Protein sequences which become available as a result of molecular cloning techniques can be synthesized chemically in large quantities for structural, functional, and immunological studies. Peptides corresponding to immunologically important epitopes found on viral and bacterial proteins have also proven to be highly specific reagents which can be used for antibody detection and the diagnosis of infection.

Despite the many advantages synthetic peptides offer, there are a number of disadvantages associated with their use. Because of their relatively short size (generally less than 50 amino acids in length), their structure may fluctuate between many different conformations in the absence of the stabilizing influence of intramolecular interactions present in the full-length protein. Furthermore, the small size of these peptides means that their chemical properties and solubilities will frequently be quite different from those of the full-length protein and that the contribution of individual amino acids in the peptide sequence toward determining the overall chemical properties of the peptide will be proportionally greater.

Many immunological assays require that the antigen used for antibody detection be immobilized on a solid support. Most enzyme-linked immunosorbent assays (ELISA) make use of polystyrene as the solid phase. Many proteins can be stably adsorbed to the solid phase and present sequences which are accessible for subsequent interactions with antibodies. Because of their small size, direct adsorption of peptides to the solid phase frequently gives rise to unsatisfactory results for any of a number of reasons.

Firstly, the peptide may not possess the correct overall charge or amino acid composition which would enable the peptide to bind to the solid phase. Secondly, the same amino acid residues which are required for binding to the solid phase may also be required for antibody recognition and therefore not available for antibody binding. Thirdly, the peptide may become fixed in an unfavorable conformation upon binding to the solid phase which renders it unrecognizable to antibody molecules. In many cases, it is neither possible nor necessary to distinguish between these possibilities. Binding to the solid phase can be increased and made less sensitive to the specific chemical properties of a peptide by first coupling the peptide to a large carrier molecule. Typically, the carrier molecule is a protein.

While the amount of peptide bound to the solid phase, albeit indirectly, can in some cases be increased by this method, this approach suffers from the fact that the linkage between the peptide and the carrier protein frequently involves the side chains of internal trifunctional amino acids whose integrity may be indispensable for recognition by antibodies. The binding avidity of antisera for the internally modified peptide is frequently very much reduced relative to the unmodified peptide or the native protein.

The production of antisera to synthetic peptides also requires in most cases that the peptide be coupled to a carrier. Again, the coupling reaction between an internal trifunctional amino acid of the peptide and the carrier is likely to alter the immunogenic properties of the peptide.

There exist many methods for performing coupling reactions and most of the procedures in current use are discussed in detail in Van Regenmortel, M. H. V., Briand, J. P., Muller, S., and Plaue, S.; Laboratory Techniques in Biochemistry and Molecular Biology, vol. 19, Synthetic Polypeptides as Antigens, Elsevier Press, Amsterdam, New York, Oxford, 1988. In addition to these procedures, unprotected peptides can also be biotinylated using commercially available reagents such as N-hydroxysuccinimidobiotin or biotinamidocaproate N-hydroxysuccinimide ester. Many of these reagents are discussed in Billingsley, M. L., Pennypacker, K. R., Hoover, C. G., and Kincaid, R. L., Biotechniques (1987) 5(1):22–31. Biotinylated peptides are capable of being bound by the proteins streptavidin and avidin, two proteins which exhibit extraordinarily high affinity binding to biotin.

In certain instances, it is possible to selectively couple biotin to an unprotected peptide or an unprotected peptide to a carrier. This may be accomplished by synthesizing the peptide with an additional trifunctional amino acid added to one of the ends which is capable of participating in the coupling reaction. This approach will only be successful, however, as long as this amino acid is not a critical residue in the immunogenic sequence of interest and as long as the coupling agent chosen is sufficiently selective. No single technique is applicable to all unprotected peptides regardless of their amino acid composition.

The etiological agent responsible for non-A, non-B hepatitis has been identified and termed hepatitis C virus (HCV). Patent application EP-A-0 318 216 discloses sequences corresponding to approximately 80% of the viral genome. The availability of these sequences rapidly led to the elucidation of the remainder of the coding sequences, particularly those located in the 5' end of the genome (Okamoto; J. Exp. Med. 60, 167–177, 1990). The HCV genome is a linear, positive-stranded RNA molecule with a length of approximately 9400 nucleotides. With the exception of rather short untranslated regions at the termini, the genome consists of one large, uninterrupted, open reading frame encoding a polyprotein of approximately 3000 amino acids. This polyprotein has been shown to be cleaved co-translationally into individual viral structural and non-structural (NS) regions. The structural protein region is further divided into capsid (Core) and envelope (E1 and E2) proteins. The NS regions are divided into NS-1 to NS-5 regions.

A number of independent patent applications have employed a variety of strategies to determine the locations of diagnostically important amino acid sequences and many of these studies have led to the identification of similar regions of the HCV polyprotein.

The NS4 region has mainly been studied in EP-A-0 318 216, EP-A-0 442 394, U.S. Pat. No. 5,106,726, EP-A-0 489 986, EP-A-0 484 787, and EP-A-0 445 801. Unfortunately only 70% of HCV-infected individuals produce antibodies to NS4, neither the synthetic nor recombinant proteins containing sequences from this region are adequate for identifying all infected serum samples. The nucleocapsid or Core region has been studied in patent applications EP-A-0 442 394, U.S. Pat. No. 5,106,726, EP-A-0 489 986, EP-A-0 445

801, EP-A-0 451 891 and EP-A-0 479 376. It was found that these peptides often used as mixtures, were more frequently recognized by antibodies (85–90%) in sera from chronically infected individuals than were the peptides derived from NS4. The NS5 region was studied in patent applications EP-A-0 489 986 and EP-A-0 468 527. Depending on the serum panel used, more than 60% of NANB hepatitis can be shown to contain antibodies directed against these peptides. The NS3 region was also studied in patent application EP-A-0 468 527. All available evidence suggests that the most dominant epitope of NS3 are discontinuous in nature and cannot be adequately represented by synthetic peptides. The E1 region which is potentially interesting as a region from the outer surface of the virus particles (possible immunogenic epitopes) was studied in both patent applications EP-A-0 468 527 and EP-A-0 507 615. The E2/NS1 region was studied for the same reason as E1. Comparisons of this region from different HCV variants elucidated that this protein contains variable region which are reminiscent of the HIV V3 loop region of gp120 envelope protein. Four peptides were found in EP-A-0 468 527 which were shown to contain relatively infrequently recognized epitopes. Finally, the NS2 region of HCV was analyzed in EP-A-0 486 527. However, the diagnostic value of this region is not clear yet. Virtually all patent applications concerning diagnostically useful synthetic peptides for antibody detection describe preferred combinations of peptides. Most of these include peptides from the HCV core protein and NS4. In some cases, peptides from NS5 (EP-A-0 489 968 and EP-A-0 468 527), and E1 and E2/NS1 are included (EP-A-0 507 615 and EO-A-0 468 527).

Different patent applications have addressed the problem of finding diagnostically useful epitopes of human immunodeficiency virus (HIV). An important immunodominant region containing cyclic HIV-1 and HIV-2 peptides was found in patent application EP-A-0 326 490. In EP-A-0 379 949, this region was asserted to be even more reactive with HIV-specific antibodies in case a biotin molecule was coupled to these cyclic HIV peptides. SU-A-161 22 64 also describes the use of a biotinylated peptide in a solid phase immunoassay for the detection of HIV antibodies.

Other applications have looked for useful HIV epitopes in the hypervariable V3 loop region of gp120 (such as EP-A-0 448 095 and EP-A-0 438 332).

U.S. Pat. No. 4,833,071 provides peptide compositions for detection of HTLV I antibodies.

Deciding whether or not an epitope is diagnostically useful is not always straightforward and depends to an extent on the specific configuration of the test into which it is incorporated. It should be ideally an immunodominant epitope which is recognized by a large percentage of true positive sera or should be able to complement other antigens in the test to increase the detection rate. Epitopes which are not frequently recognized may or may not be diagnostically useful depending on the contribution they make towards increasing the detection rate of antibodies in true positive sera and the extent to which incorporation of these epitopes has an adverse effect on the sensitivity of the test due to dilution of other stronger epitopes.

Peptides can thus be used to identify regions of proteins which are specifically recognized by antibodies produced as a result of infection or immunization. In general, there are two strategies which can be followed. One of these strategies has been described by Geysen, H. M., Meloen, R. H., and Barteling, S. J.; Proc. Natl. Acad. Sci. USA (1984) 81:3998–4002. This approach involves the synthesis of a large series of short, overlapping peptides on polyethylene rods derivatized with a noncleavable linker such that the entire length of the protein or protein fragment of interest is represented.

The rods are incubated with antisera and antibody binding is detected using an anti-immunoglobulin: enzyme conjugate. A positive reaction immediately identifies the location and sequence of epitopes present in the protein sequence. This technique has the advantage that all peptides are uniformly linked to the solid support through their carboxy-terminus. While this method allows for very accurate mapping of linear epitopes, the length of the peptides which can be reliably synthesized on the rods is limited. This may sometimes present problems if the length of the epitope exceeds the length of the peptides synthesized.

A second approach to epitope mapping involves the synthesis of larger peptides, generally between fifteen and thirty amino acids in length, along the sequence of the protein to be analyzed. Consecutive peptides may be contiguous but are preferably overlapping. Following cleavage, the evaluation of antibody binding to the individual peptides is assessed and the approximate positions of the epitopes can be identified. An example of this approach is given in Neurath, A. R., Strick, N., and Lee, E. S. Y.; J. Gen. Virol. (1990) 71:85–95. This approach has the advantage that longer peptides can be synthesized which presumably more closely resemble the homologous sequence in the native protein and which offer better targets for antibody binding. The disadvantage of this approach is that each peptide is chemically unique and that the conditions under which each peptide can be optimally coated onto a solid phase for immunological evaluation may vary widely in terms of such factors as pH, ionic strength, and buffer composition. The quantity of peptide which can be adsorbed onto the solid phase is also an uncontrolled factor which is unique for each peptide.

The main purpose of the present invention is to provide modified peptides corresponding to immunologically useful epitopes with said modified peptides having superior immunological properties over non-modified versions of these peptides.

Another aim of the present invention is to provide modified peptides corresponding to immunologically useful epitopes which could not be identified through classical epitope mapping techniques.

Another aim of the present invention is to provide a process for the in vitro determination of antibodies using said peptides, with said process being easy to perform and amenable to standardization.

Another aim of the invention is to provide a process for the determination of peptides corresponding to immunologically important epitopes on bacterial and viral proteins.

Another aim of the invention is to provide a method for preparing protein sequences used in any of said methods.

Another aim of the invention is to provide a method for preparing protein sequence which can be used in a process for the determination of their epitopes or in an in vitro method for the determination of antibodies.

Another aim of the invention is to provide intermediary compounds useful for the preparation of peptides used in the above-mentioned methods.

Another aim of the present invention is also to provide compositions containing peptides determined to correspond to immunologically important epitopes on proteins for diagnostic purposes.

Another aim of the present invention is also to provide compositions containing peptides determined to correspond to immunologically important epitopes on proteins for vaccine purposes.

According to the present invention, a series of biotinylated peptides representing immunologically important regions of viral proteins have been identified and prepared by solid phase peptide synthesis. These peptides have been identified to be very useful for (i) the detection of antibodies to HCV, and/or HIV, and/or HTLV-I or II. In some preferred arrangements, these peptides were also found or are at least expected, to be useful in stimulating the production of antibodies to HCV, and/or HIV, and/or HTLV-I or II in healthy animals such as BALB/C mice, and in a vaccine composition to prevent HCV and/or HIV, and/or HTLV-I or II infection.

As demonstrated in the Examples section of the present invention, the use of biotinylated peptides also allows the determination of immunologically important epitopes within a previously determined protein sequence. The determination of immunologically important epitopes using non-biotinylated peptides, which are covalently coupled to the solid phase, often fails to localize these epitopes. Especially in case of localization of structural epitopes, the use of biotinylated peptides seems to be quite successful.

(1) According to the present invention, a peptide composition useful for the detection of antibodies to HCV, and/or HIV, and/or HTLV-I or II comprise peptides corresponding to immunologically important epitopes being of the structure:

(A)—(B)—(X)—Y-[amino acids]$_n$—Y—(X)—Z where

[amino acids]$_n$ is meant to designate the length of the peptide chain where n is the number of residues, being an integer from about 4 to about 50, preferably less than about 35, more preferably less than about 30, and advantageously from about 4 to about 25;

B represents biotin;

X represents a biotinylated compound which is incorporated during the synthetic process;

Y represents a covalent bond or one or more chemical entities which singly or together form a linker arm separating the amino acids of the peptide proper from the biotinyl moiety B or X, the function of which is to minimize steric hindrance which may interfere with the binding of the biotinyl moiety B or X to avidin or streptavidin, wherein Y is not a covalent bond, it is advantageously at least one chemical entity and may consist of as many as 30 chemical entities but will consist most frequently of 1 to 10 chemical entities, which may be identical or different, more preferably glycine residues, β-alanine, 4-aminobutyric acid, 5-aminovaleric acid, or 6-aminohexanoic acid;

B and X being enclosed in parentheses to indicate that the presence of biotin or a biotinylated compound in these positions is optional, the only stipulation being that B or X be present in at least one of the positions shown;

A, when present, as indicated by parentheses, represents (an) amino acid(s), an amino group, or a chemical modification of the amino terminus of the peptide chain;

Z represents (an) amino acid(s), an OH-group, an NH2-group, or a linkage involving either of these two chemical groups wherein the amino acids are selectively chosen to be immunodominant epitopes which are recognized by a large percentage of true posistive sera or are able to complement other antigens in the test to increase the detection rate and B interacts with the selected amino acids to produce a compound with greater diagnostic senstivity.

The peptide composition comprises at least one and preferably a combination of two, three, four or more biotinylated peptides chosen from the following sequences:

1. Human immunodeficiency Virus type 1 Envelope Peptides:

a. gp41
1. (SEQ ID NO:1) gp41, isolate HTLV-IIIB
(A)-(B)-(X)-Y-Ile-Trp-Gly-Cys-Ser-Gly-Lys-Ile-Cys-Y-(X)-Z
2. (SEQ ID NO:2)
(A)-(B)-(X)-Y-Ile-Trp-Gly-Cys-Ser-Gly-Lys-Leu-Ile-Cys-Thr-Thr-Ala-Val-Pro-Trp-Asn-Ala-Ser-Y-(X)-Z
3. (SEQ ID NO:3)
(A)-(B)-(X)-Y-Glu-Arg-Tyr-Leu-Lys-Asp-Gln-Gln-Leu-Leu-Gly-Ile-Trp-Gly-Cys-Ser-Gly-Lys-Leu-Ile-Y-(X)-Z
4. (SEQ ID NO:4)
(A)-(B)-(X)-Y-Leu-Gln-Ala-Arg-Ile-Leu-Ala-Val-Glu-Arg-Tyr-Leu-Lys-Asp-Gln-Gln-Leu-Y-(X)-Z
5. (SEQ ID NO:5) gp41, isolate Ant70
(A)-(B)-(X)-Y-Leu-Trp-Gly-Cys-Lys-Gly-Lys-Leu-Val-Cys-Y-(X)-Z
6. (SEQ ID NO:6) gp41, isolate ELI
(A)-(B)-(X)-Y-Asp-Gln-Gln-Leu-Leu-Gly-Ile-Trp-Gly-Cys-Ser-Gly-Lys-His-Ile-Cys-Thr-Thr-Asn-Val-Pro-Trp-Asn-Y-(X)-Z b. gp 120
1. (SEQ ID NO:7) Partial V3 loop sequence, consensus
(A)-(B)-(X)-Y-Asn-Asn-Thr-Arg-Lys-Ser-Ile-His-Ile-Gly-Pro-Gly-Arg-Ala-Phe-Tyr-Thr-Thr-Gly-Glu-Ile-Ile-Gly-Y-(X)-Z
1.a. (SEQ ID NO:8) Complete V3 loop sequence, consensus
(A)-(B)-(X)-Y-Cys-Thr-Arg-Pro-Asn-Asn-Thr-Arg-Lys-Ser-Ile-His-Ile-Gly-Pro-Gly-Arg-Ala-Phe-Tyr-Thr-Thr-Gly-Glu-Ile-Ile-Gly-Asp-Ile-Arg-G ln-Ala-His-Cys-Y-(X)-Z -(X)-Z
2. (SEQ ID NO:9) Partial V3 loop sequence, isolate HIV-1 SF2
(A)-(B)-(X)-Y-Asn-Asn-Thr-Arg-Lys-Ser-Ile-Tyr-Ile-Gly-Pro-Gly-Arg-Ala-Phe-His-Thr-Thr-Gly-Arg-Ile-Ile-Gly-Y-(X)-Z
3. (SEQ ID NO:10) Partial V3 loop sequence, isolate HIV-1 SC
(A)-(B)-(X)-Y-Asn-Asn-Thr-Thr-Arg-Ser-Ile-His-Ile-Gly-Pro-Gly-Arg-Ala-Phe-Tyr-Ala-Thr-Gly-Asp-Ile-Ile-Gly-Y-(X)-Z
4. (SEQ ID NO:11) Partial V3 loop sequence, isolate HIV-1 MN
(A)-(B)-(X)-Y-Tyr-Asn-Lys-Arg-Lys-Arg-Ile-His-Ile-Gly-Pro-Gly-Arg-Ala-Phe-Tyr-Thr-Thr-Lys-Asn-Ile-Ile-Gly-Y-(X)-Z
5. Partial V3 loop sequence, isolate HIV-1 RF
(SEQ ID NO:12) (A)-(B)-(X)-Y-Asn-Asn-Thr-Arg-Lys-Ser-Ile-Thr-Lys-Gly-Pro-Gly-Arg-Val-Ile-Tyr-Ala-Thr-Gly-Gln-Ile-Ile-Gly-Y-(X)-Z
6. Partial V3 loop sequence, isolate HIV-1 mal
(SEQ ID NO:13) (A)-(B)-(X)-Y-Asn-Asn-Thr-Arg-Arg-Gly-Ile-His-Phe-Gly-Pro-Gly-Gln-Ala-Leu-Tyr-Thr-Thr-Gly-Ile-Val-Gly-Y-(X)-Z
7. Partial V3 loop sequence, isolate HTLV-IIIB
(SEQ ID NO:14) (A)-(B)-(X)-Y-Asn-Asn-Thr-Arg-Lys-Ser-Ile-Arg-Ile-Gln-Arg-Gly-Pro-Gly-Arg-Ala-Phe-Val-Thr-Ile-Gly-Lys-Ile-Gly-Y-(X)-Z
8. Partial V3 loop sequence, isolate HIV-1 ELI
(SEQ ID NO:15) (A)-(B)-(X)-Y-Gln-Asn-Thr-Arg-Gln-Arg-Thr-Pro-Ile-Gly-Leu-Gly-Gln-Ser-Leu-Tyr-Thr-Thr-Arg-Ser-Arg-Ser-Y-(X)-Z 9. Partial V3 loop sequence, isolate ANT70
(SEQ ID NO:16) (A)-(B)-(X)-Y-Gln-Ile-Asp-Ile-Gln-Glu-Met-Arg-Ile-Gly-Pro-Met-Ala-Trp-Tyr-Ser-Met-Gly-Ile-Gly-Gly-Y-(X)-Z 10. Partial V3 loop sequence, Brazilian isolate, Peptide V3-368
(SEQ ID NO:17) (A)-(B)-(X)-Y-Asn-Asn-Thr-Arg-Arg-Gly-Ile-His-Met-Gly-Trp-Gly-Arg-Thr-Phe-Tyr-Ala-Thr-Gly-Glu-Ile-Ile-Gly-Y-(X)-Z 11. Carboxy-terminus, HIV-1 gp120
(SEQ ID NO:18) (A)-(B)-(X)-Y-Arg-Asp-Asn-Trp-Arg-Ser-Glu-Leu-Tyr-Lys-Tyr-Lys-Val-Val-Lys-Ile-Glu-Pro-Leu-Gly-Val-Ala-Pro -Thr-Lys-Ala-Lys-Arg-Arg-Val-Val-Gln-Arg-Glu-Lys-Arg-Y-(X)-Z 2. Human immunodeficiency Virus type 2 Envelope Peptide
a. gp41, isolate HIV-2 rod
(SEQ ID NO:19) (A)-(B)-(X)-Y-Ser-Trp-Gly-Cys-Ala-Phe-Arg-Gln-Val-Cys-Y-(X)-Z
b.
(SEQ ID NO:20) (A)-(B)-(X)-Y-Lys-Tyr-Leu-Gln-Asp-Gln-Ala-Arg-Leu-Asn-Ser-Trp-Gly-Cys-Ala-Phe-Arg-Gln-Val-Cys-Y-(X)-Z
c. gp120, isolate HIV-2 NIHZ
(SEQ ID NO:21) (A)-(B)-(X)-Y-Asn-Lys-Thr-Val-Leu-Pro-Ile-Thr-Phe-Met-Ser-Gly-Phe-Lys-Phe-His-Ser-Gln-Pro-Val-Ile-Asn-Lys-Y-(X)-Z
d. Partial V3 loop sequence, Peptide V3-GB12
(SEQ ID NO:22) (A)-(B)-(X)-Y-Asn-Lys-Thr-Val-Val-Pro-Ile-Thr-Leu-Met-Ser-Gly-Leu-Val-Phe-His-Ser-Gln-Pro-Ile-Asn-Lys-Y-(X)-Z
e. Partial V3 loop sequence, Peptide V3-239
(SEQ ID NO:23) (A)-(B)-(X)-Y-Asn-Lys-Thr-Val-Leu-Pro-Val-Thr-Ile-Met-Ser-Gly-Leu-Val-Phe-His-Ser-Gln-Pro-Ile-Asn-Asp-Y-(X)-Z 3. Chimpanzee immunodeficiency Virus
a. gp41
(SEQ ID NO:24) (A)-(B)-(X)-Y-Leu-Trp-Gly-Cys-Ser-Gly-Lys-Ala-Val-Cys-Y-(X)-Z 4. Simian immunodeficiency Virus
a. Transmembrane protein, isolate SIVagm(TY01)
(SEQ ID NO:25) (A)-(B)-(X)-Y-Ser-Trp-Gly-Cys-Ala-Trp-Lys-Gln-Val-Cys-Y-(X)-Z.
b. Transmembrane protein, isolate SIVmnd
(SEQ ID NO:26) (A)-(B)-(X)-Y-Gln-Trp-Gly-Cys-Ser-Trp-Ala-Gln-Val-Cys-Y-(X)-Z 5. HTLV-I and HTLV-II Virus
Peptide I-gp46-3
(SEQ ID NO:27) (A)-(B)-(X)-Y-Val-Leu-Tyr-Ser-Pro-Asn-Val-Ser-Val-Pro-Ser-Ser-Ser-Ser-Thr-Leu-Leu-Tyr-Pro-Ser-Leu-Ala-Y-(X)-Z
Peptide I-gp46-5
(SEQ ID NO:28) (A)-(B)-(X)-Y-Tyr-Thr-Cys-Ile-Val-Cys-Ile-Asp-Arg-Ala-Ser-Leu-Ser-Thr-Trp-His-Val-Leu-Tyr-Ser-Pro-Y-(X)-Z
Peptide I-gp46-4
(SEQ ID NO:29) (A)-(B)-(X)-Y-Asn-Ser-Leu-Ile-Leu-Pro-Pro-Phe-Ser-Leu-Ser-Pro-Val-Pro-Thr-Leu-Gly-Ser-Arg-Ser-Arg-Arg-Y-(X)-Z
Peptide I-gp46-6
(SEQ ID NO:30) (A)-(B)-(X)-Y-Asp-Ala-Pro-Gly-Tyr-Asp-Pro-Ile-Trp-Phe-Leu-Asn-Thr-Glu-Pro-Ser-Gln-Leu-Pro-Pro-Thr-Ala-Pro-Pro-Leu -Leu-Pro-His-Ser-Asn-Leu-Asp-His-Ile-Leu-Glu-Y-(X)-Z
Peptide I-p21-2
(SEQ ID NO:31) (A)-(B)-(X)-Y-Gln-Tyr-Ala-Ala-Gln-Asn-Arg-Arg-Gly-Leu-Asp-Leu-Leu-Phe-Trp-Glu-Gln-Gly-Gly-Leu-Cys-Lys-Ala-Leu-Gln -Glu-Gln-Cys-Arg-Phe-Pro-Y-(X)-Z Peptide I-p19
(SEQ ID NO:32) (A)-(B)-(X)-Y-Pro-Pro-Pro-Pro-Ser-Ser-Pro-Thr-His-Asp-Pro-Pro-Asp-Ser-Asp-Pro-Gln-Ile-Pro-Pro-Pro-Tyr-Val-Glu-Pro -Thr-Ala-Pro-Gln-Val-Leu-Y-(X)-Z
Peptide II-gp52-1
(SEQ ID NO:33) (A)-(B)-(X)-Y-Lys-Lys-Pro-Asn-Arg-Gln-Gly-Leu-Gly-Tyr-Tyr-Ser-Pro-Ser-Tyr-Asn-Asp-Pro-Y-(X)-Z
Peptide II-gp52-2
(SEQ ID NO:34) (A)-(B)-(X)-Y-Asp-Ala-Pro-Gly-Tyr-Asp-Pro-Leu-Trp-Phe-Ile-Thr-Ser-Glu-Pro-Thr-Gln-Pro-Pro-Pro-Thr-Ser-Pro-Pro-Leu -Val-His-Asp-Ser-Asp-Leu-Glu-His-Val-Leu-Thr-Y-(X)-Z
Peptide II-gp52-3:
(SEQ ID NO:35) (A)-(B)-(X)-Y-Tyr-Ser-Cys-Met-Val-Cys-Val-Asp-Arg-Ser-Ser-Leu-Ser-Ser-Trp-His-Val-Leu-Tyr-Thr-Pro-Asn-Ile-Ser-Ile -Pro-Gln-Gln-Thr-Ser-Ser-Arg-Thr-Ile-Leu-Phe-Pro-Ser-Y-(X)-Z
Peptide II-p19
(SEQ ID NO:36) (A)-(B)-(X)-Y-Pro-Thr-Thr-Pro-Pro-Pro-Pro-Pro-Pro-Ser-Pro-Glu-Ala-His-Val-Pro-Pro-Pro-Tyr-Val-Glu-Pro-Thr -Thr-Thr-Gln-Cys-Phe-Y-(X)-Z These above-mentioned biotinylated peptides were synthesized and found to be specifically recognized by antisera from infected humans or primates are considered particularly advantageous. All these above-mentioned peptides are new.

The process of the invention enables to increase the antigenicity of these HIV peptides, which can however be bound to a support, even when they are not biotinylated.

The HCV peptide sequences which follow have been found to be specifically recognized by antisera from infected humans or primates and which are considered particularly advantageous. The non-biotinylated amino acid sequences can be synthesized according to classical methods.

The peptides of interest are intended to mimic immunologically proteins or domains of proteins encoded by HCV. Since sequence variability has been observed for HCV, it may be desirable to vary one or more amino acids so as to better mimic the epitopes of different strains. It should be understood that the peptides described need not be identical to any particular HCV sequence as long as the subject compounds are capable of providing for immunological competition with at least one strain of HCV. The peptides may therefore be subject to insertions, deletions and conservative as well as non-conservative amino acid substitutions where such changes might provide for certain advantages in their use. The peptides will preferably be as short as possible while still maintaining all of the sensitivity of the larger sequence. In certain cases, it may be desirable to join two or more peptides together into a single structure. The formation of such a composite may involve covalent or non-covalent linkages.

Of particular interest are biotinylated peptides of HCV into which cysteine, thioglycollic acid, or other thiol-containing compounds have been incorporated into the peptide chain for the purpose of providing mercapto-groups which can be used for cyclization of the peptides.

The following peptides from the Core region of HCV were determined as corresponding to immunologically important epitopes.

1. Peptide I or Core 1 (aa. 1–20) has the following amino acid sequence:
(I)
(SEQ ID NO:37) (A)-(B)-(X)-Y-Met-Ser-Thr-Ile-Pro-Lys-Pro-Gln-Arg-Lys-Thr-Lys-Arg-Asn-Thr-Asn-Arg-Arg-Pro-Gln-Y-(X)-Z 2. Peptide II or Core 2 (aa. 7–26) has the amino acid sequence:
(II)
(SEQ ID NO:38) (A)-(B)-(X)-Y-Pro-Gln-Arg-Lys-Thr-Lys-Arg-Asn-Thr-Asn-Arg-Arg-Pro-Gln-Asp-Val-Lys-Phe-Pro-Gly-Y-(X)-Z Of particular interest is the oligopeptide IIA (aa. 8 to 18):
(IIA)
(SEQ ID NO:39) (A)-(B)-(X)-Y-Gln-Arg-Lys-Thr-Lys-Arg-Asn-Thr-Asn-Arg-Arg-Y-(X)-Z.

3. Peptide III or Core 3 (aa 13–32) has the sequence:
(III)
(SEQ ID NO:40) (A)-(B)-(X)-Y-Arg-Asn-Thr-Asn-Arg-Arg-Pro-Gln-Asp-Val-Lys-Phe-Pro-Gly-Gly-Gly-Gln-Ile-Val-Gly-Y-(X)-Z 4. Peptide IV or Core 7 (aa 37–56) has the sequences:
(IV)
(SEQ ID NO:41) (A)-(B)-(X)-Y-Leu-Pro-Arg-Arg-Gly-Pro-Arg-Leu-Gly-Val-Arg-Ala-Thr-Arg-Lys-Thr-Ser-Glu-Arg-Ser-Y-(X)-Z Of particular interest is the oligopeptide IVa or Core 6 (aa. 31 to 50):
(IVa)
(SEQ ID NO:42) (A)-(B)-(X)-Y-Val-Gly-Gly-Val-Tyr-Leu-Leu-Pro-Arg-Arg-Gly-Pro-Arg-Leu-Gly-Val-Arg-Ala-Thr-Arg-Y-(X)-Z 5. Peptide V or Core 9 (aa 49–68) has the sequence:
(V)
(SEQ ID NO:43) (A)-(B)-(X)-Y-Thr-Arg-Lys-Thr-Ser-Glu-Arg-Ser-Gln-Pro-Arg-Gly-Arg-Arg-Gln-Pro-Ile-Pro-Lys-Val-Y-(X)-Z Of particular interest is the oligopeptide Va (aa. 55 to 74):
(Va)
(SEQ ID NO:44) (A)-(B)-(X)-Y-Arg-Ser-Gln-Pro-Arg-Gly-Arg-Arg-Gln-Pro-Ile-Pro-Lys-Val-Arg-Arg-Pro-Glu-Gly-Arg-Y-(X)-Z 6. Peptide VI or Core 11 (aa 61–80) has the following sequence:
(VI)
(SEQ ID NO:45) (A)-(B)-(X)-Y-Arg-Arg-Gln-Pro-Ile-Pro-Lys-Val-Arg-Arg-Pro-Glu-Gly-Arg-Thr-Trp-Ala-Gln-Pro-Gly-Y-(X)-Z 7. Peptide VII (aa 73–92) or core 13 has the sequence:
(VII)
(SEQ ID NO:46) (A)-(B)-(X)-Y-Gly-Arg-Thr-Trp-Ala-Gln-Pro-Gly-Tyr-Pro-Trp-Pro-Leu-Tyr-Gly-Asn-Glu-Gly-Cys-Gly-Y-(X)-Z 8. Peptide Core 123 (aa. 1–32):
(SEQ ID NO:47) (A)-(B)-(X)-Y-Met-Ser-Thr-Ile-Pro-Gln-Arg-Lys-Thr-Lys-Arg-Asn-Thr-Asn-Arg-Arg-Pro-Gln-Asp-Val-Lys-Phe-Pro-Gly-Gly-Gly -Gln-Ile-Val-Gly-Y-(X)-Z 9. Peptide Core 7910 (aa. 37–80):
(SEQ ID NO:48) (A)-(B)-(X)-Y-Gly-Gly-Val-Tyr-Leu-Leu-Pro-Arg-Arg-Gly-Pro-Arg-Leu-Gly-Val-Arg-Arg-Ala-Thr-Arg-Lys-Thr-Ser-Glu-Arg -Ser-Gln-Pro-Arg-Gly-Arg-Arg-Gln-Pro-Ile-Pro-Lys-Val-Arg-Arg-Y-(X)-Z The following peptides from the NS4 region of HCV were found to correspond to immunologically important epitopes.
Peptide VIII or NS4-1 or HCV1 (aa 1688–1707) has the sequence:
(VIII)
(SEQ ID NO:49) (A)-(B)-(X)-Y-Leu-Ser-Gly-Lys-Pro-Ala-Ile-Ile-Pro-Asp-Arg-Glu-Val-Leu-Tyr-Arg-Glu-Phe-Asp-Glu-Y-(X)-Z Peptide IX or HCV2 (aa 1694–1713) has the sequence:
(IX)
(SEQ ID NO:50) (A)-(B)-(X)-Y-Ile-Ile-Pro-Asp-Arg-Glu-Val-Leu-Tyr-Arg-Glu-Phe-Asp-Glu-Met-Glu-Glu-Cys-Ser-Gln-Y-(X)-Z Peptide HCV3
(SEQ ID NO:51) (A)-(B)-(X)-Y-Val-Leu-Tyr-Arg-Glu-Phe-Asp-Glu-Met-Glu-Glu-Cys-Ser-Gln-His-Leu-Pro-Tyr-Ile-Glu-Y-(X)-Z Peptide X or HCV4 (aa 1706–1725) has the sequence:
(X)
(SEQ ID NO:52) (A)-(B)-(X)-Y-Asp-Glu-Met-Glu-Glu-Cys-Ser-Gln-His-Leu-Pro-Tyr-Ile-Glu-Gln-Gly-Met-Met-Leu-Ala-Y-(X)-Z 11. Peptide XI or NS4-5 or HCV5 (aa 1712–1731) has the sequence:
(XI)
(SEQ ID NO:53) (A)-(B)-(X)-Y-Ser-Gln-His-Leu-Pro-Tyr-Ile-Glu-Gln-Gly-Met-Met-Leu-Ala-Glu-Gln-Phe-Lys-Gln-Lys-Y-(X)-Z 12. Peptide XII or HCV6 (aa 1718–1737) has the sequence:
(XII)
(SEQ ID NO:54) (A)-(B)-(X)-Y-Ile-Glu-Gln-Gly-Met-Met-Leu-Ala-Glu-Gln-Phe-Lys-Gln-Lys-Ala-Leu-Gly-Leu-Leu-Gln-Y-(X)-Z 13. Peptide XIII or NS4-7 or HCV7 (aa 1724–1743) has the sequence:
(XIII)
(SEQ ID NO:55) (A)-(B)-(X)-Y-Leu-Ala-Glu-Gln-Phe-Lys-Gln-Lys-Ala-Leu-Gly-Leu-Leu-Gln-Thr-Ala-Ser-Arg-Gln-Ala-Y-(X)-Z 14. Peptide XIV or HCV8 (aa 1730–1749) has the sequence:
(XIV)
(SEQ ID NO:56) (A)-(B)-(X)-Y-Gln-Lys-Ala-Leu-Gly-Leu-Leu-Gln-Thr-Ala-Ser-Arg-Gln-Ala-Glu-Val-Ile-Ala-Pro-Ala-Y-(X)-Z 15. Peptide NS4-27 or HCV9 (aa. 1712–1743):
(SEQ ID NO:57) (A)-(B)-(X)-Y-Ser-Gln-His-Leu-Pro-Tyr-Ile-Glu-Gln-Glu-Met-Leu-Ala-Glu-Gln-Phe-Lys-Gln-Lys-Ala-Leu-Gly-Leu-Leu-Gln -Thr-Ala-Ser-Arg-Gln-Ala-Y-(X)-Z 16. Peptide NS4e:
(SEQ ID NO:58) (A)-(B)-(X)-Y-Gly-Glu-Gly-Ala-Val-Gln-Trp-Met-Asn-Arg-Leu-Ile-Ala-Phe-Ala-Ser-Arg-Gly-Asn-His-Y-(X)-Z The following peptides of the NS5 region of HCV were found to correspond to immunologically important epitopes.
Peptide XV or NS5-25 (aa 2263–2282) has the sequence:
(XV)
(SEQ ID NO:59) (A)-(B)-(X)-Y-Glu-Asp-Glu-Arg-Glu-Ile-Ser-Val-Pro-Ala-Glu-Ile-Leu-Arg-Lys-Ser-Arg-Arg-Phe-Ala-Y-(X)-Z Peptide XVI or NS5-27 (aa 2275–2294) has the sequence:
(XVI)
(SEQ ID NO:60) (A)-(B)-(X)-Y-Leu-Arg-Lys-Ser-Arg-Arg-Phe-Ala-Gln-Ala-Leu-Pro-Val-Trp-Ala-Arg-Pro-Asp-Tyr-Asn-Y-(X)-Z Peptide XVII or NS5-29 (aa 2287–2306) has the sequence:
(XVII)
(SEQ ID NO:61) (A)-(B)-(X)-Y-Val-Trp-Ala-Arg-Pro-Asp-Tyr-Asn-Pro-Pro-Leu-Val-Glu-Thr-Trp-Lys-Lys-Pro-Asp-Tyr-Y-(X)-Z Peptide XVIII or NS5-31 (aa 2299–2318) has the sequence:
(XVIII)
(SEQ ID NO:62) (A)-(B)-(X)-Y-Glu-Thr-Trp-Lys-Lys-Pro-Asp-Tyr-Glu-Pro-Pro-Val-Val-His-Gly-Cys-Pro-Leu-Pro-Pro-Y-(X)-Z Peptide XIX or NS5-33(aa 2311–2330) has the sequence:
(XIX)

(SEQ ID NO:63) (A)-(B)-(X)-Y-Val-His-Gly-Cys-Pro-Leu-Pro-Pro-Pro-Lys-Ser-Pro-Pro-Val-Pro-Pro-Pro-Arg-Lys-Lys-Y-(X)-Z

Peptide NS5-2527 (aa. 2263 to 2294):

(SEQ ID NO:64) (A)-(B)-(X)-Y-Glu-Asp-Glu-Arg-Glu-Ile-Ser-Val-Pro-Ala-Glu-Ile-Leu-Arg-Lys-ser-Arg-Lys-ser-Arg-Arg-Phe-Ala-Gln-Ala-Leu -Pro-Val-Trp-Ala-Arg-Pro-Asp-Tyr-Asp-Tyr-Asn-Y-(X)-Z The following peptides from the N-terminal region of the E2/NS1 region of HCV were found to correspond to immunologically important epitopes.

peptide XXa (aa. 383–416)

(SEQ ID NO:65) (A)-(B-(X)-Y-Gly-Glu-Thr-Tyr-Thr-Ser-Gly-Gly-Ala-Ala-Ser-His-Thr-Thr-Ser-Thr-Leu-Ala-Ser-Leu-Phe-Ser-Pro-Gly-Ala -Ser-Gln-Arg-Ile-Gln-Leu-Val-Asn-Thr-Y-(X)-Z peptide XXa-1 (aa. 383–404)

(SEQ ID NO:66) (A)-(B)-(X)-Y-Gly-Glu-Thr-Tyr-Thr-Ser-Gly-Gly-Ala-Ala-Ser-His-Thr-Thr-Ser-Thr-Leu-Ala-Ser-Leu-Phe-Ser-Y-(X)-Z peptide XXa-2 (aa. 393–416)

(SEQ ID NO:67) (A)-(B)-(X)-Y-Ser-His-Thr-Thr-Ser-Thr-Leu-Ala-Ser-Leu-Phe-Ser-Pro-Gly-Ala-Ser-Gln-Arg-Ile-Gln-Leu-Val-Asn-Thr-Y-(X)-Z peptide XXb (aa. 383–416)

(SEQ ID NO:68) (A)-(B)-(X)-Y-Gly-His-Thr-Arg-Val-Ser-Gly-Gly-Ala-Ala-Ala-Ser-Asp-Thr-Arg-Gly-Leu-Val-ser-Leu-Phe-Ser-Pro-Gly-Ser-Ala -Gln-Lys-Ile-Gln-Leu-Val-Asn-Thr-Y-(X)-Z peptide XXb-1 (aa. 383–404)

(SEQ ID NO:69) (A)-(B)-(X)-Y-Gly-His-Thr-Arg-Val-Ser-Gly-Gly-Ala-Ala-Ala-Ser-Asp-Thr-Arg-Gly-Leu-Val-Ser-Leu-Phe-Ser-Y-(X)-Z peptide XXb-2 (aa. 393–416)

(SEQ ID NO:70) (A)-(B)-(X)-Y-Ala-Ser-Asp-Thr-Arg-Gly-Leu-Val-Ser-Leu-Phe-Ser-Pro-Gly-Ser-Ala-Gln-Lys-Ile-Gln-Leu-Val-Asn-Thr-Y-(X)-Z peptide XXc (aa. 383–416)

(SEQ ID NO:71) (A)-(B)-(X)-Y-Gly-His-Thr-Arg-Val-Thr-Gly-Gly-Val-Gln-Gly-His-Val-Thr-Cys-Thr-Leu-Thr-Ser-Leu-Phe-Arg-Pro-Gly-Ala-Ser -Gln-Lys-Ile-Gln-Leu-Val-Asn-Thr-Y-(X)-Z peptide XXc-1 (aa. 383–404)

(SEQ ID NO:72) (A)-(B)-(X)-Y-Gly-His-Thr-Arg-Val-Thr-Gly-Gly-Val-Gln-Gly-His-Val-Thr-Cys-Thr-Leu-Thr-Ser-Leu-Phe-Arg-Y-(X)-Z peptide XXc-2 (aa. 393–416)

(SEQ ID NO:73) (A)-(B)-(X)-Y-Gly-His-Val-Thr-Cys-Thr-Leu-Thr-Ser-Leu-Phe-Arg-Pro-Gly-Ala-Ser-Gln-Lys-Ile-Gln-Leu-Val-Asn-Thr-Y-(X)-Z peptide XXd (aa. 383–416)

(SEQ ID NO:74) (A)-(B)-(X)-Y-Gly-His-Thr-His-Val-Thr-Gly-Gly-Arg-Val-Ala-Ser-Ser-Thr-Gln-Ser-Leu-Val-Ser-Trp-Leu-ser-Gln-Gly-Pro-Ser -Gln-Lys-Ile-Gln-Leu-Val-Asn-Thr-Y-(X)-Z peptide XXd-1 (aa. 383–404)

(SEQ ID NO:75) (A)-(B)-(X)-Y-Gly-His-Thr-His-Val-Thr-Gly-Gly-Arg-Val-Ala-Ser-Ser-Thr-Gln-Ser-Leu-Val-Ser-Trp-Leu-Ser-Y-(X)-Z peptide XXd-2 (aa. 393–416)

(SEQ ID NO:76) (A)-(B)-(X)-Y-Ala-Ser-Ser-Thr-Gln-Ser-Leu-Val-Ser-Trp-Leu-Ser-Gln-Gly-Pro-Ser-Gln-Lys-Ile-Gln-Leu-Val-Asn-Thr-Y-(X)-Z peptide XXe (aa. 383–416)

(SEQ ID NO:77) (A)-(B)-(X)-Y-Gly-Asp-Thr-His-Val-Thr-Gly-Gly-Ala-Gln-Ala-Lys-Thr-Thr-Asn-Arg-Leu-Val-Ser-Met-Phe-Ala-Ser-Gly-Pro-Ser -Gln-Lys-Ile-Gln-Leu-Ile-Asn-Thr-Y-(X)-Z peptide XXe-1 (aa. 383–404)

(SEQ ID NO:78) (A)-(B)-(X)-Y-Gly-Asp-Thr-His-Val-Thr-Gly-Gly-Ala-Gln-Ala-Lys-Thr-Thr-Asn-Arg-Leu-Val-Ser-Met-Phe-Ala-Y-(X)-Z peptide XXe-2 (aa. 393–416)

(SEQ ID NO:79) (A)-(B)-(X)-Y-Ala-Lys-Thr-Thr-Asn-Arg-Leu-Val-Ser-Met-Phe-Ala-Ser-Gly-Pro-Ser-Gln-Lys-Ile-Gln-Leu-Ile-Asn-Thr-Y-(X)-Z peptide XXf (aa. 383–416)

(SEQ ID NO:80) (A)-(B)-(X)-Y-Ala-Glu-Thr-Tyr-Thr-Ser-Gly-Gly-Asn-Ala-Gly-His-Thr-Met-Thr-Gly-Ile-Val-Arg-Phe-Phe-Ala-Pro-Gly-Pro-Lys -Gln-Asn-Val-His-Leu-Ile-Asn-Thr-Y-(X)-Z peptide XXf-1 (aa. 383–404)

(SEQ ID NO:81) (A)-(B)-(X)-Y-Ala-Glu-Thr-Tyr-Thr-Ser-Gly-Gly-Asn-Ala-Gly-His-Thr-Met-Thr-Gly-Ile-Val-Arg-Phe-Phe-Ala-Y-(X)-Z peptide XXf-2 (aa. 393–416)

(SEQ ID NO:82) (A)-(B)-(X)-Y-Gly-His-Thr-Met-Thr-Gly-Ile-Val-Arg-Phe-Phe-Ala-Pro-Gly-Pro-Lys-Gln-Asn-Val-His-Leu-Ile-Asn-Thr-Y-(X)-Z peptide XXg (aa. 383–416)

(SEQ ID NO:83) (A)-(B)-(X)-Y-Ala-Glu-Thr-Ile-Val-Ser-Gly-Gly-Gln-Ala-Ala-Arg-Ala-Met-Ser-Gly-Leu-Val-Ser-Leu-Phe-Thr-Pro-Gly-Ala-Lys -Gln-Asn-Ile-Gln-Leu-Ile-Asn-Thr-Y-(X)-Z peptide XXg-1 (aa. 383–404)

(SEQ ID NO:84) (A)-(B)-(X)-Y-Ala-Glu-Thr-Ile-Val-Ser-Gly-Gly-Gln-Ala-Ala-Arg-Ala-Met-Ser-Gly-Leu-Val-Ser-Leu-Phe-Thr-Y-(X)-Z peptide XXg-2 (aa. 393–416)

(SEQ ID NO:85) (A)-(B)-(X)-Y-Ala-Arg-Ala-Met-Ser-Gly-Leu-Val-Ser-Leu-Phe-Thr-Pro-Gly-Ala-Lys-Gln-Asn-Ile-Gln-Leu-Ile-Asn-Thr-Y-(X)-Z peptide XXh (aa. 383–416)

(SEQ ID NO:86) (A)-(B)-(X)-Y-Ala-Glu-Thr-Tyr-Thr-Thr-Gly-Gly-Ser-Thr-Ala-Arg-Thr-Thr-Gln-Gly-Leu-Val-Ser-Leu-Phe-Ser-Arg-Gly-Ala-Lys -Gln-Asp-Ile-Gln-Leu-Iie-Asn-Thr-Y-(X)-Z peptide XXh-1 (aa. 383–404)

(SEQ ID NO:87) (A)-(B)-(X)-Y-Ala-Glu-Thr-Tyr-Thr-Thr-Gly-Gly-Ser-Thr-Ala-Arg-Thr-Thr-Gln-Gly-Leu-Val-Ser-Leu-Phe-Ser-Y-(X)-Z peptide XXh-2 (aa. 393–416)

(SEQ ID NO:88) (A)-(B)-(X)-Y-Ala-Arg-Thr-Thr-Gln-Gly-Leu-Val-Ser-Leu-Phe-Ser-Arg-Gly-Ala-Lys-Gln-Asp-Ile-Gln-Leu-Ile-Asn-Thr-Y-(X)-Z

The above-mentioned sequences correspond to epitopes localized on the HCV type-1 isolate HCV-1 (Choo et al. Proc; Natl. Acad. Sci. 88, 2451–2455, 1991) and HC-J1 (Okamoto et al., Jap. J. Exp. Med. 60, 167–177, 1990) sequence. It is, however, to be understood that also peptides from other type-1 HCV isolate sequences which correspond to the above-mentioned immunologically important regions may also be comprised in the composition according to the invention. An example of variant HCV sequences also falling within the present invention may be derived from the HCV-J isolate (Kato et al., Proc. Natl. Acad. Sci. 87, 9524–9528).

The following peptides derived from the same regions as the above-cited peptide regions from the type 2 HCV sequences.

peptide XX/2

(SEQ ID NO:89) (A)-(B)-(X)-Y-Ala-Gln-Thr-His-Thr-Val-Gly-Gly-Ser-Thr-Ala-His-Asn-Ala-Arg-Thr-Leu-Thr-Gly-Met-Phe-Ser-Leu-Gly-Ala-Arg -Gln-Lys-Ile-Gln-Leu-Ile-Asn-Thr-Y-(X)-Z peptide XX/2-1

(SEQ ID NO:90) (A)-(B)-(X)-Y-Ala-Gln-Thr-His-Thr-Val-Gly-Gly-Ser-Thr-Ala-His-Asn-Ala-Arg-Thr-Leu-Thr-Gly-Met-Phe-Ser-Y-(X)-Z peptide XX/2-2

(SEQ ID NO:91) (A)-(B)-(X)-Y-Ala-His-Asn-Ala-Arg-Thr-Leu-Thr-Gly-Met-Phe-Ser-Leu-Gly-Ala-Arg-Gln-Lys-Ile-Gln-Leu-Ile-Asn-Thr-Y-(X)-Z peptide VIII-2 or NS4-1 (2)

(SEQ ID NO:92) (A)-(B)-(X)-Y-Val-Asn-Gln-Arg-Ala-Val-Val-Ala-Pro-Asp-Lys-Glu-Val-Leu-Tyr-Glu-Ala-Phe-Asp-Glu-Y-(X)-Z peptide IX-2

(SEQ ID NO:93) (A)-(B)-(X)-Y-Val-Ala-Pro-Asp-Lys-Glu-Val-Leu-Tyr-Glu-Ala-Phe-Asp-Glu-Met-Glu-Glu-Cys-Ala-Ser-Y-(X)-Z peptide X-2

(SEQ ID NO:94) (A)-(B)-(X)-Y-Asp-Glu-Met-Glu-Glu-Cys-Ala-Ser-Arg-Ala-Ala-Leu-Ile-Glu-Glu-Gly-Gln-Arg-Ile-Ala-Y-(X)-Z peptide XI-2 or NS4-5 (2)

(SEQ ID NO:95) (A)-(B)-(X)-Y-Ala-Ser-Arg-Ala-Ala-Leu-Ile-Glu-Glu-Gly-Gln-Arg-Ile-Ala-Glu-Met-Leu-Lys-Ser-Lys-Y-(X)-Z peptide XII-2

(SEQ ID NO:96) (A)-(B)-(X)-Y-Ile-Glu-Glu-Gly-Gln-Arg-Ile-Ala-Glu-Met-Leu-Lys-Ser-Lys-Ile-Gln-Gly-Leu-Leu-Gln-Y-(X)-Z peptide XIII-2 or NS4-7(2)

(SEQ ID NO:97) (A)-(B)-(X)-Y-Ile-Ala-Glu-Met-Leu-Lys-Ser-Lys-Ile-Gln-Gly-Leu-Leu-Gln-Gln-Ala-Ser-Lys-Gln-Ala-Y-(X)-Z peptide XIV-2

(SEQ ID NO:98) (A)-(B)-(X)-Y-Ser-Lys-Ile-Gln-Gly-Leu-Leu-Gln-Gln-Ala-Ser-Lys-Gln-Ala-Gln-Asp-Ile-Gln-Pro-Ala-Y-(X)-Z peptide XV-2

(SEQ ID NO:99) (A)-(B)-(X)-Y-Arg-Ser-Asp-Leu-Glu-Pro-Ser-Ile-Pro-Ser-Glu-Tyr-Met-Leu-Pro-Lys-Lys-Arg-Phe-Pro-(X)-Y-Z peptide XVI-2

(SEQ ID NO:100) (A)-(B)-(X)-Y-Met-Leu-Pro-Lys-Lys-Arg-Phe-Pro-Pro-Ala-Leu-Pro-Ala-Trp-Ala-Arg-Pro-Asp-Tyr-Asn-Y-(X)-Z peptide XVII-2

(SEQ ID NO:101) (A)-(B)-(X)-Y-Ala-Trp-Ala-Arg-Pro-Asp-Tyr-Asn-Pro-Pro-Leu-Val-Glu-Ser-Trp-Lys-Arg-Pro-Asp-Tyr-Y-(X)-Z peptide XVIII-2

(SEQ ID NO:102) (A)-(B)-(X)-Y-Glu-Ser-Trp-Lys-Arg-Pro-Asp-Tyr-Gln-Pro-Ala-Thr-Val-Ala-Gly-Cys-Ala-Leu-Pro-Pro-Y-(X)-Z peptide XIX-2

(SEQ ID NO:103) (A)-(B)-(X)-Y-Val-Ala-Gly-Cys-Ala-Leu-Pro-Pro-Pro-Lys-Lys-Thr-Pro-Thr-Pro-Pro-Pro-Arg-Arg-Y-(X)-Z

The above-mentioned sequences correspond to epitopes localized on the HCV type-2 isolate HC-J6 sequence (Okamoto et al., J. Gen. Virology 72, 2697–2704, 1991). It is, however, to be understood that also peptides from other type-2 HCV isolate sequences which correspond to the above-mentioned immunologically important regions may also be comprised in the composition according to the invention. Examples of variant sequences also falling within the present invention may be derived from HCV isolate HC-J8 (Okamato et al., Virology 188, 331–341, 1992).

The following peptides from the NS4 region of HCV type 3 are also preferred peptides according to the present invention:

Peptide NS4-1 (3)

(SEQ ID NO:107) (A)-(B)-(X)-Y-Leu-Gly-Gly-Lys-Pro-Ala-Ile-Val-Pro-Asp-Lys-Glu-Val-leu-Tyr-Gln-Gln-Tyr-Asp-Glu-Y-(X)-Z Peptide NS4-5 (3)

(SEQ ID NO:108) (A)-(B)-(X)-Y-Ser-Gln-Ala-Ala-Pro-Tyr-Ile-Glu-Gln-Ala-Gln-Val-Ile-Ala-His-Gln-Phe-Lys-Glu-Lys-Y-(X)-Z

Peptide NS4-7 (3)

(SEQ ID NO:109) (A)-(B)-(X)-Y-Ile-Ala-His-Gln-His-Gln-Phe-Lys-Glu-Lys-Val-Leu-Gly-Leu-Leu-Gln-Arg-Ala-Thr-Gln-Gln-Gln-Y-(X)-Z

It is to be understood that also other peptides corresponding to HCV type-3 isolate sequences which correspond to immunologically important regions as determined for HCV type-1 and type-2 may also be comprised in the composition according to the invention.

The composition according to the present invention may also comprise hybrid HCV peptide sequences consisting of combinations of the core epitopes of the HCV core (table 9) HCV NS4 (table 10) or th HCV NS5 (table 11) region separated by Gly and/or Ser residues, and preferentially the following hybrid HCV sequences:

Epi-152

(SEQ ID NO:104) (A)-(B)-(X)-Y-Ile-Pro-Asp-Arg-Glu-Val-leu-Tyr-Arg-Gly-Gly-Lys-Pro-Asp-Tyr-Glu-Pro-Pro-Val-Gyl-Gyl-Arg-Arg-Pro-Gln-Asp-Val-Lys-Phe-Pro-Y-(X)-Z Epi-33B3A (SEQ ID NO:105) (A)-(B)-(X)-Y-Trp-Ala-Arg-Pro-Asp-Tyr-Asn-Pro-Pro-Gly-Gly-Gln-Phe-Lys-Gln-Lys-Ala-Leu-Gyl-Leu-Gyl-Ser-Gyl-Ser-Gly-Val-Tyr-Leu-Leu-Pro-Arg-Arg-Gyl-Y-(X)-Z Epi-4B2A6

(SEQ ID NO:106) (A)-(B)-(X)-Y-Arg-Gyl-Arg-Gly-Arg-Arg-Gln-Pro-Ile-Pro-Lys-Gly-Gly-Ser-Gln-His-Leu-Pro-Tyr-Ile-Glu-Gln-Ser-Gly-Pro-Val-Val-His-Gly-Cys-Pro-Leu-Pro-Y-(X)-Z

The composition according to the present invention may also comprise so called biotinylated mixotope sequences amino acids found in the naturally occurring isolates, with said peptidees being derived from any of the above-mentioned immuologically important regions (see FIG. 14).

(2) A preferred mixture of biotinylated peptides for detecting and/or immunizing against Hepatitis C virus, Human Immunodeficiency Virus type 1 and Human Immunodeficiency Virus type 2 consists of:

A. II, III, IVa, Va, IX, XI, XIII, XV, XVI, XVIII, 1a.3, 1a.4, 1a.b, 1b.1a, 2b, 2d,

B. II, III, IVa, Va, IX, XI-2, XI, XI-2, XIII, XIII-2,XV, XV-2, XVI, XVI-2, XVIII, XVIII-2, 1a.3, 1a.4, 1a.b, 1b.1a, 2b, 2d.

(3) A preferred mixture of biotinylated peptides for detecting and/or immunizing against Human Immunodeficiency Virus type 1 and type 2 Human Lymphotropic Virus Types I and II consists of:

1a.3, 1a.4, 1b.1, 2b, 2c, 2d, I-gp46-3, I-gp46-4, I-gp46-5, I-gp46-6, II-gp52-2, II-gp52-3, I-p21-2, I-p19, II-p19.

(4) Another preferred mixture of biotinylated peptides for detecting and/or immunizing against Hepatitis C Virus, Human Immunodeficiency Virus types 1 and 2 and Human Lymphotropic Virus types I and II consists of:

1a.3, 1a.4, 1a.6, 1b.1a, 2d, II, III, IVa, Va, IX, XI, XIII, Xv, XVI, XVIII, XXa-2, XXc-2, XXg-2, XXh-2, I-gp46-3, I-gp46-4, I-gp46-5, I-gp46-6, II-gp52-3, I-p21-2, I-p19, II-p19.

(5) The present invention relates also to compositions of biotinylated peptides which are considered particularly advantageous, for diagnostic as well as immunogenic purposes for Hepatitis C Virus, and which advantageously comprise the following mixtures:

A. I, III, IVa, Va,

B. II, III, IVa, Va,

C. IX, XI, XIII,

D. XV, XVI, XVIII, XIX,

E. XXc-2, XXa-1, XXa-2, XXh-1, XXh-2, XXg-2, XX/2-2,

F. IX-2, XI-2, XIII-2,

G. XV-2, XVI-2, XVIII-2, XIX-2,

H. IX, IX-2, XI, XI-2, XIII, XIII-2,

I. XV, XV-2, XVI, XVI-2, XVIII, XVIII-2, XIX, XIX-2,

J. II, III, IVa, Va, IX, IX-2, XI, XI-2, XIII, XIII-2, XV, XV-2, XVI, XVI-2, XVIII, XVIII-2,

K. II, III, IVa, Va, IX, XI, XIII, XV, XVI, XVIII,

L. II, III, IV, V, IX, XI, XIII, XV, XVI, XVIII,

M. II, III, IVa, Va, IX, XI, XIII, XV, XVI, XVIII, XXa-2, XXc-2, XXg-2, XXh-2.

(6) The present invention relates also to compositions of biotinylated peptides which are considered particularly advantageous, for diagnostic as well as immunogenic purposes for Human Immunodeficiency Virus, and which are advantageously selected from the following mixtures: for type 1:

A. 1a.3, 1a.4, 1a.5, 1a.b

B. 1a.3, 1a.4, 1b.1, 1b.3, 1b.6, 1b.10,

C. 1b.1, 1b.2, 1b.3, 1b.4, 1b.5, 1b.6, 1b.7, 1b.8, 1b.9, 1b.10

D. 1b.1, 1b.2, 1b.3, 1b.4, 1b.6, 1b.10,

E. 1a.3, 1a.4, 1a.5, 1a.b, 1b.1a. for type 2:

A. 2b, 2c, 2d, 2e. for types 1 and 2:

A. 1a.3, 1a.4, 1b.1, 2b, 2c, 2d,

B. 1a.3, 1a.4, 1b.1a, 2b, 2d.

(7) The present invention relates also to compositions comprising biotinylated peptides which are considered particularly advantageous, for diagnostic as well as immunogenic purposes for Human T-cell Lymphotropic Virus and are advantageously selected from the following mixtures:

for Human T-Lymphotropic virus type I:

Peptides I-gp46-3, I-gp46-4, I-gp46-5, I-gp46-6, I-p21-2, I-p19 for Human T-Lymphotropic virus type II:

Peptides II-gp52-1, II-gp52-2, II-gp52-3, I-gp46-4, II-p19, I-p21-2.

for Human lymphotropic virus types I and II:

Peptides I-gp46-3, I-gp46-4, I-gp46-5, I-gp46-6, II-gp52-1, IIgp52-2, II-gp52-3, I-p21-2, I-p19, II-p19.

The synthesis of the peptides may be achieved in solution or on a solid support. Synthesis protocols generally employ t-butyloxycarbonyl- or 9-fluorenylmethoxycarbonyl- protected activated amino acids. The procedures for carrying out the synthesis, the amino acid activation techniques, the types of side-chain production, and the cleavage procedures used are amply described in, for example, Stewart and Young, Solid Phase Peptide Synthesis, 2nd Edition, Pierce Chemical Company, 1984; and Atherton and Sheppard, Solid Phase Peptide Synthesis, IRL Press, 1989.

(8) The present invention also relates to a process for in vitro determination of antibodies using the above defined biotinylated peptides, wherein said biotinylated peptides are preferably in the form of streptavidin-biotinylated peptide complexes or avidin-biotinylated peptide complexes.

In the complex of streptavidin-biotinylated peptides or avidin-biotinylated peptides, the peptides may be biotinylated either N-terminally, C-terminally or internally.

This approach for the determination of antibodies is not limited with respect to peptide length and avoids the difficulties inherent in coating peptides directly onto the solid phase for immunological evaluation.

The use of biotinylated peptides, in the process of the invention, makes the anchorage of peptides to a solid support such that it leaves their essential amino acids free to be recognized by antibodies.

The expression anchoring peptide to a solid support means the attachment of the peptide to a support via covalent bonds or non-covalent interactions such that the peptide becomes immobilized.

The solid support can be nitrocellulose, polystyrene, nylon or any other natural or synthetic polymer.

The expression "their essential amino acids are left free to be recognized by antibodies" means that amino acid side chains of the peptide proper are neither chemically modified in any way nor involved in the interaction between the peptide and the solid phase.

The use of biotinylated peptides in the process of the invention enables said biotinylated peptides to be free to assume a wide range of conformations, among which at least one is appropriate for the binding of antibodies to said biotinylated peptides.

Any biotinylated peptide can be selected to be used in the process of the invention. However, some of them are able to be anchored on solid support and to react with antibodies specifically recognizing the epitope within this peptide even without being biotinylated and without being involved in a complex of avidin of streptavidin. In this case, the use of biotinylated peptides results in an apparent increase of the antigenicity of peptides with respect to the antigenicity observed when the peptides are not biotinylated. The expression "apparent" is meant to indicate an observed change obtained under similar test conditions without regard to the absolute cause of the observed change.

By "antigenicity" is meant the property of a peptide to be bound by an antibody.

By "increase of antigenicity" is meant that a positive signal is obtained for a dilution which is at least two times the dilution of the non-biotinylated peptides. Said positive signal is of the same magnitude as the one obtained for non-biotinylated peptides.

In other words, obtaining a positive signal can be obtained for a smaller amount of biotinylated peptide, compared to the amount of non-biotinylated peptide.

The present invention also illustrated a process for the identification of epitopes in a protein sequence comprises the following steps:

the preparation of peptides corresponding to portions of the amino acid sequence of the protein or polypeptide to be analyzed, said peptides being either contiguous, or preferably overlapping each other, the amount of overlapping being at least 3 amino acids, and preferably about 6 to about 12, the length of the peptides being at least about 5 amino acids and no more than about 50, preferably no more than about 40 amino acids, and more preferably from 9 to about 30 amino acids, with said peptides being characterized in that they are biotinylated;

binding the peptides to a solid phase through the interaction between the biotinyl group and streptavidin or avidin and measuring antibody binding to the individual peptides using classical methods.

(9) The present invention also relates to a process for the in vitro determination of antibodies to HIV or diagnosis of HIV infection by using a peptide composition as defined above in an immunoassay procedure, wherein the biotinylated peptides used are in the form of complexes of streptavidin-biotinylated or of avidin-biotinylated peptides.

(10) The present invention relates also to a process for the in vitro determination of antibodies to HCV or diagnosis of HCV infection by using a peptide composition as defined above in an immunoassay procedure, wherein the biotinylated peptides used are in the form of complexes of streptavidin-biotinylated or of avidin-biotinylated peptides.

(11) The present invention relates also to a process for the in vitro determination of antibodies to HTLV I or II or diagnosis of HTLV I or II infection by using a peptide composition as defined above in an immunoassay procedure, wherein the biotinylated peptides used are in the form of complexes of streptavidin-biotinylated or of avidin-biotinylated peptides.

A preferred method for carrying out the in vitro determination of antibodies is by means of an enzyme-linked immunosorbant assay (ELISA). This assay employs a solid phase which is generally a polystyrene microtiter plate or bead. The solid phase may, however, be any material which is capable of binding a protein, either chemically via a covalent linkage or by passive adsorption. In this regard, nylon-based membranes are also considered to be particularly advantageous. The solid phase is coated with streptavidin or avidin and after a suitable period, excess unbound protein is removed by washing. Any unoccupied binding sites on the solid phase are then blocked with an irrelevant protein such as bovine serum albumin or casein.

A solution containing the mixture or selection of biotinylated peptides is subsequently brought into contact with the streptavidin- or avidin-coated surface and allowed to bind. Unbound peptide is removed by washing. Alternatively, biotinylated peptides are allowed to form complexes with either avidin or streptavidin. The resulting complexes are used to coat the solid phase. After a suitable incubation period, unbound complex is removed by washing. An appropriate dilution of an antiserum or other body fluid is brought into contact with the solid phase to which the peptide is bound. The incubation is carried out for a time necessary to allow the binding reaction to occur. Subsequently, unbound components are removed by washing the solid phase. The detection of immune complexes is achieved by using heterologous antibodies which specifically bind to the antibodies present in the test serum and which have been conjugated with an enzyme, preferably but not limited to either horseradish peroxidase, alkaline phosphatase, or β-galactosidase, which is capable of converting a colorless or nearly colorless substrate or co-substrate into a highly colored product or a product capable of forming a colored complex with a chromogen which can be detected visually or measured spectrophotometrically.

Other detection systems known in the art may however be employed and include those in which the amount of product formed is measured electrochemically or luminometrically. The detection system may also employ radioactively labeled antibodies, in which case the amount of immune complex is quantified by scintillation counting or counting. In principle, any type of immunological test for the detection of antibodies may be used, as long as the test makes use of the complex between either streptavidin or avidin and (a) biotinylated peptide(s) synthesized as described.

Also included are competition assays in which streptavidin- or avidin-biotinylated peptide complexes in solution are permitted to compete with the solid phase-bound antigen for antibody binding or assays in which free peptide in solution is permitted to compete with solid phase-bound streptavidin or avidin: biotinylated peptide complexes. By way of example, the many types of immunological assays for the detection and quantitation of antibodies and antigen are discussed in detail (Tijssen, P., Practice and Theory of Enzyme Immunoassays, Elsevier Press, Amsterdam, Oxford, N.Y. 1985).

The immunological assays may be restricted to single biotinylated peptides. Preferably, however, a mixture of biotinylated peptides is used which includes more than one epitope derived from the infectious agent(s) to which the presence of specific antibodies is to be measured.

Another preferred method for carrying out the in vitro determination of antibody detection is the line immunoassay (LIA).

This method of antibody detection consists essentially of the following steps:

the antigens, in the form of biotinylated peptide: streptavidin or avidin complexes, to be tested or used are applied as parallel lines onto a membrane which is capable of binding, covalently or non-covalently, the antigen to be tested, unoccupied binding sites on the membrane are blocked with an irrelevant protein such as casein or bovine serum albumin, the membrane is cut into strips in a direction perpendicular to the direction in which the antigen (biotinylated peptide) lines are applied, an appropriate dilution of an antiserum or other body fluid (containing antibodies to be detected) is brought into contact with a strip to which the antigens are bound and allowed to incubate for a period of time sufficient to permit the binding reaction to occur, unbound components are removed by washing the strip, the detection of immune complexes is achieved by incubating the strip with heterologous antibodies which specifically bind to the antibodies in the test serum and which have been conjugated to an enzyme such as horseradish peroxidase, the incubation is carried out for a period sufficient to allow binding to occur, the presence of bound conjugate is detected by addition of the required substrate or co-substrates which are converted to a colored product by the action of the enzyme, the reactions are detected visually or may be quantified by densitometry.

(12) As demonstrated in the Examples section the present invention relates also the the use of a peptide composition as defined above, for immunization against HIV, and/or HCV, and/or HTLV I or II infection.

(13) The present invention also relates to a method for preparing the biotinylated peptides used in the invention involves the use of N-α-Fmoc-X (N-y-biotin) or N-α-Fmoc-X (N-y-biotin) derivative, wherein X represents

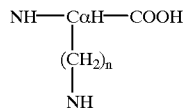

where n is at least 1 but less than 10 and is preferably between 2 and 6, one amino group being attached to the Cα atom while the other being attached to carbon Cy, which is the most distal carbon in the side chain; or their esters obtained with alcohol ROH and more particularly pentafluorophenyl ester;

y representing position y with respect to the carbon atom carrying the COOH group in the radical.

This biotin derivative will be called intermediary product, and the above-defined intermediary products are new compounds determined according to the process of the invention.

(14) In an advantageous method for preparing the compounds of the invention, the intermediary product can be represented by one of the following formula: N-α-Fmoc-(N-y-biotin) is N-α-Fmoc-lysine (ε-biotin) or N-α-Fmoc-ornithine (N-δ-biotin)

(15) The N-terminal biotinylated peptides can be prepared according to the method which comprises the following steps:

addition of the successive amino acids duly protected onto the resin to give: Fmoc-AA$_n$ . . . AA$_1$-resin, deprotection of the NH$_2$-terminal for instance by means of piperidine, addition of the intermediary product:

through its COOH onto the NH$_2$-terminal to obtain:

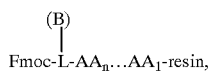

deprotection of the NH$_2$-terminal group of the compound obtained, cleavage from the resin, extraction and purification of the peptide obtained, biotinylated at its amino terminal, the steps of side chain deprotection and peptide cleavage being liable to be performed simultaneously or separately, and particularly deprotection of the NH$_2$-terminal group of the intermediary group, for instance by means of piperidine, cleavage from the resin for instance with an acid such as trifluoroacetic acid, in the presence of scavengers such as ethanedithiol, thioanisole, or anisole, extraction of the peptide with a solvent such as diethyl-ether to remove most the acid and scavengers, purification, such as with HPLC to obtain:

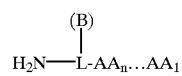

Biotin can be conveniently coupled to the free amino-terminus of an otherwise fully protected peptide chain using also conventional activation procedures. Since biotin possesses one carboxyl group and no amino groups, biotin essentially functions as a chain terminator. Preferred activating agents for in situ activation include but are not limited to benzotriazol-1-yl-oxy-tripyrrolidinophosphonium hexafluorophosphate(PyBOP), O-benzotriazol-1-yl-N,N,N',N'-tetramethyluronium hexafluorophosphate (HBTU), and O-(1H-benzotriazol-1-yl)-N,N,N',N'-tetramethyluronium tetrafluoroborate (TBTU). The activation procedures employing these and related compounds are known to those versed in the art of solid phase peptide synthesis and the coupling of biotin does not entail a significant departure from standard coupling protocols.

Biotin in a pre-activated form may also be used. Either N-hydroxysuccinimidobiotin or biotinamidocaproate N-hydroxysuccinimide ester are conveniently employed and both are commercially available. This method of coupling has been described by Lobl, T. J., Deibel, M. R., and Yem, A. W., Anal. Biochem. (1988) 170(2):502–511. Following addition of the N-terminal biotin, the peptide is cleaved from the resin in the presence of scavengers, the choice of which will depend on the usual considerations of peptide amino acid composition and the nature of the protecting groups used.

(16) The carboxy terminal biotinylated peptides involved in the process of the invention can be prepared according to a method which comprises coupling of a carboxy-activated form of the intermediary product as defined above to a cleavable linker attached to the resin, for instance to obtain the following compound:

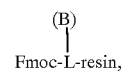

deprotection of the α amino group of the intermediary compound, for instance by means of piperidine to obtain:

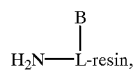

successive addition of the subsequent amino acids AA$_1$ . . . AA$_n$ duly protected onto

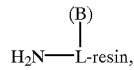

to obtain:

Fmoc-AA$_n$...AA$_1$-L-resin, deprotection of the NH$_2$-terminal for instance by means of piperidine, deprotection of the compound obtained, cleavage from the resin, extraction and purification of the peptide obtained, biotinylated at its carboxy terminal end, the steps of side chain deprotection and peptide cleavage being liable to be performed simultaneously or separately, and particularly deprotection of the NH$_2$-terminal, for instance by means of piperidine, cleavage from the resin for instance with trifluoroacetic acid, in the presence of scavengers such as ethanedithiol, or thioanisole, or anisole, extraction of the peptide with a solvent such as diethyl-ether to remove most of the acid and scavengers, purification, such as with HPLC to obtain:

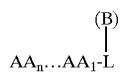
AA$_n$...AA$_1$-L

(17) The internally biotinylated peptides can be prepared according to a method which comprises the following steps:

addition of successive amino acids duly protected onto the resin to give:

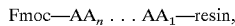
Fmoc—AA$_n$ . . . AA$_1$—resin, deprotection of the NH$_2$-terminal, addition of the intermediary product:

Fmoc-L through its COOH onto the NH$_2$-terminal to obtain:

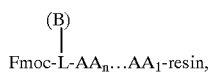
Fmoc-L-AA$_n$...AA$_1$-resin, deprotection of the α amino group of the intermediary compound, for instance by means of piperidine to obtain:

L-AA$_n$...AA$_1$-resin, addition of the subsequent amino acids duly protected onto the resin to give:

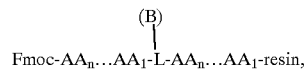
Fmoc-AA$_n$...AA$_1$-L-AA$_n$...AA$_1$-resin, deprotection of the NH2 terminal group of the compound obtained, cleavage from the resin, extraction and purification of the peptide obtained, biotinylated at its amino-terminal, the steps of side chain deprotection and peptide cleavage being liable to be performed simultaneously or separately, and particularly, deprotection of the NH$_2$-terminus, for instance by means of piperidine, cleavage from the resin for instance with trifluoroacetic acid, in the presence of scavengers such as ethanedithiol, or thioanisole, or anisole, extraction of the peptide with a solvent such as diethyl-ether to remove most of the acid and scavengers, purification, such as with HPLC to obtain:

AA$_n$...AA$_1$-L-AA$_n$...AA$_1$

Under certain circumstances, it may prove particularly advantageous to be able to biotinylate a peptide internally or at its carboxy-terminus. Such instances arise, for example, when the amino acid sequence of a peptide corresponds to the amino-terminal sequence of a protein. Attachment of a biotin to the amino-terminus of such a peptide results in a structure which is significantly different from that found in the native protein and may, as a consequence, adversely affect the binding properties of biochemical properties of the peptide. It is also possible that even for peptides corresponding to internal protein sequences, their recognition by binding proteins or immunoglobulins may depend on which end of the peptide and the manner in which it is presented for binding. The importance of peptide orientation has been described by Dyrberg, T. and Oldstone, M. B. A., J. Exp. Med. (1986) 164:1344–1349.

In order to be able to incorporate a biotinyl moiety into a peptide in a position and sequence independent manner, efforts were made to synthesize a suitable reagent which can be coupled using conventional procedures. A convenient reagent for C-terminal or internal biotinylation is N-ε-biotinyl-lysine. Provided the α-amino group of this compound is suitably protected (Fmoc and tBoc), this reagent may be used to introduce a biotin anywhere in the peptide chain, including at the amino terminus, by the standard procedures used in solid phase peptide synthesis. The synthesis of the t-Boc-protected derivative has been described (Bodansky, M., and Fagan, D T., J. Am. Chem. Soc. (1977) 99:235–239) and was used to synthesize short peptides for use in studying the enzyme activities of certain transcarboxylases.

Unlike the t-Boc derivative, the synthesis of N-α-Fmoc-Lys (N-ε-biotin) has not been described and given the growing interest in Fmoc-based synthesis strategies, this compound is considered particularly advantageous.

There are a number of possible routes which can be taken to arrive at the desired Fmoc-protected compound. These are shown in FIG. 1. In the first approach, commercially available N-α-Fmoc-Lys (N-ε-tBoc) can be used as the starting material. The N-ε-tBoc protection is removed using trifluoroacetic acid and a scavenger such as water. A slight molar excess of the N-α-Fmoc-lysine so obtained is then reacted with carboxy-activated biotin. The resulting product can be readily purified by selective extractions and standard chromatographic techniques. In an alternative approach, N-α-Fmoc-Lys (N-ε-biotin) can be produced from commercially available N-ε-biotinyl lysine (biocytin) by reaction with fluorenylmethylsuccinimidyl carbonate. Numerous examples of these reactions which can be used as guidelines are given in Atherton and Sheppard, Solid Phase Peptide Synthesis, IRL Press, 1989.

The strategy shown in FIG. 1 (method A) may also be applied to synthesize N-α-Fmoc-ornithine (N-δ-biotin) from commercially available N-α-Fmoc-ornithine (N-δ-tBoc). The ornithine derivative differs from the lysine derivative only in the length of the side chain which, for the ornithine derivative, is shorter by one carbon atom. The N-α-Fmoc-Lys can be conveniently incorporated into the peptide chain using the same reagents for in situ activation described for free biotin.

Alternatively, N-α-Fmoc-Lys (N-ε-biotin)-O-pentafluorophenyl ester can be conveniently synthesized from N-α-Fmoc-Lys (N-ε-biotin) and pentafluorophenyl trifluoroacetate using the base-catalyzed transesterification reaction described by Green, M. and Berman, J., Tetrahedron Lett. (1990) 31:5851–5852, for the preparation of O-pentafluorophenyl esters of amino acids. This active ester can be used directly to incorporate N-α-Fmoc-Lys (N-ε-biotin) into the peptide chain. The class of above-defined intermediary products can be prepared according to a method which comprises the following steps:

reaction of a diamino-, monocarboxylic acid previously described with fluorenylmethysuccinimidylcarbonate or fluorenylmethyl chloroformate under conditions of carefully controlled pH to give the singly protected N-α-Fmoc derivative, or alternatively, use of commercially available N-α-Fmoc-protected diamino-monocarboxylic acids when the side chain amino group is provided with a protecting group which is different from the Fmoc group used to protect the α-amino group, the side chain amino group protection being liable to be selectively removed under conditions which leave the N-α-Fmoc group intact, purification of the mono-protected N-α-Fmoc-diamino-monocarboxylic acid derivative by selective extractions and chromatography, reaction of the derivative obtained with a carboxy-activated derivative of biotin, such as N-hydroxysuccinimide biotin, to obtain the (N-α-Fmoc)-(N-y-biotin) derivative which is the desired intermediary product, purification of the intermediary product by selective extractions, precipitations, or chromatography.

When the biotinylated peptides used in the process of the invention are to be provided with linker arms, these chemical entities may be conveniently attached to either the N- or C-terminus of a peptide sequence during solid phase synthesis using standard coupling protocols, as long as the amino groups of these compounds are provided with appropriate temporary amino group protection.

All these specific biotinylated peptides are new.

DESCRIPTION OF THE FIGURES

All the samples and sera mentioned in the figures and tables are randomly chosen samples and sera, containing antibodies produced as a result of naturally occurring infection by a viral agent.

More particularly:

Method A corresponds to the synthesis of (N-α-Fmoc-Lys(N-ε-biotin) from N-ε-Fmoc-Lys(N-ε-tBoc) and Method B corresponds to the synthesis of (N-α-Fmoc-Lys(N-ε-biotin) from N-ε-biotinyl lysine.

Figure 1A:
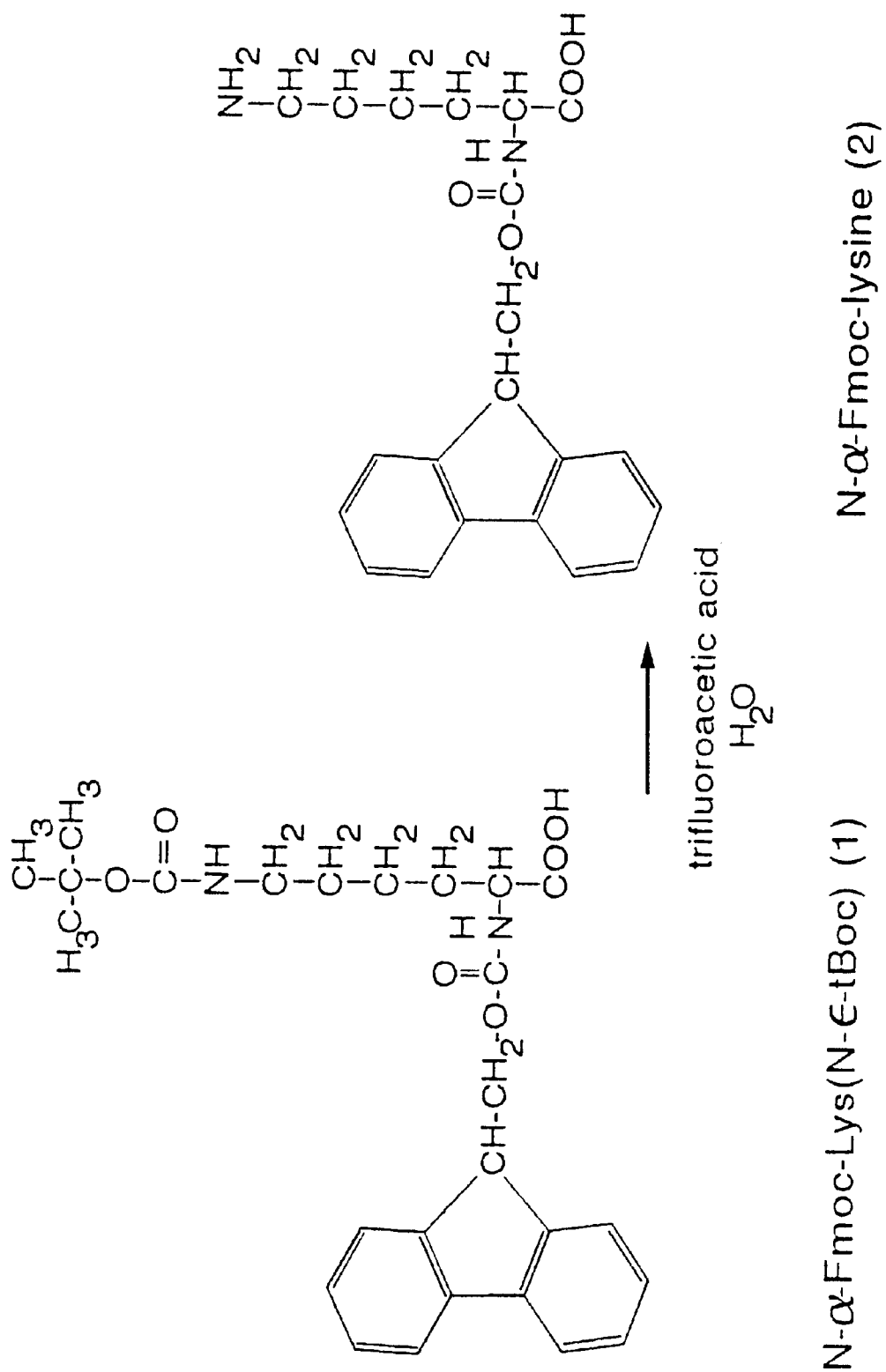
FIG. 1 represents the strategies for the synthesis of N-α-Fmoc-lysine (N-ε-Biotin).
Figure 1B:
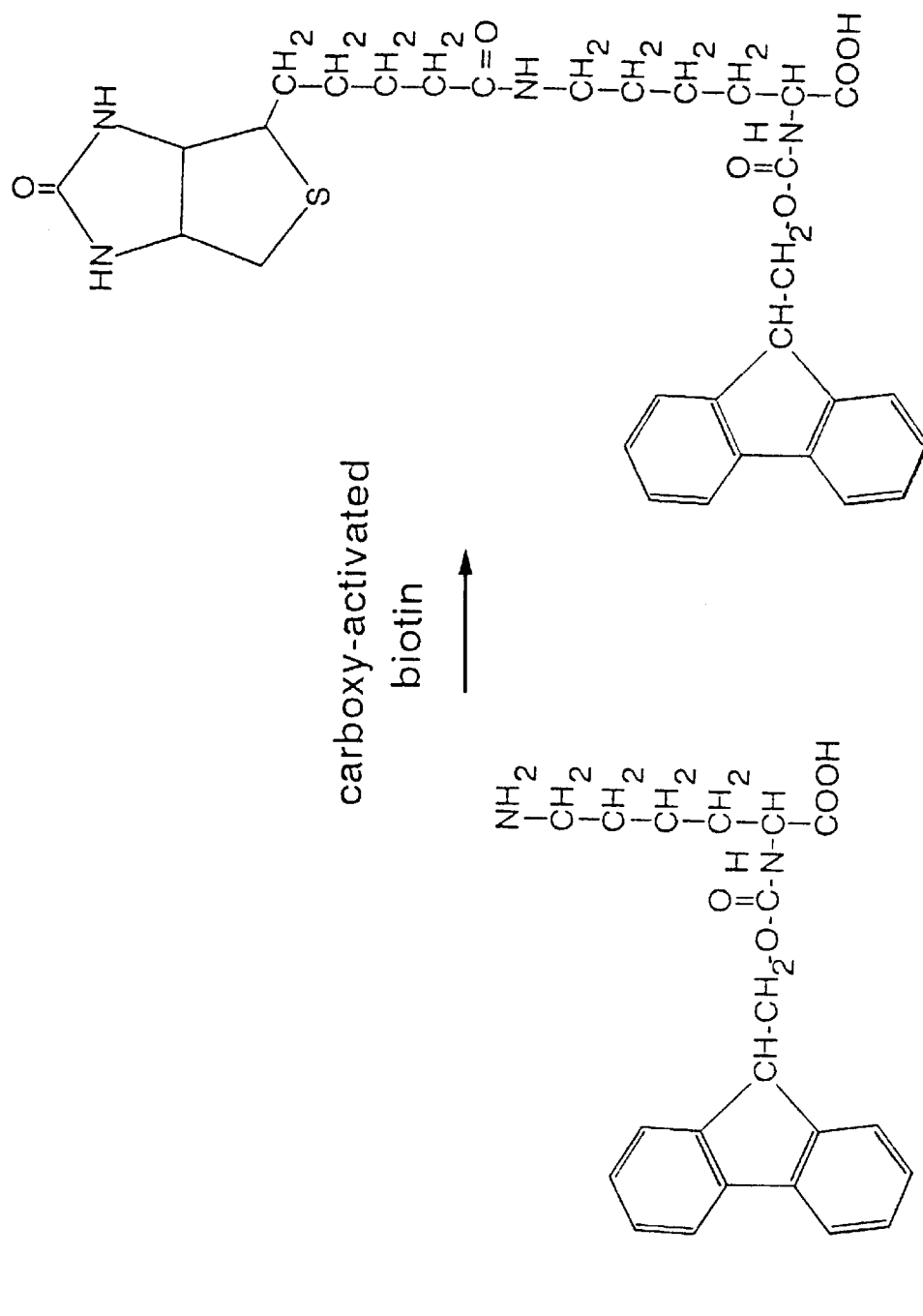
Figure 1C:
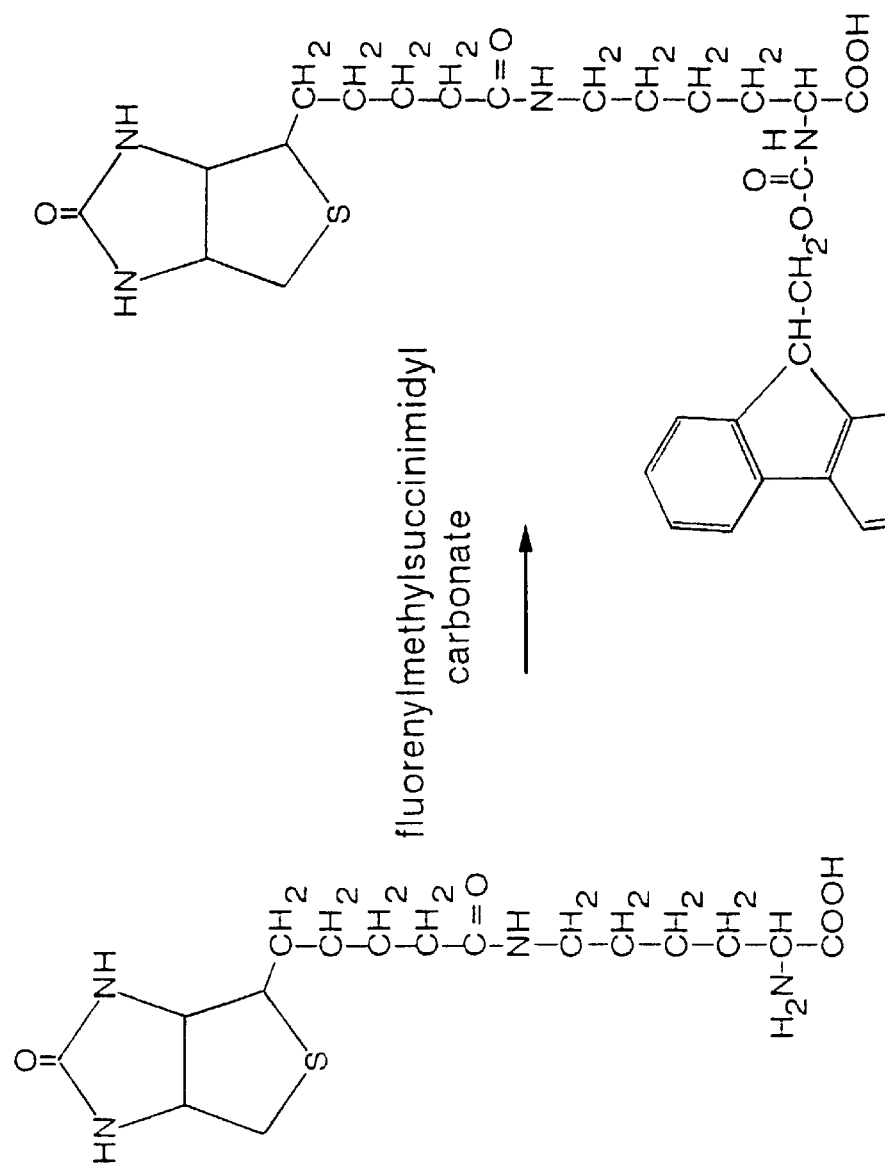
Figure 2A:
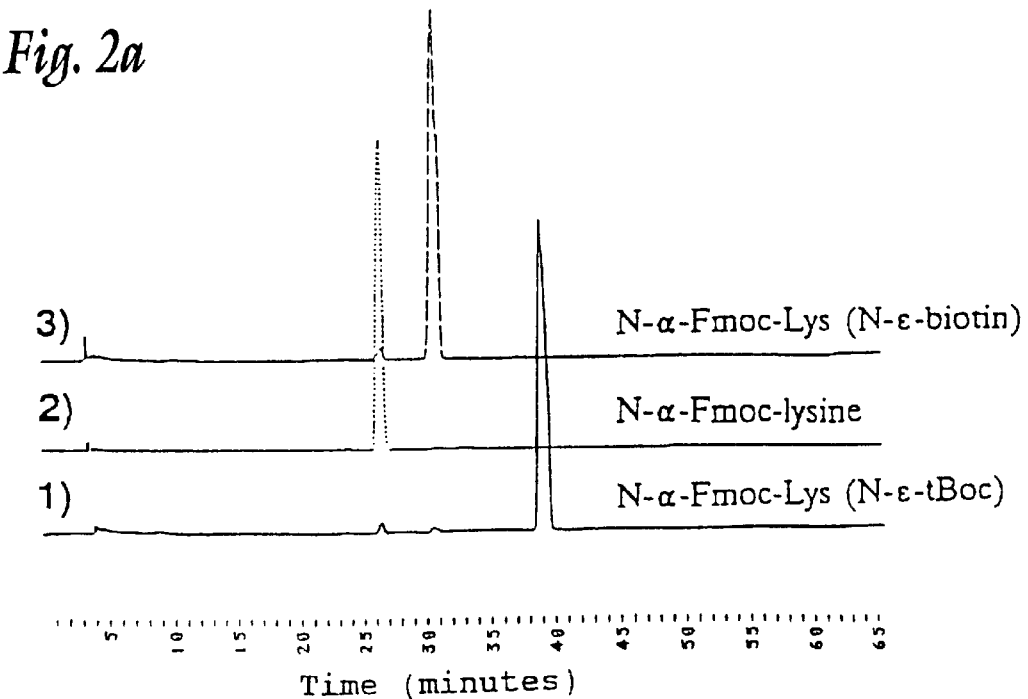
Figure 2B:
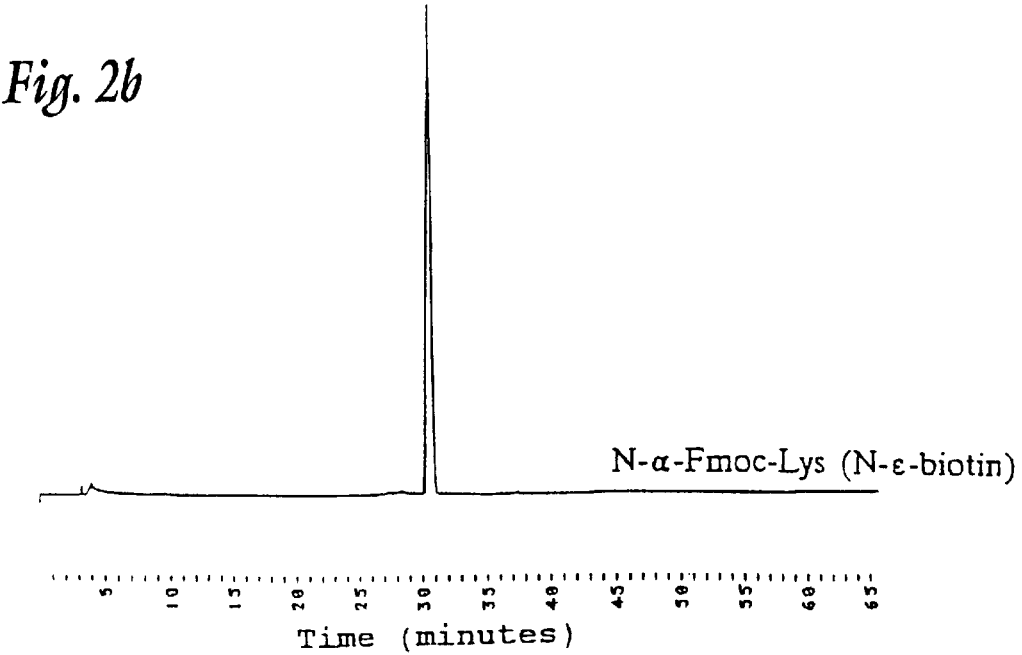
Figure 2:
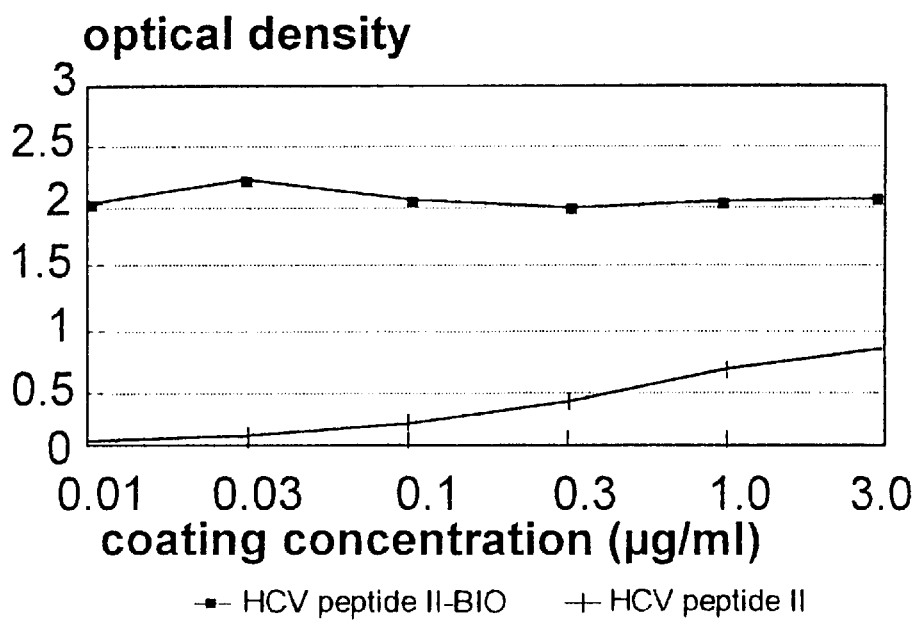

FIG. 2 represents the diagram obtained in reverse phase chromatography of the precursors involved in the preparation of the intermediary products defined above, and of the intermediary compounds.

The reverse phase chromatography has been carried out in the following conditions:
gradient specifications:
buffer A: 0.1% TFA in H2O,
buffer B: 0.1% TFA in acetonitrile,
column: C2/C18 reverse phase (Pharmacia, Pep-S), detection wavelength: 255 nanometers;
gradient:
0% B from 0 to 1 minute,
0% B to 100% B from 1 minute to 60 minutes,
0% B from 60 minutes to 70 minutes.

Figure 1:
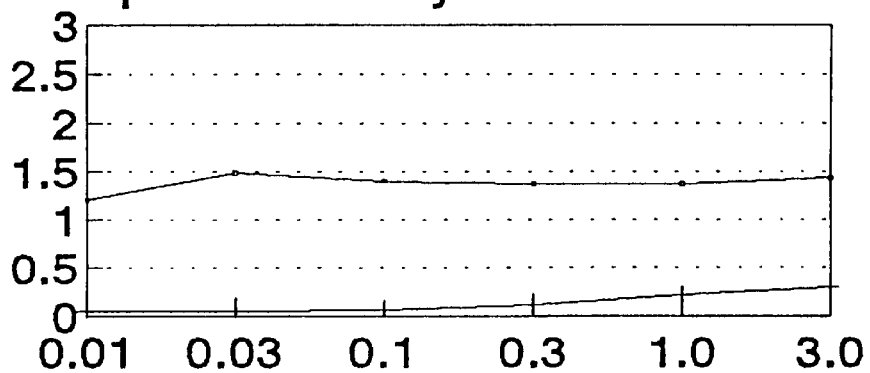
Figure 3A:
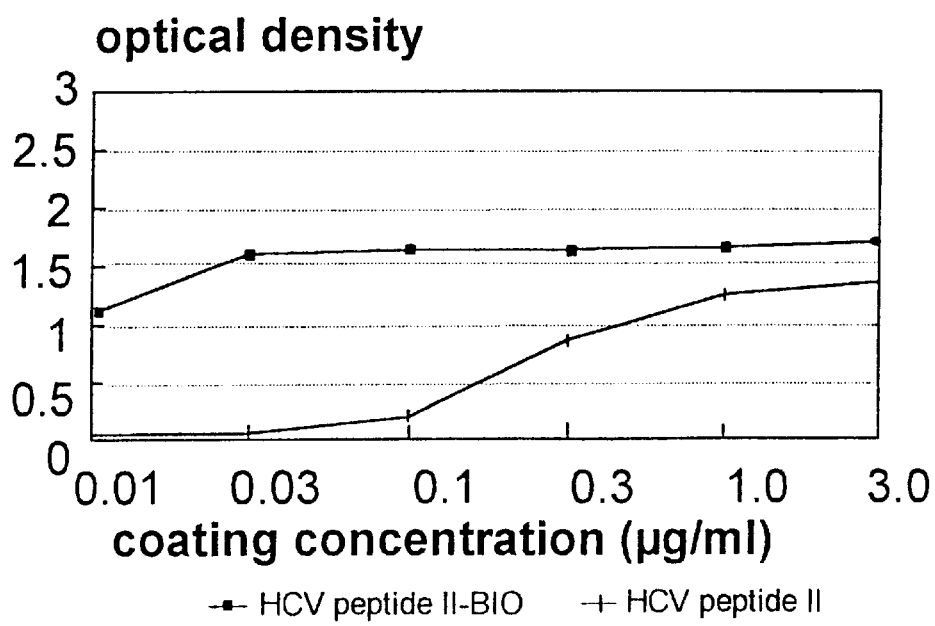

The first diagram corresponds to method A (see FIG. 1) and the second diagram corresponds to method B (see FIG. 1).

Figure 3A:
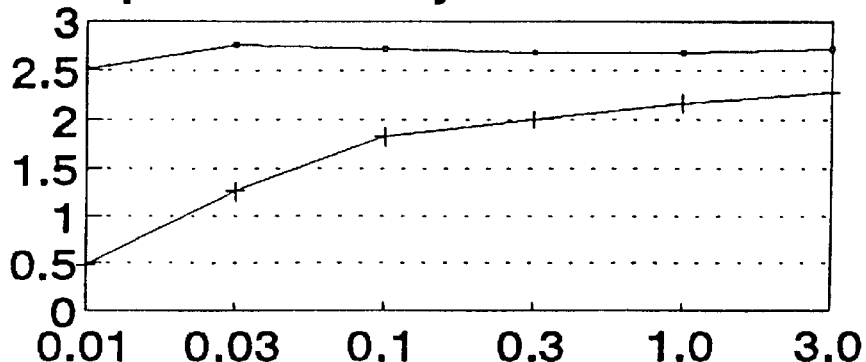

FIG. 3a represents the antibody binding to HCV peptide II (in an ELISA).

The upper left curve corresponds to sample 8320.
The upper right curve corresponds to sample 8242.
The lower left curve corresponds to sample 8243.
The lower right curve corresponds to sample 8318.

In each of these samples, the optical density (at 450 nm) is plotted against the coating concentration expressed in μg/ml.

The curve with crosses corresponds to non-biotinylated HCV peptide II and the curve with dots corresponds to biotinylated HCV peptide II.

Figure 3B:
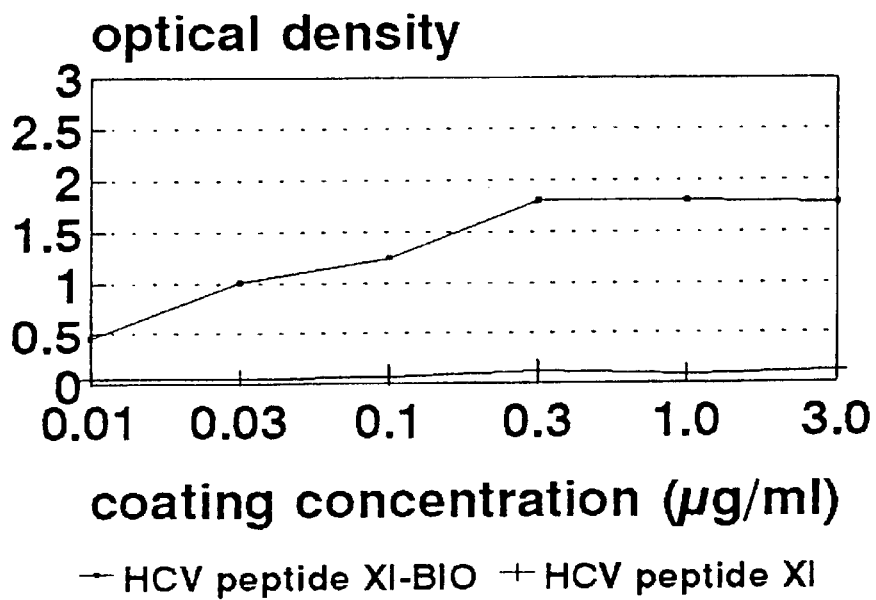
Figure 1:
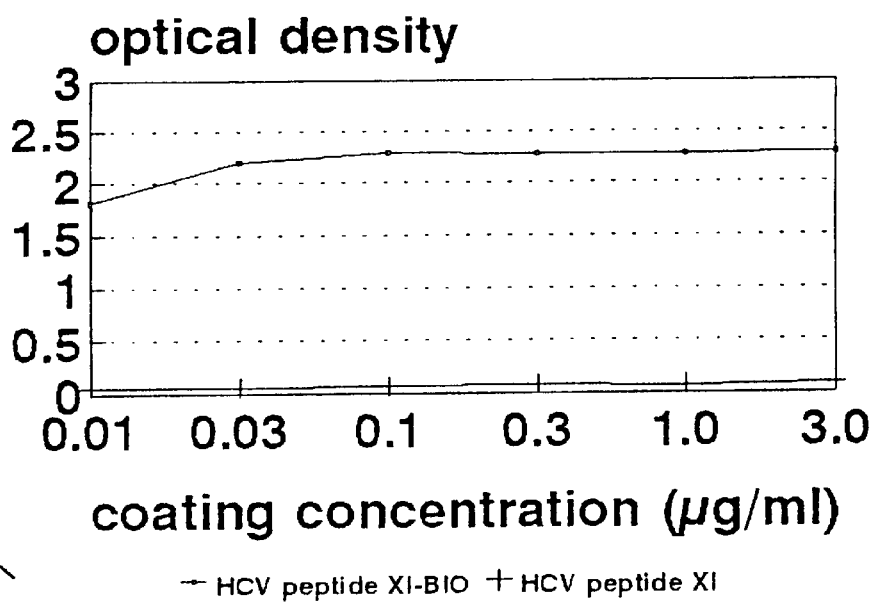
Figures 2, 3B:
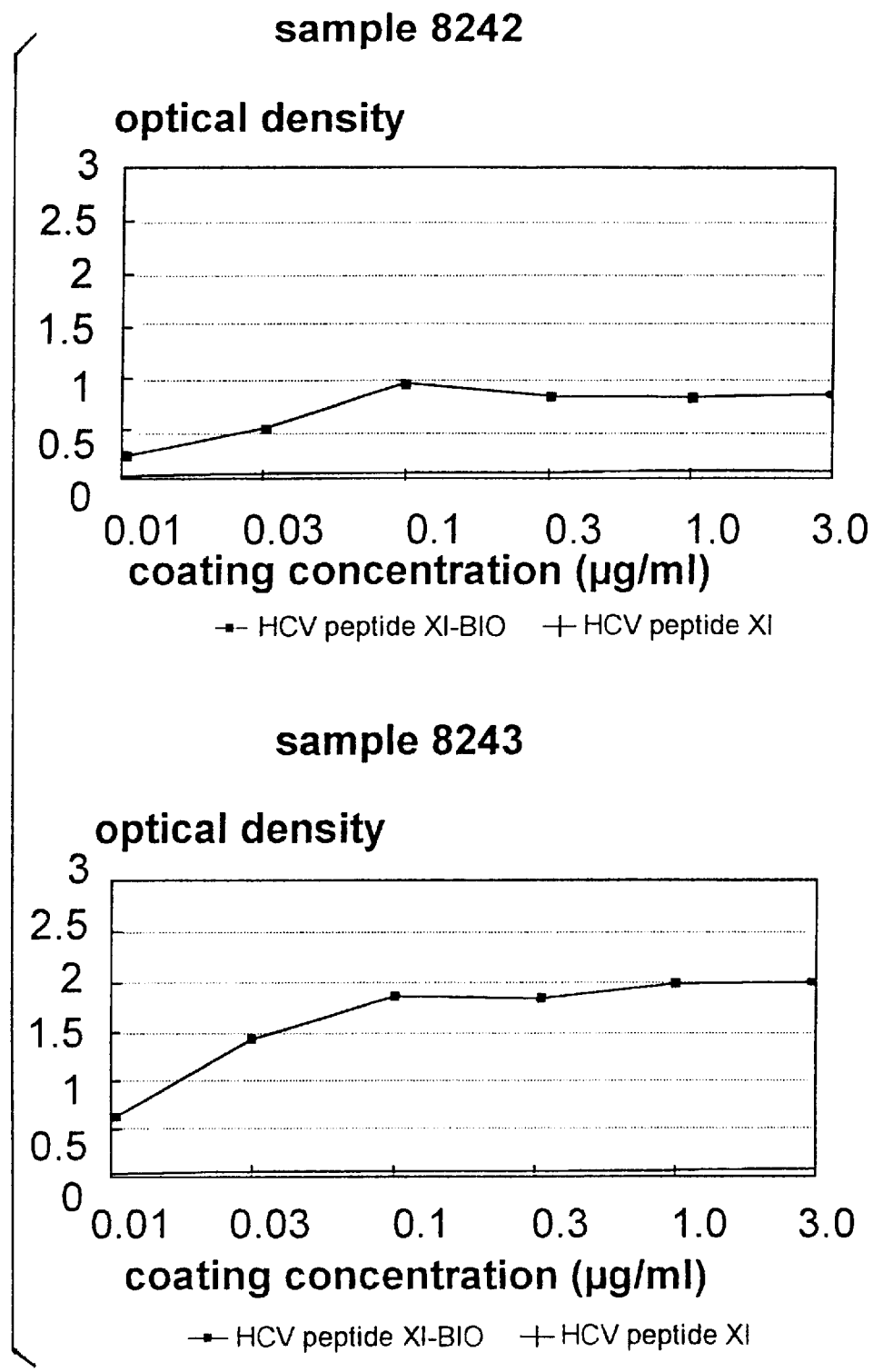

FIG. 3b represents the antibody binding to HCV peptide XI (in an ELISA).

The upper left curve corresponds to sample 8320.
The upper right curve corresponds to sample 8326.
The lower left curve corresponds to sample 8242.
The lower right curve corresponds to sample 8243.

In each of these samples, the optical density (at 450 nm) is plotted against the coating concentration expressed in μg/ml.

The curve with crosses corresponds to non-biotinylated HCV peptide XI and the curve with dots corresponds to biotinylated HCV peptide XI.

Figure 3C:
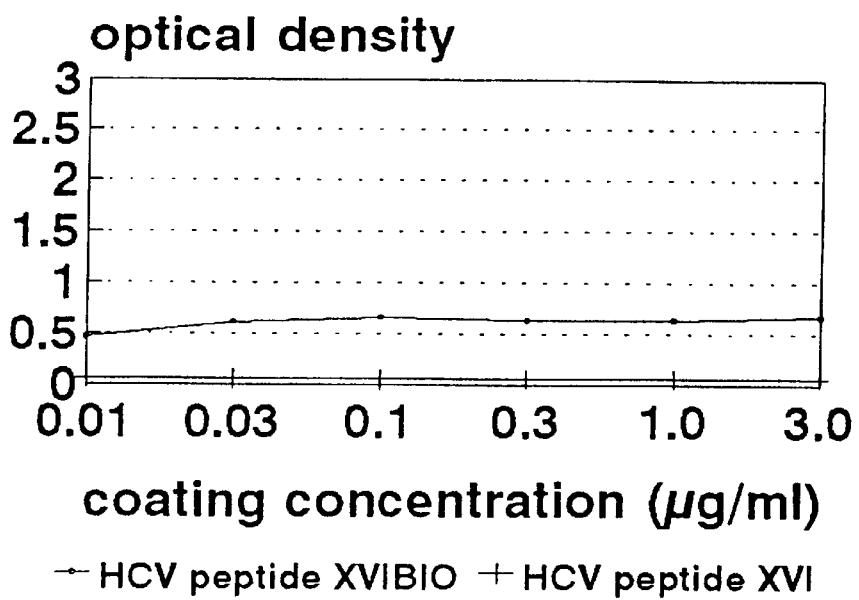
Figure 1:
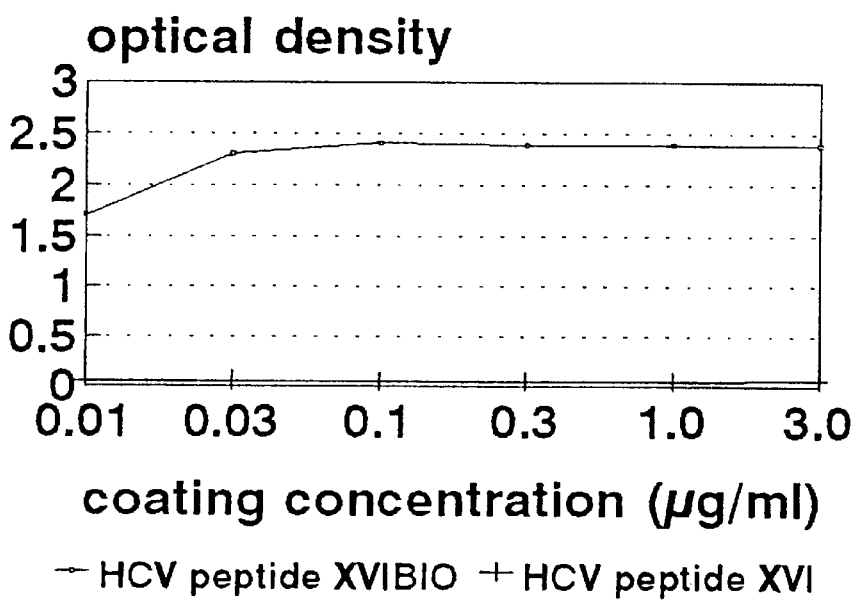
Figure 3C:
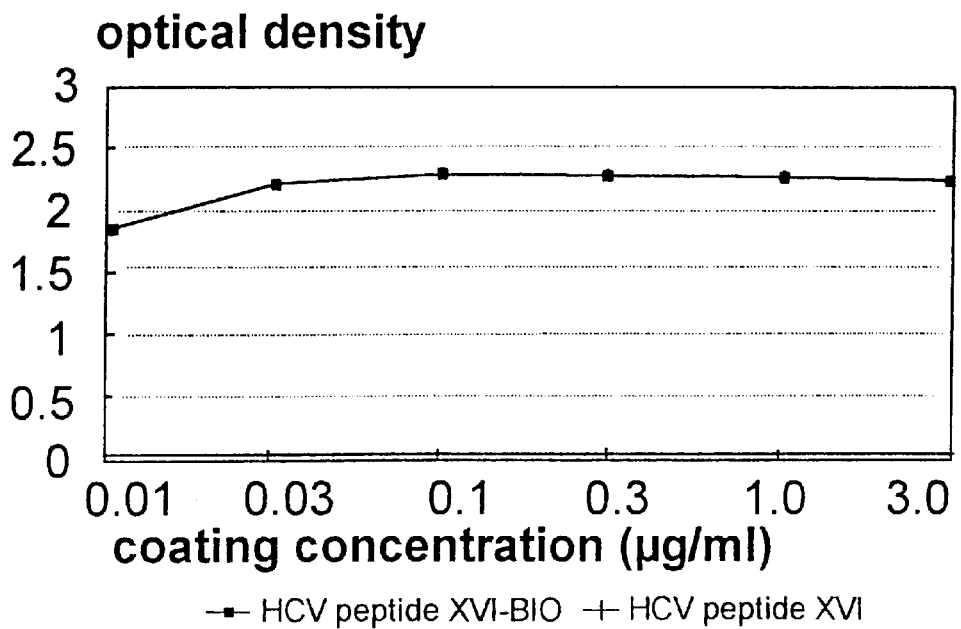
Figure 2:
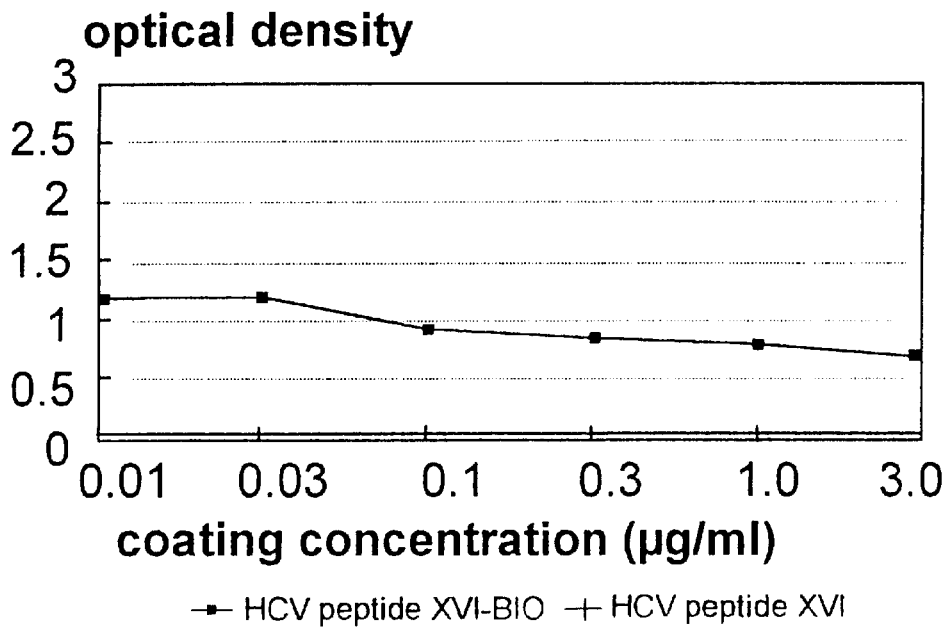
Figure 4A:
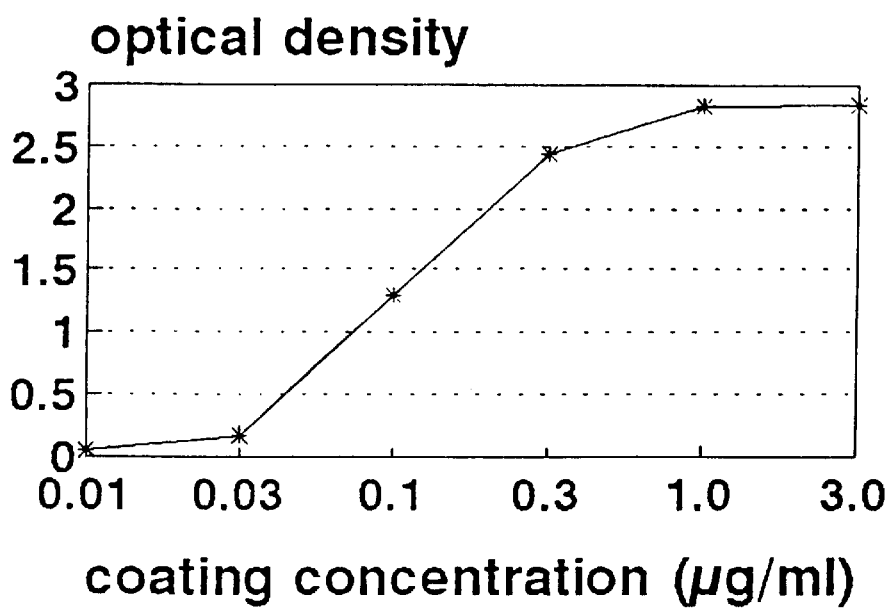
Figure 4A:
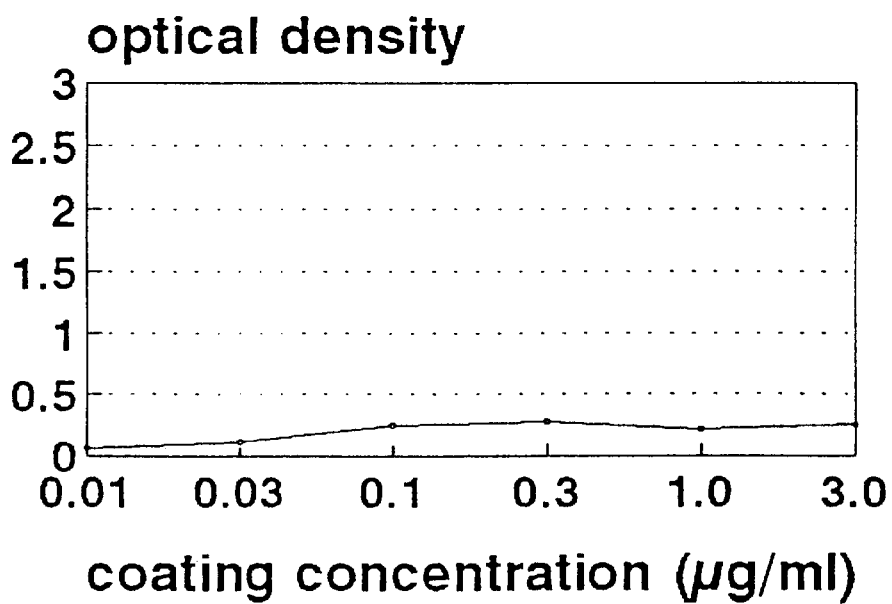
Figure 4B:
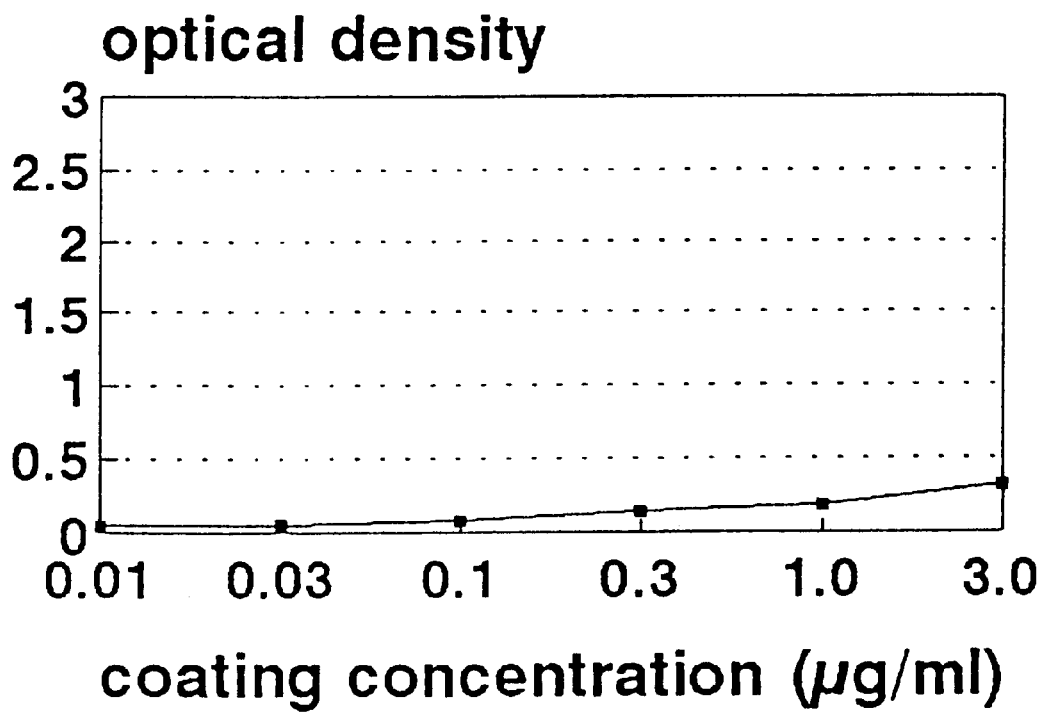
Figure 5A:
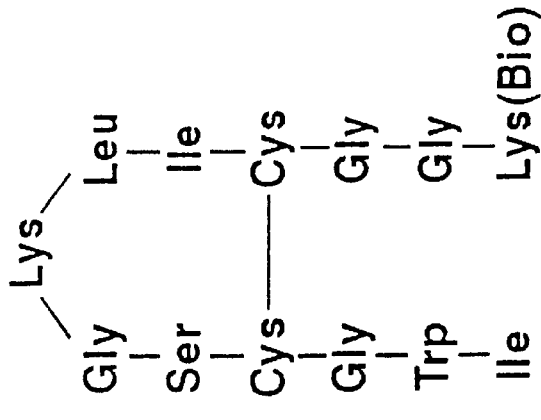
Figure 5B:
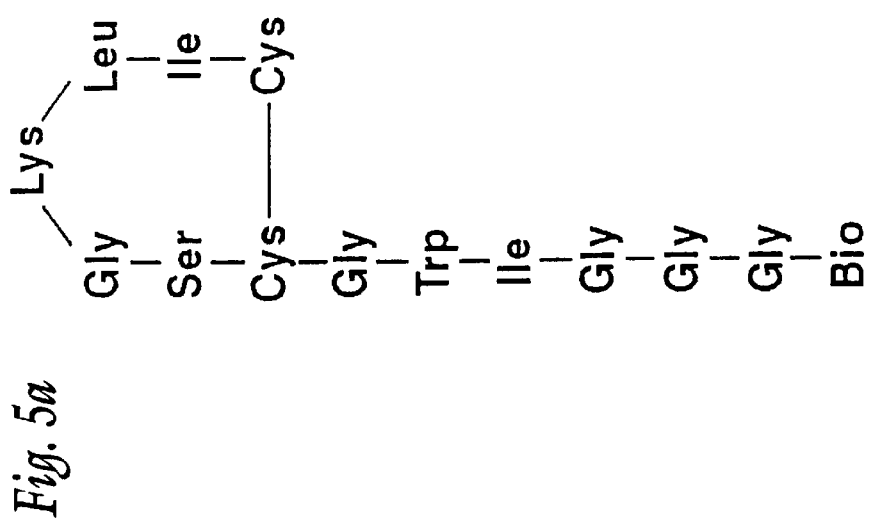

FIG. 3c represents the antibody binding to HCV peptide XVI (in an ELISA).

The upper left curve corresponds to sample 8326.
The upper right curve corresponds to sample 8242.
The lower left curve corresponds to sample 8243.
The lower right curve corresponds to sample 8318.

In each of these samples, the optical density (at 450 nm) is plotted against the coating concentration expressed in μg/ml.

The curve with crosses corresponds to non-biotinylated HCV peptide XVI and the curve with dots corresponds to biotinylated HCV peptide XVI.

Figures 1, 6A:
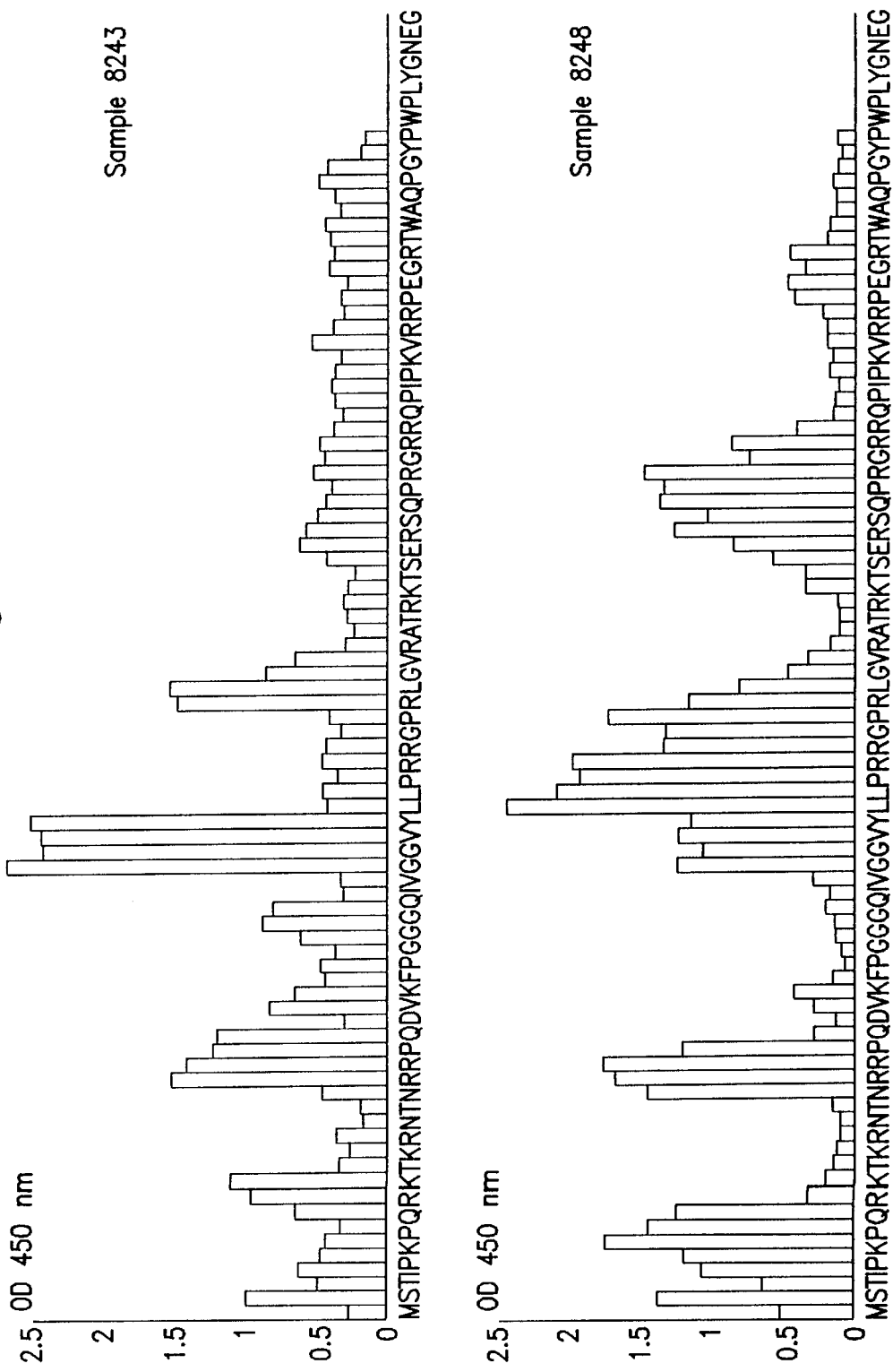
Figures 2, 6A:
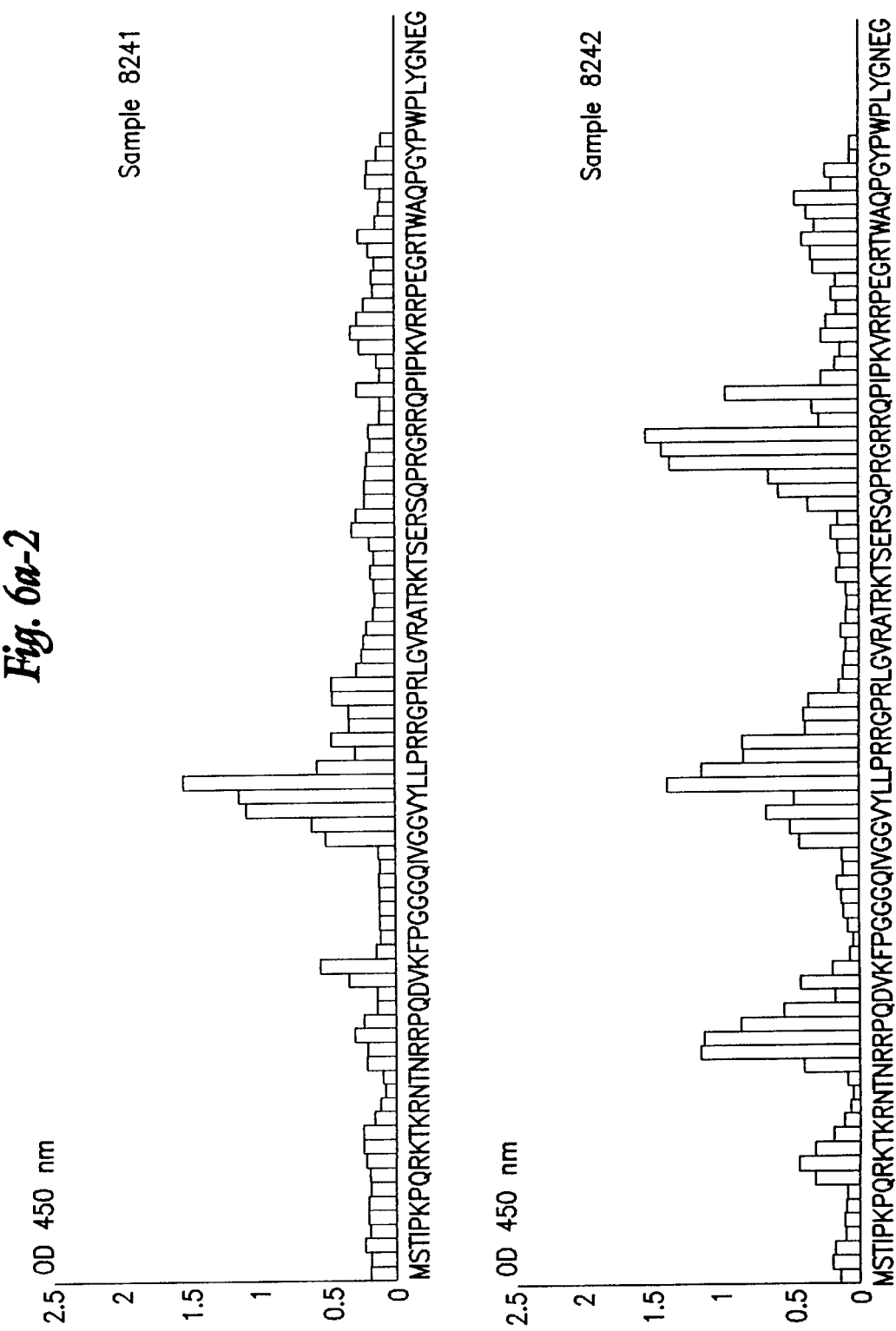
Figures 3, 6A:
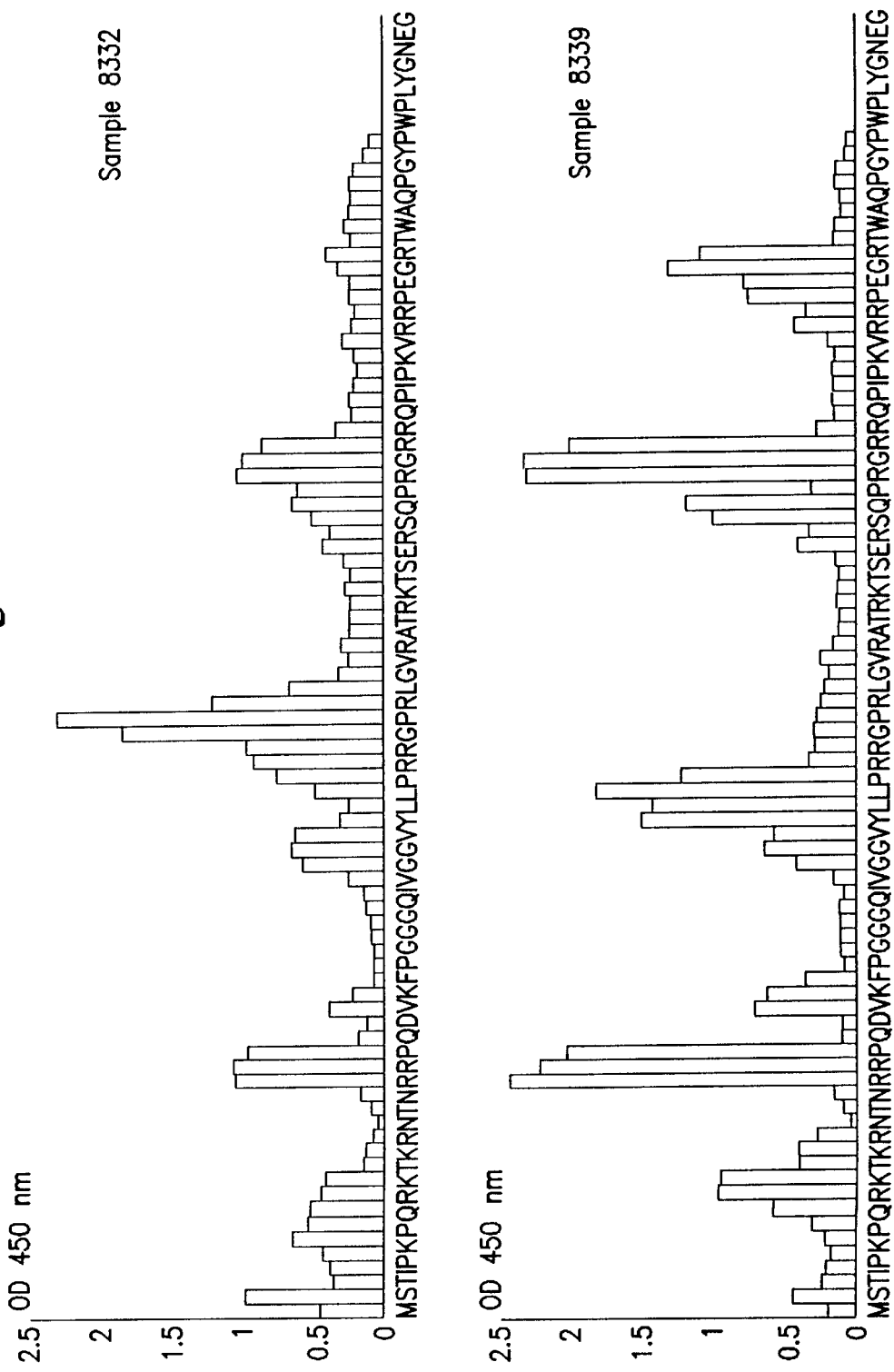
Figures 4, 6A:
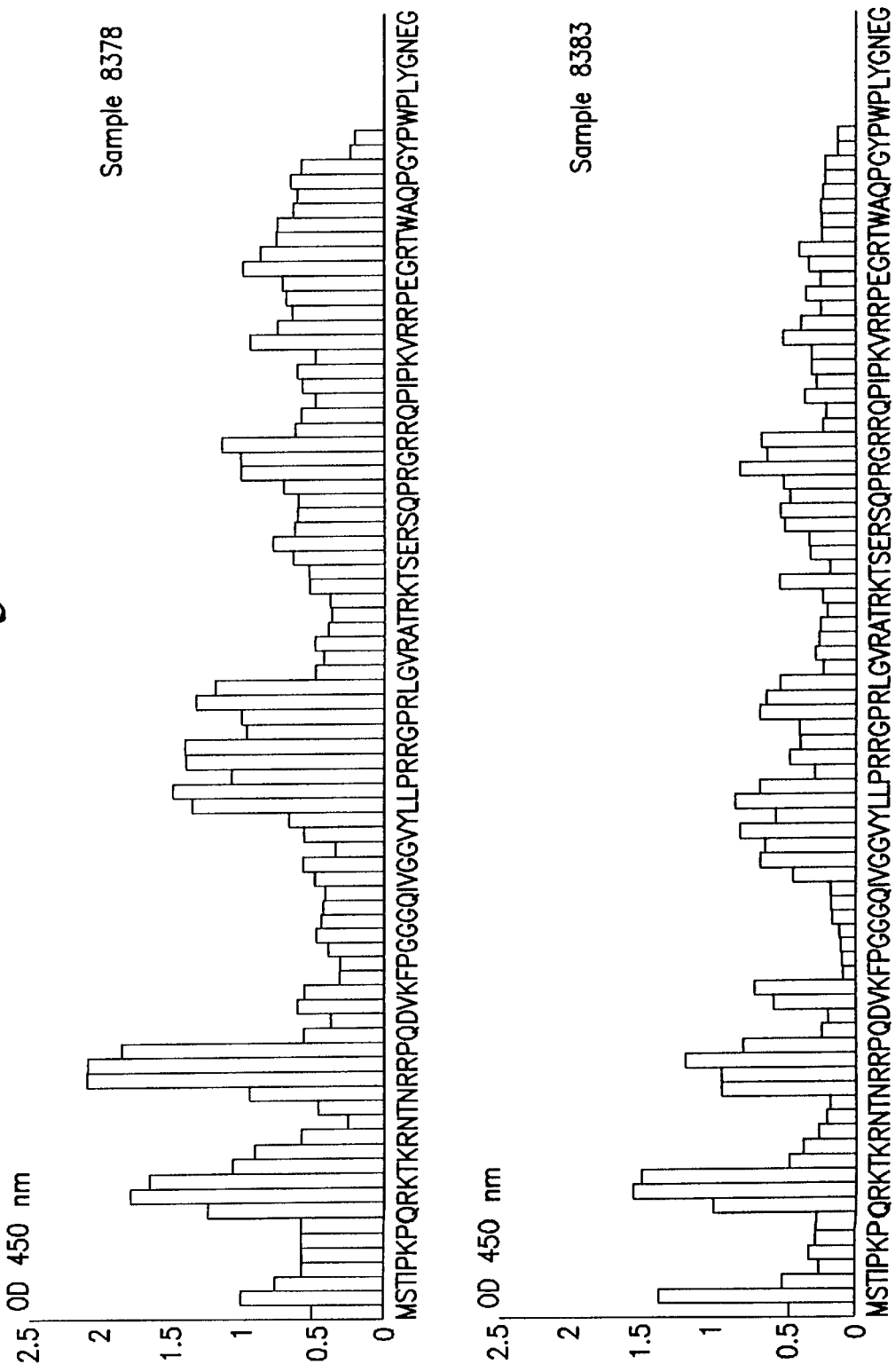

FIG. 4 corresponds to the detection of biotinylated peptides coated directly (in an ELISA).

The first curve corresponds to biotinylated HCV peptide II, the second curve to biotinylated HCV peptide XI and the third curve to biotinylated HCV peptide XVI.

In each of these samples, the optical density (at 450 nm) is plotted against the coating concentration expressed in μg/ml.

Figures 5, 6A:
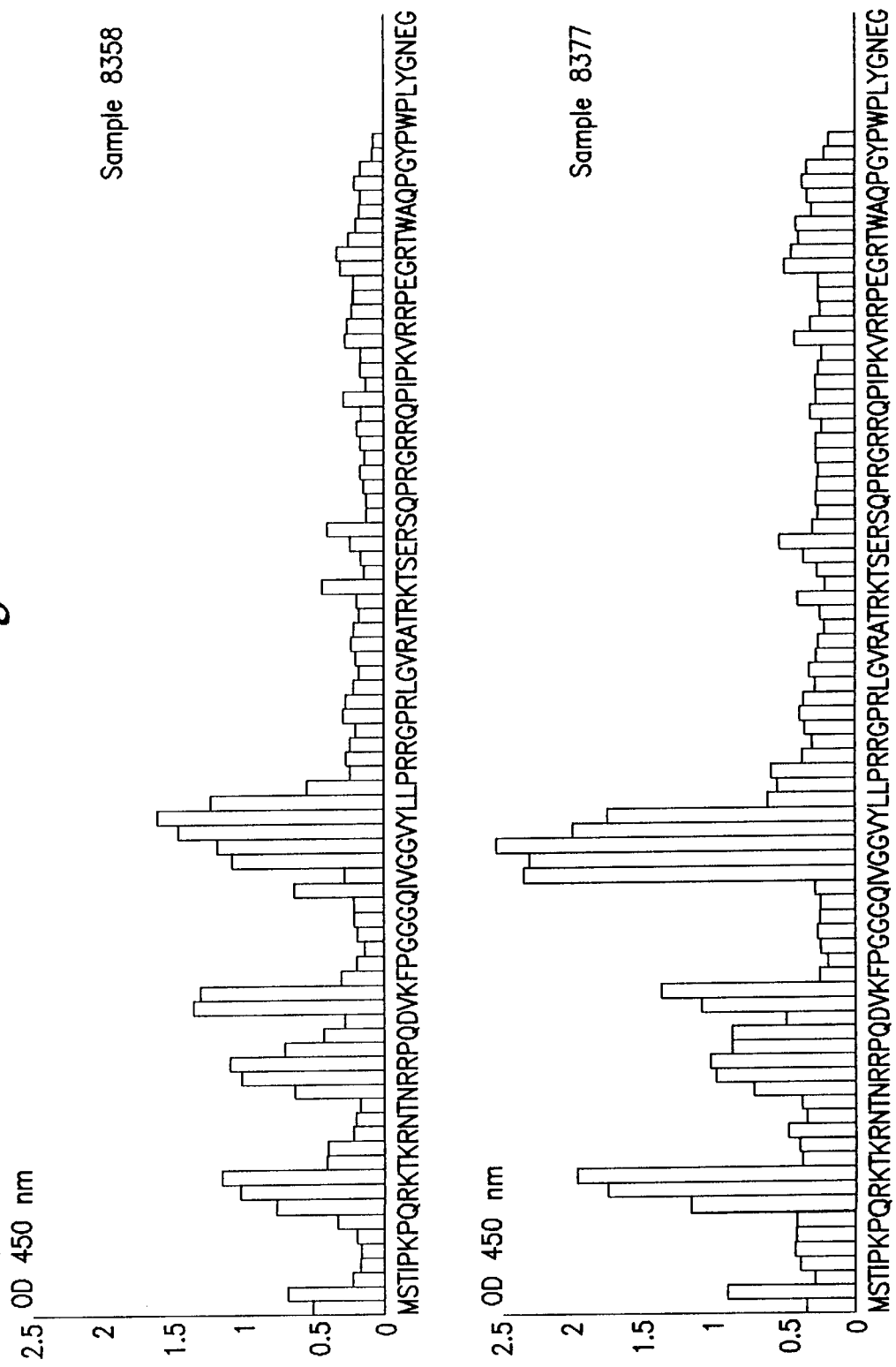

FIG. 5 represents the structures of N- and C-terminally biotinylated HIV-1 peptides (hereabove designated by 1a.1) originating from the transmembrane (TM) protein of HIV-1.

FIG. 6a represents the detection of core epitopes in the Core region of HCV using overlapping 9-mers (in an ELISA).

The sera used are indicated above each diagram.

The ordinates correspond to the optical density at 450 nm.

The abscissae correspond to the sequence of the protein in which the location of the epitope(s) is to be determined. For purposes of graphic illustration, the optical density is assigned to the first amino acid in the respective nine-mer sequences.

Figures 1, 6B:
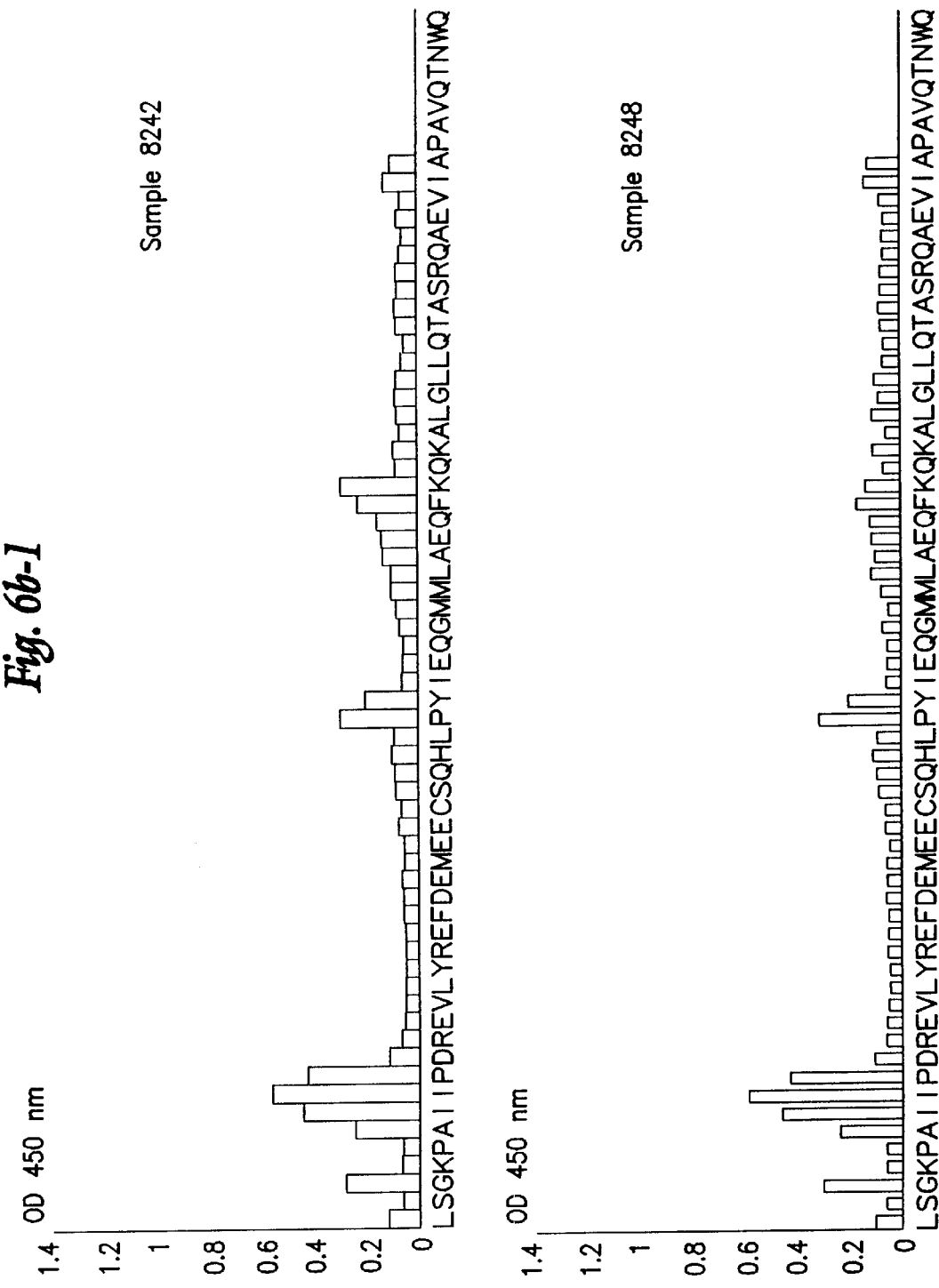
Figures 2, 6B:
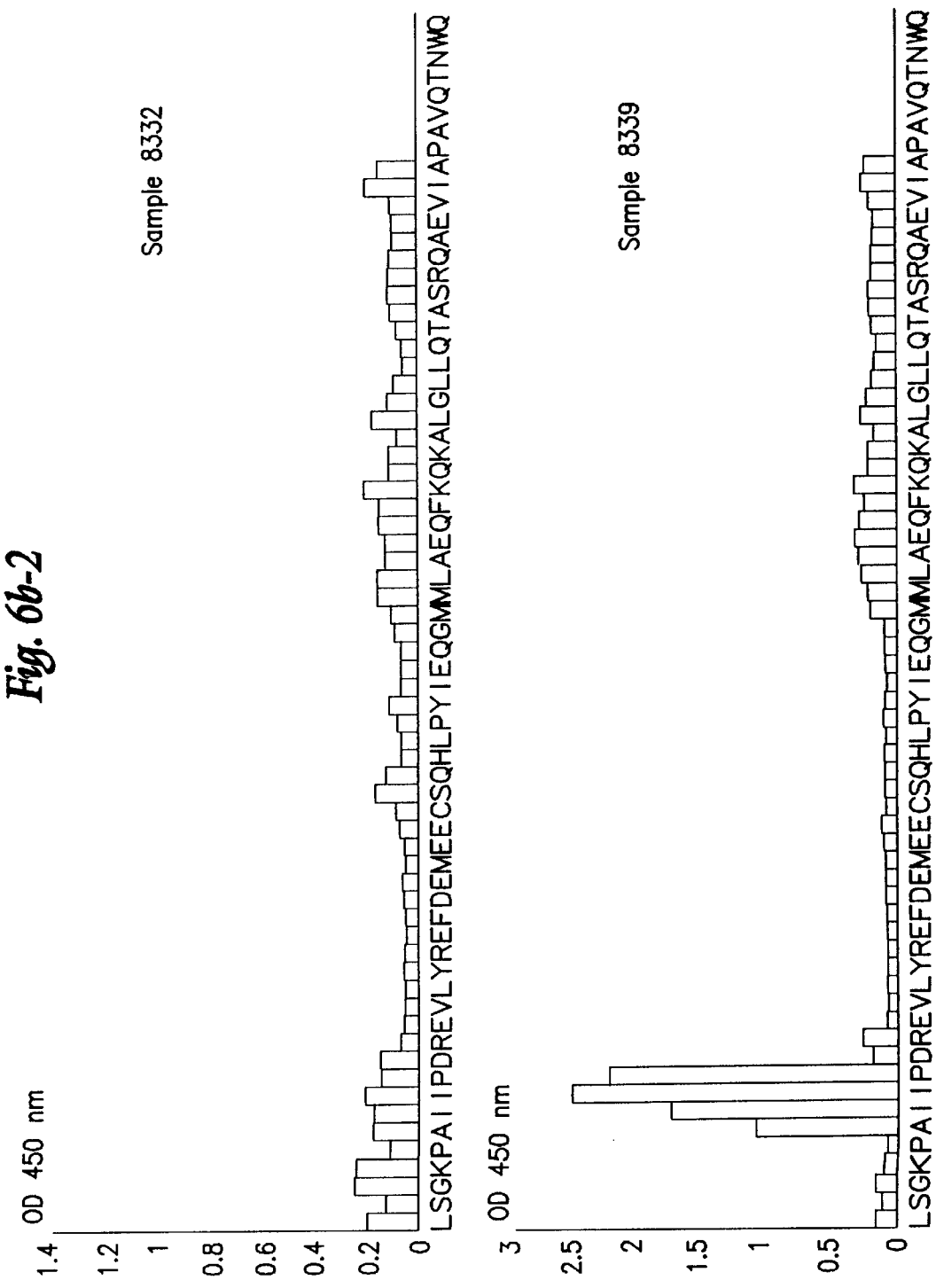
Figures 5, 6B:
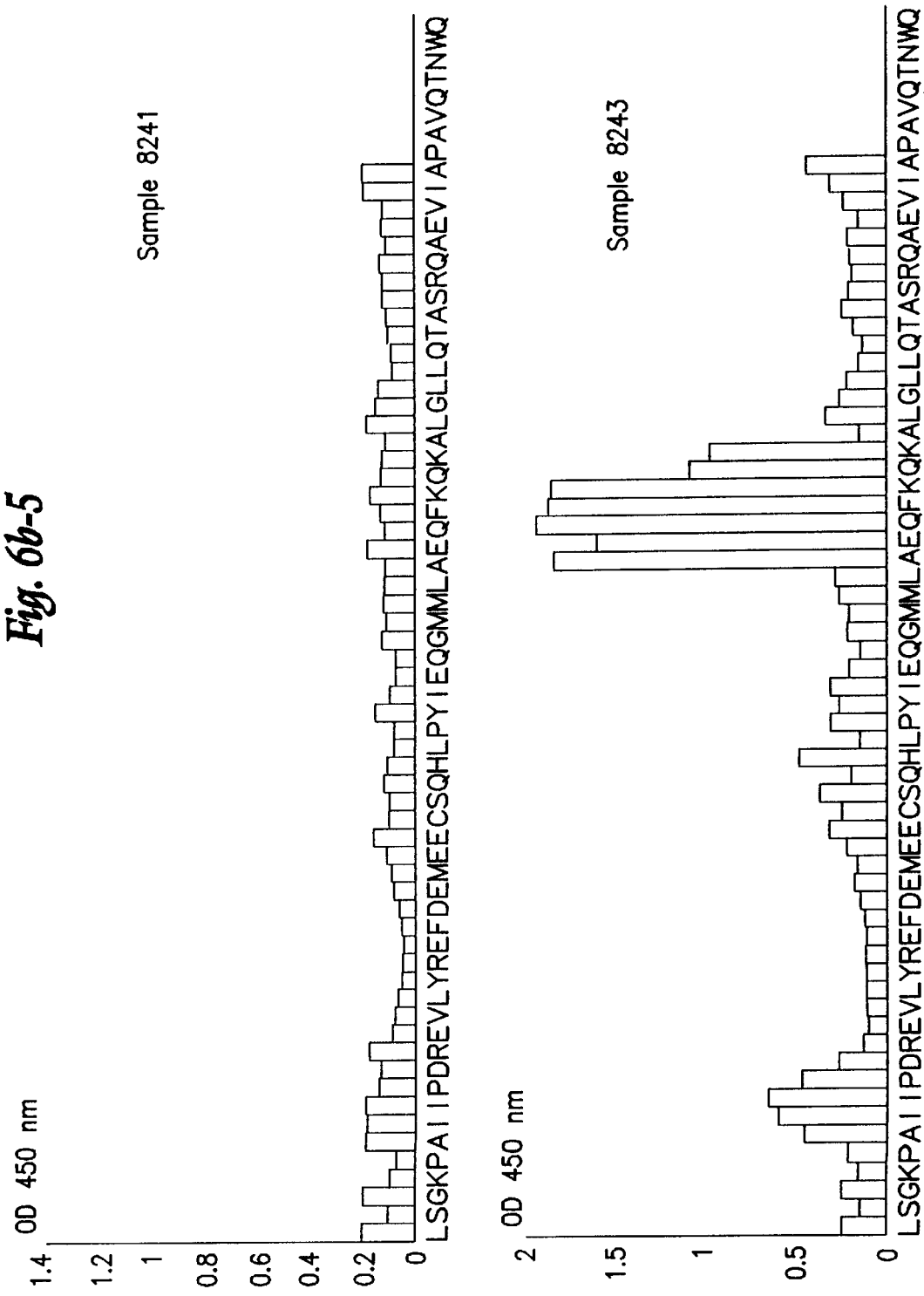

FIG. 6b represents the detection of core epitopes in the NS4 region of HCV using overlapping 9-mers (in an ELISA).

The sera used are indicated above each diagram.

The ordinates correspond to the optical density at 450 nm.

The abscissae correspond to the sequence of the protein in which the location of the epitope(s) is to be determined. For purposes of graphic illustration, the optical density is assigned to the first amino acid in the respective nine-mer sequences.

Figures 1, 6C:
Figures 2, 6C:
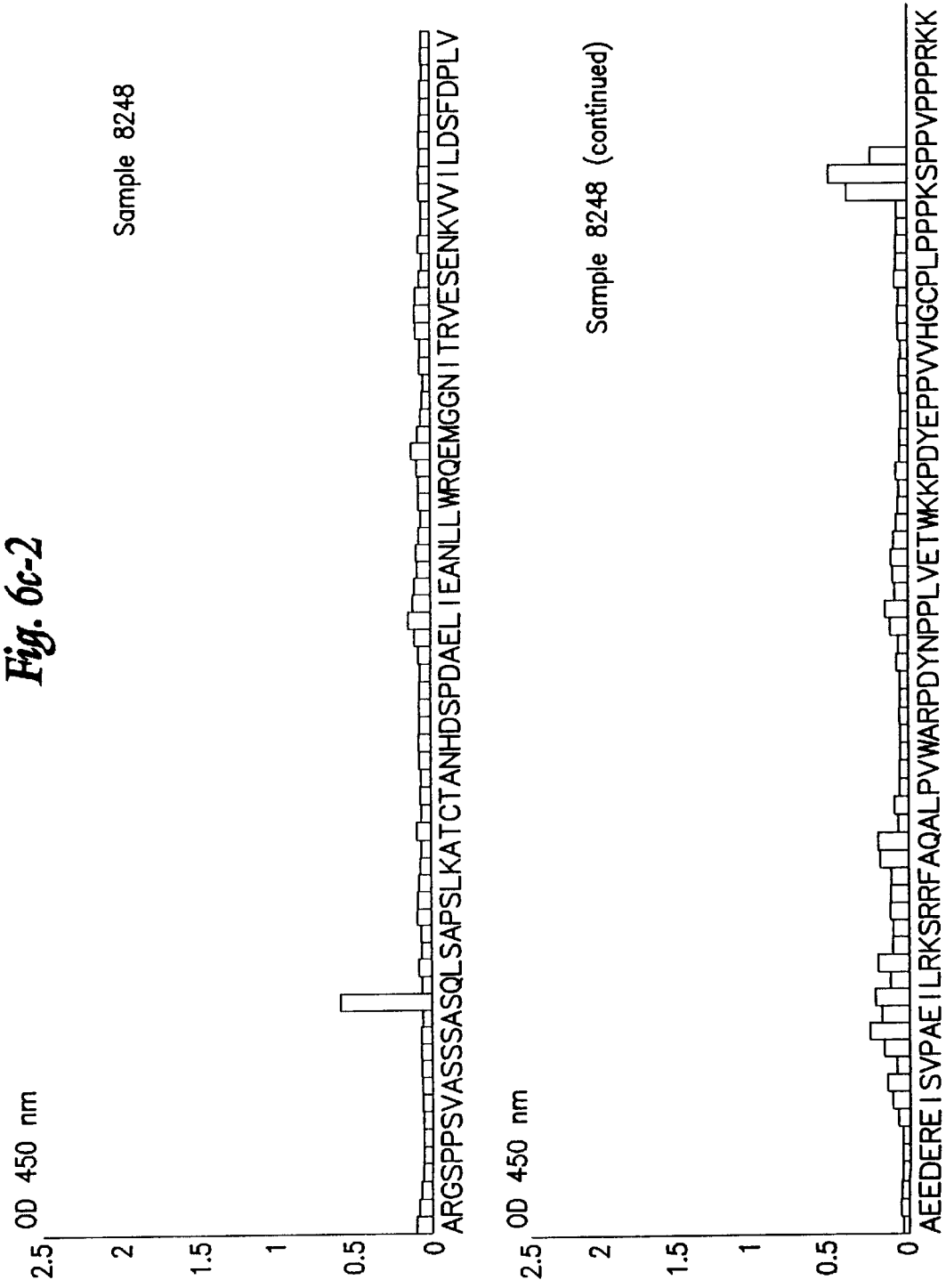
Figures 4, 6C:
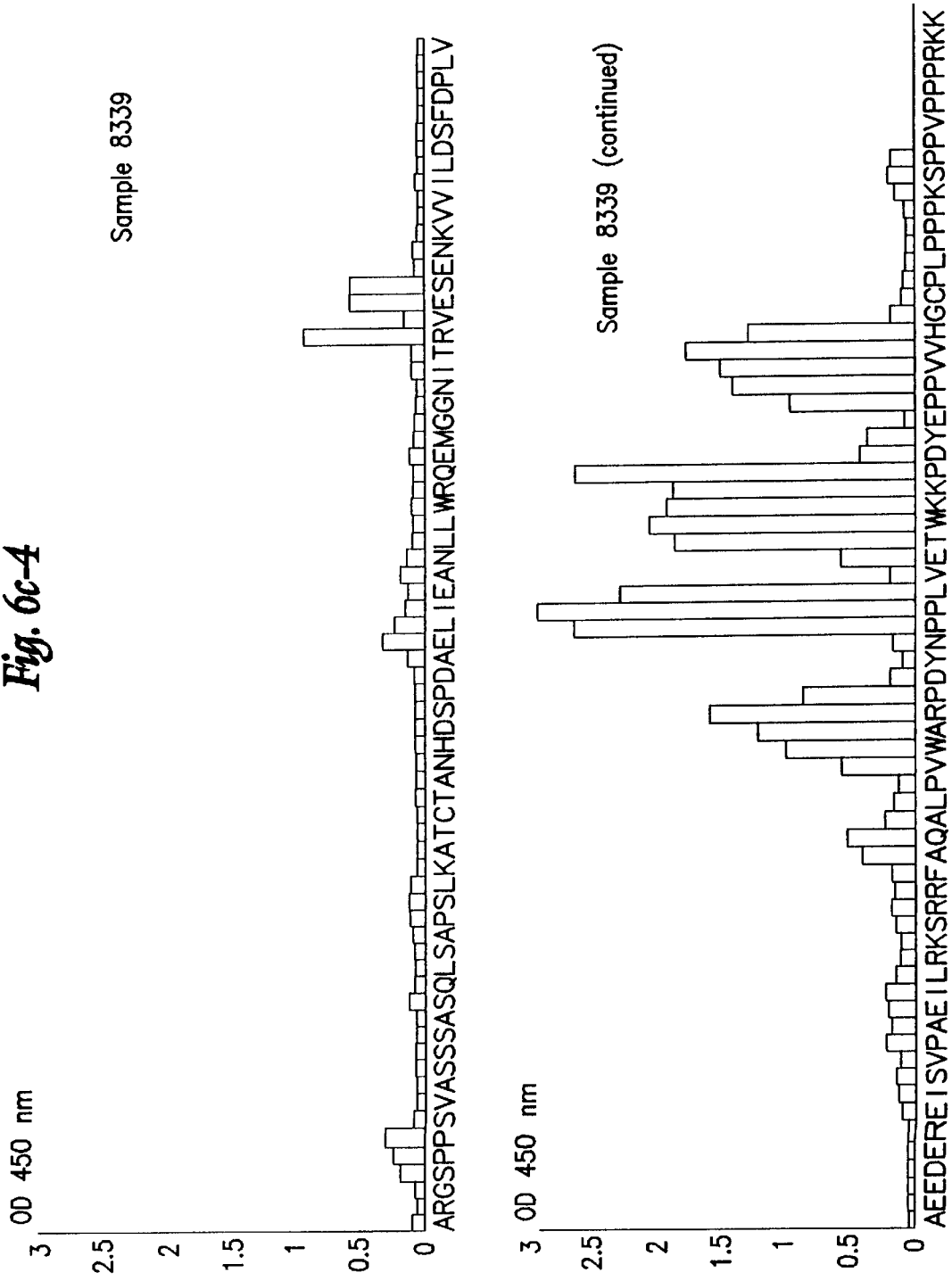
Figures 6, 6C:
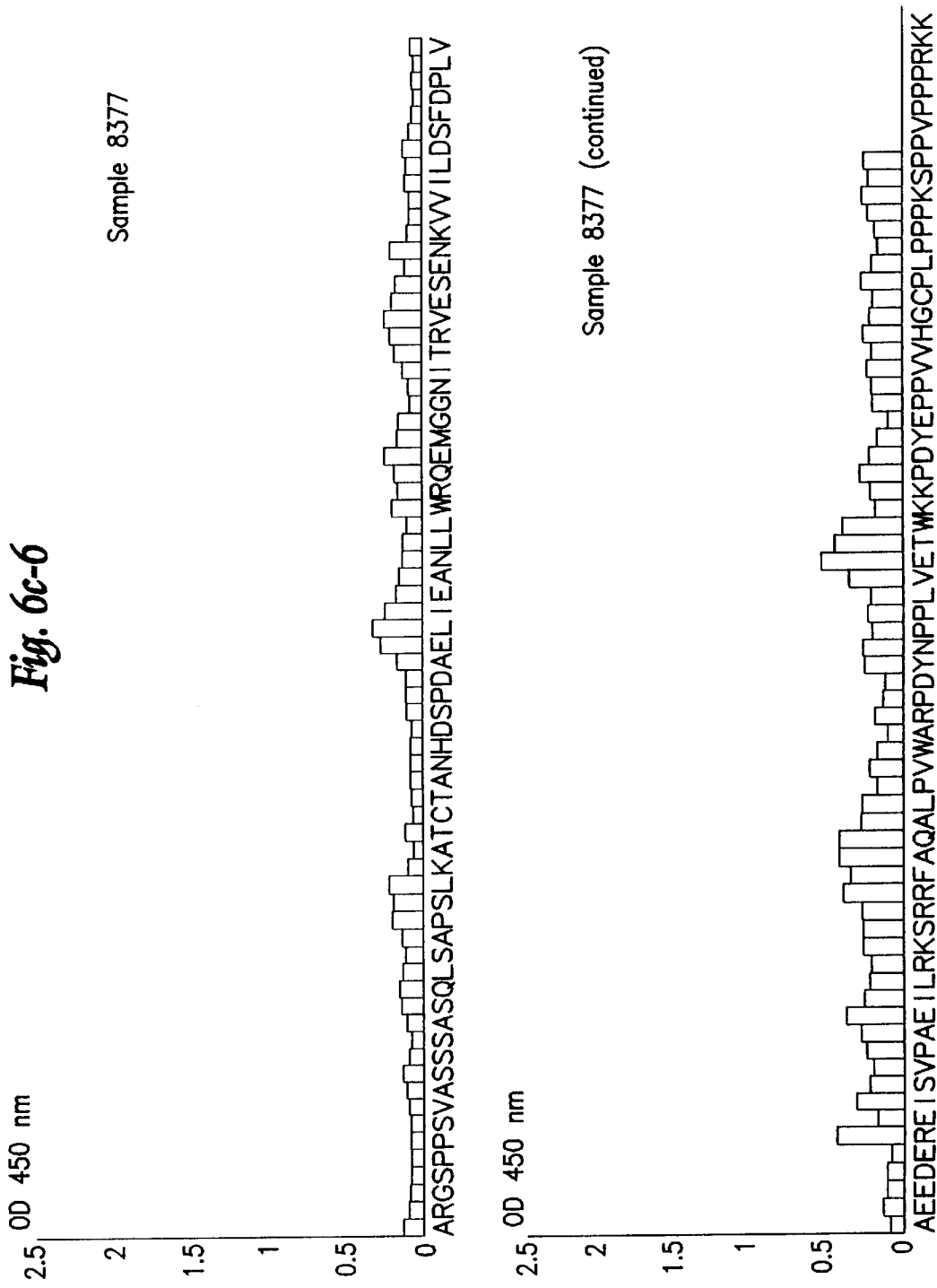

FIG. 6c represents the detection of core epitopes in the NS5 region of HCV using overlapping 9-mers (in an ELISA).

The sera used are indicated above each diagram.

The ordinates correspond to the optical density at 450 nm.

The abscissae correspond to the sequence of the protein in which the location of the epitope(s) is to be determined. For purposes of graphic illustration, the optical density is assigned to the first amino acid in the respective nine-mer sequences.

Figures 3, 7A:
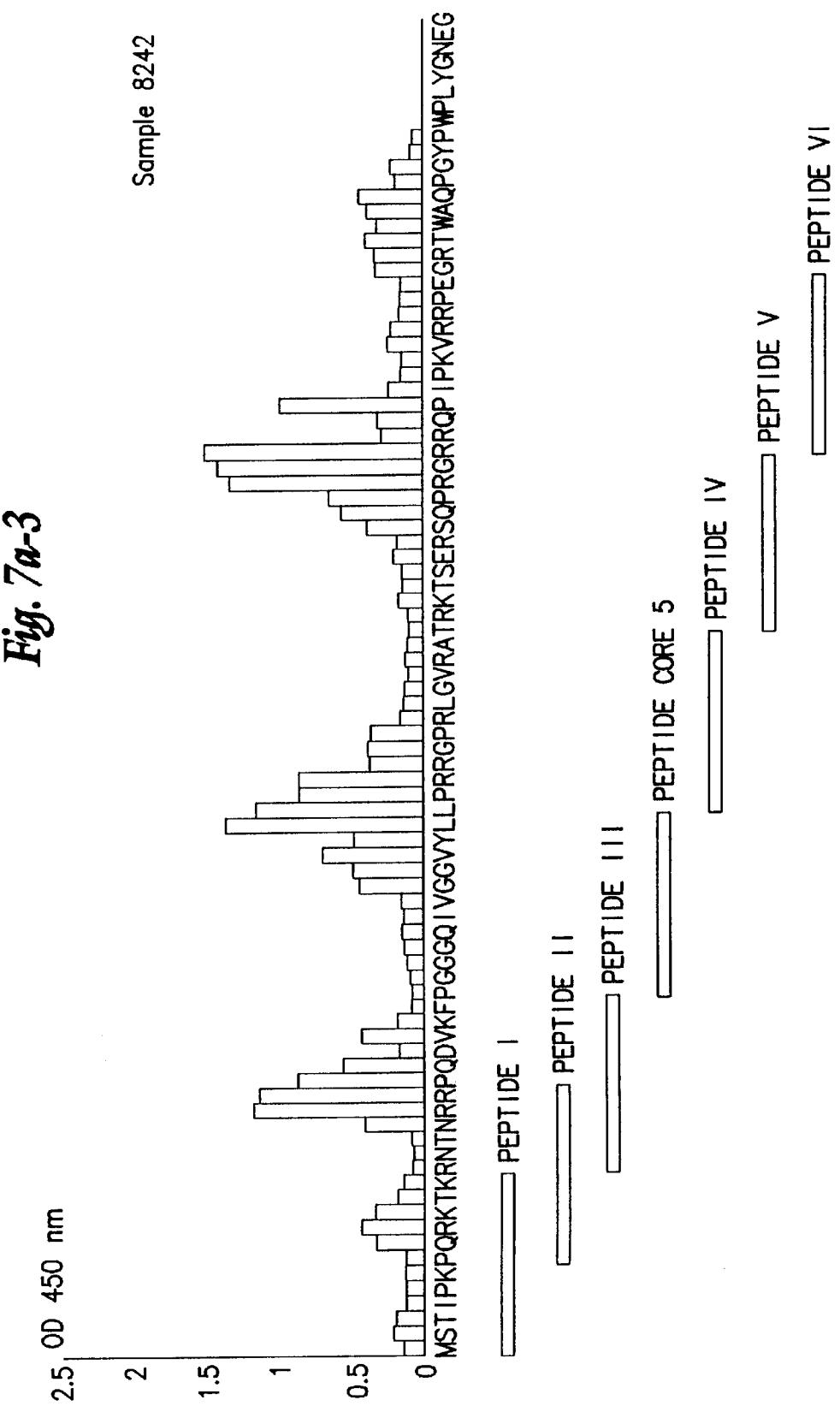

FIG. 7a corresponds to the positions of biotinylated 20-mers with respect to overlapping 9-mers (in an ELISA).

The abscissae corresponds to the protein sequence in which the epitope(s) is to be determined.

Figures 6, 6C, 7:
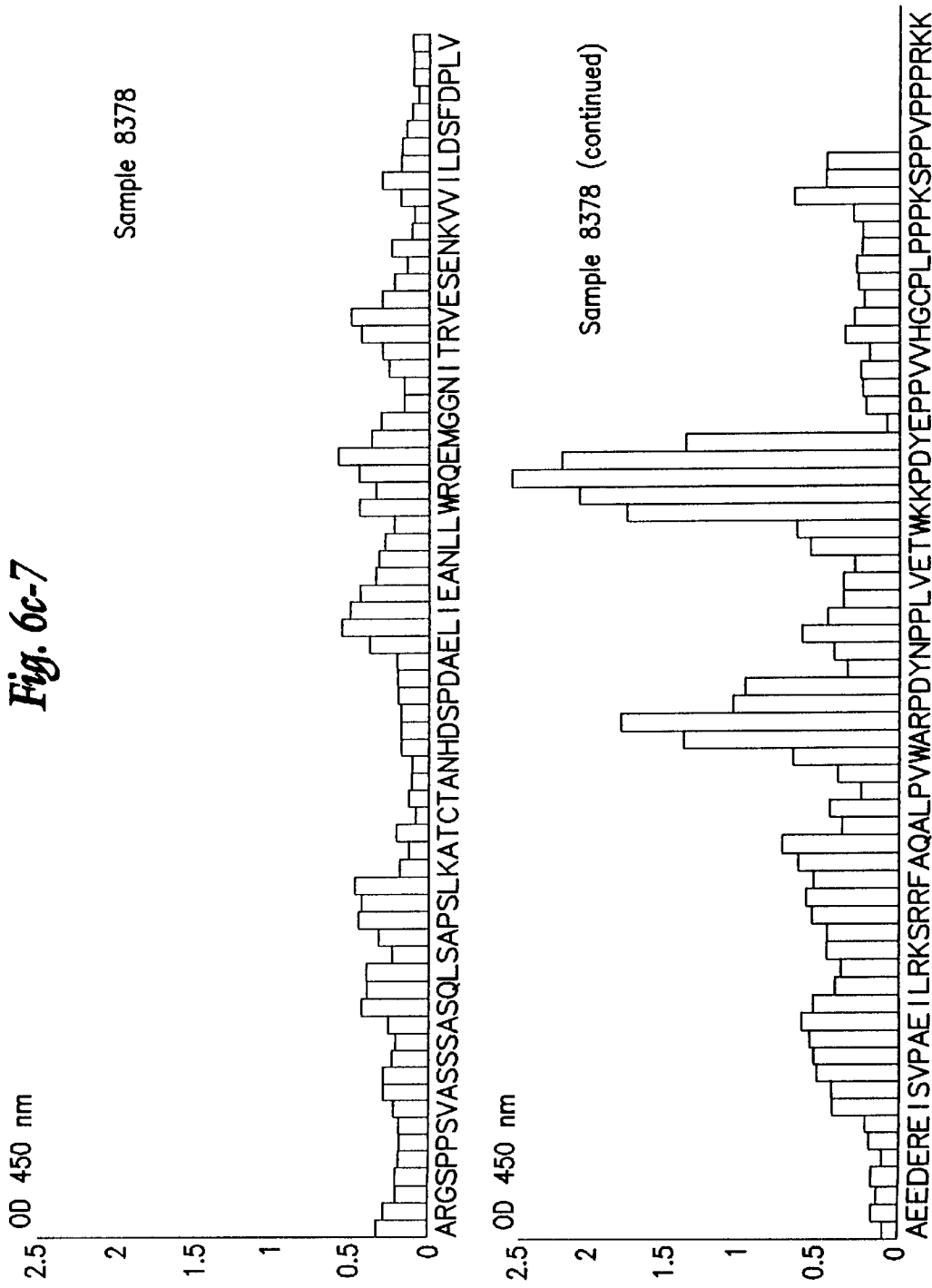

FIG. 7b corresponds to the positions of biotinylated 20-mers with respect to overlapping 9-mers (in an ELISA).

The abscissae corresponds to the protein sequence in which the epitope(s) is to be determined.

Figures 3, 7C:
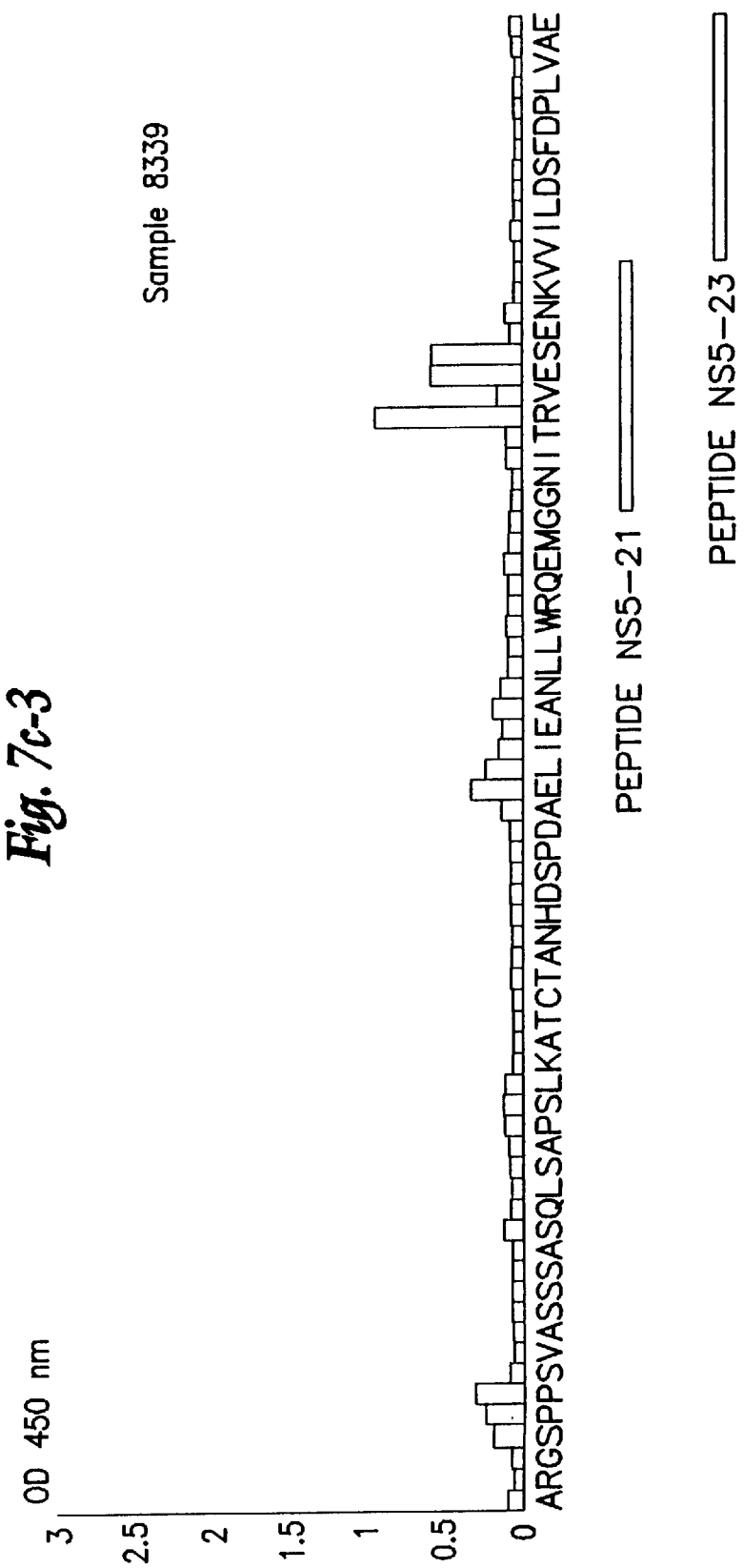

FIG. 7c corresponds to the positions of biotinylated 20-mers with respect to overlapping 9-mers (in an ELISA).

The abscissae corresponds to the protein sequence in which the epitope(s) is to be determined.

Figure 8:
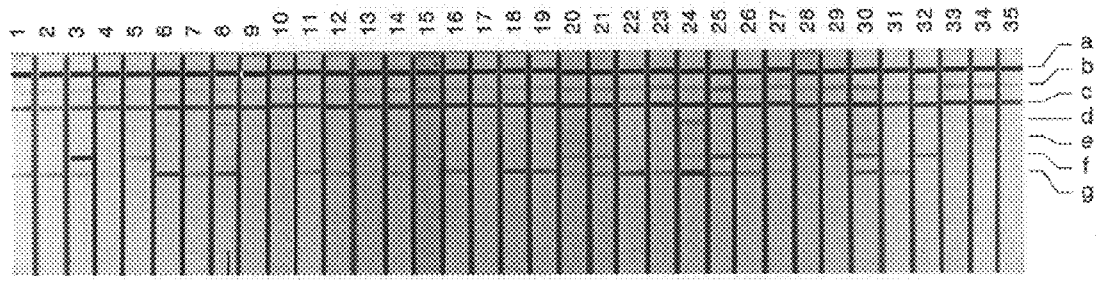

FIG. 8 (SEQ ID NO:176 and SEQ ID NO:177) represents a comparison of antibody recognition of biotinylated and unbiotinylated HCV peptides by line immunoassay (LIA).

Figure 9:
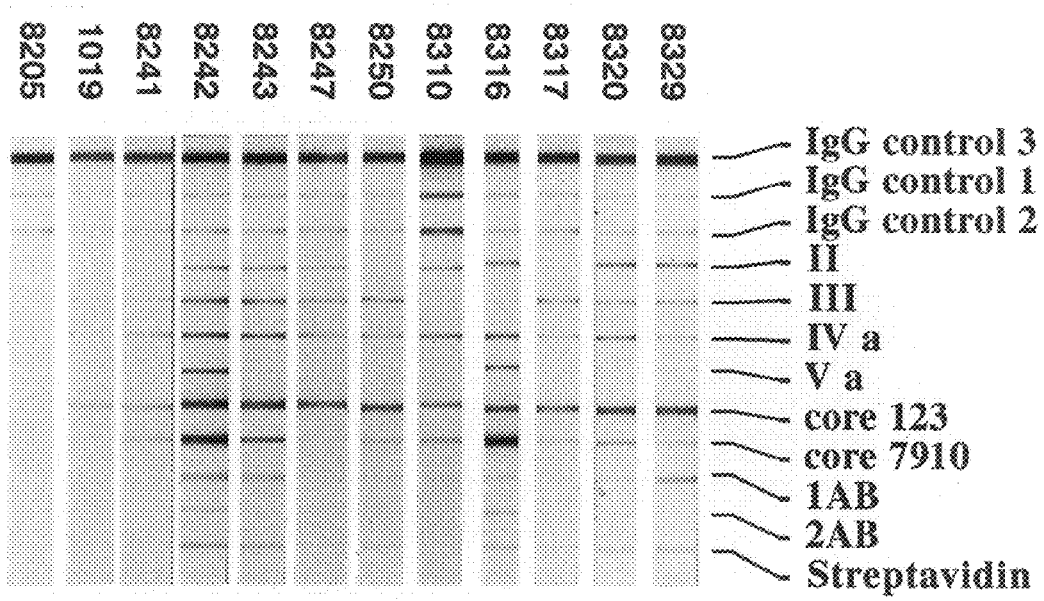

FIG. 9 represents a comparison of antibody recognition of biotinylated core peptides by line immunoassay (LIA).

The shorter and longer peptides are compared.

Figure 10:
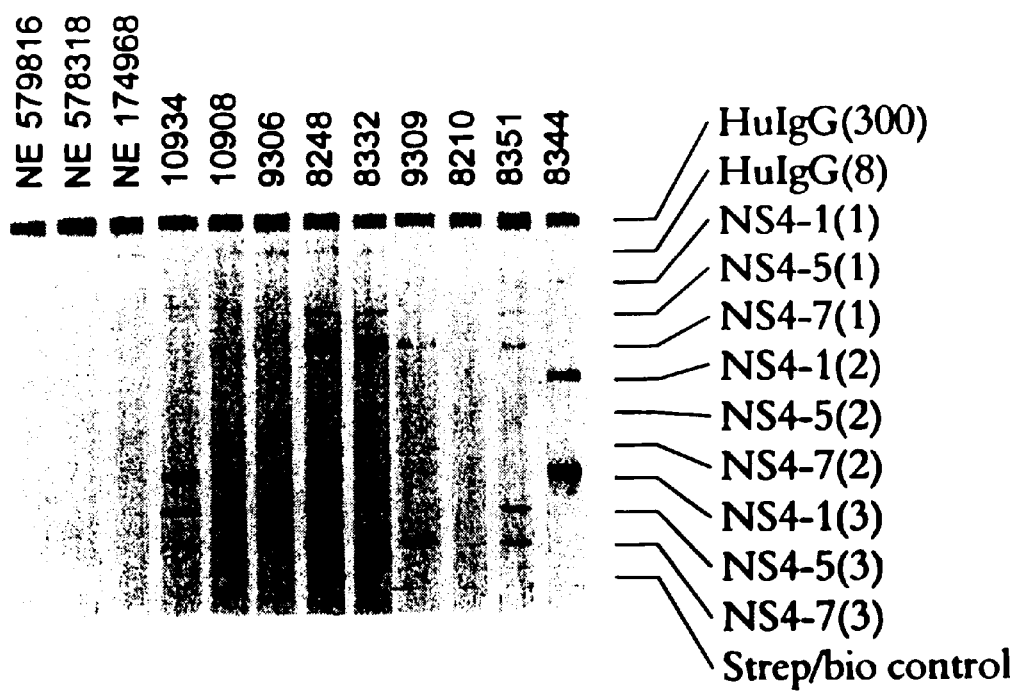

FIG. 10 represents an evaluation of type-specific HCV NS4 peptides by Line immunoassay (LIA).

FIG. 11 represents the amino acid sequence of peptides NS4-a to NS4-e.

FIG. 12 represents the composition of hybrid HCV peptides.

Figure 13:
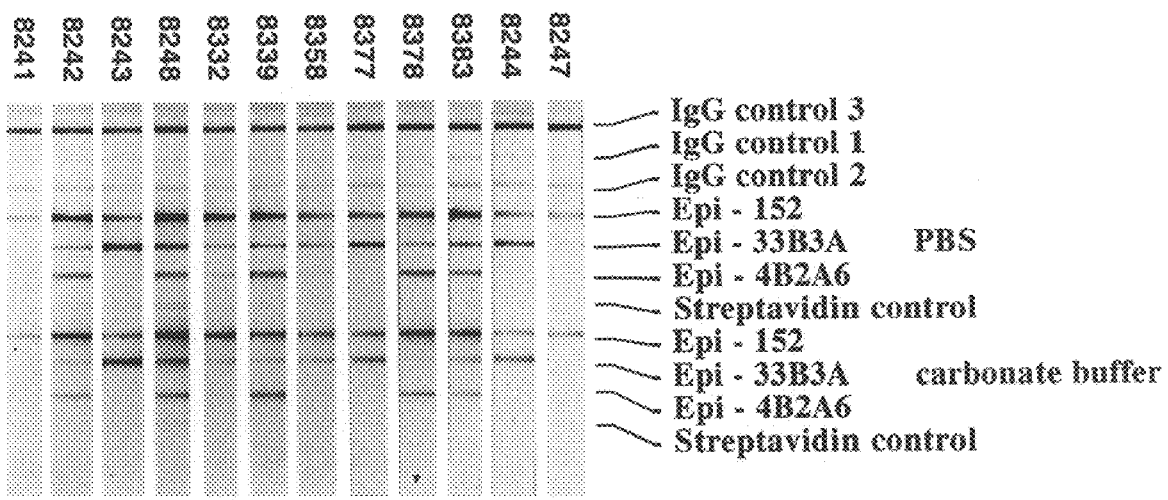

FIG. 13 represents the antibody recognition of hybrid HCV peptides.

Figures 14A, 14B:
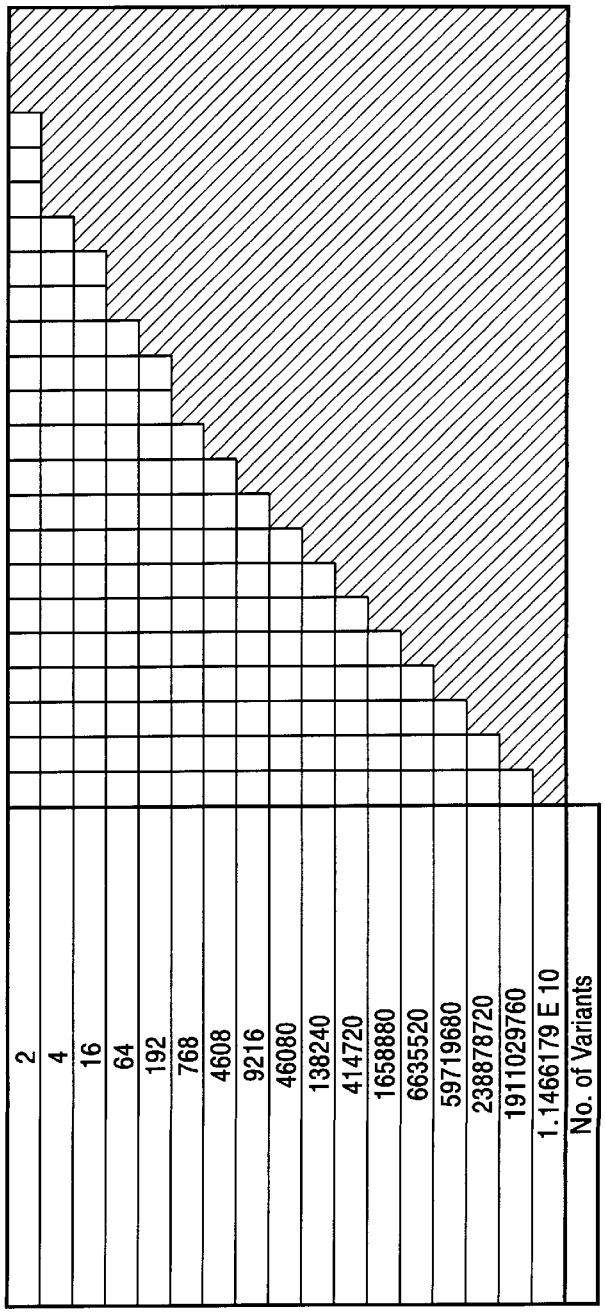
Figure 14C:
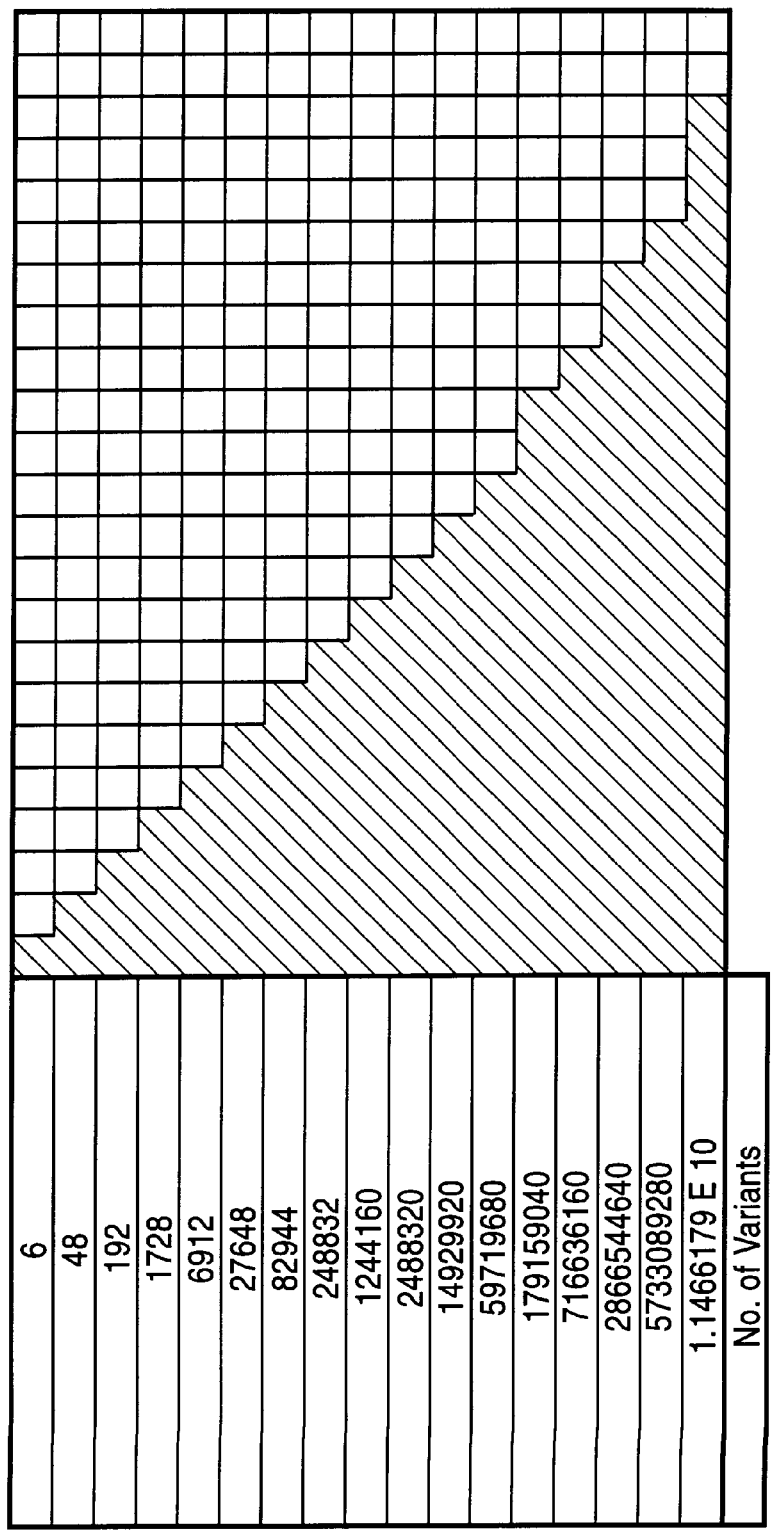
Figure 14D:
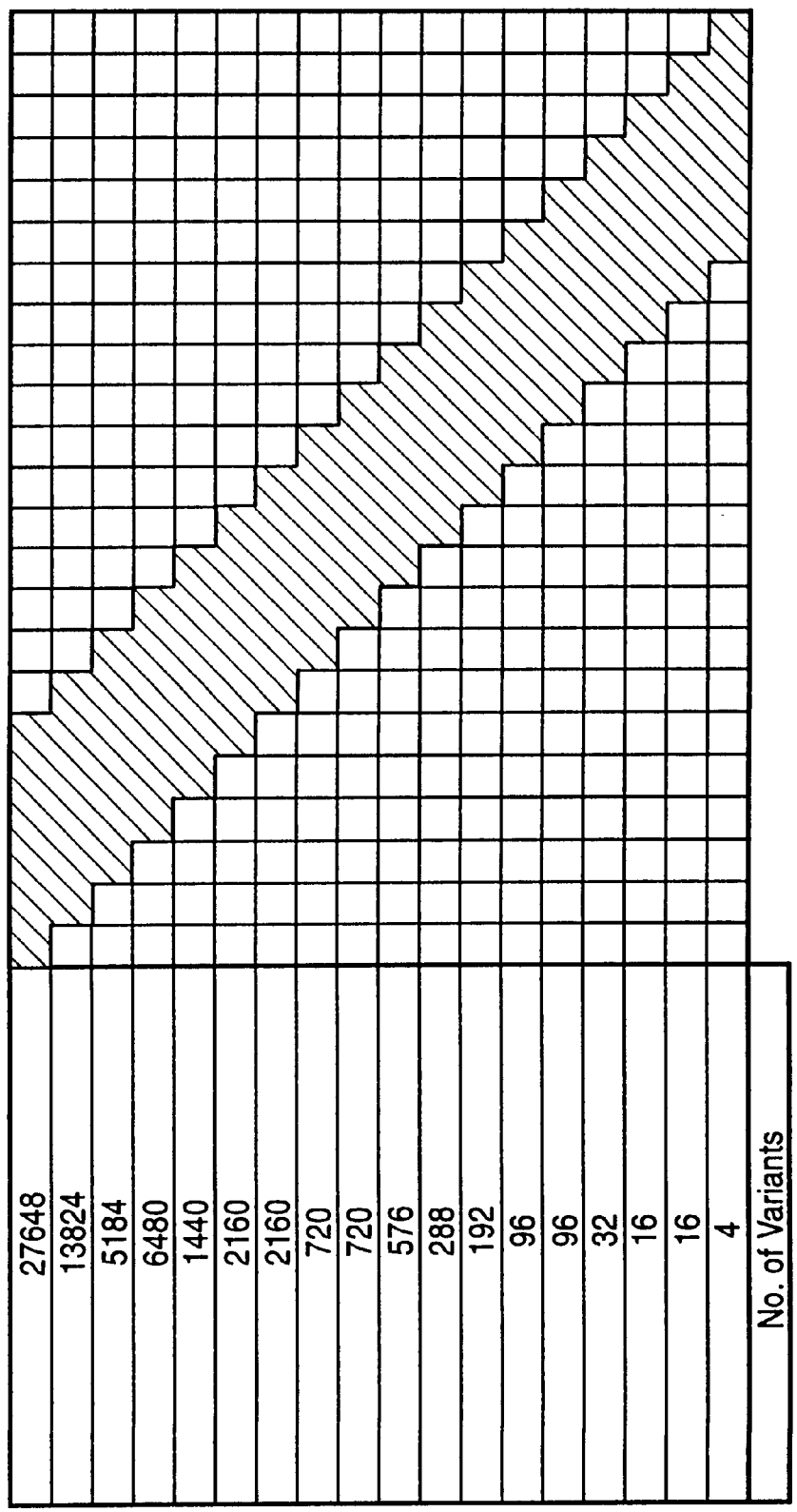

FIG. 14 represents the construction scheme for mixotope peptides from the N-terminus of E2/NS1 of HCV type 1.

Figure 15:
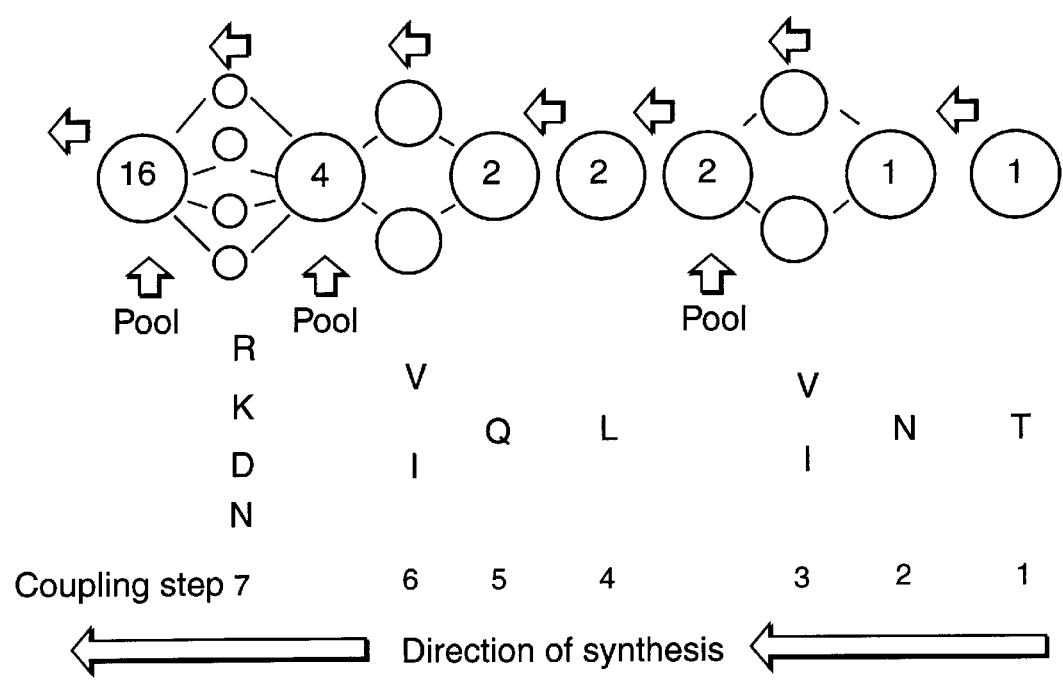
Figure 16A:
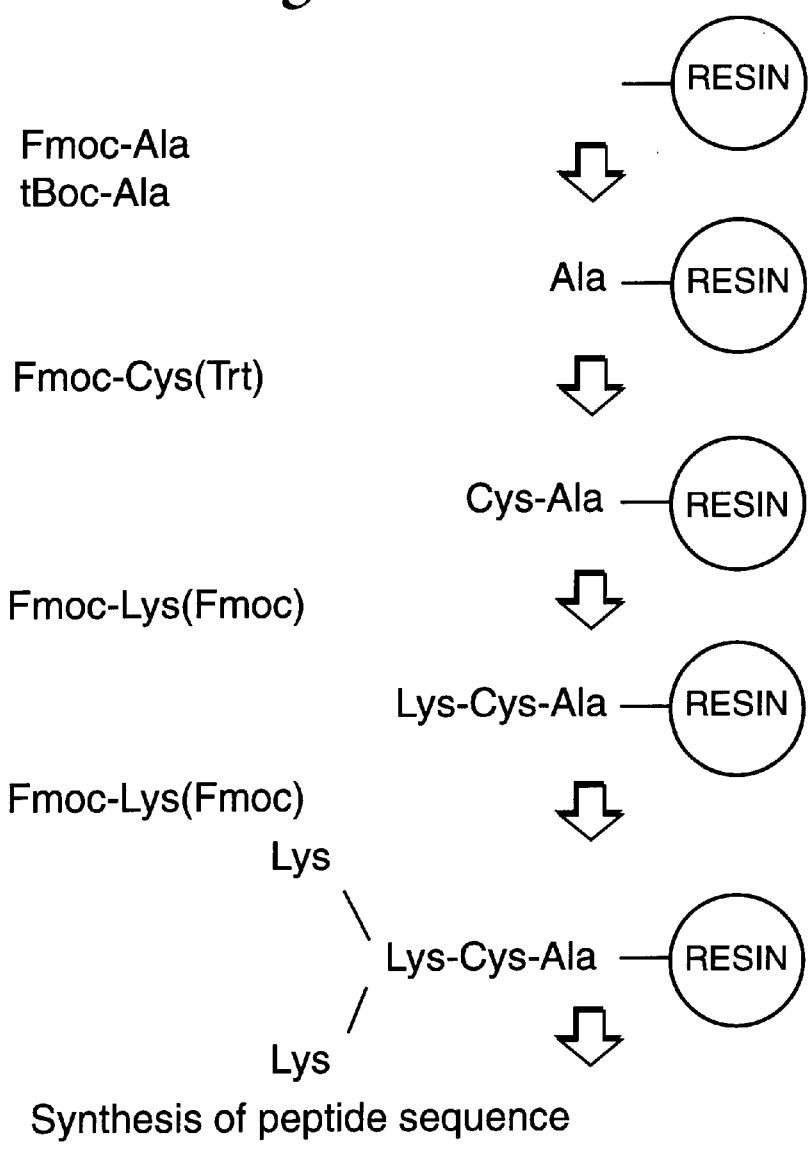
Figure 16A:
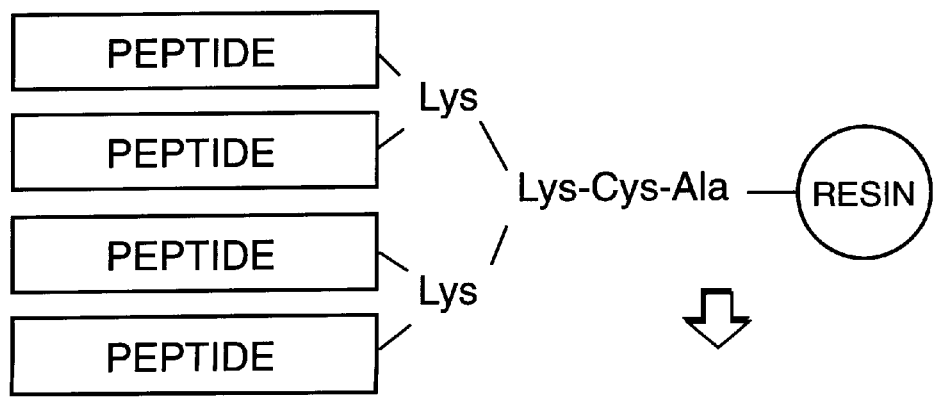
Figure 16B:
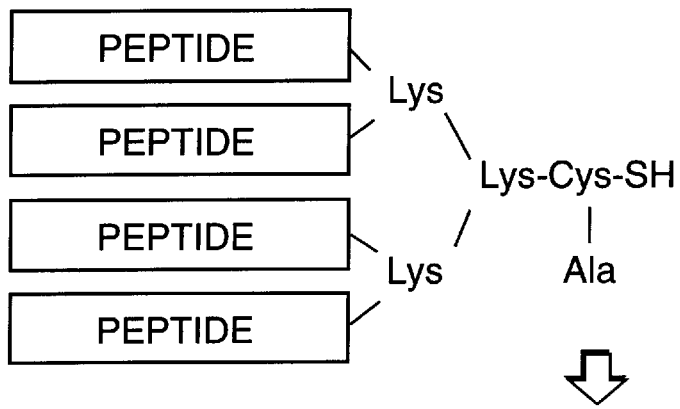
Figure 16B:
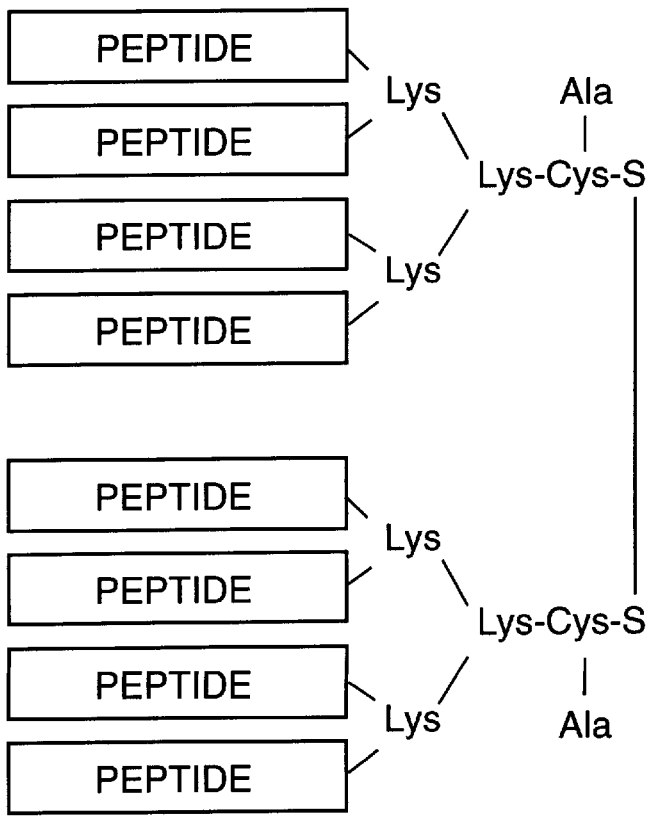

FIG. 15 (SEQ ID NO:178 to SEQ ID NO:261) represents the mixotope synthesis strategy.

FIG. 16 (SEQ ID NO:262 to SEQ ID NO:369) represents the synthesis of multiple antigen peptides (MAPs).

Figure 17A:
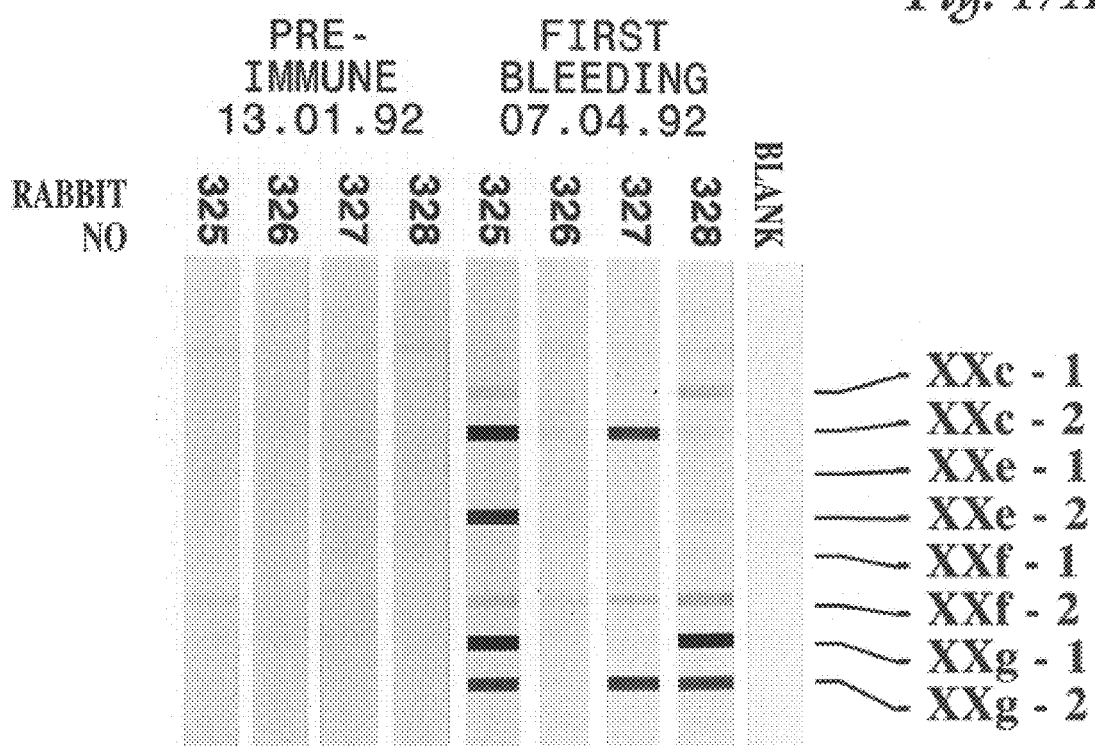
Figure 17B:
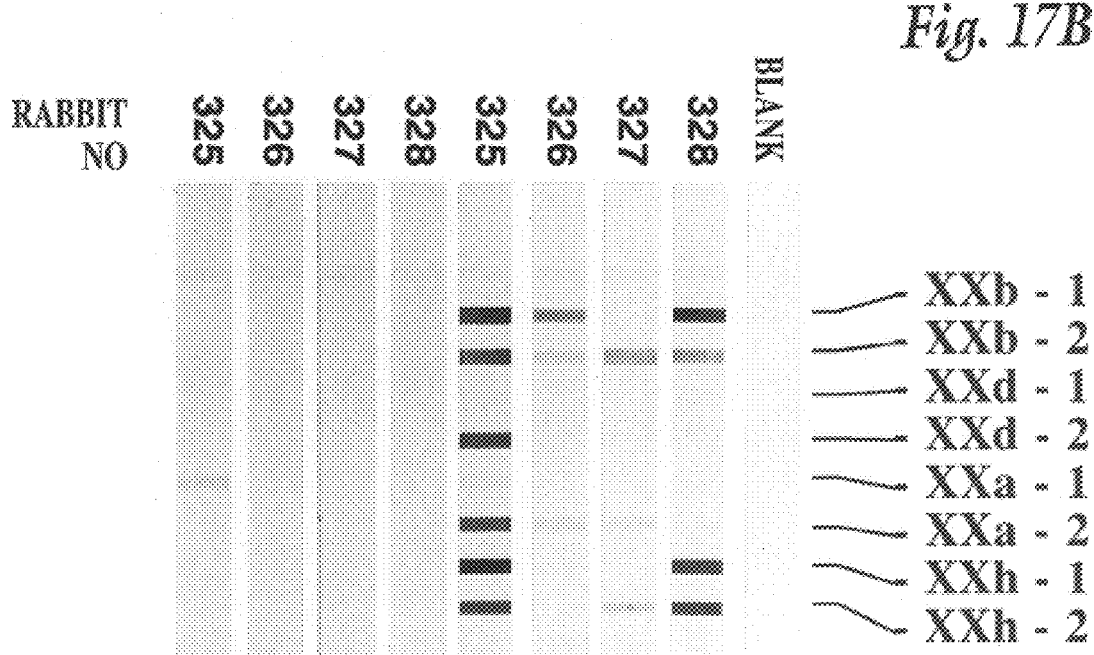

FIG. 17 (SEQ ID NO:370 to SEQ ID NO:453) represents the recognition of E2/NS1 peptides by sera from rabbits immunized with E2/NS1 "b" peptide MAPs.

Figure 18:
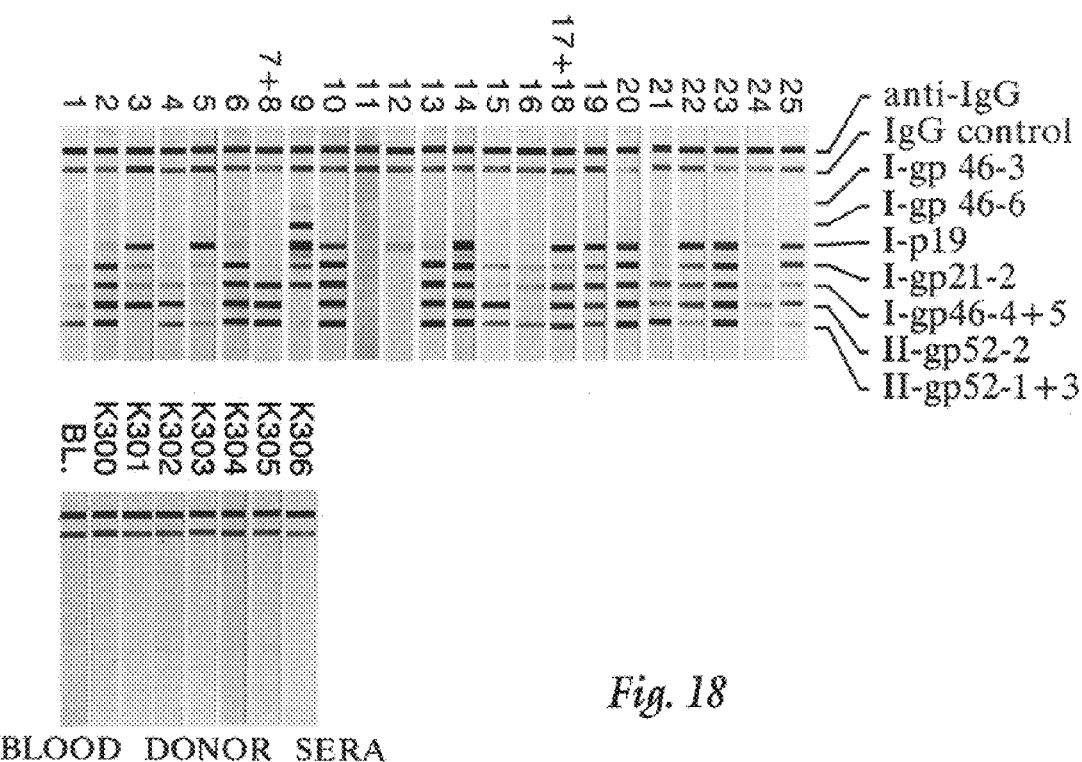

FIG. 18 represents the recognition of a commercially available serum panel with a number of biotinylated HTLV-I and HTLV-II peptides incorporated into LIA strips.

Table 1 represents the antibody recognition of unbiotinylated HIV-1 and HIV-2 peptides (designated by TM-HIV-1 and TM-HIV-2) and biotinylated HIV-1 and HIV-2 peptides (hereabove referred to as 1a.1 and 2a, and also designated by TM-HIV-1 Bio and TM-HIV-2 Bio) in an ELISA.

Table 2 represents the comparison of antibody recognition of unbiotinylated and biotinylated peptides from the V3 sequence of isolate HIV-1 mn (also referred as 1b.4) in an ELISA.

Table 3 represents the comparison of antibody recognition of the biotinylated V3-mn peptide (referred to as 1b.4) bound to streptavidin and avidin, in an ELISA.

Table 4 represents the comparison of antibody recognition of biotinylated and unbiotinylated HCV peptides, in an ELISA.

More particularly

Table 4A corresponds to the antibody binding to HCV peptide XI.

Table 4B corresponds to the antibody binding to HCV peptide XVI.

Table 4C corresponds to the antibody binding to HCV peptide II.

Table 4D corresponds to the antibody binding to HCV peptide III.

Table 4E corresponds to the antibody binding to HCV peptide V.

Table 4F corresponds to the antibody binding to HCV peptide IX.

Table 4G corresponds to the antibody binding to HCV peptide XVIII.

Table 5 represents a comparison of antibody binding to biotinylated and non-biotinylated peptides, at different peptide coating concentrations, in an ELISA.

Table 6 represents the comparison of N- and C-terminally biotinylated TM-HIV-1 peptide (referred to as 1a.1), in an ELISA.

Table 7 represents a comparison of antibody recognition of unbiotinylated and carboxy-biotinylated HCV peptide I.

Table 8 represents the use of mixtures of biotinylated HIV and HCV peptides for antibody detection, in an ELISA.

Table 9 represents sequences of the core epitopes of the HCV Core protein.

Table 10 represents sequences of the core epitopes of the HCV NS4 protein.

Table 11 represents sequences of the core epitopes of the HCV NS5 protein.

Table 12 represents the antibody binding of various Core, NS4, and NS5 biotinylated 20-mers by 10 test sera.

Table 13 represents the antibody recognition of individual E2/NS1 peptides (percent of all sera giving a positive reaction).

Table 14 represents the overall recognition of HIV V3-loop peptides.

Table 15 represents the recognition of HIV peptides according to the geographical region.

Table 16 represents the recognition of European, African and Brazilian HIV-1-positive sera to HIV-I V3-loop peptides V3-con and V3-368.

Table 17 represents the recognition of HIV-2 positive sera to two HIV-2 V3 loop peptides.

Table 18 represents the antibody recognition of hybrid peptides.

Table 19 represents the antibody recognition of mixed HTLV I and II peptides.

All amino acid sequences are given in the conventional and universally accepted three-letter code and where indicated in the one-letter code. The peptide sequences are given left to right which, by convention, is the direction from the amino terminus to the carboxy-terminus.

A number of unconventional codes are also used to represent chemical groups or modifications and are defined as follows:

| Group | Code |
|-------|------|
| Ac | acetyl |
| Bio | D-biotinyl |
| Fmoc | 9-fluorenylmethoxycarbonyl |
| tBoc | tertiary butyloxycarbonyl |

EXAMPLE 1
Peptide Synthesis

All of the peptides described were synthesized on Tenta-Gel S-RAM (Rapp Polymere, Tübingen, Germany), a polystyrene-polyoxyethylene graft copolymerfunctionalized with the acid-labile linker4-(α-Fmoc-amino-2',4'-dimethoxybenzyl) phenoxyaceticacid (Rink, Tetrahedron Lett. (1987) 28:3787) in order to generate peptide carboxy-terminal amides upon cleavage. t-Butyl-based side chain protection and Fmoc-α-amino-protection was used. The guanidine-group of arginine was protected with the 2,2,5,7, 8-pentamethylchroman-6-sulfonyl moiety. The imidazole group of histidine was protected with either t-Boc or trityl and the sulfhydryl group of cysteine was protected with a trityl group. Couplings were carried out using preformed O-pentafluorophenyl esters except in the case of arginine where TBTU was used as the activating agent in the presence of 1.5 equivalents of the base N-methylmorpholine. Occasionally, glutamine and asparagine were also coupled using TBTU activation. In these cases, the trityl-protected derivatives of these amino acids were employed. Biotin was coupled using either TBTU or HBTU. All syntheses were carried out on a Milligen 9050 PepSynthesizer (Novato, Calif.) using continuous flow procedures. Following cleavage with trifluoroacetic acid in the presence of scavengers and extraction with diethylether, all peptides were analyzed by C18-reverse phase chromatography.

EXAMPLE 2
Synthesis of N-α-Fmoc-Lys (N-ε-Biotin)

A. Method A

Commercially available N-α-Fmoc-L-lysine (N-ε-tBoc) (1.5 grams) was treated with 20 milliliters of 95% trifluoroacetic acid, 5% H$_2$O for 2 hours at room temperature. Most of the acid was then evaporated under a stream of nitrogen. Ten milliliters of water was added and the solution was extracted 3 times with diethylether. The aqueous phase was then evaporated to dryness in vacuo over phosphorus pentoxide. The resulting powder(N-α-Fmoc-L-lysine) was analyzed by reverse phase chromatography and revealed a homogeneous product which was, as expected, more hydrophilic than the starting material.

N-α-Fmoc-lysine (190 mg, 0.49 mmol) was dissolved in 8 milliliters of 0.1 M borate buffer, pH 8.7. N-hydroxysuccinimidobiotin (162 mg, 0.47 mmol) was dissolved in 4 milliliters of dimethylformamide and added to the solution of N-α-Fmoc-lysine. The pH was monitored and titrated as necessary, with NaOH. After 2 hours, the solution was acidified with HCl to pH 2.0, at which time a white precipitate was obtained.

Following extraction with ethylacetate and centrifugation, the white precipitate was found at the H2O: ethylacetate interface. Both phases were removed and the precipitate extracted twice with 10 mM HCl, once with ethylacetate, followed by two extractions with diethylether. The precipitate was dissolved in DMF and precipitated by addition of diethylether. The crystalline powder was then dried in vacuo over phosphorus pentoxide. The resulting product was analyzed by reverse phase chromatography and revealed a major peak which, as expected, eluted later than N-α-Fmoc-Lys. A very small peak of N-α-Fmoc-Lys was also observed. (FIG. 2a).

B. Method B

Commercially available N-ε-biotinyl lysine (biocytin, Sigma, 249 mg, 0.67 mmol) was dissolved in 8 milliliters of 1 M Na2CO3 and cooled on ice. Fluorenylmethylsuccinimidyl carbonate (222 mg, 0.66 mmol) was dissolved in 2 milliliters of acetone and was added to the biotinyl lysine solution over a period of 30 minutes with vigorous stirring. Stirring was continued for 5 hours at room temperature. The pH was maintained between 8 and 9 by addition of 1 M Na$_2$CO$_3$ as necessary. The acetone was then evaporated off under vacuum, and 1.0 M HCl was added until the pH of the solution was approximately 2. Upon acidification of the solution, a white precipitate appeared which was washed twice with 10 mM HCl, twice with ethyl acetate, and twice with diethylether. The precipitate was dissolved in DMF and precipitated by addition of diethylether. The crystalline powder was then thoroughly dried in vacuo over phosphorus pentoxide. The resulting product was analyzed by reverse phase chromatography and revealed a major peak which eluted with the same retention time (30.5 minutes) as the product obtained using method 1 (FIG. 2b).

EXAMPLE 3
Methods for the Determination of Peptides Corresponding to Immunologically Important Epitopes in an Enzyme-linked Immunosorbent Assay (ELISA) Using Specific Antibodies Where peptides were to be coated directly, stock solutions of the peptides were diluted in sodium carbonate buffer, pH 9.6 and used to coat polystyrene microtiter plates at a peptide concentration of 2 to 5 micrograms per milliliter for 1 hour at 37° C.

In cases where biotinylated peptides were to be evaluated, plates were first coated with streptavidin in sodium carbonate buffer, pH 9.6 at a concentration of 3 micrograms per milliliter for 1 hour at 37° C. The plates were then washed to remove excess, unbound protein. A working solution of the biotinylated peptide at 1 microgram per milliliter in sodium carbonate buffer was then added to the wells of the microtiter plate and incubated for 1 hours at 37° C.

Once the plates had been coated with antigen, any remaining free binding sites on the plastic were blocked with casein. After washing, a dilution of the appropriate antisera, usually 1:100, was added to the wells of the plates and incubated for 1 hour at 37° C.

After washing to remove unbound material, specific antibody binding was detected by incubating the plates with goat anti-human immunoglobulin antibodies conjugated to the enzyme horseradish peroxidase. Following removal of unbound conjugate by washing, a solution containing H$_2$O$_2$ and 3,3',5,5'-tetramethylbenzidine was added.

Reactions were stopped after a suitable interval by addition of sulfuric acid. Positive reactions gave rise to a yellow color which was quantified using a conventional microtiter plate reader. Absorbance measurements were made at a wavelength of 450 nanometers and all data are expressed as an optical density value at this wavelength.

EXAMPLE 4
Use of Biotinylated HIV Peptides for the Detection of HIV-specific Antibodies Experiments were performed to evaluate antibody recognition of short, 10 amino acid-long, N-acetylated peptides corresponding to other contained within the transmembrane proteins of HIV-1 and HIV-2. Direct coating of these peptides in the wells of microtiter plates gave very poor results when antibody binding was evaluated in an ELISA. Since it was suspected that the peptides did not bind well to the polystyrene solid phase, the peptides were resynthesized in the same way except that biotin was attached to the amino terminus of the peptides, separated from the decamer peptide sequence by three glycine residues whose function it was to serve as a linker arm. The peptides used for the comparison were as follows:

TM-HIV-1:
(SEQ ID NO:110) Ac-Ile-Trp-Gly-Cys-Ser-Gly-Lys-Leu-Ile-Cys-NH2
TM-HIV-1 Bio
(SEQ ID NO:111) Bio-Gly-Gly-Gly-Ile-Trp-Gly-Cys-Ser-Gly-Lys-Leu-Ile-Cys-NH2
TM-HIV-2
(SEQ ID NO:112) Ac-Ser-Trp-Gly-Cys-Ala-Phe-Arg-Gln-Val-Cys-NH2
TM-HIV-2 Bio
(SEQ ID NO:113) Bio-Gly-Gly-Gly-Ser-Trp-Gly-Cys-Ala-Phe-Arg-Gln-Val-Cys-NH2

The biotinylated peptides were loaded onto microtiter plates which had been coated with streptavidin. Antibody binding to these peptides was compared to antibody binding to the unbiotinylated peptides which were coated directly onto microtiter plates. The results are shown in Table 1. It is evident that the biotinylated peptides from the HIV-1 or HIV-2 transmembrane proteins bound to streptavidin are recognized very well by antisera from HIV-1 or HIV-2 infected persons respectively. This is in contrast to the unbiotinylated versions of these peptides coated directly onto the polystyrene plates. Addition control experiments showed that the increase in antibody binding was the result of the specific interaction between the biotinylated peptide and streptavidin, since there was no difference in antibody recognition of the biotinylated or unbiotinylated peptides when both were coated directly onto the microtiter plate.

Some peptides, particularly ones which are 15 amino acids in length or longer, bind sufficiently to the solid phase to allow the detection of specific antibodies which recognize (an) epitope(s) present in the peptide sequence.

To ascertain whether biotinylation would also improve antibody recognition of longer peptides, both the biotinylated and unbiotinylated versions of the partial V3 loop sequence of isolate HIV-1 mn were synthesized. The sequence and method of synthesis of both peptides were identical except at the amino terminus. The unbiotinylated peptide was simply acetylated whereas in the biotinylated version, two glycine residues were added as a linker arm to separate the peptide from the biotinyl moiety.

The sequences of the two peptides used are as follows:
unbiotinylated V3 mn peptide
(SEQ ID NO:114) Ac-Tyr-Asn-Lys-Arg-Lys-Arg-Ile-His-Ile-Gly-Pro-Gly-Arg-Ala-Phe-Tyr-Thr-Thr-Lys-Asn-Ile-Ile-Gly-NH2.

biotinylated V3 mn peptide (peptide 1b.4)
(SEQ ID NO:115) Bio-Gly-Gly-Tyr-Asn-Lys-Arg-Lys-Arg-Ile-His-Ile-Gly-Pro-Gly-Arg-Ala-Phe-Tyr-Thr-Thr-Lys-Asn-Ile-Ile-Gly-NH2.

The unbiotinylated peptide was coated directly onto the wells of a polystyrene microtiter plate while the biotinylated peptide was bound to wells which had previously been coated with streptavidin. The results shown in Table 2 demonstrate that antibody binding to the biotinylated peptide is superior to antibody binding to peptide coated directly onto the plastic.

EXAMPLE 5
Use of Biotinylated Peptides—Avidin Complexes for Antibody Detection

Having demonstrated that antibody recognition of this peptide is improved when the peptide is biotinylated and bound to streptavidin, an additional experiment was performed to determine whether streptavidin could be substituted by avidin. The results shown in Table 3 indicate that this is the case and that biotinylated peptides bound to avidin are recognized very efficiently by specific antibodies.

EXAMPLE 6
Use of Biotinylated HCV Peptides for Detection of HCV Specific Antibodies In order to determine whether the enhanced antibody recognition of biotinylated peptides was a general phenomenon, a number of additional twenty amino acid-long peptides were synthesized which correspond to sequences derived from the hepatitis C virus (HCV) polyprotein. The amino acid sequences evaluated were as follows:

a. HCV peptide XI
(SEQ ID NO:116) Ser-Gln-His-Leu-Pro-Tyr-Ile-Glu-Gln-Gly-Met-Met-Leu-Ala-Glu-Gln-Phe-Lys-Gln-Lys
b. HCV peptide XVI
(SEQ ID NO:117) Leu-Arg-Lys-Ser-Arg-Arg-Phe-Ala-Gln-Ala-Leu-Pro-Val-Trp-Ala-Arg-Pro-Asp-Tyr-Asn
c. HCV peptide II
(SEQ ID NO:118) Pro-Gln-Arg-Lys-Thr-Lys-Arg-Asn-Thr-Asn-Arg-Arg-Pro-Gln-Asp-Val-Lys-Phe-Pro-Gly
d. HCV peptide III
(SEQ ID NO:119) Arg-Asn-Thr-Asn-Arg-Arg-Pro-Gln-Asp-Val-Lys-Phe-Pro-Gly-Gly-Gly-Gln-Ile-Val-Gly
e. HCV peptide V
(SEQ ID NO:120) Thr-Arg-Lys-Thr-Ser-Glu-Arg-Ser-Gln-Pro-Arg-Gly-Arg-Arg-Gln-Pro-Ile-Pro-Lys-Val
f. HCV peptide IX
(SEQ ID NO:121) Ile-Ile-Pro-Asp-Arg-Glu-Val-Leu-Tyr-Arg-Glu-Phe-Asp-Glu-Met-Glu-Glu-Cys-Ser-Gln
g. HCV peptide XVIII
(SEQ ID NO:122) Glu-Thr-Trp-Lys-Lys-Pro-Asp-Tyr-Glu-Pro-Pro-Val-Val-His-Gly-Cys-Pro-Leu-Pro-Pro In each case, two versions of the peptide were synthesized. In the unbiotinylated version, the peptide was acetylated at the amino terminus. The biotinylated versions were all N-terminally biotinylated. A linker arm consisting of two glycine residues separated the biotinyl moiety from the amino acids comprising the HCV sequence.

The unbiotinylated peptides were adsorbed onto the wells of polystyrene microtiter plates at a concentration of 3 micrograms per milliliter.

The biotinylated peptides were bound at a concentration of 1 microgram per milliliter to streptavidin-coated microtiter plates. Sera known to contain antibodies to these peptides were used for the evaluation and were tested at a 20-fold dilution. The results of these comparisons are shown in Table 4, a to g.

These results clearly indicate that antibody recognition of biotinylated peptides bound to streptavidin is enhanced relative to that of peptides coated directly onto the wells of the microtiter plate.

EXAMPLE 7
Influence of Coating Concentration on Antibody Detection

To investigate further the enhanced antibody recognition of biotinylated HCV peptides bound to streptavidin or avidin as compared to direct adsorption on plastic, the influence of peptide coating concentration was investigated. Three peptides (HCV peptides II, XI, and XVI) were coated in concentrations ranging from 10 nanograms per milliliter to 3 micrograms per milliliter in a volume of 200 microliters per microtiter plate well. For direct coating, the unbiotinylated versions of these peptides were used. The biotinylated versions of these peptides were used to coat wells to which streptavidin had previously been adsorbed. Sera known to contain antibodies to these peptides were used at a dilution of 1 to 100 to evaluate the magnitude of antibody binding.

The numerical results of this experiment are shown in Table 5 and are depicted graphically in FIG. 3, a–c.

It is evident that with few exceptions, the biotinylated peptide is recognized very well even at the lowest concentration tested (10 nanograms per milliliter, 2 nanograms per well). In many cases, optical density values close to the maximum attainable are observed at a peptide concentration of only 30 nanograms per milliliter (6 nanograms per well). In contrast, however, the unbiotinylated peptides adsorbed directly onto the plastic are poorly bound by antibody, if at all.

EXAMPLE 8
Influence of Biotinylation of Peptides on Coating Efficiency of the Peptides on a Solid Phase To determine if the absence of a signal was due to lack of peptide adsorption when the peptides were coated directly, an additional experiment was performed. In this case, the biotinylated versions of the peptides were coated directly onto the plastic at the same concentrations used in the previous experiment for the unbiotinylated versions. To ascertain whether biotin-labeled peptide was bound, the microtiter plates were incubated with a streptavidin: horseradish peroxidase conjugate. Since each peptide contains a single biotinyl group, the resulting optical densities are a measure of the amount of peptide bound, although the absolute amount of bound peptide is not known. The results presented graphically in FIG. 4 demonstrate that plastic-bound peptide can be detected. As expected, the curves are different for each peptide which is a reflection of their chemical uniqueness. Two of the peptides, HCV peptides XI and XVI, appear to bind only weakly to the wells of the polystyrene microtiter plate and this poor binding is reflected in the low optical density values obtained in the ELISA. Since the binding of the biotinylated peptides to streptavidin-coated wells results in very good antibody recognition, it is obvious that poor binding of the peptide to the solid phase is not a limitation when use is made of interaction between biotin and streptavidin.

On the other hand, one of the peptides, HCV peptide II, shows very significant binding to the solid phase, particularly at higher coating concentrations. However, at no coating concentration did the signal obtained when the peptide was coated directly ever equal the signal obtained when the biotinylated peptide was bound to streptavidin. Since even at the lowest concentration tested, the streptavidin-bound biotinylated versions of this peptide clearly gives a positive signal with the antisera tested, the results would seem to indicate either that the direct coating of this peptide is extraordinarily inefficient or that other factors are important besides the simple binding of peptide to the solid phase.

Although difficult to quantify, one of the factors almost certainly involves the manner in which the peptide is bound and available for antibody binding. In the case of peptides coated directly onto the solid phase, it is virtually inevitable that some proportion of the peptide molecules will interact with the solid phase through amino acid side chains which are also essential for antibody recognition. These peptide molecules will therefore be unable to participate in the binding reaction with antibodies. This problem is not encountered with the biotinylated peptides which are all bound to the solid phase through the interaction between biotin and the solid phase-bound streptavidin.

EXAMPLE 9
Use of C-terminally Biotinylated HIV Peptides for Specific Antibody Recognition In order to determine whether the peptides biotinylated at their carboxy-terminus also give use to enhanced antibody recognition, a carboxy-biotinylated version of the TM-HIV-1 peptide was synthesized. N-α-Fmoc-Lys N-ε-biotin) prepared by method A as described was coupled directly to resin functionalized with the acid labile linker 4-(α-Fmoc-amino-2',4'-dimethoxybenzyl) phenoxyacetic acid after removal of the linker-bound Fmoc group with 20 percent piperidine. The coupling was performed using a 3-fold molar excess of N-α-Fmoc-Lys (N-ε-biotin) relative to resin functional groups. Carboxyl group activation was achieved using one equivalent of HBTU, one equivalent of 1-hydroxybenzotriazole and 1.5 equivalents of N-methylmorpholine. N-methyl morpholine was dispensed as a 0.6 M solution in dimethylformamide containing 40 percent dimethylsulfoxide which was necessary to achieve complete dissolution of the N-α-Fmoc-Lys (N-ε-biotin). Inspection of the Fmoc deprotection peak following coupling of the N-α-Fmoc-Lys (N-ε-biotin) indicated that coupling had proceeded smoothly and efficiently. Two glycine residues were coupled to separate the biotinyl lysine from the TM-HIV-1 amino acid sequence. Following synthesis of the peptide, the amino terminus was acetylated with acetic anhydride. The resulting structure of the carboxy-biotinylated peptide differs significantly from the peptide biotinylated at the amino terminus. A comparison of these structures is shown in FIG. 5.

In order to evaluate antibody recognition of these two peptides, the peptides were bound individually to streptavidin-coated microtiter plates and tested using a panel of antisera from HIV-1 seropositive donors. The results of this comparison is shown in Table 6. Clearly, antibody recognition of the C-terminally biotinylated peptide compares very favorably with that of the N-terminally biotinylated peptide. These results also confirm the utility of the reagent N-α-Fmoc-Lys (N-ε-biotin) for carboxy-terminal biotinylation.

EXAMPLE 10
Comparison of Antibody Recognition of HCV Peptide I, Coated Directly (Unbiotinylated) or Bound to Streptavidin-coated Plated (Carboxy-terminal Biotinylation)

A similar experiment was performed using a peptide which binds relatively well to polystyrene ELISA plates in order to determine whether the carboxy-biotinylated form of the peptide would result in superior antibody recognition relative to the unbiotinylated form of the peptide. The peptide chosen was HCV peptide I, which was synthesized in the following versions:

a. unbiotinylated version:
(SEQ ID NO:123) H2N-Met-Ser-Thr-Ile-Pro-Lys-Pro-Gln-Arg-Lys-Thr-Lys-Arg-Asn-Thr-Asn-Arg-Arg-Pro-Gln-CONH2 b. carboxy-biotinylated version:
(SEQ ID NO:124) H2N-Met-Ser-Thr-Ile-Pro-Lys-Pro-Gln-Arg-Lys-Thr-Lys-Arg-Asn-Thr-Asn-Arg-Arg-Pro-Gln-Gly-Gly-Lys(Bio)-CONH2.

A spacer consisting of two glycine residues was added at the carboxy-terminus to physically separate the HCV portion of the peptide proper from the Lys(N-ε-Bio). Synthesis was performed on resin functionalized with 4-(α-Fmoc-amino-2',4'-dimethoxybenzyl) phenoxyacetic acid linker in order to generate carboxy-terminal amides upon cleavage. Coupling of the N-α-Fmoc-Lys(N-ε-biotin) to the linker was performed using a 3-fold molar excess of the intermediate product relative to the linker. Activation of the N-α-Fmoc-Lys(N-ε-biotin) was achieved using one equivalent of TBTU, one equivalent of 1-hydroxybenzotriazole, and 1.5 equivalents of N-methylmorpholine. The coupling of all other amino acids was performed according to conventional protocols. Following cleavage of the peptides in trifluoroacetic acid in the presence of the appropriate scavengers, the peptides were precipitated and extracted with diethylether.

Unbiotinylated HCV peptide I was coated directly onto the wells of a polystyrene ELISA plate at a concentration of 3 micrograms per milliliter in sodium carbonate buffer, pH 9.6. Biotinylated HCV peptide I was bound to streptavidin-coated wells using a stock solution containing the peptide at a concentration of 1 microgram per milliliter. The resulting plates were then incubated in parallel with a panel of sera from HCV-seropositive donors. The results of this comparison are shown in Table 7. The biotinylated peptide clearly gives superior results relative to the unbiotinylated version of the same sequence. Two of the sera (8326 and 8244) recognize the biotinylated version of this peptide far better than the unbiotinylated version. The specificity of the antibody reaction is also reflected by the low optical density values obtained for 5 serum samples from uninfected donors (F88, F89, F76, F136, and F6).

EXAMPLE 11
Use of Mixtures of Biotinylated HIV and HCV Peptides

In many cases, the use of mixtures of peptides is required to give the desired result. Mixtures of peptides may be used for the detection of antibodies directed against one or more proteins of a single virus, or for the detection of antibodies directed against proteins of several viruses in a single test. Such tests are considered particularly advantageous for the screening of blood donations for their suitability for use in transfusions and as a source of blood products. In such cases, ELISA plates or other solid supports coated with suitable mixtures of peptides may be used to screen samples for the presence of antibodies to one or more infectious agents whose presence would render the sample unsuitable for use. For the diagnosis of specific infectious agents, appropriate mixtures of peptides are required in order to obtain accurate determinations. Antibodies to individual viral antigens derived from one or more infectious agents may be individually detected and identified simultaneously when use is made of test systems in which individual peptides or mixtures of peptides are bound to the solid phase but are physically separated as they are, for example, in the line immunoassay, such that individual reactions can be observed and evaluated. Such tests require the use of an appropriate combination of peptide mixtures to achieve the desired result.

It is frequently preferable to use mixtures of peptides rather than a single peptide for the diagnosis of ongoing or past infections. Since individual responses to single epitopes may be quite variable, more reliable results are often obtained when several immunologically important epitopes are present in the antibody test. However, since each peptide is chemically unique, it is frequently difficult to incorporate all of the desired peptides into one test, particularly when the peptides are to be coated directly onto the solid phase. Not all peptides are capable of binding to the solid phase and the peptides in the mixture may also exhibit very different optimal coating conditions in terms of pH, ionic strength, and buffer composition.

To determine how well biotinylated peptides would function in a mixture when bound to streptavidin- or avidin-coated plates, two mixtures were made of the N-terminally biotinylated versions of the HIV-1 peptides TM-HIV1 (hereabove referred to as 1a.1) and V3-mn (hereabove referred to as 1b.4), the HIV-2 peptide TM-HIV-2 (hereabove referred to as 2a), and the hepatitis C virus peptides II, IX, and XVIII. Mixture A contained each of the six biotinylated peptides at a concentration of 1 microgram per milliliter (6 micrograms per milliliter peptide, total) while in mixture B, each peptide was present at a concentration of 0.1 microgram per milliliter (0.6 microgram per milliliter peptide, total). The individual peptides were coated at a concentration of 1 microgram per milliliter. For purposes of comparison, mixtures A and B were also coated directly onto the wells of a microtiter plate. Samples from HIV-1, HIV-2, and HCV-seropositive donors were tested and compared to sera from seronegative blood donors. A cut-off absorbance value of 0.250 was used to determine whether a reaction was positive or negative. Absorbance values equal or greater than 0.250 were considered positive while absorbance values below this value were considered negative. The results of this experiment are shown in Table 8.

Based on the reactions to the individual peptides, all of the HCV serum samples were negative for antibodies to either HIV-1 or HIV-2. One HIV-2 sample (no. 1400) had antibodies to HCV peptide XVIII. Of the HIV samples tested, there was no indication of cross reactivity and the ELISA based on individual peptides is specific.

Both mixtures A and B gave good results when bound to avidin-coated microtiter plates. As expected, these mixtures were recognized by HIV-1, HIV-2, and HCV-positive sera but not by sera from seronegative blood donors. In contrast, when these mixtures were coated directly onto the microtiter plates, the results were considerably less satisfactory, with many samples giving a reaction which fell below the cut-off value applied. These results serve to illustrate quite convincingly the enhanced immunological recognition of biotinylated peptides bound to avidin as compared to peptides coated directly onto the solid phase as well as the advantages of using mixtures of peptides for multiple antibody detection.

EXAMPLE 12
Use of Biotinylated Peptides for Mapping of Epitopes in Diagnostically Useful Regions of HCV It was demonstrated in Example 6 that several diagnostically important regions of the HCV polyprotein, such as Core, NS4, and NS5, can be identified using overlapping 20-mer biotinylated peptides. Extensive serological testing identified the most useful 20-mer biotinylated peptides which permitted to develop a line immunoassay utilizing these biotinylated peptides. However, it was desirable to know more exactly where in these 20 amino acid-long sequences the epitopes were located. One reason is that, if shorter sequences could be identified, it would be possible to make synthetic peptides containing two or three epitopes without the peptide becoming prohibitively long.

Epitopes present in a position of the putative HCV proteins were mapped using the method originally described by Geysen, H. M., Meloen, R. H., and Barteling, S. J.; Proc. Natl. Acad. Sci. USA (1984) 81:3998–4002. Consecutive peptides nine amino acids in length with an eight amino acid overlap were synthesized on polyethylene pins derivatized with a non-cleavable linker. This peptide length was chosen because it is larger than the size of typical linear epitopes which are generally between 5 and 7 amino acids in length. By synthesizing 9-mers, the probability that epitopes would be missed was minimized.

The regions in the HCV polyprotein which were scanned contain Core sequences (aa. 1 to 80), NS4 (aa. 1688 to 1755), and NS5 (aa. 2191 to 2330). These regions correspond to the previously determined 20-mers: Peptide I to VII (Core 1 to 13), Peptide VIII to XIV (NS4-1 to 9), and peptide XV to XIX (NS5-13 to 33).

Following synthesis, all peptides were N-acetylated prior to side chain deprotection in order to remove the unnatural positive charge at the amino terminus.

The peptides were then assayed for their ability to be recognized by antibodies present in sera from HCV seropositive donors. The results of these experiments are shown in FIGS. 6a to 6c. The optical density values shown are the average of duplicate determinations and have been assigned to the first amino acid of the 9-mer sequence.

The antibody binding profiles for 10 different HCV sera are shown in FIG. 6a. It is clear that the core protein of HCV presents well-defined linear epitopes which are readily stimulated by synthetic peptides. At least superficially, most sera appear to give very similar patterns. Closer inspection, however, reveals that there are individual differences. The various regions of the HCV core protein which are recognized by antibodies are perhaps more properly termed epitopic clusters rather than epitopes as such, since each region is undoubtedly composed of several overlapping epitopes which are difficult, if not impossible, to distinguish using polyclonal sera. An attempt was made to identify core epitopes in each of the epitopic clusters. Used in this sense, the word "core" refers to the minimal amino acid sequence recognizable by antibodies. It should be emphasized, however, that amino acids in addition to the core sequence may improve reactivity particularly in the case of polyclonal sera. An analysis of the epitopes is given in Table 9. By comparing the reactions of the various sera, subdomains of epitopic clusters could be identified. Some sera react predominantly with one subdomain and not with others, while other sera recognize all of the subdomains but still allow the subdomains to be distinguished because each forms a shoulder in the large peak which defines that particular epitopic clusters. Table 9 and FIG. 7a shows the locations of the core epitopes with respect to the sequences of the 20-mers.

The series of 9-mers corresponding to each of the 20-mer Core peptides are shown in FIG. 7a together with the placement of each of these sequences in relation to an antibody recognition profile for one of the antisera tested.

The antigenic profiles for the NS4 protein obtained with the 10 sera are shown in FIG. 6b. In general, the reaction of these sera with the 9-mers was less pronounced than with the peptides from the Core protein. It was, nevertheless, still possible to identify epitopic regions in the N-terminal sequences of the viral NS4 protein. The core sequences of these epitopes are analyzed in Table 10 and show their relation to the 20-mer synthetic peptides which are diagnostically important in this region. The 9-mers corresponding to the different 20-mers are shown in FIG. 7b together with their placement in relation to an example of an antigenic profile. It can be seen that the 20-mers correspond quite well to the epitopes in this region.

The portion of the NS5 protein which was scanned corresponds to the region covered by the 20-mer peptides 13 to 33. The antigenic profiles obtained in this region are shown in FIG. 6c. Again, an attempt was made to define core epitopes and these are listed in Table 11. Little antibody binding was observed in the amino terminal portion of this sequence. In FIG. 7c, the 9-mers corresponding to the 20-mer peptides NS5-21 to NS5-31 are listed and their positions are shown relative to one of the antigenic profiles.

In particular, it is apparent that, the importance of the sequence represented by HCV peptide XVI (NS5-27) would be severely underestimated based on the results obtained with the overlapping 9-mers. The importance of this sequence would also be underestimated if unbiotinylated HCV peptide XVI (NS5-27) were evaluated in an ELISA following direct coating onto the microtiter plate (see Table 4B). However, the biotinylated version of this peptide when bound to streptavidin- or avidin-coated plates reveals the presence of a very important epitope which is of diagnostic value.

In contrast to the often weak binding observed with the 9-mers, the binding with the 20-mers was frequently quite strong (see table 12). In several cases the differences are dramatic. For example, serum 8241 does not recognize any of the 9-mers, whereas the binding to the peptides HCV2 (peptide IX) and HCV5 (peptide XI) is very strong. Moderate binding was also observed to the peptide HCV7 (peptide XIII). This would seem to indicate that there is an important structural component to these epitopes which is present in the 20-mers but which is absent in the 9-mers.

EXAMPLE 13

Use of Biotinylated Peptides for Identification of Epitopes in the N-Terminus of NS1 Region of HCV Line Immunoassay Epitopes can also be identified using the line immunoassay (LIA). In general, unbiotinylated peptides bind better to nylon membranes than to polystyrene ELISA plates. Nevertheless, biotinylated peptides complexed with streptavidin or avidin give superior results in the line immunoassay than do their unbiotinylated counterparts bound directly to the membrane. In order to illustrate this, unbiotinylated and N-terminally biotinylated versions of HCV peptides XXg-1 and XXg-2 were synthesized. The unbiotinylated peptides were applied to the membrane as a stock solution containing 100 micrograms per milliliter peptide, whereas the biotinylated peptides were bound to streptavidin and applied as a stock solution of 100 micrograms per milliliter complex. The amount of biotinylated peptide in the stock solution was therefore approximately 10 micrograms per milliliter. Three human IgG control lines were also applied to the strips in order to assist in evaluating the intensity of the reactions. Following application of the antigen lines, excess binding sites on the membrane were blocked with casein in phosphate-buffered saline. The membrane was subsequently cut into strips perpendicular to the direction in which the antigen lines were applied and the resulting strips were incubated with a panel of sera from HCV-seropositive donors. Bound antibody was detected visually using goat anti-human IgG antibodies conjugated to the enzyme alkaline phosphatase after addition of 5-bromo-4-chloro-3-indolylphosphate and Nitro Blue tetrazolium. The results are shown in FIG. 8.

The specificity of the reactions is demonstrated by the absence of detectable antibody binding to any of the HCV peptides by three sera (33, 34, and 35) obtained from HCV-seronegative donors. The reactions of sera 1 to 32 to the unbiotinylated HCV peptides XX-1 and XX-2 are generally absent or exceedingly weak. In contrast, many of the sera tested recognized the biotinylated versions of these peptides when complexed to streptavidin. The antibody reactions to the biotinylated peptides are significantly stronger in spite of the fact that only approximately one-tenth the amount of peptide was present in these stock solutions compared to the amount present in the stock solutions of the unbiotinylated peptides. The results obtained using the biotinylated peptides demonstrate the presence of a diagnostically useful epitope in these peptide sequences which is not evident when the unbiotinylated versions of the peptides are used.

A total of 8 sequences spanning the hypervariable N-terminus of the HCV E2-NS1 region (aa 383 to 416 of the HCV polyprotein) of different HCV isolates were chosen for further evaluation. These aligned sequences (One-letter code) are as following:

(SEQ ID NO: 125) XXa GETYTSGGAASHTTSTLASLF-SPGASQRIQLVNT (1)
(SEQ ID NO: 126) XXb GHTRVSGGAAASDTRGLVSLF-SPGSAQKIQLVNT (2)
(SEQ ID NO: 127) XXc GHTRVTGGVQGH-VTCTLTSLFRPGASQKIQLVNT (3)
(SEQ ID NO: 128) XXd GHTHVTGGRVASSTQS-LVSWLSQGPSQKIQLVNT (4)
(SEQ ID NO: 129) XXe GDTHVTGGAQAKTTNRLVSM-FASGPSQKIQLINT (5)
(SEQ ID NO: 130) XXf AETYTSGGNAGHTMTGIVRF-FAPGPKQNVHLINT (6)
(SEQ ID NO: 131) XXg AETIVSGGQAARAMSGLVS-LFTPGAKQNIQLINT (7)
(SEQ ID NO: 132) XXh AETYTTGGSTARTTQGLVSLF-SRGAKQDIQLINT (8)

These sequences are derived from isolates described by the following groups:
(1) Hijikata et al., Biochem. Biophys. Res. Comm. 175:220–228, 1991.
(2) unpublished results
(3) Hijikata et al., Biochem. Biophys. Res. Comm. 175:220–228, 1991.
(4) Kato et al., Proc. Natl. Acad. sci. USA 87:9524–9528, 1990.
(5) Takamizawa et al., J. Virology 65:1105–1113, 1991.
(6) Weiner et al., Virology 180:842–848, 1991.
(7) Okamoto et al., Japan. J. Exptl. Med. 60:167–177, 1990.
(8) Kremsdorfl et al., Abstract V64, Third International Symposium on HCV, Strasbourg, France, September, 1991.

Since the sequences are rather long and because secondary structure—related difficulties were predicted to occur during synthesis, it was decided to split the sequences into two overlapping parts ("a"=amino acid 383 to 404 and "b"= amino acid 393 to 416 of the HCV polyprotein). Subdividing the sequence also allows the position of the epitopes to be more accurately defined.

All of the peptides were N-terminally biotinylated, complexed with streptavidin and used to prepare LIA-strips (data not shown).

When only the LIA-positive samples are considered, the detection rate on the E2/NS1 peptides was found to be on the order of 90 percent. The correlations between recognition of the E2/NS1 peptides and LIA reactivity as well as the scores for the individual peptides are shown in Table 13. It was also clear from the observed reactions that the primary epitope in this sequence is located towards the carboxy-terminus of the hypervariable region. There were exceptions to this, however. Each serum appeared to have its own recognition pattern which underscores the importance of using a mixture of different sequences if this epitope is to be included as a line in the LIA. It would also appear that either there is a considerable degree of crossreactivity between the type 1a and type 1b sequences, or that most people are doubly infected. It is a simple matter to distinguish between these two possibilities by selectively removing the antibodies which bind to one sequence and looking to see what the effect is on antibody recognition of the other sequences. A number of samples gave a rather weak reaction to one or more E2/NS1 peptides but were LIA negative. While most probably false positive reactions, these sera may also be from people who where previously infected but who have resolved the infection.

EXAMPLE 14

Use of Combined HCV Peptides from the Core Region of HCV for the Detection of Antibodies by LIA In order to reduce the overall number of peptides in a HCV ELISA or LIA, biotinylated peptides can be synthesize which span other immunologically important peptides. Examples of such "combined" HCV peptides from the core protein NS3 region of HCV are given below: (SEQ ID NO:133–SEQ ID NO:141, respectively)

| Peptide | Sequence |
|---|---|
| core 1 (I) | M S T I P K P Q R N T K R N T N R R P Q |
| core 2 (II) | P K P Q R K T K R N T N R R P |
| core 3 (III) | R N T N R R P Q D V K F P G G G Q I V G |
| core 123 | M S T I P K P Q R N T K R N T N R R P Q D V K F P G G G Q I V G |
| core 6 (IVa) | V G G V Y L L P R R G P R L G V R A T R |
| core 7 (IV) | L P R R G P R L G V R A T R K T S E R S |
| core 9 (V) | T R K T S E R S Q P R G R R Q P I P E V |
| core 10 (VI) | R S Q P R G R R Q P I P E V R R P E G R |
| core 7910 | G G V Y L L P R R G P R L G V R A T R K T S E R S Q P R G R R Q P I P E V R R |

All of these peptides have been provided with a Gly-Gly spacers and a biotin at the amino terminus. The peptides were evaluated in a line immunoassay experiment (LIA) and compared to the shorter core peptides. The results are shown in FIG. 9. The longer core peptides compare very favorably to the shorter peptides and consistently give a more intense reaction. This is could be explained if (i) the longer peptides incorporate two or more epitopes which were previously spread over two separate peptides and/or (2) there is any conformational contribution which may be more prominent in the longer peptides.

EXAMPLE 15
Use of Combined HCV Peptides from the NS4 and NS5 Regions of HCV for the Detection of Antibodies by LIA Other peptides combine sequences in NS4 and NS5 which are as following: (SEQ ID NO:142–SEQ ID NO:147, respectively)

| Peptide | Sequence |
|---|---|
| NS4-5 (XI) | S Q H L P Y I E Q G M M L A E Q F K Q K |
| NS4-7 (XIII) | L A E Q F K Q K A L G L L Q T A S R Q A |
| NS4-57 | S Q H L P Y I E Q G M M L A E Q F K Q K A L G L L Q T A S R Q A |
| NS5-25 (XV) | E D E R E I S V P A E I L R K S R R F A |
| NS5-27 (XVI) | L R K S R R F A Q A L P V W A R P D Y N |
| NS5-2527 | E D E R E I S V P A E I L R K S R R F A Q A L P V W A R P D Y N |

The general advantage in using the longer peptides lies in the fact that their use in an ELISA or LIA leaves more space for the incorporation of other peptides carrying immunologically important epitopes.

EXAMPLE 16
Use of Type-Specific HCV NS4 Peptides for the Detection of Antibodies by LIA Equivalent peptides containing HCV type 2 and type 3 NS4 sequences which correspond to the type 1 peptides found to contain epitopes in NS4 were synthesized. The sequences of these peptides are shown below for comparison:

| Peptide | Sequence |
|---|---|
| NS4-1 (1) | L S G K P A I I P D R E V L Y R E F D E |
| NS4-1 (2) | V N Q R A V V A P D K E V L Y E A F D E |
| NS4-5 (1) | S Q H L P Y I E Q G M M L A E Q F K Q K |
| NS4-5 (2) | A S R A A L I E E G Q R I A E M L K S K |
| NS4-7 (1) | L A E Q F K Q K A L G L L Q T A S R Q A |
| NS4-7 (2) | I A E M L K S K I Q G L L Q Q A S K Q A |

LIA strips were prepared using these nine peptides which were subsequently incubated with different sera. The results are shown in FIG. 10. Two of the sera which were previously negative on type 1 NS4 peptides gave a positive reaction to the type 3 and type 2 peptides. This indicates that it is possible to increase the NS4 detection rate using these peptides.

EXAMPLE 17
Use of Biotinylated Peptides from the V3 Loop Region of GP120 of Different HIV-1 Isolates in a Line Immunoassay for the Detection of HIV Antibodies In order to determine the general diagnostic value of the V3 loop region of gp120, nine peptides derived from this region of nine different HIV-1 isolates were synthesized and included in a LIA. All nine peptides were provided with a Gly-Gly spacer and an N-terminal biotin. The aligned peptides (one-letter amino acid code) sequences are as following:

CON NNTRKSIHI—GPGRAFYTTGEIIG 23 (SEQ ID NO:154)
SF2 NNTRKSIYI—GPGRAFHTTGRIIG 23 (SEQ ID NO:155)
SC NNTTRSIHI—GPGRAFYATGDIIG 23 (SEQ ID NO:156)
MN YNKRKRIHI—GPGRAFYTTKNIIG 23 (SEQ ID NO:157)
RF NNTRKSITK—GPGRVIYATGQIIG 23 (SEQ ID NO:158)
MAL NNTRRGIHF—GPGQALYTTG-IVG 22 (SEQ ID NO:159)
BH NNTRKSIRIQRGPGRAFVTIGKI-G 24 (SEQ ID NO:160)
ELI QNTRQRTPI—GLGQSLYTT-RSRS 22 (SEQ ID NO:161)
ANT70 QIDIQEMRI—GP-MAWYSMG-IGG 21 (SEQ ID NO:162)

The peptides were mixed with streptavidin in a slight molar excess over biotin binding sites and the peptide:streptavidin complexes were separated from unbound material over Sephadex G-25. Material eluting in the void volume was used in the preparation of the LIA.

A total of 332 sera were tested which had been obtained from various geographical regions. Since it is known that virus strains isolated in Europe or North America exhibit less strain-to-strain variability than African isolates, geographical differences in the V3-loop sequence recognition were to be expected. The reactions of the various lines were evaluated as positive (i) or negative (o) (data not shown).

A complete evaluation of the sera is given in Table 14. In total, 307 of the 332 sera gave a reaction to at least one peptide on the V3-loop LIA. Those sera which failed to give a reaction to any peptide on the V3-loop LIA were tested by Western Blot to determine whether the sera were indeed positive for anti-HIV-I antibodies. It was found that 6 sera were in fact negative. The total number of positive sera tested was therefore 326. There were, however, 19 sera which contained antibodies to gp120 which failed to react with any of the V3-loop LIA, the percentage of sera giving a positive reaction was, in global terms, 94%. There were, however, significant geographical differences. These differences are shown in Table 15.

The total percentage of sera from the different geographical regions giving at least one positive reaction can be summarized as follows:

| | |
|---|---|
| European | 100% |
| African | 94% |
| Brazilian | 92% |

Additional evaluations with European samples indicate that this percentage is, in fact, some what less than 100% (data not shown). African samples which failed to give a reaction in the LIA have not been tested by Western Blot to confirm the presence of other HIV antibodies.

That the European sera would score well was expected. The lower score obtained for the African sera was also not totally unexpected, since it is known that there is more viral heterogeneity in Africa. Since V3-loop sequences of African strains of HIV have not been as extensively characterized as the European or North American strains, it is clear that we either do not have a representative sequence, or that attempting to characterize African strains in terms of a consensus sequence is not possible exercise since there is too much sequence divergence. The results obtained with the Brazilian sera were unexpected since nothing has ever been reported concerning HIV variability in Brazil. From these results, it appears that the situation in Brazil more closely resembles the situation in Africa and not the situation in North America or Europe.

EXAMPLE 18
Improved Detection of HIV-1 ANTI-V3 Domain Antibodies in Brazilian Sera Using a V3 Sequence Derived from a Brazilian Isolate Brazilian serum samples which failed to recognize any HIV-1 V3 loop sequences present on the previously described LIA strips but which were positive for antibodies which recognized the HIV-1 gp120 protein on Western blots were selected for further study. In one of these samples, V3 loop sequences of virus present in the serum sample could be amplified using the polymerase chain reaction using primers derived from the more constant regions flanking the hypervariable domain. The resulting DNA fragment was subsequently cloned and the nucleotide sequence was determined. A peptide corresponding to the deduced amino acid sequence encoded by this fragment was synthesized and tested for its ability to be recognized by various HIV-1 antibody-positive sera. The sequence of this peptide was as follows:

Peptide V3-368 (SEQ ID NO: 168):
Asn Asn Thr Arg Arg Gly Ile His Met Gly Trp Gly Arg Thr Phe Tyr Ala Thr Gly Glu Ile Ile Gly A spacer consisting of two glycine residues was added to the amino terminus. Thereafter, the resulting N-terminal glycine residue was biotinylated. The ability of European, African, and Brazilian HIV-1 antibody-positive sera to recognize this peptide was investigated and compared to the ability of these same sera to recognize the consensus sequence peptide in an ELISA. The two peptides were also evaluated together as a mixture. These results are summarized in table 16. These results demonstrate that with sera of European or African origin, the V3-368 peptide does not result in an increased anti-V3 loop antibody detection over that which is observed with the V3con peptide. In contrast, the use of the V3-368 peptide results in a marked improvement in V3 antibody detection with Brazilian sera. Although this peptide is recognized less frequently than the V3con peptide, the two peptides complement each other to raise the detection rate from 83.3 percent using the V3con peptide alone to 97.2 percent when the two peptides are used together.

EXAMPLE 19
Antibody Recognition of HIV-2 V3 Loop Sequences

The outer membrane glycoprotein of HIV-2 (gp105) is similar to that of HIV-1 with respect to its organization. Like the gp120 protein of HIV-1, the gp105 protein of HIV-2 consists of domains of variable sequence flanked by domains of relatively conserved amino acid sequence. In order to detect antibodies specific for the V3 domain of HIV-2 produced in response to infection by this virus, biotinylated peptides were synthesized corresponding to the V3 sequences of the HIV-2/SIV isolates GB12 and isolate SIV mm 239 (Boeri, E., Giri, A., Lillo, F. et al.; J. Virol. (1992) 66(7):4546–4550). The sequences of the peptides synthesized are as follows:

V3-GB12 (SEQ ID NO:164):
Asn Lys Thr Val Val Pro Ile Thr Leu Met Ser Gly Leu Val Phe His Ser Gln Pro Ile Asn Lys

V3-239 (SEQ ID NO:165):
Asn Lys Thr Val Leu Pro Val Thr Ile Met Ser Gly Leu Val Phe His Ser Gln Pro Ile Asn Asp

Two glycine residues were added at the N-terminus of each peptide to serve as a spacer and a biotin was coupled to the α-amino group of the resulting N-terminal glycine. The peptides were bound to streptavidin and coated in the wells of microwell plates. HIV-2 antibody-positive sera were used to evaluate these two peptides in an ELISA. These results are summarized in Table 17. The results clearly demonstrate the usefulness of these two peptide sequences for the diagnosis of HIV-2 infection.

EXAMPLE 20
Localization of the Epitope at the Carboxy Terminus of C-100 with Biotinylated Peptides There have been various reports of an epitope located towards the carboxy-terminal portion of the C-100 protein (EP-A-0 468 527, EP-A-0 484 787). Reactivity of certain sera toward this epitope and not to epitopes located within the 5-1-1 fragment could explain why these sera give a positive reaction on C-100 but not to the above-described peptides described in the above-mentioned examples. The five overlapping biotinylated peptides synthesized NS4-a, b, c, d and e are shown n FIG. 11 and cover the carboxy-terminus of C-100 except for the last three amino acids. LIA strips prepared with these peptides were tested using a series of HCV Ab-positive and negative sera. The results of this experiment (data not shown) are summarized below:

| Peptide | Nr. of reactive sera | Percentage |
|---------|---------------------|------------|
| NS4-a   | 0                   | 0%         |
| NS4-b   | 2                   | 3%         |
| NS4-c   | 0                   | 0%         |
| NS4-d   | 0                   | 0%         |
| NS4-e   | 16                  | 27%        |

EXAMPLE 21
Use of Biotinylated Hybrid Peptides Containing Epitopes from Different HCV Proteins A fine mapping of the epitopes in the immunologically most important regions of the HCV polyprotein using 9-mers was performed as illustrated in Example 12. Using this information, 3 peptide sequences were devised which consisted of three 9-mer stretches of HCV sequence separated by 2 amino acid-long spacers. In general, Gly-Gly, Gly-Ser or Ser-Gly spacers were used to provide chain flexibility. The arrangement of the epitopes in the three hybrid peptides synthesized and their sequences are shown in FIG. 12. The three peptides were evaluated on a LIA strip. In the first evaluation, the sera originally used for the epitope fine mapping experiments were used since the precise interactions of these sera with the epitopes is known. These results are shown in FIG. 13 and are summarized in Table 16. The order in which the epitopes were incorporated into these three hybrid peptides was arbitrary. It is advantageous, however, to link the epitopes together in a limited number of peptide chains rather than attempting to develop a test based on individual 9-mers. The use of separate 9-mers would rapidly saturate the streptavidin binding sites on the plate (one biotin binding site/9-mer) whereas incorporating the 9-mers into a limited number of peptides as was done in these experiments would enable one to bind 3 times as much (one biotin binding site/three 9-mers).

EXAMPLE 22
E2/NS1 "b" Sequence Mixotope Peptides

The results using synthetic peptides (see Examples above) have indicated that most HCV seropositive sera contain antibodies directed towards the hypervariable N-terminus of E2/NS1. However, because of the hypervariable nature of this region of the protein, it is necessary to use a rather wide spectrum of sequences in order to detect these antibodies in an acceptably high percentage of sera. Analysis of available sequences revealed that the observed amino acid substitutions were not entirely random and that certain amino acids were preferred in certain positions within the sequence. Since the hypervariable sequence is rather long, this sequence who divided into two overlapping portions ("a" and "b") to improve the quality of the product and simplify the synthesis. Subdividing this region also permitted the determination of that the portion of this N- terminal segment of the E2/NS1 protein which was most frequently recognized by antibodies was located in the region encompassed by the "b" versions of these sequences. Given the sequence information shown in FIG. 14 a "mixotope" was synthesized which contains at each position all the amino acids found in the naturally occurring isolates examined. The strategy followed in the synthesis of the mixotope is depicted in FIG. 15. The strategy for designing mixotopes is reviewed in Gras-masse et al., Peptide Res. (1992) 5:211–216. The resin was divided into a number of portions equal to the number of amino acids to be coupled. The coupling reactions were carried out individually so as to avoid problems arising due to differences in coupling kinetics between the various amino acids. Following the coupling reactions, the resin portions were pooled and mixed thoroughly. The total number of variants obtained for this 23 amino acid-long sequence was +1.147×10$^{10}$. The increasing number of variants as a function of chain length as measured from the carboxy-terminus or amino-terminus is shown in FIG. 14. The rationale behind the mixotope approach is that epitopes are composed of amino acids whose contribution to antibody binding is not equal. Antibodies may recognize an epitope even though there may be a relatively large number of (generally not random) substitutions in certain positions. In this respect, the antigenic complexity of the mixotope should be substantially less than the number of variants comprising the mixture. For the sake of illustration, if it is assumed that an average epitope is 6 amino acids in length, it is possible to calculate the number variants for each successive 6 amino acid long segment in the sequence. The number of variants as a function of position in the sequence is shown in FIG. 14. The actual number of functional variant sequences will be equal to the number shown for any 6 amino acid-long sequence which happens to correspond to an epitope, divided by a degeneracy factor equal to the number if tolerated substitutions in each position of the epitope but modified to reflect the degree to which the particular substitutions are tolerated. Unfortunately, the exact position(s) of the epitope(s) are not known. It should be stated explicitly that this is not a random peptide library. Key positions in the total sequence which do not tolerate substitutions, as evidenced by the absence of amino acid variations in naturally occurring isolates, are preserved. one disadvantage to this synthetic approach is that rare amino acid substitutions are overrepresented and will tend to dilute out the more commonly encountered amino acids. On the other hand, the possibility existed that overrepresentation of rare substitutions might allow the detection of antibodies not detectable with epitope sequences comprised of more frequently encountered amino acids. Following completion of the synthesis of the mixotope, all peptide chains were provided with a (Gly)2 spacer and a biotin to facilitate immunological evaluation. A multiple antigen peptide (MAP) version of the mixotope may also be synthesized in parallel.

One result of previous studies was that while approximately 90 percent of HCV-positive sera could be shown to contain anti-E2/NS1 antibodies directed against the N-terminal hypervariable region with the 16 "a" and "b" sequences investigated. The apparent lack of these antibodies in the remaining 10 percent of HCV antibody-positive sera could be due to two factors: 1) these patients fail to produce antibodies against this portion of E2/NS1, or 2) has not yet been identified the correct sequence with which to detect these antibodies. Based on experiments with the HIV-1 V3 loop, this latter possibility did not seem at all unrealistic. LIA strips were prepared which contained the 8 "b" sequences previously used in addition to the mixotope. Sera were selected which previously scored positive on at least one of the eight defined sequences as well as sera which scored negative. In total, 60 sera were tested, of which 56 previously gave a positive reaction and 4 were previously found to be negative. Of the 56 sera which had previously scored positive, 21 reacted with only one or two of the peptides on the strip or only gave a very weak reaction. (data not shown) The mixotope was recognized by approximately one-third of all the sera tested. The reaction of some sera to the mixotope was surprisingly strong, however, it may be possible that the collection of E2/NS1 sequences on which the mixotope was based is not truly representative. It is expected that the mixotope MAP will elicit the production of broad specificity antisera directed against the amino-terminus of E2/NS1.

EXAMPLE 23

Use of Branched HCV N-Terminal E2/NS1 Region Peptides for Raising Antibodies

Several sequences from the N-terminus of E2/NS1 were selected for synthesis as multiple antigen peptides (MAP's) using the technique described by Tam (Proc. Natl. Acad. Sci. USA 85:5409–5413,1988). The strategy used to synthesize the branched peptides is shown schematically in FIG. 16. Rabbits (two for each MAP) were given an initial injection and were boosted once before blood was drawn for a first evaluation of antibody production. The antisera were tested on LIA strips containing a total of 16 E2 peptides (sequences derived from 8 type 1 isolates, "aa" and "b" versions of each). Examination of the LIA strips reveals that there is considerable cross-reaction between the antibodies raised in the rabbits and the various E2 peptides on the strips (FIG. 17). The fact that both "a" and "b" versions can be found which are recognized by the different antisera indicates that there is at least one. epitope located in the region where these two versions overlap.

EXAMPLE 24

Diagnosis of HTLV Infection Using Biotinylated Synthetic Peptides

HTLV-I and II are antigenically related members of a family of oncogenic retroviruses. HTLV-I infection has been shown to be associated with two disease syndromes: HTLV-I-associated myelopathy/tropical spastic paraparesis (neurological disorders) and adult T-cell leukemia (ATL). In contrast, HTLV-II has not been conclusively linked to any known disease syndrome. This virus was originally isolated from a patient with hairy cell leukemia, however, no causal relationship between HTLV-II infection and the disease state could be established. Since HTLV-I infection has definitely been demonstrated to have the potential to result in human disease while HTLV-II infection has not, it is of clinical interest to be able to differentiate between these two infectious agents. Since these two viruses are antigenically highly related, it is difficult to discriminate between HTLV-I and HTLV-II infections when viral or recombinant antigens are used for antibody detection. A number of biotinylated peptides were synthesized and evaluated for their ability to detect antibodies raised in response to infection by either HTLV-I or HTLV-II. Some of the peptides were chosen because they contain epitopes which are highly conserved between HTLV-I and HTLV-II and should therefore be useful reagents for detecting HTLV infection without regard to virus type. Still other peptides were chosen because they contain epitopes which should allow HTLV-I and HTLV-II infections to be discriminated. The peptides synthesized are as follows:

I-gp46-3:
(SEQ ID NO:166) Bio Gly Gly Val Leu Tyr Ser Pro Asn Val Ser Val Pro Ser Ser Ser Thr Leu Leu Tyr Pro Ser Leu Ala

I-gp46-5:
(SEQ ID NO: 167) Bio Gly Gly Tyr Thr Cys Ile Val Cys Ile Asp Arg Ala Ser Leu Ser Thr Trp His Val Leu Tyr Ser Pro

I-gp46-4:
(SEQ ID NO:168) Bio Gly Gly Asn Ser Leu Ile Leu Pro Pro Phe Ser Leu Ser Pro Val Pro Thr Leu Gly Ser Arg Ser Arg Arg

I-gp46-6:
(SEQ ID NO:169) Bio Gly Gly Asp Ala Pro Gly Tyr Asp Pro Ile Trp Phe Leu Asn Thr Glu Pro Ser Gln Leu Pro Pro Thr Ala Pro Pro Leu Leu Pro His Ser Asn Leu Asp His Ile Leu Glu

I-p21-2:
(SEQ ID NO:170) Bio Gly Gly Gln Tyr Ala Ala Gln Asn Arg Arg Gly Leu Asp Leu Leu Phe Trp Glu Gln Gly Gly Leu Cys Lys Ala Leu Gln Glu Gln Cys Arg Phe Pro

I-p19:
(SEQ ID NO:171) Bio Gly Gly Pro Pro Pro Pro Ser Ser Pro Thr His Asp Pro Pro Asp Ser Asp Pro Gln Ile Pro Pro Pro Tyr Val Glu Pro Thr Ala Pro Gln Val Leu

II-gp52-1:
(SEQ ID NO:172) Bio Gly Gly Lys Lys Pro Asn Arg Gln Gly Leu Gly Tyr Tyr Ser Pro Ser Tyr Asn Asp Pro

II-gp52-2:
(SEQ ID NO:173) Bio Gly Gly Asp Ala Pro Gly Tyr Asp Pro Leu Trp Phe Ile Thr Ser Glu Pro Thr Gln Pro Pro Pro Thr Ser Pro Pro Leu Val His Asp Ser Asp Leu Glu His Val Leu Thr

II-gp52-3:
(SEQ ID NO:174) Bio Gly Gly Tyr Ser Cys Met Val Cys Val Asp Arg Ser Ser Leu Ser Ser Trp His Val Leu Tyr Thr Pro Asn Ile Ser Ile Pro Gln Gln Thr Ser Ser Arg Thr Ile Leu Phe Pro Ser

II-p19:
(SEQ ID NO:175) Bio Gly Gly Pro Thr Thr Thr Pro Pro Pro Pro Pro Pro Pro Ser Pro Glu Ala His Val Pro Pro Pro Tyr Val Glu Pro Thr Thr Thr Gln Cys Phe

A number of these peptides were used to prepare LIA strips for the detection of antibodies to HTLV. Several of the peptides, such as I-p19 and I-gp46-4, which are derived from regions of the HTLV-I p19 gag protein and envelope glycoprotein, respectively, are expected to be recognized by antibodies produced as a result of both HTLV-I and HTLV-II infection since these sequences are highly homologous in the two viruses. Others, such as I-gp46-3, I-gp46-6 for HTLV-I, and II-gp52-1, II-gp52-2 and II-gp52-3 for HTLV-II may be useful for detection of antibodies as well as discrimination. Since there is some homology between the HTLV-I and HTLV-II sequences, cross-reactions are to be expected. Nevertheless, the intensities of the reactions to the various peptides should reveal the identity of the virus to which the antibodies were produced.

An example of LIA strips prepared with a number of the biotinylated HTLV-I and HTLV-II peptides is shown in figure XXX. The LIA strips were evaluated using a commercially available serum panel (Boston Biomedica Inc., mixed titer panel, PRP203). The test results are in complete agreement with the analysis provided by distributor. Only one sample (nr. 9) is positive for HTLV-I. Sample nr.12 is detected as positive because of the positive reaction to the peptide I-p19. This sample could not be differentiated using these peptides, nor could this sample be differentiated by any other test used by the distributor of the serum panel. Sample nr. 11 was found to be negative and all other samples were found to be positive for HTLV-II. In an additional experiment, an ELISA was performed using all 10 of the biotinylated HTLV-I and HTLV-II peptides. The peptides were complexed with streptavidin individually and then mixed prior to coating. Some of the samples from the panel used to evaluate the LIA strips were used to evaluate the peptides in the ELISA. These results are shown in table. The ELISA in this configuration cannot be used to differentiate HTLV-I and -II infections but should identify HTLV-positive samples in general regardless of virus type. The results further demonstrate the utility of these peptides for the diagnosis of HTLV infection.

TABLE 1

Antibody recognition of biotinylated and unbiotinylated HIV-1 and HIV-2 peptides

| Serum | TM-HIV-1 | TM-HIV-1 Bio | TM-HIV-2 | TM-HIV-2 Bio |
|---|---|---|---|---|
| HIV-1 positive | | | | |
| 0724 | 0.174 | 2.570 | 0.000 | 0.000 |
| mm | 0.051 | 2.579 | 0.000 | 0.000 |
| YEMO | 0.162 | 2.357 | 0.000 | 0.000 |
| PL | 0.000 | 1.559 | 0.000 | 0.000 |
| VE | 0.052 | 2.551 | 0.000 | 0.000 |
| HIV-2 positive | | | | |
| 1400 | 0.000 | 0.000 | 0.000 | 1.982 |
| AG | 0.000 | 0.000 | 0.000 | 2.323 |
| 53-3 | 0.000 | 0.000 | 0.000 | 2.365 |
| Seronegative Donors | | | | |
| 194 | 0.000 | 0.000 | 0.000 | 0.000 |
| 195 | 0.000 | 0.000 | 0.000 | 0.000 |
| 180 | 0.000 | 0.005 | 0.000 | 0.000 |
| 204 | 0.000 | 0.001 | 0.000 | 0.000 |

TABLE 2

Comparison of antibody recognition of biotinylated and unbiotinylated peptides from the V3 sequence of isolate HIV-1 mn.

| Sample identity | V3-mn | V3-mn Bio |
|---|---|---|
| negative control | 0.063 | 0.069 |
| blank | 0.053 | 0.051 |
| YS | 1.442 | 2.784 |
| DV | 1.314 | 2.881 |
| VE | 1.717 | overflow* |
| OOST 6 | 1.025 | 2.855 |
| OOST 8 | 1.389 | overflow* |
| 3990 | 1.442 | overflow* |
| PL | 0.531 | 2.351 |
| MM | 0.791 | 2.542 |
| 4436 | 0.388 | 2.268 |
| 4438 | 0.736 | 2.554 |
| 266 | 0.951 | 2.591 |
| OOST 4 | 1.106 | overflow* |

*: Absorbance value greater than 3.000

TABLE 3

Comparison of antibody recognition of the biotinylated V3-mn peptide bound to streptavidin and avidin

| Serum | Streptavidin | Avidin |
|---|---|---|
| YS | 1.236 | 1.721 |
| DV | 1.041 | 1.748 |
| PL | 0.222 | 0.983 |
| 3990 | 1.391 | 1.854 |
| VE | 1.526 | 1.908 |
| 4436 | 0.596 | 1.519 |
| Control | 0.050 | 0.063 |

TABLE 4

Comparison of antibody recognition of biotinylated and unbiotinylated HCV peptides.

Antibody binding to HCV peptide XI

| Serum | Unbiotinylated peptide XI | Peptide XI |
|---|---|---|
| 2 | 0.090 | 1.971 |
| 3 | 0.443 | 2.086 |
| 4 | 0.473 | 1.976 |
| 6 | 0.053 | 0.518 |
| 8 | 1.275 | 2.624 |
| 10 | 0.764 | 2.321 |
| 11 | 0.569 | 2.378 |
| 23 | 0.775 | 2.503 |
| 31 | 0.497 | 2.104 |
| 77 | 0.093 | 0.159 |
| 33 | 0.832 | 1.857 |
| 49 | 0.515 | 2.180 |
| negative serum | 0.053 | 0.095 |

Antibody binding to HCV peptide XVI

| Serum | Unbiotinylated peptide XVI | Peptide XVI |
|---|---|---|
| 1 | 1.038 | 2.435 |
| 2 | 0.616 | 1.239 |
| 6 | 0.100 | 1.595 |
| 8 | 0.329 | 1.599 |
| 10 | 1.033 | 2.847 |
| 26 | 0.053 | 1.522 |
| 83 | 0.912 | 2.221 |
| 88 | 1.187 | 2.519 |
| 89 | 0.495 | 1.530 |
| 91 | 0.197 | 2.169 |
| 95 | 0.109 | 1.484 |
| 99 | 0.814 | 2.045 |
| 100 | 0.474 | 1.637 |
| 104 | 0.205 | 0.942 |
| 105 | 0.313 | 2.186 |
| 110 | 0.762 | 1.484 |
| 111 | 0.193 | 1.465 |
| 112 | 0.253 | 1.084 |
| 113 | 0.833 | 2.535 |
| 116 | 0.058 | 1.918 |
| 120 | 0.964 | 2.332 |
| 11476 | 0.068 | 2.197 |
| 24724 | 0.071 | 0.062 |
| 266 | 0.712 | 2.262 |
| 8247 | 0.059 | 0.618 |
| negative serum | 0.063 | 0.067 |

Antibody binding to HCV peptide II

| Serum | Unbiotinylated peptide II | Peptide II |
|---|---|---|
| 8241 | 0.444 | 0.545 |
| 8242 | 1.682 | 2.415 |
| 8243 | 2.181 | 2.306 |
| 8247 | 1.518 | 1.975 |
| 8250 | 0.110 | 0.357 |
| 8271 | 0.912 | 1.284 |
| 8273 | 2.468 | 2.769 |
| 8274 | 2.700 | 2.943 |
| 8275 | 1.489 | 2.030 |
| 8276 | 2.133 | 2.348 |
| 8277 | 1.771 | 2.572 |
| 8278 | 1.907 | 2.022 |
| negative serum | 0.047 | 0.070 |

Antibody binding to HCV peptide III

| Serum | Unbiotinylated peptide III | Peptide III |
|---|---|---|
| 8241 | 1.219 | 2.066 |
| 8242 | 1.976 | 2.197 |
| 8243 | 1.859 | 2.368 |
| 8247 | 1.072 | 2.398 |
| 8248 | 2.742 | 2.918 |

TABLE 4-continued

Comparison of antibody recognition of biotinylated and unbiotinylated HCV peptides.

| | | |
|---|---|---|
| 8250 | 2.471 | 2.626 |
| 8271 | 1.471 | 2.066 |
| 8272 | 2.471 | 2.638 |
| 8273 | 1.543 | 2.697 |
| 8274 | 2.503 | 2.905 |
| 8275 | 1.595 | 2.640 |
| 8276 | 1.976 | 2.674 |
| 8277 | 0.735 | 2.327 |
| negative serum | 0.050 | 0.06 |

Antibody binding to HCV peptide V

| Serum | Unbiotinylated peptide V | Peptide V |
|---|---|---|
| 8272 | 0.589 | 1.220 |
| 8273 | 0.294 | 1.026 |
| 8274 | 1.820 | 2.662 |
| 8275 | 1.728 | 1.724 |
| 8276 | 2.194 | 2.616 |
| 8277 | 0.770 | 1.796 |
| 8278 | 1.391 | 1.746 |
| 8284 | 0.040 | 0.757 |
| negative serum | 0.047 | 0.070 |

Antibody binding to HCV peptide IX

| Serum | Unbiotinylated peptide IX | Peptide IX |
|---|---|---|
| 8315 | 2.614 | 2.672 |
| 8316 | 0.133 | 0.367 |
| 8317 | 0.855 | 1.634 |
| 8318 | 1.965 | 2.431 |
| 8320 | 0.721 | 0.896 |
| 8321 | 0.283 | 0.457 |
| 8326 | 2.219 | 2.540 |
| negative serum | 0.052 | 0.005 |

Antibody binding to HCV peptide XVIII

| Serum | Unbiotinylated peptide XVIII | Peptide XVIII |
|---|---|---|
| 79 | 1.739 | 2.105 |
| 83 | 1.121 | 1.232 |
| 88 | 0.972 | 1.858 |
| 89 | 2.079 | 2.309 |
| 91 | 2.202 | 2.132 |
| 99 | 1.253 | 1.526 |
| 104 | 1.864 | 1.998 |
| 105 | 1.522 | 2.053 |
| 110 | 1.981 | 2.065 |
| 111 | 1.363 | 1.542 |
| 112 | 1.172 | 1.408 |
| 116 | 1.534 | 1.978 |
| 120 | 1.599 | 2.031 |
| 1 | 2.523 | 2.691 |
| 33 | 1.463 | 1.813 |
| 39 | 0.068 | 0.213 |
| 47 | 2.117 | 2.611 |
| negative serum | 0.001 | 0.001 |

TABLE 4E

Antibody binding to HCV peptide V

| Serum | Unbiotinylated peptide V | Peptide V |
|---|---|---|
| 8272 | 0.589 | 1.220 |
| 8273 | 0.294 | 1.026 |
| 8274 | 1.820 | 2.662 |
| 8275 | 1.728 | 1.724 |
| 8276 | 2.194 | 2.616 |
| 8277 | 0.770 | 1.796 |
| 8278 | 1.391 | 1.746 |
| 8284 | 0.040 | 0.757 |
| negative serum | 0.047 | 0.070 |

TABLE 4F

Antibody binding to HCV peptide IX

| Serum | Unbiotinylated peptide IX | Peptide IX |
|---|---|---|
| 8315 | 2.614 | 2.672 |
| 8316 | 0.133 | 0.367 |
| 8317 | 0.855 | 1.634 |
| 8318 | 1.965 | 2.431 |
| 8320 | 0.721 | 0.896 |
| 8321 | 0.283 | 0.457 |
| 8326 | 2.219 | 2.540 |
| negative serum | 0.052 | 0.005 |

TABLE 4G

Antibody binding to HCV peptide XVIII

| Serum | Unbiotinylated peptide XVIII | Peptide XVIII |
|---|---|---|
| 79 | 1.739 | 2.105 |
| 83 | 1.121 | 1.232 |
| 88 | 0.972 | 1.858 |
| 89 | 2.079 | 2.309 |
| 91 | 2.202 | 2.132 |
| 99 | 1.253 | 1.526 |
| 104 | 1.864 | 1.998 |
| 105 | 1.522 | 2.053 |
| 110 | 1.981 | 2.065 |
| 111 | 1.363 | 1.542 |
| 112 | 1.172 | 1.408 |
| 116 | 1.534 | 1.978 |
| 120 | 1.599 | 2.031 |
| 1 | 2.523 | 2.691 |
| 33 | 1.463 | 1.813 |
| 39 | 0.068 | 0.213 |
| 47 | 2.117 | 2.611 |
| negative serum | 0.001 | 0.001 |

TABLE 5

| Peptide concentration* | 30 | | 10 | | 0.3 | | 0.1 | | 0.03 | | 0.01 | |
|---|---|---|---|---|---|---|---|---|---|---|---|---|
| coating method** | 1 | 2 | 1 | 2 | 1 | 2 | 1 | 2 | 1 | 2 | 1 | 2 |
| Unbiotinylated HCV peptide II and HCV peptide II | | | | | | | | | | | | |
| sample positive | | | | | | | | | | | | |
| 8320 | 2.718 | 2.278 | 2.684 | 2.163 | 2.684 | 2.001 | 2.718 | 1.828 | 2.757 | 1.272 | 2.519 | 0.479 |
| 8242 | 1.427 | 0.539 | 1.368 | 0.408 | 1.365 | 0.234 | 1.399 | 0.058 | 1.481 | 0.048 | 1.196 | 0.051 |
| 8243 | 1.668 | 1.341 | 1.652 | 1.221 | 1.608 | 0.831 | 1.639 | 0.181 | 1.597 | 0.057 | 1.088 | 0.056 |
| 8318 | 2.016 | 0.791 | 1.993 | 0.626 | 1.958 | 0.347 | 2.001 | 0.181 | 2.181 | 0.095 | 2.002 | 0.048 |
| sample negative | | | | | | | | | | | | |
| 1747 | 0.064 | 0.049 | 0.071 | 0.046 | 0.046 | 0.011 | 0.045 | 0.044 | 0.045 | 0.043 | 0.045 | 0.041 |
| 1781 | 0.057 | 0.053 | 0.055 | 0.053 | 0.051 | 0.045 | 0.047 | 0.046 | 0.049 | 0.053 | 0.053 | 0.046 |
| Unbiotinylated HCV peptide IX and HCV peptide IX | | | | | | | | | | | | |
| sample positive | | | | | | | | | | | | |
| 8320 | 1.779 | 0.129 | 0.802 | 0.093 | 1.798 | 0.122 | 1.244 | 0.063 | 1.007 | 0.057 | 0.461 | 0.059 |
| 8326 | 2.284 | 0.081 | 2.271 | 0.068 | 2.271 | 0.078 | 2.281 | 0.068 | 2.193 | 0.051 | 1.812 | 0.049 |
| 8242 | 0.791 | 0.059 | 0.777 | 0.052 | 0.795 | 0.048 | 0.911 | 0.046 | 0.496 | 0.047 | 0.215 | 0.049 |
| 8243 | 1.959 | 0.063 | 1.953 | 0.053 | 1.892 | 0.051 | 1.834 | 0.051 | 1.421 | 0.051 | 0.639 | 0.054 |
| sample negative | | | | | | | | | | | | |
| 1747 | 0.051 | 0.046 | 0.049 | 0.046 | 0.046 | 0.044 | 0.042 | 0.045 | 0.044 | 0.045 | 0.043 | 0.045 |
| 1781 | 0.053 | 0.053 | 0.051 | 0.052 | 0.051 | 0.051 | 0.047 | 0.052 | 0.048 | 0.049 | 0.049 | 0.051 |
| Unbiotinylated HCV peptide XVIII and HCV peptide XVIII | | | | | | | | | | | | |
| sample positive | | | | | | | | | | | | |
| 8326 | 2.315 | 0.052 | 2.331 | 0.053 | 2.331 | 0.053 | 2.331 | 0.049 | 2.219 | 0.051 | 1.848 | 0.051 |
| 8242 | 0.749 | 0.053 | 0.839 | 0.049 | 0.873 | 0.048 | 0.946 | 0.047 | 1.188 | 0.049 | 1.185 | 0.048 |
| 8243 | 0.671 | 0.057 | 0.627 | 0.053 | 0.629 | 0.054 | 0.661 | 0.051 | 0.611 | 0.053 | 0.462 | 0.053 |
| 8318 | 2.391 | 0.051 | 2.396 | 0.045 | 2.392 | 0.047 | 2.409 | 0.047 | 2.308 | 0.047 | 1.711 | 0.048 |
| sample negative | | | | | | | | | | | | |
| 1747 | 0.047 | 0.048 | 0.042 | 0.045 | 0.061 | 0.046 | 0.044 | 0.045 | 0.058 | 0.044 | 0.042 | 0.047 |
| 1781 | 0.053 | 0.055 | 0.048 | 0.054 | 0.048 | 0.051 | 0.048 | 0.051 | 0.051 | 0.051 | 0.045 | 0.053 |

*In micrograms per milliliter
**1. biotinylated peptide on streptavidin coated plate
   2. unbiotinylated peptide coated directly

TABLE 6

Comparison of N- and C-terminally biotinylated TM-HIV-1 peptide.

| | Serum | TM-HIV-1 C-terminal biotin | TM-HIV-1 N-terminal biotin |
|---|---|---|---|
| HIV positive | VE | 2.079 | 2.240 |
| | OOST 6 | 1.992 | 2.003 |
| | MM | 2.097 | 2.308 |
| | 0724 | 2.322 | 2.291 |
| | DV | 0.903 | 1.579 |
| | PL | 1.893 | 1.849 |
| | 2049 | 1.780 | 2.058 |
| | 3990 | 1.959 | 1.870 |
| | 4438 | 1.622 | 1.697 |
| | 4436 | 2.190 | 2.110 |
| | OOST 7 | 1.728 | 2.027 |
| | OOST 8 | 2.117 | 2.237 |
| | OOST 9 | 2.119 | 2.222 |
| | VCM | 2.131 | 2.263 |
| | 1164 | 1.865 | 1.919 |
| | 1252 | 2.244 | 2.356 |
| | 0369/87 | 2.059 | 2.042 |
| Seronegative blood donors | 1784 | 0.000 | 0.000 |
| | 1747 | 0.000 | 0.000 |
| | 1733 | 0.014 | 0.000 |

TABLE 7

| | HCV peptide I (coated directly) | HCV peptide I carboxy-biotinylated (bound to streptavidin-coated wells) |
|---|---|---|
| HCV antibody-positive sera | | |
| 8316 | 2.394 | 2.541 |
| 8318 | 2.385 | 2.404 |
| 8320 | 2.760 | 2.762 |
| 8326 | 0.525 | 1.775 |
| 8329 | 2.633 | 2.672 |
| 8333 | 2.143 | 2.545 |
| 8334 | 2.271 | 2.549 |
| 8336 | 1.558 | 2.016 |
| 8344 | 1.878 | 2.010 |
| 8248 | 2.042 | 2.493 |
| 8244 | 0.077 | 1.399 |
| 8243 | 2.211 | 2.541 |
| 8242 | 1.367 | 2.389 |
| 8364 | 2.705 | 2.705 |
| 8374 | 1.070 | 2.151 |
| 8378 | 2.161 | 2.531 |
| 8330 | 1.985 | 2.651 |
| 8387 | 1.427 | 2.628 |

TABLE 7-continued

|  | HCV peptide I (coated directly) | HCV peptide I carboxy-biotinylated (bound to streptavidin-coated wells) |
|---|---|---|
| HCV antibody-negative sera | | |
| F88 | 0.000 | 0.026 |
| F89 | 0.017 | 0.001 |
| F76 | 0.000 | 0.022 |
| F136 | 0.006 | 0.002 |
| F8 | 0.000 | 0.000 |

TABLE 8

Use of mixtures of biotinylated peptides for antibody detection.

| Serum | IM-HIV-1-BIO Avidin | IM-HIV-2-BIO Avidin | V3-mn-BIO Avidin | HCV peptide II-BIO Avidin | HCV peptide IX-BIO Avidin | HCV peptide XVIII-BIO Avidin | Mixture A Avidin | Mixture B Avidin | Mixture A Direct coating | Mixture B Direct coating |
|---|---|---|---|---|---|---|---|---|---|---|
| HCV | | | | | | | | | | |
| 8243 | 0.108 | 0.109 | 0.114 | 1.430 | 1.213 | 0.118 | 1.590 | 1.638 | 0.542 | 0.184 |
| 8247 | 0.042 | 0.048 | 0.052 | 1.356 | 0.756 | 0.046 | 0.840 | 1.149 | 0.049 | 0.049 |
| 8248 | 0.043 | 0.046 | 0.048 | 2.287 | 0.047 | 0.905 | 1.859 | 2.154 | 0.407 | 0.064 |
| 8269 | 0.053 | 0.049 | 0.056 | 1.213 | 0.051 | 1.513 | 0.923 | 1.268 | 0.078 | 0.067 |
| 8290 | 0.045 | 0.047 | 0.050 | 0.060 | 0.048 | 2.323 | 1.210 | 1.761 | 0.559 | 0.717 |
| 8278 | 0.046 | 0.045 | 0.053 | 1.878 | 0.074 | 0.052 | 1.806 | 1.944 | 0.540 | 0.152 |
| 8273 | 0.053 | 0.050 | 0.056 | 2.017 | 0.053 | 0.052 | 2.037 | 2.113 | 0.773 | 0.185 |
| 8285 | 0.134 | 0.163 | 0.143 | 1.592 | 0.270 | 0.146 | 1.746 | 1.822 | 0.908 | 0.401 |
| 8291 | 0.048 | 0.050 | 0.053 | 1.539 | 0.052 | 0.049 | 1.591 | 1.809 | 0.335 | 0.098 |
| HIV-2 | | | | | | | | | | |
| AG | 0.054 | 2.065 | 0.068 | 0.081 | 0.064 | 0.058 | 1.833 | 1.880 | 0.054 | 0.056 |
| 1400 | 0.051 | 1.781 | 0.055 | 0.121 | 0.052 | 1.362 | 1.692 | 2.031 | 0.214 | 0.326 |
| HIV-1 | | | | | | | | | | |
| YS | 0.046 | 0.046 | 2.201 | 0.048 | 0.049 | 0.049 | 2.045 | 1.845 | 0.200 | 0.052 |
| PL | 1.974 | 0.051 | 1.321 | 0.052 | 0.056 | 0.052 | 1.587 | 1.776 | 0.052 | 0.055 |
| DV | 1.329 | 0.048 | 2.340 | 0.047 | 0.049 | 0.047 | 1.969 | 1.742 | 0.100 | 0.049 |
| 3990 | 1.602 | 0.054 | 2.319 | 0.054 | 0.066 | 0.056 | 2.217 | 1.926 | 0.390 | 0.031 |
| Blood donor | | | | | | | | | | |
| 1785 | 0.046 | 0.047 | 0.048 | 0.045 | 0.050 | 0.047 | 0.047 | 0.049 | 0.045 | 0.049 |
| 1794 | 0.124 | 0.090 | 0.091 | 0.153 | 0.098 | 0.104 | 0.152 | 0.161 | 0.050 | 0.058 |
| 1784 | 0.044 | 0.046 | 0.046 | 0.045 | 0.050 | 0.047 | 0.047 | 0.047 | 0.045 | 0.048 |
| 1782 | 0.052 | 0.057 | 0.059 | 0.057 | 0.062 | 0.053 | 0.057 | 0.059 | 0.049 | 0.056 |

TABLE 9

Sequences of the Core Epitopes of the HCV Core Protein
HCV CORE PROTEIN AMINO ACIDS T–90
Positions of core epilopes

| Epitope 1A: | I P K [P O R K T K] | | | | | CORE 1 |
|---|---|---|---|---|---|---|
| | P K [P O R K T K] R | | M S T I P K P O R K T K R N T N R R P O | | | |
| | K [P O R K T K] R N | | P O R K T K R N T N R R P O D V K F P G | | | CORE 2 |
| | [P O R K T K] R N T | | | | | |
| Epitope 1B: | O P [K T K R N T N] | | M S T I P K P O R K T K R N T N R R P O | | | CORE 1 |
| | R [K T K R N T N] R | | P O R K T K R N T N R R P O D V K F P G | | | |
| | [K T K R N T N] R R | | | | | CORE 2 |

TABLE 9-continued

Sequences of the Core Epitopes of the HCV Core Protein
HCV CORE PROTEIN AMINO ACIDS T–90
Positions of core epilopes

| Epitope 2: | R R P O D V K F P<br>R P O D V K F P G<br>P O D V K F P G G | P O R K T K R N T N R R P O D V K F P G<br>R N T N R R P O D V K F P G G G O I V G | CORE 2<br>CORE 2 |
|---|---|---|---|
| Epitope 2A: | G G V T L L P R R<br>G V T L L P R R G<br>V T L L P R R G P<br>T L L P R R G P R | P G G G O I V G G V T L L P R R G P R L | CORE 5 |
| Epitope 2B: | L L P R R G P R L<br>L P R R G P R L G<br>P R R G P R L G V | P G G G O I V G G V T L L P R R G P R L<br>L P R R G P R L G V R A T R K I S E R S | CORE 5<br>CORE 7 |
| Epitope 3C: | G P R L G V R A T<br>P R L G V R A T R<br>R L G V R A T R K | L P R R G P R L G V D A T R K T G E R S | CORE 7 |
| Epitope 4A: | E R S O P R G R G<br>R S O P R G R G O<br>S O P R G R G O P | T R K T S E R S O P R G R R O P I P K Y | CORE 9 |
| Epitope 4B: | R G R R O P I P K<br>G R R O P I P K Y<br>R R O P I P K Y R | T R K T S E R S O P R G R R O P I P K Y<br>R R O P I P K V R R P E G R T W A O P G | CORE 9<br>CORE 11 |
| Epitope 5A: | P E G R T W A O P<br>E G R T W A O P G<br>G R T W A O P G T<br>R T W A O P G T P | R R O P I P K Y R R P E G R T W A O P G<br>G R T W A O P G T P W P L T G N E G G G | CORE 11<br>CORE 13 |
| Epitope 5B:<br>runner 1 | A O P G T P W P L<br>O P G T P W P L T | G R T W A O P G T P W P L T G N E G G G | CORE 13 |

TABLE 10

Sequences of the Core Epitopes of the HCV NS4 Protein
HCV NS4 PROTEIN
Positions of core epitopes

| Epitope 1: | A I I P D R E V L<br>I I P D R E V L T<br>I P D R E V L T R<br>P D R E V L T R E | L S G K P A I I P D R E V L Y R E F D E<br>I I P D R E V L Y R E F D E M E E C S O | HCV1<br>HCV2 |
|---|---|---|---|
| Epitope 2A: | O S O M L P T I E<br>S O M L P T I E O<br>O M L P T I E O G<br>M L P T I E O G M | V L T R E F D E M E E C S O M L P V L E<br>D E M E E C S O M L P V L E O G M M L A<br>S O M L P V L E O G M M L A E O F K O K | HCV3<br>HCV4<br>HCV5 |
| Epitope 2B:<br>runner 1 | P T I E O G M M L<br>T I E O G M M L A | D E M E E C S O M L P T I E O G M M L A<br>S O M L P T I E O G M M L A E O F K O K | HCV4<br>HCV5 |
| Epitope 3A: | M L A E G F K O K<br>L A E G F K O K A<br>A E G F K O K A L | S O M L P Y I E O G M M L A E O E K O K<br>I E O G M M L A E O E K O K A L G L L O<br>L A E O E K O K A L G L L O T A S R O A | HCV5<br>HCV6<br>HCV7 |
| Epitope 3B: | E O F K O K A L O<br>O F K O K A L O L<br>F K O K A L O L L<br>K O K A L O L L O | I E O C M M L A E O F K O K A L O L L O<br>L A E O F K O K A L O L L O T A S R O A | HCV6<br>HCV7 |

TABLE 10-continued

Sequences of the Core Epitopes of the HCV NS4 Protein
HCV NS4 PROTEIN
Positions of core epitopes

| Epitope 4: | K A L G L L O T A<br>A L G L L O T A S<br>L G L L O T A S R | L A E O F K O K A L O L L O T A S R O A<br>O K A L O L L O T A S R O A E V I A P A | HCV7<br>HCV8 |
|---|---|---|---|

TABLE 11

Sequences of the Core Epitopes of the HCV NS5 Protein
−31 NS5 PROTEIN
Positions of the core epitopes

| Epitope 1A: | S V P A E I L R K<br>V P A E I L R K S | E D E R E I S V P A E I L P M S R R F A | NSS-25 |
|---|---|---|---|
| Epitope 1B: | F A E I L R K S R<br>A E I L R K S R R<br>E I L R K S R R F | E D E R E I S V P A E I L P M S R R F A | NSS-25 |
| Epitope 2: | F A O A L P V W A<br>A O A L P V W A R<br>O A L P V W A R P | L R K S R R F A G A L P V W L R P D Y N | NSS-27 |
| Epitope 3: | W A P P D T N P P<br>A P P D T N P P L<br>P P D T N P P L Y<br>P D T N P P L Y E | V W A S P S T M P P L V E T W K K P D T | NSS-29 |
| Epitope 4: runner 1 | F F L V E T W K K<br>F L V E T W K K P<br>L V E T W K K P P | V W A S P S T M P P L V E T W K K P D T | NSS-29 |
| Epitope 5: | K K P O Y E P P V<br>K P O Y E P P V V<br>P O Y E P P V V M<br>O Y E P P V V M G | E T K K K P D T E P P V V M G C P L P P | NSS-31 |
| Epitope 6: | P P V V M G C P L<br>P V V M G C P L P<br>V V M G C P L P P<br>V M G C P L P P P<br>M G C P L P P P K | E T K K K P D T E P P V V M G C P L P P<br>V M G C P L P P P K S P P V P P P R K K | NSS-31<br>NSS-33 |

TABLE 12

Antibody Binding of Various Core. NS4 and NS5 Biotinylated 20 mers by the 10 Test Sera

PEPTIDE ELISA O.D.

| SERUM | Core-2 | Core-3 | Core-7 | Core-9 | HCV-2 | HCV-5 | HCV-7 | NS5-25 | NS5-27 | NS5-31 |
|---|---|---|---|---|---|---|---|---|---|---|
| 8242 | 2.415 | 2.197 | 0.632 | 2.315 | 2.114 | 1.625 | 1.252 | 0.268 | 2.318 | 2.453 |
| 8248 | 2.441 | 2.918 | 1.529 | 2.021 | 0.142 | 0.182 | 1.963 | 0.054 | 0.388 | 1.511 |
| 8332 | 1.977 | 2.054 | 1.387 | 1.455 | 0.392 | 0.575 | 0.945 | 0.047 | 2.130 | 2.290 |
| 8339 | 2.030 | 2.765 | 0.166 | 2.598 | 2.497 | 0.043 | 0.041 | 1.495 | 2.359 | 2.757 |
| 8358 | 1.982 | 2.135 | 0.357 | 0.685 | 1.779 | 0.623 | 0.598 | 0.069 | 2.249 | 0.182 |
| 8377 | 2.181 | 2.368 | 0.221 | 0.076 | 2.368 | 2.227 | 1.829 | 1.092 | 2.336 | 1.378 |
| 8378 | 2.140 | 2.369 | 1.089 | 1.228 | 1.859 | 1.449 | 2.006 | 0.279 | 1.602 | 2.337 |
| 8383 | 2.463 | 2.463 | 0.970 | 2.162 | 2.300 | 1.018 | 2.504 | 0.055 | 2.390 | 2.358 |
| 8241 | 0.545 | 2.066 | 0.448 | 0.274 | 2.421 | 2.280 | 0.968 | 0.050 | 2.456 | 0.278 |
| 8243 | 2.306 | 2.368 | 1.251 | 1.378 | 2.203 | 2.268 | 2.251 | 0.062 | 1.444 | 0.127 |

TABLE 13

Antibody recognition of individual E2/NS1 peptides (percent of all sera giving a positive reaction.)

| Peptide | Count | Percent |
|---|---|---|
| CL14-A | 7(51) | 13.7% |
| B | 36(51) | 70.6% |
| KATO-A | 2(51) | 3.92% |
| B | 26(51) | 50.98% |
| HCJ4-A | 32(51) | 62.74% |
| B | 41(51) | 80.39% |
| FRENCH-A | 30(51) | 58.8% |
| B | 42(51) | 82.35% |
| YEK-A | 7(51) | 13.72% |
| B | 49(51) | 96.07% |
| TAMI-A | 12(51) | 23.52% |
| B | 36(51) | 70.58% |
| 18CHl-A | 5(51) | 9.8% |
| B | 30(51) | 58.82% |
| CHIR-A | 32(51) | 62.7% |
| B | 40(51) | 78.43% |

TABLE 14

Overall Recognition of V3-Loop Peptides

| | CON | SC | MN | SF2 | BH | RF | MAL | ELI | 70 |
|---|---|---|---|---|---|---|---|---|---|
| Total | | | | | | | | | |
| SUM | 287 | 261 | 275 | 258 | 108 | 146 | 140 | 24 | 6 |
| COUNT | 326 | 326 | 326 | 326 | 326 | 326 | 326 | 326 | 326 |
| gp120 positive | | | | | | | | | |
| % Reactive | 88 | 80 | 84 | 79 | 33 | 45 | 43 | 7 | 2 |
| Total | | | | | | | | | |
| SUM | 287 | 261 | 275 | 258 | 108 | 146 | 140 | 24 | 6 |
| COUNT | 307 | 307 | 307 | 307 | 307 | 307 | 307 | 307 | 307 |
| HIV-V3 positive | | | | | | | | | |
| % Reactive | 93 | 85 | 90 | 84 | 35 | 48 | 46 | 8 | 2 |

TABLE 15

Recognition of Peptides According to Geographical Region

| EUROPEAN | % | AFRICAN | % | BRAZILIAN | % |
|---|---|---|---|---|---|
| Consensus | 98 | Consensus | 89 | Consensus | 82 |
| HIV-1 (SC) | 98 | HIV-1 (MN) | 85 | HIV-1 (MN) | 78 |
| HIV-1 (SF2) | 98 | HIV-1 (SF2) | 79 | HIV-1 (SC) | 75 |
| HIV-1 (MN) | 97 | HIV-1 (SC) | 73 | HIV-1 (SF2) | 72 |
| HIV-1 (RF) | 75 | HIV-1 (MAL) | 60 | HIV-1 (RF) | 38 |
| HIV-1 (MAL) | 68 | HIV-1 (RF) | 34 | HIV-1 (MAL) | 30 |
| HIV-1 (IIIB) | 61 | HIV-1 (IIIB) | 27 | HIV-1 (IIIB) | 26 |
| HIV-1 (ELI) | 8 | HIV-1 (ELI) | 13 | HIV-1 (ELI) | 5 |
| ANT 70 | 2 | ANT 70 | 2 | ANT 70 | 2 |

TABLE 16

Recognition of European, African and Brazilian HIV 4 antibody-positive sera to HIV-1 V3 loop peptides V3-con and V3-368

| | V3-con | V3-368 | V3con-V3-368 |
|---|---|---|---|
| European sera | | | |
| number tested | 36 | 36 | 36 |
| number positive | 33 | 4 | 33 |
| number negative | 0 | 12 | 0 |
| number borderline | 3 | 20 | 3 |
| percent positive | 92 | 11 | 92 |
| percent negative | 0 | 33 | 0 |
| percent borderline | 8 | 56 | 8 |
| African sera | | | |
| number tested | 45 | 45 | 45 |
| number positive | 40 | 5 | 40 |
| number negative | 4 | 31 | 2 |
| number borderline | 1 | 9 | 3 |
| percent positive | 89 | 11 | 89 |
| percent negative | 9 | 69 | 4 |
| percent borderline | 2 | 20 | 7 |
| Brazilian sera | | | |
| number tested | 36 | 36 | 36 |
| number positive | 30 | 16 | 35 |
| number negative | 1 | 5 | 1 |
| number borderline | 5 | 15 | 0 |
| percent positive | 83.3 | 44.4 | 97.2 |
| percent negative | 2.8 | 13.9 | 2.8 |
| percent borderline | 13.9 | 41.7 | 0 |

TABLE 17

Recognition of HIV-2 positive sera to peptides from the V2 loop region of HIV-2

| | V3-GB12 | V3-239 |
|---|---|---|
| number tested | 21 | 21 |
| number positive | 21 | 19 |
| number negative | 0 | 0 |
| number borderline | 0 | 2 |
| percent positive | 100 | 90.5 |
| percent negative | 0 | 0 |
| percent borderline | 0 | 9.5 |

TABLE 18

Antibody recognition of hybrid peptides

| A. | Serum | NS4 Epitope 1 | NS5 Epitope 5 | Core Epitope 2 | LIA Epi-152 | Discrepancies |
|---|---|---|---|---|---|---|
| | 8241 | — | — | — | — | weak |
| | 8242 | — | — | — | — | |
| | 8243 | — | — | — | — | |
| | 8246 | — | — | — | — | |
| | 8332 | — | — | — | — | |
| | 8339 | — | — | — | — | |
| | 8377 | — | — | — | — | |
| | 8378 | — | — | — | — | |
| | 8383 | — | — | — | — | |

| B. | Serum | NS5 Epitope 3 | NS4 Epitope 3B | Core Epitope 3A | LIA Epi-33934 | Discrepancies |
|---|---|---|---|---|---|---|
| | 8241 | — | — | — | — | |
| | 8242 | — | — | — | — | |
| | 8245 | — | — | — | — | |
| | 8246 | — | — | — | — | |
| | 8332 | — | — — | — | — | |
| | 8339 | — | — | — | — | |
| | 8355 | — | — | — | — | |
| | 8377 | — | — | — | — | |
| | 8376 | — | — | — | — | |
| | 8383 | — | — | — | — | |

| C. | Serum | Core Epitope 4B | NSA4 Epitope 2A | NS5 Epitope 6 | LIA Epi-48245 | Discrepancies |
|---|---|---|---|---|---|---|
| | 8241 | — | — | — | — | |
| | 8242 | — | — | — | — | |
| | 8243 | — | — — | — | — | |
| | 8248 | — | — | — | — | |
| | 8332 | — | — — | — | — | weak |
| | 8339 | — | — | — | — | |
| | 8358 | — | — | — | — — | |
| | 8377 | — | — | — | — | |
| | 8378 | — | — | — | — | |
| | 8383 | — | — | — | — | |

TABLE 19

ANTIBODY RECOGNITION OF HTLV PEPTIDES

| Serum number | Optical density |
|---|---|
| 1 | 0.303 |
| 2 | 3.001 |
| 3 | 0.644 |
| 4 | 1.262 |
| 6 | 3.001 |
| 7 | 2.623 |
| 9 | 2.607 (HTLV-I) |
| 10 | 3.001 |
| 11 | 0.058 (negative) |
| 13 | 3.001 |
| 14 | 3.001 |
| 15 | 0.850 |
| 16 | 0.278 |
| 19 | 1.048 |
| 20 | 3.001 |
| 21 | 0.805 |
| 22 | 0.812 |
| 23 | 3.001 |
| 24 | 0.405 |
| 25 | 1.521 |

What is claimed is:

1. A peptide having the amino acid sequence set forth in SEQ ID NO:162 and the following chemical structure:

(A) (B) (X) Y Gln-Ile-Asp-Ile-Gln-Glu-Met-Arg-Ile-Gly-Pro-Met-Ala-Trp-Tyr-Ser-Met-Gly-Ile-Gly-GlyY (X) (Z);

wherein

B represents biotin,

X represents a biotinylation compound which is incorporated during the synthetic process, Y represents a covalent bond or a linker arm, A represents at least one amino acid, amino group, or chemically modified amino terminus of the peptide, Z represents at least amino acid, OH-group, $NH_2$-group or a linkage involving these two groups, and the parentheses indicate that the presence of any given group in this position is optional.

2. The peptide of claim 1 wherein Y is selected from the group consisting of a glycine reside, β alanine, 4-aminobutyric acid, 5-amino valeric acid and 6-aminohexanoic acid.

3. A peptide having an amino acid sequence consisting of: Gln-Ile-Asp-Ile-Gln-Glu-Met-Arg-Ile-Gly-Pro-Met-Ala-Trp-Tyr-Ser-Met-Gly-Ile-Gly-Gly (SEQID NO:162).

4. The peptide according to claim 1, wherein said peptide is biotinylated N-terminally, C-terminally or internally.

5. The peptide according to claim 4 which is coupled to streptavidin or avidin, with said streptavidin or avidin optionally coupled to a solid phase.

6. The peptide according to claim 1, with said peptide being anchored to a solid support via covalent or non-covalent bonds.

7. An immunoassay process for determining the presence of antibodies to HIV in a biological sample using a peptide according to claim 1, the process comprising:

contacting the biological sample with a composition comprising the peptide according to claim 1, and detecting any immune complex formed between said antibodies and said peptide.

8. An immunological assay kit for detecting antibodies to HIV comprising a peptide according to claim 1.

9. A Line immunoassay kit for detecting antibodies to HIV comprising a peptide according to claim 6.

* * * * *